US 7,495,089 B2

(12) United States Patent
O'Reilly et al.

(10) Patent No.: US 7,495,089 B2
(45) Date of Patent: Feb. 24, 2009

(54) THERAPEUTIC ANTIANGIOGENIC ENDOSTATIN COMPOSITIONS

(75) Inventors: Michael S. O'Reilly, Missouri City, TX (US); M. Judah Folkman, Brookline, MA (US); George S. Abrams, legal representative, Waban, MA (US)

(73) Assignee: The Children's Medical Center Corporation, Boston, MA (US)

( * ) Notice: Subject to any disclaimer, the term of this patent is extended or adjusted under 35 U.S.C. 154(b) by 183 days.

(21) Appl. No.: 11/089,945

(22) Filed: Mar. 25, 2005

(65) Prior Publication Data
US 2005/0282253 A1 Dec. 22, 2005

Related U.S. Application Data

(60) Continuation of application No. 10/042,347, filed on Jan. 11, 2002, now abandoned, which is a division of application No. 09/315,689, filed on May 20, 1999, now Pat. No. 6,346,510, and a continuation-in-part of application No. 09/154,302, filed on Sep. 16, 1998, now Pat. No. 6,630,448, which is a division of application No. 08/740,168, filed on Oct. 22, 1996, now Pat. No. 5,854,205.

(60) Provisional application No. 60/106,343, filed on Oct. 30, 1998, provisional application No. 60/026,263, filed on Sep. 17, 1996, provisional application No. 60/023,070, filed on Aug. 2, 1996, provisional application No. 60/005,835, filed on Oct. 23, 1995.

(51) Int. Cl.
C07H 21/02 (2006.01)
A61K 38/00 (2006.01)

(52) U.S. Cl. .................. 536/23.1; 536/23.5; 435/320.1; 514/44

(58) Field of Classification Search ........................ None
See application file for complete search history.

(56) References Cited

U.S. PATENT DOCUMENTS

| 2,584,271 | A | 2/1952 | Huffman |
|---|---|---|---|
| 2,830,991 | A | 4/1958 | Keller et al. |
| 2,846,453 | A | 8/1958 | Hoehn |
| 3,166,577 | A | 1/1965 | Ringold et al. |
| 3,410,879 | A | 11/1968 | Smith et al. |
| 3,470,218 | A | 9/1969 | Farah |
| 3,492,321 | A | 1/1970 | Crabbe |
| 3,496,272 | A | 2/1970 | Krueger |
| 3,560,495 | A | 2/1971 | Frankus et al. |
| 3,562,260 | A | 2/1971 | De Ruggieri et al. |
| 3,563,986 | A | 2/1971 | Frankus et al. |
| 3,625,946 | A | 12/1971 | Heinrich et al. |
| 3,705,162 | A | 12/1972 | Graudums et al. |
| 3,728,351 | A | 4/1973 | Counsell et al. |
| 3,817,837 | A | 6/1974 | Rubenstein et al. |
| 3,956,348 | A | 5/1976 | Hilscher |
| 4,003,996 | A | 1/1977 | Pappo et al. |
| 4,150,149 | A | 4/1979 | Wolfsen et al. |
| 4,172,132 | A | 10/1979 | Draper et al. |
| 4,212,864 | A | 7/1980 | Tax |
| 4,241,046 | A | 12/1980 | Papahadjopoulos et al. |
| 4,289,689 | A | 9/1981 | Friesen et al. |
| 4,307,086 | A | 12/1981 | Tax |
| 4,347,245 | A | 8/1982 | Shapiro |
| 4,444,767 | A | 4/1984 | Torelli et al. |
| 4,502,989 | A | 3/1985 | Kamata et al. |
| 4,522,758 | A | 6/1985 | Ward et al. |
| 4,551,271 | A | 11/1985 | Hochuli |
| 4,552,758 | A | 11/1985 | Murphy et al. |
| 4,552,888 | A | 11/1985 | Koppel et al. |
| RE32,112 | E | 4/1986 | Shapiro |
| 4,599,331 | A | 7/1986 | Schreiber et al. |
| 4,604,284 | A | 8/1986 | Kung et al. |
| 4,621,930 | A | 11/1986 | Gu et al. |
| 4,634,705 | A | 1/1987 | DeBernardis et al. |
| 4,672,108 | A | 6/1987 | Kung et al. |
| 4,677,196 | A | 6/1987 | Rausch et al. |
| 4,684,635 | A | 8/1987 | Orentreich et al. |
| 4,743,597 | A | 5/1988 | Javitt et al. |
| 4,767,720 | A | 8/1988 | Lingwood |
| 4,795,703 | A | 1/1989 | Folkman et al. |
| 4,801,685 | A | 1/1989 | Goeddel et al. |
| 4,808,402 | A | 2/1989 | Leibovich et al. |
| 4,810,645 | A | 3/1989 | Goeddel et al. |
| 4,816,566 | A | 3/1989 | DeChiara et al. |
| 4,842,855 | A | 6/1989 | Youngner et al. |
| 4,885,256 | A | 12/1989 | Alving et al. |

(Continued)

FOREIGN PATENT DOCUMENTS

DE 1907330 10/1969

(Continued)

OTHER PUBLICATIONS

Verma et al (Nature, 1997, vol. 389, pp. 239-242).*

(Continued)

Primary Examiner—Sheela J Huff
(74) Attorney, Agent, or Firm—Kilpatrick Stockton, LLP

(57) ABSTRACT

Endostatin compositions capable of inhibiting endothelial cell proliferation, inhibiting angiogenesis and causing tumor regression are described. Specifically, amino acid sequences of endostatin proteins and nucleic acid sequences coding for endostatin proteins are provided.

14 Claims, 14 Drawing Sheets

U.S. PATENT DOCUMENTS

| | | |
|---|---|---|
| 4,885,289 A | 12/1989 | Breuer et al. |
| 4,921,699 A | 5/1990 | DeChiara et al. |
| 4,929,444 A | 5/1990 | Johnston et al. |
| 4,952,569 A | 8/1990 | Simons |
| 4,966,963 A | 10/1990 | Patroni |
| 4,994,443 A | 2/1991 | Folkman et al. |
| 5,001,116 A | 3/1991 | Folkman et al. |
| 5,015,730 A | 5/1991 | Friesen et al. |
| 5,021,404 A | 6/1991 | Folkman et al. |
| 5,053,403 A | 10/1991 | Orentreich et al. |
| 5,100,662 A | 3/1992 | Bolcsak et al. |
| 5,134,127 A | 7/1992 | Stella et al. |
| 5,135,919 A | 8/1992 | Folkman et al. |
| 5,187,062 A | 2/1993 | Sato et al. |
| 5,198,340 A | 3/1993 | Mukku |
| 5,223,409 A | 6/1993 | Ladner et al. |
| 5,252,718 A | 10/1993 | Baird et al. |
| 5,260,329 A | 11/1993 | Mongelli et al. |
| 5,278,286 A | 1/1994 | Kung et al. |
| 5,288,502 A | 2/1994 | McGinity et al. |
| 5,288,704 A | 2/1994 | Ungheri et al. |
| 5,302,390 A | 4/1994 | Browne et al. |
| 5,352,664 A | 10/1994 | Carney et al. |
| 5,358,959 A | 10/1994 | Halperin et al. |
| 5,385,885 A | 1/1995 | Gasic et al. |
| 5,385,901 A | 1/1995 | Kaplan et al. |
| 5,399,352 A | 3/1995 | Hanson |
| 5,399,363 A | 3/1995 | Liversidge et al. |
| 5,405,855 A | 4/1995 | Andrulis, Jr. et al. |
| 5,409,953 A | 4/1995 | Pettit et al. |
| 5,434,170 A | 7/1995 | Andrulis, Jr. et al. |
| 5,443,824 A | 8/1995 | Piacquadio |
| 5,446,131 A | 8/1995 | Maraganore |
| 5,500,412 A | 3/1996 | Carney et al. |
| 5,502,066 A | 3/1996 | Heinemann et al. |
| 5,504,074 A | 4/1996 | D'Amato et al. |
| 5,521,168 A | 5/1996 | Clark |
| 5,523,092 A | 6/1996 | Hanson et al. |
| 5,530,095 A | 6/1996 | Vaughn et al. |
| 5,530,100 A | 6/1996 | Darling et al. |
| 5,561,122 A | 10/1996 | Pettit |
| 5,569,786 A | 10/1996 | Pettit et al. |
| 5,576,294 A | 11/1996 | Norris et al. |
| 5,589,359 A | 12/1996 | Innis et al. |
| 5,593,990 A | 1/1997 | D'Amato |
| 5,605,684 A | 2/1997 | Piacquadio |
| 5,605,914 A | 2/1997 | Muller |
| 5,610,031 A | 3/1997 | Burgeson et al. |
| 5,621,124 A | 4/1997 | Seilz et al. |
| 5,629,327 A | 5/1997 | D'Amato |
| 5,629,340 A | 5/1997 | Kuwano et al. |
| 5,635,517 A | 6/1997 | Muller et al. |
| 5,639,725 A | 6/1997 | O'Reilly et al. |
| 5,643,783 A * | 7/1997 | Olsen et al. ................. 435/325 |
| 5,643,900 A | 7/1997 | Fotsis et al. |
| 5,643,915 A | 7/1997 | Andrulis, Jr. et al. |
| 5,646,136 A | 7/1997 | Petrow |
| 5,653,744 A | 8/1997 | Khouri |
| 5,654,312 A | 8/1997 | Andrulis, Jr. et al. |
| 5,661,143 A | 8/1997 | D'Amato et al. |
| 5,679,696 A | 10/1997 | Fenton et al. |
| 5,712,291 A | 1/1998 | D'Amato |
| 5,716,981 A | 2/1998 | Hunter et al. |
| 5,726,152 A | 3/1998 | Bayne et al. |
| 5,731,325 A | 3/1998 | Andrulis, Jr. et al. |
| 5,733,876 A | 3/1998 | O'Reilly et al. |
| 5,760,029 A | 6/1998 | Jadhav et al. |
| 5,763,432 A | 6/1998 | Tanabe et al. |
| 5,770,563 A | 6/1998 | Roberts et al. |
| 5,776,704 A | 7/1998 | O'Reilly et al. |
| 5,786,328 A | 7/1998 | Dennis et al. |
| 5,792,845 A | 8/1998 | O'Reilly et al. |
| 5,795,865 A | 8/1998 | Markland et al. |
| 5,798,248 A | 8/1998 | Coughlin et al. |
| 5,798,368 A | 8/1998 | Muller et al. |
| 5,801,146 A | 9/1998 | Davidson |
| 5,837,682 A | 11/1998 | O'Reilly |
| 5,849,306 A | 12/1998 | Sim et al. |
| 5,854,205 A | 12/1998 | O'Reilly et al. |
| 5,854,221 A | 12/1998 | Cao et al. |
| 5,856,448 A | 1/1999 | Coughlin |
| 5,861,372 A | 1/1999 | Folkman et al. |
| 5,885,795 A | 3/1999 | O'Reilly et al. |
| 5,888,529 A | 3/1999 | Bunnett et al. |
| 5,892,069 A | 4/1999 | D'Amato et al. |
| 5,919,459 A | 7/1999 | Nacy et al. |
| 5,945,403 A | 8/1999 | Folkman et al. |
| 5,948,403 A | 9/1999 | Sone et al. |
| 5,958,407 A | 9/1999 | Bunnett et al. |
| 5,958,892 A | 9/1999 | Mukhopadhyay et al. |
| 5,972,896 A | 10/1999 | Davidson |
| 5,981,471 A | 11/1999 | Papathanassiu et al. |
| 5,981,484 A | 11/1999 | Davidson |
| 5,993,827 A | 11/1999 | Sim et al. |
| 6,010,880 A | 1/2000 | Markland et al. |
| 6,011,023 A | 1/2000 | Clark et al. |
| 6,011,024 A | 1/2000 | Reed |
| 6,024,688 A | 2/2000 | Folkman et al. |
| 6,046,186 A | 4/2000 | Tanabe et al. |
| 6,051,726 A | 4/2000 | Sachdeva et al. |
| 6,054,598 A | 4/2000 | Sachdeva et al. |
| 6,057,122 A | 5/2000 | Davidson |
| 6,063,847 A | 5/2000 | Chackalamannil et al. |
| 6,071,948 A | 6/2000 | D'Amato |
| 6,077,990 A | 6/2000 | Leung et al. |
| 6,080,728 A | 6/2000 | Mixson |
| 6,111,075 A | 8/2000 | Xu et al. |
| 6,114,355 A | 9/2000 | D'Amato |
| 6,136,992 A | 10/2000 | Ram et al. |
| 6,143,719 A | 11/2000 | Schmaier et al. |
| 6,174,861 B1 | 1/2001 | O'Reilly et al. |
| 6,200,966 B1 | 3/2001 | Stewart |
| 6,228,879 B1 | 5/2001 | Green et al. |
| 6,235,756 B1 | 5/2001 | D'Amato |
| 6,239,123 B1 | 5/2001 | Green et al. |
| 6,251,867 B1 | 6/2001 | Davidson |
| 6,266,380 B1 | 7/2001 | Wang et al. |
| 6,281,230 B1 | 8/2001 | Muller et al. |
| 6,284,789 B1 | 9/2001 | LaLonde et al. |
| 6,316,471 B1 | 11/2001 | Muller et al. |
| 6,323,219 B1 | 11/2001 | Costanzo |
| 6,346,510 B1 | 2/2002 | O'Reilly et al. |
| 6,352,833 B1 | 3/2002 | Mendelsohn |
| 6,358,940 B1 | 3/2002 | Conney |
| 6,361,994 B1 | 3/2002 | Hudson et al. |
| 6,379,684 B1 | 4/2002 | Lezdey et al. |
| 6,387,942 B2 | 5/2002 | Teng et al. |
| 6,399,773 B1 | 6/2002 | Liu et al. |
| 6,407,086 B2 | 6/2002 | Faarup et al. |
| 6,410,029 B1 | 6/2002 | Mukhopadhyay et al. |
| 6,413,513 B1 | 7/2002 | Holaday |
| 6,436,400 B1 | 8/2002 | Xu et al. |
| 6,448,419 B1 | 9/2002 | Paaren et al. |
| 6,461,611 B1 | 10/2002 | Bar-Shavit |
| 6,469,036 B1 | 10/2002 | Costanzo et al. |
| 6,489,308 B1 | 12/2002 | Shapiro |
| 6,514,971 B1 | 2/2003 | Thomas et al. |
| 6,528,676 B1 | 3/2003 | D'Amato et al. |
| 6,544,750 B1 | 4/2003 | Schmaier et al. |
| 6,559,128 B1 | 5/2003 | Hamm et al. |
| 6,573,249 B2 | 6/2003 | Lezdey et al. |
| 6,593,321 B2 | 7/2003 | Rao et al. |
| 6,605,622 B2 | 8/2003 | Green et al. |
| 6,627,731 B1 | 9/2003 | Carney et al. |

| | | |
|---|---|---|
| 6,645,987 B2 | 11/2003 | Chackalamannil et al. |
| 6,653,098 B1 * | 11/2003 | Violand et al. ............ 435/69.1 |
| 6,720,008 B2 | 4/2004 | Allison |
| 6,723,858 B2 | 4/2004 | D'Amato et al. |
| 6,730,665 B1 | 5/2004 | Maran et al. |
| 6,740,657 B2 | 5/2004 | Maryanoff et al. |
| 6,746,865 B1 * | 6/2004 | O'Reilly et al. ......... 435/320.1 |
| 6,750,229 B2 | 6/2004 | Seiberg et al. |
| 6,759,515 B1 | 7/2004 | Xu et al. |
| 6,773,724 B2 | 8/2004 | Franckowiak et al. |
| 6,864,220 B2 | 3/2005 | Levitt et al. |
| 6,867,190 B2 | 3/2005 | Carney |
| 6,908,910 B2 | 6/2005 | D'Amato et al. |
| 6,930,128 B2 | 8/2005 | D'Amato et al. |
| 6,995,278 B2 | 2/2006 | Agoston et al. |
| 7,012,070 B2 | 3/2006 | D'Amato et al. |
| 7,081,477 B2 | 7/2006 | D'Amato et al. |
| 7,087,592 B1 | 8/2006 | Agoston |
| 2001/0044454 A1 | 11/2001 | Nantermet et al. |
| 2002/0002294 A1 | 1/2002 | D'Amato et al. |
| 2002/0004518 A1 | 1/2002 | Teng et al. |
| 2002/0007045 A1 | 1/2002 | Barrow et al. |
| 2002/0026050 A1 | 2/2002 | Chackalammanil et al. |
| 2002/0031518 A1 | 3/2002 | Morikawa et al. |
| 2002/0035098 A1 | 3/2002 | Slaga et al. |
| 2002/0037860 A1 | 3/2002 | D'Andrea et al. |
| 2002/0045581 A1 | 4/2002 | D'Andrea et al. |
| 2002/0061599 A1 | 5/2002 | Elling et al. |
| 2002/0065300 A1 | 5/2002 | Seiberg et al. |
| 2002/0068724 A1 | 6/2002 | Slaga et al. |
| 2002/0076755 A1 | 6/2002 | Kuliopulos et al. |
| 2002/0077289 A1 | 6/2002 | MacDonald et al. |
| 2002/0082433 A1 | 6/2002 | Agoston et al. |
| 2002/0091108 A1 | 7/2002 | Franckowiak et al. |
| 2002/0098168 A1 | 7/2002 | Glorioso et al. |
| 2002/0103138 A1 | 8/2002 | D'Andrea et al. |
| 2002/0107204 A1 | 8/2002 | D'Andrea et al. |
| 2002/0164333 A1 | 11/2002 | Nemerow et al. |
| 2002/0187933 A1 | 12/2002 | Carney |
| 2002/0197244 A1 | 12/2002 | Seiberg et al. |
| 2003/0008829 A1 | 1/2003 | Costanzo et al. |
| 2003/0027209 A1 | 2/2003 | Huse |
| 2003/0027803 A1 | 2/2003 | Slaga et al. |
| 2003/0036539 A1 | 2/2003 | Slaga et al. |
| 2003/0050294 A1 | 3/2003 | Jackson et al. |
| 2003/0054409 A1 | 3/2003 | Jerome et al. |
| 2003/0073674 A1 | 4/2003 | Slaga et al. |
| 2003/0096799 A1 | 5/2003 | Rao et al. |
| 2003/0125321 A1 | 7/2003 | Bueno |
| 2003/0143218 A1 | 7/2003 | Xu et al. |
| 2003/0148449 A1 | 8/2003 | Kuliopulos et al. |
| 2003/0148921 A1 | 8/2003 | Altrogge et al. |
| 2003/0161809 A1 | 8/2003 | Houston et al. |
| 2003/0166553 A1 | 9/2003 | Araki et al. |
| 2003/0170222 A1 | 9/2003 | Jones et al. |
| 2003/0175268 A1 | 9/2003 | Saint-Remy et al. |
| 2003/0198687 A1 | 10/2003 | Bennett et al. |
| 2003/0199455 A1 | 10/2003 | Zhang et al. |
| 2003/0203849 A1 | 10/2003 | Araki et al. |
| 2003/0203927 A1 | 10/2003 | Chackalamannil et al. |
| 2003/0216403 A1 | 11/2003 | Lively et al. |
| 2003/0216437 A1 | 11/2003 | Chackalamannil et al. |
| 2003/0219497 A1 | 11/2003 | Otterbein et al. |
| 2003/0228301 A1 | 12/2003 | Li et al. |
| 2003/0229061 A1 | 12/2003 | Rao et al. |
| 2003/0236408 A1 | 12/2003 | D'Amato et al. |
| 2004/0001801 A1 | 1/2004 | Madison et al. |
| 2004/0006105 A1 | 1/2004 | Chackalamannil et al. |
| 2004/0028703 A1 | 2/2004 | Bigalke et al. |
| 2004/0033267 A1 | 2/2004 | Merisko-Liversidge et al. |
| 2004/0038369 A1 | 2/2004 | Eguchi et al. |
| 2004/0053906 A1 | 3/2004 | Slaga et al. |
| 2004/0063200 A1 | 4/2004 | Chaikof et al. |
| 2004/0063642 A1 | 4/2004 | Zhang et al. |
| 2004/0063903 A1 | 4/2004 | McComsey et al. |
| 2004/0067270 A1 | 4/2004 | Bobrowski |
| 2004/0082558 A1 | 4/2004 | Tofovic et al. |
| 2004/0082777 A1 | 4/2004 | Kamada et al. |
| 2004/0096443 A1 | 5/2004 | Traynelis et al. |
| 2004/0116397 A1 | 6/2004 | Slaga et al. |
| 2004/0116439 A1 | 6/2004 | Lively et al. |
| 2004/0131500 A1 | 7/2004 | Chow |
| 2004/0132635 A1 | 7/2004 | Nakagawa et al. |
| 2004/0132688 A1 | 7/2004 | Griffin et al. |
| 2004/0138187 A1 | 7/2004 | Reading et al. |
| 2004/0142891 A1 | 7/2004 | Groot et al. |
| 2004/0146907 A1 | 7/2004 | Smith |
| 2004/0152736 A1 | 8/2004 | Chackalamannil et al. |
| 2004/0161802 A1 | 8/2004 | Huse |
| 2004/0170580 A1 | 9/2004 | Schmidt et al. |
| 2004/0176418 A1 | 9/2004 | Thiruvengadam et al. |
| 2004/0186060 A1 | 9/2004 | Duncan et al. |
| 2004/0186086 A1 | 9/2004 | Bunschoten et al. |
| 2004/0197319 A1 | 10/2004 | Harch et al. |
| 2004/0198671 A1 | 10/2004 | Bunschoten et al. |
| 2004/0209855 A1 | 10/2004 | Tofovic et al. |
| 2004/0210040 A1 | 10/2004 | Landolfi et al. |
| 2004/0214807 A1 | 10/2004 | D'Amato et al. |
| 2004/0219682 A1 | 11/2004 | Ridgway |
| 2004/0220110 A1 | 11/2004 | Schmaier et al. |
| 2004/0220113 A1 | 11/2004 | Shapiro |
| 2004/0220239 A1 | 11/2004 | Shapiro |
| 2004/0220242 A1 | 11/2004 | Shapiro |
| 2004/0229806 A1 | 11/2004 | Shen |
| 2004/0235749 A1 | 11/2004 | Chemtob et al. |
| 2004/0242627 A1 | 12/2004 | Suzuki et al. |
| 2004/0254376 A1 | 12/2004 | Suzuki et al. |
| 2004/0259768 A1 | 12/2004 | Lauermann |
| 2004/0266687 A1 | 12/2004 | Hembrough et al. |
| 2005/0002897 A1 | 1/2005 | Haupts et al. |
| 2005/0004197 A1 | 1/2005 | Suzuki et al. |
| 2005/0004204 A1 | 1/2005 | Suzuki et al. |
| 2005/0014737 A1 | 1/2005 | Agoston et al. |
| 2005/0014770 A1 | 1/2005 | Eisert et al. |
| 2005/0032766 A1 | 2/2005 | Green et al. |
| 2005/0060028 A1 | 3/2005 | Horres et al. |
| 2005/0070488 A1 | 3/2005 | Coelingh Bennik |
| 2005/0074510 A1 | 4/2005 | Bobrowski |
| 2005/0101573 A1 | 5/2005 | Faarup et al. |
| 2005/0192258 A1 | 9/2005 | Agoston et al. |
| 2005/0203075 A1 | 9/2005 | Agoston |
| 2005/0266067 A1 | 12/2005 | Sengupta et al. |
| 2006/0025619 A1 | 2/2006 | Agoston |
| 2006/0079576 A1 | 4/2006 | D'Amato et al. |
| 2006/0135796 A1 | 6/2006 | Agoston |

FOREIGN PATENT DOCUMENTS

| | | |
|---|---|---|
| DE | 2004516 | 9/1970 |
| DE | 2309575 | 9/1974 |
| DE | 2757157 | 12/1977 |
| DE | 3625315 | 1/1988 |
| DE | 4423574 | 1/1996 |
| EP | 166937 | 8/1986 |
| EP | 8702367 | 4/1987 |
| EP | 8803151 | 5/1988 |
| EP | 281822 | 9/1988 |
| EP | 8808002 | 10/1988 |
| EP | 299706 | 1/1989 |
| EP | 8901493 | 2/1989 |
| EP | 8902275 | 3/1989 |
| EP | 325199 | 7/1989 |
| EP | 356340 | 2/1990 |
| EP | 357061 | 3/1990 |
| EP | 370711 | 5/1990 |
| EP | 9013640 | 11/1990 |

| | | |
|---|---|---|
| EP | 9015816 | 12/1990 |
| EP | 9109118 | 6/1991 |
| EP | 9110424 | 7/1991 |
| EP | 9119514 | 12/1991 |
| EP | 9205184 | 4/1992 |
| EP | 9206709 | 4/1992 |
| EP | 9214455 | 9/1992 |
| EP | 9303729 | 3/1993 |
| EP | 9310805 | 6/1993 |
| EP | 9316716 | 9/1993 |
| EP | 9318067 | 9/1993 |
| EP | 9319746 | 10/1993 |
| EP | 9324143 | 12/1993 |
| EP | 589181 | 3/1994 |
| EP | 9420085 | 9/1994 |
| EP | 9421288 | 9/1994 |
| EP | 9423302 | 10/1994 |
| EP | 9423725 | 10/1994 |
| EP | 9427635 | 12/1994 |
| EP | 9504533 | 2/1995 |
| EP | 9504535 | 2/1995 |
| EP | 9507353 | 3/1995 |
| EP | 9509908 | 4/1995 |
| EP | 657175 | 6/1995 |
| EP | 9525543 | 9/1995 |
| EP | 9529242 | 11/1995 |
| EP | 9608274 | 3/1996 |
| EP | 9635774 | 11/1996 |
| EP | 9639175 | 12/1996 |
| EP | 9640766 | 12/1996 |
| EP | 9704075 | 2/1997 |
| EP | 9735609 | 2/1997 |
| EP | 9709063 | 3/1997 |
| EP | 9711172 | 3/1997 |
| EP | 9715666 | 5/1997 |
| EP | 9716205 | 5/1997 |
| EP | 9741824 | 5/1997 |
| EP | 9723500 | 7/1997 |
| EP | 791358 | 8/1997 |
| EP | 9735881 | 10/1997 |
| EP | 9744439 | 11/1997 |
| EP | 9815179 | 4/1998 |
| EP | 9818456 | 5/1998 |
| EP | 9832763 | 7/1998 |
| EP | 867450 | 9/1998 |
| EP | 9840398 | 9/1998 |
| EP | 9854217 | 12/1998 |
| EP | 9857647 | 12/1998 |
| EP | 0890361 | 1/1999 |
| EP | 9900420 | 1/1999 |
| EP | 9901142 | 1/1999 |
| EP | 9913053 | 3/1999 |
| EP | 0911399 | 4/1999 |
| EP | 9922728 | 5/1999 |
| EP | 9926480 | 6/1999 |
| EP | 9929855 | 6/1999 |
| EP | 9929856 | 6/1999 |
| EP | 9933858 | 7/1999 |
| EP | 9933859 | 7/1999 |
| EP | 9935150 | 7/1999 |
| EP | 9935248 | 7/1999 |
| EP | 9942486 | 8/1999 |
| EP | 9948486 | 8/1999 |
| EP | 9943809 | 9/1999 |
| EP | 9945018 | 9/1999 |
| EP | 9948924 | 9/1999 |
| EP | 9950415 | 10/1999 |
| EP | 9148301 | 12/1999 |
| EP | 0004052 | 1/2000 |
| EP | 0007576 | 2/2000 |
| EP | 0010552 | 3/2000 |
| EP | 0044391 | 8/2000 |
| EP | 0044896 | 8/2000 |
| EP | 0052056 | 9/2000 |
| EP | 0055134 | 9/2000 |
| EP | 0061179 | 10/2000 |
| EP | 0068246 | 11/2000 |
| EP | 0152883 | 1/2001 |
| EP | 0107072 | 2/2001 |
| EP | 0127132 | 4/2001 |
| EP | 0164835 | 9/2001 |
| EP | 0185755 | 11/2001 |
| EP | 0215910 | 2/2002 |
| EP | 2071847 | 7/2002 |
| EP | 1314779 | 5/2003 |
| EP | 3049723 | 6/2003 |
| EP | 3079978 | 10/2003 |
| EP | 3082231 | 10/2003 |
| EP | 3099841 | 12/2003 |
| EP | 948308 | 2/2004 |
| EP | 2004080373 | 9/2004 |
| EP | 2004101595 | 11/2004 |
| GB | 768821 | 2/1957 |
| GB | 772147 | 4/1957 |
| GB | 857080 | 12/1960 |
| GB | 857081 | 12/1960 |
| GB | 1182709 | 3/1970 |
| GB | 1570597 | 7/1980 |
| GB | 2252498 | 8/1992 |
| JP | 39005480 | 4/1964 |
| JP | 4.10001 E | 1/1966 |
| JP | 42000928 | 1/1967 |
| JP | 58036391 | 3/1983 |
| JP | 58131978 | 8/1983 |
| JP | 62135472 | 6/1987 |
| JP | 63090763 | 4/1988 |
| JP | 63119500 | 5/1988 |
| JP | 2234679 | 9/1990 |
| JP | 4046120 | 2/1992 |
| JP | 9316000 | 9/1997 |
| JP | 200280367 | 3/2002 |
| WO | WO-9310141 | 5/1993 |
| WO | WO 0066095 | 11/2000 |

OTHER PUBLICATIONS

Eck et al (Gene-Based Therapy, In: The Pharmacological Basis of Therapeutics, Goodman and Gilman, Ed.s, 1996, pp. 77-101).*
Orkin ("Report and Recommendation of the Panel to Assess the NIH Investment in Research on Gene Therapy", NIH, 1995).*
*Research Plus Catalog* 1993, 50-58.
*Spectra data and Preparation sheet for C22H32O2 (2-isobutyl-13-methyl-7,8,9,11,12,13,14,15,16,17-decahydro-6H-cyclopenta(a) phenanthrene-3,17-diol.*
*Remington Pharmaceutical Sciences*, Part 8, 1080.
"(Paragraphs 583-584)," *The Merck Index 11th Edition* 1989, 88.
"2-Methoxyestradiol—An Orally Active Endogenous Inhibitor of Angiogenesis," *EntreMed Website Article* Jul. 11, 2000, 1-10.
"Amino Acid Database, Accession No. P00747," Jul. 21, 1986.
"Chapter 12: Vectors for Gene Therapy," *Current Protocols in Human Genetics* 1997.
"Lilopristone/(1-[4-(Dimethylamino)pheyl]-17hydroxy-17-(3-hydroxy-1-propenyl) estra-4,9-diene-3-one; AK 98734," *Dictionary of Drugs (1990), Dict. of Steroids (1991), Dict. of Org. Cmpds (6th Ed)(1996), Dict. of Pharm. Agents (1997)* 1990.
"News Article: Advanced Drug Delivery Systems Peak Interest of Pharmaceutical & Biotech Firms," *Genetic Engineering News*, Apr. 15, 1994.
"News Article: Hoffman-La Roche Signs $70 Million Deal with Millenium on Genomics Technology," *Genetic Engineering News* Apr. 15, 1994.
"News Article: Nasal Spray for Treating Bleeding Disorders," *Genetic Engineering News* Apr. 15, 1994.

"Recommendations Regarding Public Screenings for Measuring Blood Cholesterol. Summary of a National Heart, Lung and Blood Institute Workshop (Oct. 1988)," *Arch. Intern. Med.*, vol. 149 Dec. 1989, 2650-2654.
"Registry No. 101277-11-6," *Chemical Abstracts*.
"Registry No. 19521-72-3," *Chemical Abstracts* Feb. 6, 2003.
"Registry No. 56933-78-9," *Chemical Abstracts*.
"Registry No. 57380-15-1," *Chemical Abstracts*.
"Registry No. 71782-94-0," *Chemistry Abstracts*.
"Registry No. 71782-95-1," *Chemistry Abstracts*.
"Registry No. 101429-40-7," *Chemical Abstracts* Feb. 6, 2003.
"Registry No. 162853-20-5," *Chemical Abstracts* Feb. 10, 2003.
"Registry No. 56933-77-8," *Chemical Abstracts*.
"Thalidomide," *The Merck Index 11th Edition* 1989, 1458.
"Thalidomide in Dermatology and Leprosy," *The Lancet*, vol. 2(8446), Jul. 13, 1985, 80-81.
"Thalidomide Tested for Treatment of AIDS," *U.S. Pharmacist*, vol. 18(8), Aug. 1993, 14.
"Thalidomide: 20 Years On (Editorial)," *The Lancet*, vol. II(8245) Sep. 5, 1981, 510-511.
"Thalidomide: Potential Benefits and Risks," *Current Bioliographies in Medicine, CBM 97-3* Aug. 1, 1997, 1-72.
U.S. Appl. No. 09/580,897, filed May 30, 2000 entitled "Estrogenic Compounds as Anti-Mitotic Agents."
U.S. Appl. No. 09/641,327, filed Aug. 18, 2000 entitled "Antiangiogenic Agents."
U.S. Appl. No. 09/779,331, filed Feb. 8, 2001 entitled "Antiangiogenic Agents."
U.S. Appl. No. 09/899,702, filed Jul. 5, 2001 entitled "Estrogenic Compounds as Antiangiogenic Agents."
U.S. Appl. No. 09/939,208, filed Aug. 24, 2001 entitled "Antiangiogenic Agents."
U.S. Appl. No. 10/077,142, filed Feb. 15, 2002 entitled "Estrogenic Compounds as Anti-Mitotic Agents."
U.S. Appl. No. 10/354,921, filed Jan. 30, 2003 entitled "Non-Steroidal Analogs of 2-Methoxyestradiol."
U.S. Appl. No. 10/354,927, filed Jan. 30, 2003 entitled "Non-Steroidal Analogs of 2-Methoxyestradiol."
"Webster's II New Riverside Dictionary," *The Riverside Publishing Company* 1994, 721.
Abe, N et al., "Identification of a Novel Collagen Chain Represented by Extensive Interruptions in the Triple-Helical Region," *Biochemical and Biophysical Research Communications, 196(2)* Oct. 29, 1993, 576-582.
Aboulwafa, et al., "Synthesis and evaluation for uterotropic and antiimplantation activities of 2-substituted estradiol derivatives," *Steroids*, vol. 57 Apr. 1992, 199-204.
Adams, et al., "A family of erythrocyte binding proteins of malaria parasites," *Proceedings of the National Academy of Science*, vol. 89 1992, 7085-7089.
Adams, E. F. et al., "Steroidal regulation of oestradiol-17B dehydrogenase activity of the human breast cancer cell line MCF-7 (Chemical Abstracts Doc. No. 109:32325,1988," *Journal of Endocrinology*, vol. 118(1) Jul. 1988, 149-154.
Adams, et al., "The Duffy receptor family of *Plasmodium knowlesi* is located within the micronemes of invasive malaria merozoites," *Cell*, vol. 63(1), 1990, 141-153.
Agarwal, et al., "Antimineralocortoids," *Renal Physiology Biochemistry*, vol. 14 1991, 217-223.
Ahmad, et al., "Liposomal Amphoterician-B in the Control of Experimental Aspergillosis in Mice: Park I—Relative Therapeutic Efficacy of Free and Liposomal Amphotericin-B," *Indian Journal of Biochemistry & Biophysics*, vol. 26 Dec. 1989, 351-356.
Ahrens, et al., "Treatment of Experimental Murine Candidiasis with Liposome-Assocaited Amphotericin B," *Sabouraudia: Journal of Medical and Veterinary Mycology*, vol. 22 1984, 163-166.
Aizu-Yokota, "Natural Estrogens Induce Modulation of Microtubules in Chinese Hamster V79 Cells in Culture," *Cancer Research*, vol. 55 May 1, 1995, 1863-1868.
Al-Ani, et al., "Modified Proteinase-Activated Receptor-1 and -2 Derived Peptides Inhibit Proteinase-Activated Receptor-2 Activation by Trypson," *The Journal of Pharmacology and Experimental Therapeutics*, vol. 300(2) Feb. 2002, 702-708.

Al-Ani, et al., "Proteinase-Activated Receptor 2 (PAR2): Development of a Ligand-Binding Assay Correlating with Activation of PAR2by PAR1—and PAR2-Derived Peptide Ligands (Abstract only)," *Journal of Pharmacology*, vol. 290(2) Aug. 1999, 753-760.
Alberts, et al., "Molecular Biology of the Cell," 1983, 906-908.
Albro, et al., "A Radioimmunuassay for Chlorinated Dibenzo-p-Dioxins," *Toxicology and Applied Pharmacology*, vol. 50 1979, 137-146.
Algire, G. H. et al., "Vascular reactions of normal and malignant tumors in vivo. I. Vascular reactions of mice to wounds and to normal and neoplastic transplants," *Journal of the National Cancer Institute* vol. 6, Aug. 1945, 73-85.
Aliev, et al., "54929Q Synthesis of cycloakyl derivatives of dihydric phenols and their ethers," *Chemical Abstracts*, vol. 72 1970, 370.
Allegri, A. "Confermata I'nefficacia della Talidomide Nella Terapia dei Tumori," *Gazzetta Medica Italiana* 1964, 124-127.
Alving, et al., "Adjuvanticity of Lipid A and Lipid A Fractions in Liposomes," *Liposome and Immunobiology* 1980, 67-78.
Alving, et al., "Antibodies to Cholesterol, Cholesterol Conjugates, and Liposomes: Implications for Atherosclerosis and Autoimmunity," *Critical Reviews in Immunology*, vol. 10(5) 1991, 441-453.
Alving, "Antibodies to Liposomes, Phospholipids and Cholesterol: Implications for Autoimmunity, Atherosclerosis and Aging," *Horizons in Membrane Biotechnology*, 1990, 40-41.
Alving, "Antibodies to Liposomes, Phospholipids and Phosphate Esters," *Chemistry and Physics of Lipids*, vol. 40 1986, 303-314.
Alving, et al., "Cholesterol-Dependent Human Complement Activation Resulting In Damage To Liposomal Model Membrane," *The Journal of Immunology*, vol. 118(1) Jan. 1977, 342-347.
Alving, et al., "Liposomes as Vehicles for Vaccines," *Prog. Clin. Biol. Res.*, vol. 47 1980, 339-355.
Alving, et al., "Naturally Occuring Autoantibodies to Cholesterol in Humans," *Biochemical Transactions, 629th Meeting, London*, vol. 17 1989, 637-639.
Alving, et al., "Preparation and Use of Liposomes in Immunological Studies," *Liposome Technology 2nd. Ed.*, vol. 3 1993, 317-343.
Alving, et al., "Preparation and Use of Liposomes in Immunological Studies," *Liposome Technology*, vol. 2 1984, 157-175.
Ambs, S. et al., "Interactive Effects of Nitric Oxide and the p 53 Tumor Supressor Gene in Carcinogenesis and Tumor Progression," *The FASEB Journal*, vol. 11 May 1997, 443-448.
Angelloz-Nicoud, et al., "Autocrine Regulation of Cell Proliferation by the Insulin-Like Growth Factor (IGF) and IGF Binding Protein-3 Protease System in a Human Prostate Carcinoma Cell Line (PC3)*," *Endocrinology*, vol. 136(12) 1995, 5485-5492.
Angiolillo, A. et al., "Human Interferon-inducible Protein 10 is a Potent Inhibitor of Angiogenesis in Vivo.," *The Journal of Experimental Medicine*, vol. 182 Hepatocyte Growth Factor HGF Jul. 1995, 155-162.
Anne, et al., "*Streptomyces lividans* as host for heterologous protein production," *FEMS Microbiology Letters*, vol. 114 1993, 121-128.
Anstead, et al., "The Estradiol Pharmacophore: Ligand Structure-Estrogen Receptor Binding Affinity Relationships and a Model for the Receptor Binding Site," *Steroids*, vol. 62 1997, 268-303,
Apt, W. "Effect of Thalidomide on the Course of Experimental Chagas' Disease," *Boletin Chileno de Parasitolgia*, vol. 20(3) Jul. 1965, 84-86.
Arbiser, et al., "The Antiangiogenic Agents TNP-470 and 2-Methoxyestradiol Inhibit the Growth of Angiosarcoma in Mice," *Journal of the American Academy of Dermatology, June*, Part 1 Jun. 1999, 925-929.
Arensman, et al., "Vitamin A Effect on Tumor Angiogenesis," *Journal of Pediatric Surgery*, vol. 14(6) Dec. 1979, 809-813.
Armstrong, et al., "Detection of Vascular Endothelial Growth Factor and Tumor Necrosis Factor Alpha in Epiretinal Membranes of Proliferative Diabetic Retinopathy, Proliferative Vitroretinopathy and Macular Pucker," *Ophthalmologica*, vol. 212(6) Nov. 1998, 410-414.
Arnold, et al., "Angiogenesis in Wound Healing," *Pharmacology & Therapeutics*, vol. 52(3) Dec. 1991, 407-422.
Arnoldi, et al., "Sweet Isovanillyl Derativatives: Synthesis and Structure-Taste Relationships of Conformationally Restricted Analogs (Abstract only)," *Journal of Agric. Food Chem.*, vol. 46(10) 1998, 4002-4010.

Aronson, et al., "Thalidomide-Induced Peripheral Neuropathy. Effect of Serum Factor on Nerve Cultures," *Archives of Dermatology*, vol. 120(11) Nov. 1984, 1466-1470.

Atherton, E. et al., "Solid Phase Protein Synthesis: A Practical Approach."

Attalla, et al., "2-Methoxyestradiol Arrests Cells in Mitosis without Depolymerizing Tubulin," *Biochemical and Biophysical Research Communications*, vol. 228 1996, 467-473.

Attalla, et al., "2-Methoxyestradiol-Induced Phosphorylation of Bcl-2: Upcoupling from JNK/SAPK Activation (Abstract only)," *Biochemical and Biophysical Research Communications*, vol. 247(3) Jun. 29, 1998, 616-619.

Audier, et al., "Orientation de la fragmentation en spectrometrie de masse par introduction de groupements fonctionnels. VII.— Etheylenecetals de ceto-2 stroides," *Bulletin De La Societe Chimique De France*, vol. 10 1965, 3088-3090.

Aulenta, et al., "Fragrance Release from the Surface of Branched Poly(amides)," *Molecules*, vol. 10 Jan. 31, 2005, 81-97.

Ausubel, et al., vol. 1 & 2 1994-1998.

Awakumov, et al., "Crystal Structure of Human Sex Hormone-binding Globulin in Complex with 2-Methoxyestradiol Reveals the Molecular Basis for High Affinity Interactions with C-2 Derivatives of Estradiol," *The Journal of Biological Chemistry*, vol. 277(47) Nov. 22, 2002, 45219-45225.

Ayala, et al., "The Induction of Accelerated Thymic Programmed Cell Death During Polymicrobial Sepsis: Control by Corticosteroids but not Tumor Necrosis Factor (Abstract Only)," *Shock*, vol. 3(4) Apr. 1995, 259-267.

Bach, "Initiation of Coagulation by Tissue Factor," *CRC Crit Rev Biochem*, vol. 23(4) 1988, 339-368.

Bach, et al., "Studies on the Possible Anti-Neoplastic Effect of Thalidomide," *ACTA Pathologica Et Microbiologica Scandinavica*, vol. 59 1963, 491-499.

Bach, et al., "Thalidomide in Cancer Chemotherapy," *The Lancet*, vol. 1 Jun. 8, 1963, 1271.

Bachovchin, W. W. "15N NMR Spectroscopy of Hydrogen-Bonding Interactions in the Active Serine Proteases: Evidence for a Moving Histidine Mechanism," *Biochemistry*, vol. 25 1986, 7751-7759.

Bahmer, F. A. "Therapie bel lymphozytischer Infiltration," *Der Hautarzt*, vol. 43 Oct. 1992, 663.

Bailey, W. et al., "Heparin and Basic Fibroblast Growth Factor are Associated with Preservation of Latissimus Cardiomyoplasties in Goats: A Retrospective Study," *Journal of Cardiac Surgery*, vol. 11(4) Jul. 1996, 247-255.

Bailey, et al., "Immunization with a Synthetic Cholesterol-ester Antigen and Induced Atherosclerosis in Rabbits," *Nature*, vol. 201(4917), Jan. 25, 1964, 407-408.

Balabanova, et al., "Lupus Erythematosus Hypertrophicus et Profundus," *Zeitschrift fur Hautkrankheiten*, vol. 67(9) Sep. 1992, 812-815.

Balian, et al., "Structure of Rat Skin Collagen a1-CB8, Amino Acid Sequence of the Hydroxylamine-Produced Fragment HA2," *Biochemistry*, vol. 11(20) 1972, 2798-3806.

Banerji, et al., "Antibodies to Liposomal Phosphatidylserine and Phosphatidic Acid," *Biochemical Cell Biology*, vol. 68 1990, 96-101.

Banerji, et al., "Membrane Lipid Composition Modulates the Binding Specificity of a Monoclonal Antibody Against Liposomes," *Biochimia et Biophysica Acta*, vol. 689 1982, 319-326.

Bangham, et al., "Diffision of Univalent Ions Across the Lamellae of Swollen Phospholipids," *Journal of Molecular Biology*, vol. 13 1965, 238-252.

Banik, et al., "Orally Active Long-Acting Estrogen (AY-20, 121) (3-(2-propynyloxy)- estra-1,3,5,(10)-triene-17. beta.-ol trimethylacetate)(Identifier only)," *Steroids*, vol. 16(3) 1970, 289-296.

Barchiesi, et al., "Differential Regulation of Estrogen Receptor Subtypes a and b in Human Aortic Smooth Muscle Cells by Oligonucleotides and Estradiol," *The Journal of Clinical Endocrinology and Metabolism*, vol. 89(5) Jun. 6, 2005, 2373-2381.

Bardon, et al., "Steroid Receptor-Mediated Cytotoxicity of an Antiestrogen and an Antiprogestin in Breast Cancer Cells (Abstract only)," *Cancer Research*, vol. 47(5) Mar. 1, 1987, 1441-1448.

Barnes, et al., "Tumor Necrosis Factor Production in Patients with Leprosy," *Infection and Immunity*, vol. 60(4) Apr. 1992, 1441-1446.

Barnhill, R. et al., "Studies on the Anti-Inflammatory Properties of Thalidomide: Effects on Polymorphonuclear Leukocytes and Monocytes," *Journal of the American Acadmy of Dermatology*, vol. 11(5) Nov. 1984, 814-819.

Barnhill, et al., "Thalidomide: Use and Possible Mode of Action in Reactional Lepromatous Leprosy and in Various Other Conditions," *Journal of the American Academy of Dermatology*, vol. 7(3) Sep. 1992, 317-323.

Barriere, H. "Traitement par la thalidomide," *La Presse Medicale*, vol. 12(15) Apr. 2, 1983, 963.

Bartels, et al., "Automated sequence-specific NMR assignment of homologous proteins using the program GARANT," *Journal of Biomolecular NMR*, vol. 7 1996, 207-213.

Bartels, et al., "GARANT—A General Algorithm for Resonance Assignment of Multidimensional Nuclear Magnetic Resonance Spectra," *Journal of Computational Chemistry*, vol. 18(1) 1997, 139-149.

Bartels, et al., "The program XEASY for computer-supported NMR Spectral analysis of biological macromolecules," *Journal of Biomolecular NMR*, vol. 5 1995, 1-10.

Bartolazzi, et al., "Interaction between CD44 and Hyaluronate is Directly Implicated in the Regulation of Tumor Development," *Journal of Experimental Medicine*, vol. 180 Jul. 1994, 53-66.

Bazzoli, et al., "The Effects of Thalidomide and Two Analogues on the Regenerating Forelimb of the Newt," *Journal of Embyology and Experimental Morphology*, vol. 41 Oct. 1977, 125-135.

Bearz, et al., "Expression, purification and functional characterization of a Kunitz-type module from chicken type VI collagen," *Biochemical & Biophysical Research Communications*, vol. 215(3) Oct. 24, 1995, 1050-1055.

Beccerica, E. "L'approccio terapeutico al paziente anziano con artrite reumatoide," *La Clinica Terapeutica*, vol. 122 1987, 289-298.

Beck, Jr., L. et al., "Vascular Development: Cellular and Molecular Regulation," *The FASEB Journal*, vol. 11 Apr. 1997, 365-374.

Beckner, Marie E. "Factors Promoting Tumor Angiogenesis," *Cancer Investigation*, vol. 17(8) 1999, 594-623.

Bek, et al., "Entothelins are Angiogenic (Abstract only)," *Journal of Cardiovascular Pharmacology*, vol. 36(5)-Supp 1 2000, S136.

Belaube, P. et al., "Should Thalidomide be Rehabilitated?," *Sem. Hop. Paris*, vol. 59(45) Dec. 8, 1983, 3101-3104.

Bensinger, W. I. "Supportive Care in Marrow Transplantation," *Current Opinion in Oncology*, vol. 4(4) 1992, 614-623.

Berger, et al., "On the Specificity of Antibodies to Substances from the Lipoid Class," *Z. Immunitaet*, vol. 76 1932, 16-35.

Berger, et al., "The Angiogenesis Inhibitor, Endostation, Does Not Affect Murine Cutaneous Wound Healing," *Journal of Surgical Research*, vol. 91 2000, 26-31.

Bergers, et al., "Effects of Angiogenesis Inhibitors on Multistage Carcinogenesis in Mice," *Science*, vol. 284 Apr. 30, 1999, 808-812.

Berglund, et al., "Cloning and Characterization of the Bovine Plasminogen cDNA (abstract only)," *International Dairy Journal*, vol. 5(6) 1995, 596-603.

Bernal, et al., "Cellular Immune Effects of Thalidomide in Actinic Prurigo," *International Journal of Dermatology*, vol. 31(8) Aug. 1992, 599-600.

Best, et al., "Cloning of A Full-Length cDNA Sequence Encoding A cdc2-Related Protein Kinase from Human Endothelial Cells," *Biochemical and Biophysical Research Communications*, vol. 208(2) Mar. 17, 1995, 562-568.

Bhat, et al., "Estradiol-Inducted Mitotic Inhibition in the Bursa of Fabricius of Male Domestic Duckling (Chemical Abstracts Doc. No. 98:31837, 1982)," *Mikroskopie*, vol. 39 May 1982, 113-117.

Bhattacharyya, et al., "Tubulin aggregation and disaggregation: Mediation by two distinct vinblastine-binding sites," *National Academy of Sciences*, vol. 73(7) Jul. 1976, 2375-2378.

Bianchi, et al., "Ricerche su compositi strutturalmente analoghi all' a-ftalimidoglutarimide (talidomide) nota I," *Il Farmaco*, vol. XX(9) Sep. 1965, 611-628.

Bianchi, et al., "Richerche Su Compositi Strutturalmente Analoghi All' a -Ftalimidoglutarimide (Talidomide) Nota III," *Il Farmaco*, vol. XXI(2) Feb. 1966, 121-130.

Bibb, et al., "Unusual Features of Transcription and Translation of Antibiotic Resistance Genes in Antibiotic-Producing *Streptomyces*," *Fifth International Symposium on the Genetics of Industrial Microorganisms* 1986, 309-318.

Bignami, et al., "Effects of Thalidomide and Related Compounds in Rat Pregnancy," *Forensic Immunology, Medicine, Pathology and Toxicology—Report of the Third International Meeting* Apr. 1963, 124-125.

Billeter, et al., "Comparison of the High-resolution Structures of the a-Amylase Inhibitor Tendamistat Determined by Nuclear Magnetic Resonance in Solution and by X-Ray Diffraction in Single Crystals," *Journal of Molecular Biology*, vol. 206 1989, 677-687.

Billeter, et al., "Restrained Energy Refinement with Two Different Alrotithms and Force fields of the Structure of the a-Amylase Inhibitor Tendamistat Determined by NMR in Solution," *Biopolymers*, vol. 29 1990, 695-706.

Bindra, et al., "Studies in Antifertility Agents.8.Seco Steroids. 2. 5,6-Secoestradiol and Some Related Compounds," *Journal of Medicinal Chemistry*, vol. 18(9) 1975, 921-385.

Binnie, et al., "Heterologous biopharmaceutical protein expression in *Streptomyces*," *Tibtech*, vol. 15 Aug. 1997, 315-320.

Blagosklonny, et al., "Raf-1/bcl-2 Phosphorylation: A Step from Microtubule Damage to Cell Death," *Cancer Research*, vol. 57 Jan. 1, 1997, 130-135.

Blair, R et al., "Human Mast Cells Stimulate Vascular Tube Formation," *The Journal of Clinical Investigation*, vol. 99(11) Jun. 1997, 2691-2700.

Blaschke, V. et al., "Chromatographische Racemattrennung von Thalidomid und teratogene Wirkung der Enantiomere," *Arzneimittel Forschung/Drug Research*, vol. 29(11) 1979, 1640-1642.

Blickenstaff, et al., "Estrogen-*Catharanthus* (Vinca) Alkaloid Conjugates (Chemical Abstracts Doc. No. 94:114277, 1981)," *Cytotoxic Estrogens i nHormone Receptive Tumors* 1980, 89-105.

Blickenstaff, et al., "Synthesis of Some Analogs of Estradiol," *Steroids*, vol. 46(4,5) Oct. 1985, 889-902.

Bloch, et al., "The angiogenesis inhibitor endostatin impairs blood vessel maturation during wound healing," *The FASEB Journal*, vol. 14 Dec. 2000, 2373-2376.

Bodenhausen, et al., "Natural Abundance Nitrogen-15 NMR by Enhanced Heteronuclear Spectroscopy," *Chemical Physics Letters*, vol. 69(1) Jan. 1, 1980, 185-189.

Boehm, et al., "Antiangiogenic therapy of experimental cancer does not induce acquired drug resistance," *Nature*, vol. 390 Nov. 27, 1997, 404-407.

Boehm, et al., "Distruption of the KEX1 Gene in *Pichia pastoris* Allows Expression of Full-Length Murine and Human Endostatin," *Yeast*, vol. 15 1999, 563-572.

Boehm, et al., "Zinc-Binding of Endostatin is Essential for its Antiangiogenic Activity," *Biochemical and Biophysical Research Communications*, vol. 252 1998, 190-194.

Bogdan, Christian "The Multiplex Function of Nitric Oxide in (Auto)immunity," *Journal of Experimental Medicine*, vol. 187(9) May 4, 1998, 1361-1365.

Bohm, M. et al., "Alpha-Melanocyte-Stimulating Hormone Modulates Activation of NF-kappa B and AP-1 and Secretion of Interleukin-8 in Human Derman Fibroblasts (Abstract only)," *Annals of the New York Academy of Sciences*, vol. 885 1999, 277-286.

Bok, R. A. et al., "Quantitative Characterization of the Binding of Plasminogen to Intact Fibrin Clots, Lysine-Sepharose, and Fibrin Cleaved by Plasmin," *Biochemistry*, vol. 24 1985, 3279-3286.

Bonifacino, J. et al., "A Peptide Sequence Confers Retention and Rapid Degradation in the Endoplasmic Reticulum," *Science*, vol. 2 Jan. 5, 1990, 79-80.

Bonnetblanc, et al., "Thalidomide and Recurrent Aphthous Stomatitis: A Follow-Up Study," *Determatology*, vol. 193(4) 1996, 321-323.

Boodman, S. G. "Questions About a Popular Prenatal Test," *The Washington Post* Nov. 3, 1992.

Boussif, O. et al., "A versatile fector for gene and oligonucleotide transfer into cells in culture and in vivo: Polyethylenimine," *Proc. Natl. Acad. Sci. USA*, vol. 92 Aug. 1995, 7297-7301.

Bowers, et al., "Effect of Thalidomide on Orogential Ulceration," *British Medical Journal*, vol. 287 (6395) Sep. 17, 1983, 799-800.

Boyce, et al., "Some Preliminary Synthetical Studies with 5,6,7,8-Tetra-hydro-8-methylindane -1,5-dione," *Unknown* 1960, 4547-4553.

Boyd, et al., "The Generation of Phase-Sensitive 2D 15N-1H Spectra Using Gradient Pulses for Coherence-Transfer-Pathway Selection," *Journal of Magnetic Resonance*, vol. 98 1992, 660-664.

Boye, et al., "185. Deaminocolchinyl Methyl Ether: Synthesis from 2,3,4,4'-Tetramethoxybiphelyl- 2-carbaldehyde. Comparision of Antitubulin Effects of Deaminocolchinyl Methyl Ether and Dehydro Analogs," *Helvetica Chimica Acta*, vol. 72 1989, 1690-1696.

Boylen, J. B. et al., "Teratogenic Effects of Talidomide and its Metabolites on the Developing Chick Embryo," *Canadian Journal of Biochemistry*, vol. 42 Jan. 1, 1964, 35-42.

Boylen, et al., "Teratogenic Effects of Thalidomide and Related Substances," *The Lancet*, vol. 1(728) Mar. 9, 1963, 552.

Brandi, et al., "Bone endothelial cells as estrogen targets (Abstract only)," *Calcif. Tissue Int.*, vol. 53(5) 1993, 312-317.

Braun, W. "Local Deformation Studies of Chain Molecules: Differential Conditions for Changes of Dihedral Angles," *Biopolymers*, vol. 26 1987, 1691-1704.

Braun, et al., "Thalidomide Metabolite Inhibits Tumor Cell Attachment to Concanavalin a Coated Surfaces," *Biochemical and Biophysical Research Communications*, vol. 98(4) Feb. 27, 1981, 1029-1034.

Brawer, et al., "Predictors of Pathologic Stage in Prostatic Carcinoma," *Cancer*, vol. 73 Feb. 1, 1994, 678-687.

Brem, H. et al., "Interstitial chemotherapy with drug polymer implants for the treatment of recurrent," *Journal of Neurosurgery*, vol. 74 Hepatocyte Growth Factor HGF Mar. 1, 1991, 441-446.

Brent, R. et al., "Clinical and Basic Science Lessons from the Thalidomide Tragedy: What have we learned about the causes of limb defects?," *Teratology*, vol. 38 Jan. 1, 1988, 241-251.

Bressler, S. "Clinicopathologic Correlation of Occult Choroidal Neovascularization in Age-Related Macular Degeneration," *Archives of Opthalmology*, vol. 110 Jun. 1, 1992, 827.

Brochu, et al., "Monoclonal Antibodies for Use with Iodine-Labeled Radioligands in Progesterone Radiummunoassay," *Journal of Steroid Biochemistry*, vol. 21(4) 1984, 405-411.

Brockway, W. J. et al., "Measurement of the Binding of Antifibrinolytic Amino Acids to Various Plaminogens," *Archives of Biochemistry and Biophysics*, vol. 151 Apr. 18, 1972, 194-199.

Brodie, A. M. "Aromatase Inhibitors in the Treatment of Breast Cancer (Abstract only)," *Journal of Steroid Biochemistry and Molecular Biology*, vol. 49(4-6) Jun. 1994, 287-287.

Brodthagen, H. "Significant Response of Oral Aphthosis to Thalidomide Treatment," *Journal of the American Academy of Determatology*, vol. 13(3) Sep. 1, 1985, 509.

Bromberg, et al., "Tissue Factor-Factor VIIa Induces Phosphylation of p 44/42 Mitogen-Activated Protein Kinase Mainly by the Generation of Factor Xa in Human Breast Cancer Cells (Abstract only #1048)," *Blood*, vol. 98(11) Dec. 7, 2001, 250a.

Brooks, P. C. et al., "Integrin avb3 antagonists promote tumor regression by inducing apoptosis of angiogenic blood vessels," *Cell*, vol. 79 Dec. 30, 1994, 1157-1164.

Brosens, et al., "Comparative Study of the Estrogenic Effect of Ethinylestradiol and Mestranol on the Endometrium," *Contracteption (Laboratory for Genecological Physiopathology)*, vol. 14(6) Dec. 1, 1976, 678-685.

Brovarone, F. V. et al., "Occhio e gravidanza," *Minerva Ginecologica*, vol. 43 Apr. 1, 1991, 141-167.

Browder, et al., "Antiangiogenic Scheduling of Chemotherapy Improves Efficacy against Experimental Drug-resistant Cancer," *Cancer Research*, vol. 60 Apr. 1, 2000, 1878-1886.

Brown, et al., "A Receptor-Mediated Pathway for Cholesterol Homeostatis," *Science*, vol. 232 Apr. 4, 1986, 34-47.

Brown, G. C. et al., "Ischaemia and neovascularization," *Transactions of the Ophthalmological Societies of the United Kingdom*, vol. C Part III Sep. 1, 1980, 377-380.

Browne, "Expression of Recombinant Human Plasminogen and Aglycoplasminogen in HeLa cells," *Fibinolysis* vol. 5 Apr. 13, 1991, 257-260.

Broze, et al., "Regulation of Coagulation by a Multivalent Kunitz-Type Inhibitor," *Biochemistry*, vol. 29(33) Aug. 21, 1990, 7539-7546.

Bruckdorfer, et al., "The Effect of Partial Replacements of Membrane Cholesterol by Other Steroids on the Osmotic Fragility and Glycerol Permeability of Erythrocytes," *Bichimica et Biophysica Acta*, vol. 183 1969, 334-345.

Bruckdorfer, et al., "The Incorporation of Steroid Molecules into Lecithin Sols, Ã?Â¢- Lipoproteins and Cellular Membranes," *European Journal of Biochemistry*, vol. 4 1968, 512-518.

Brueggemeier, et al., "2-Methoxymethylestradiol: a new 2-methoxy estrogen analog that exhibits antiproliferative activity and alters tubulin dynamics," *Journal of Steroid Biochemistry 78 & Molecular Biology*, vol. 78 2001, 145-156.

Bruno, et al., "New drugs for treatment of multiple myeloma," *The Lancet*, vol. 5(7) Jul. 1, 2004, 430-437.

Bu, et al., "Mechanisms for 2-Methoxyestradiol-induced apoptosis of prostate cancer cells," *FEBS Letters*, vol. 531 Jan. 2002, 141-151.

Bu, et al., "p38 Mitogen-activated protein kinases is required for counteraction of 2-Methoxyestradiol to estradio-stimulated cell proliferation and induction of apoptosis in ovarian carcinoma cells via phosphorylation Bcl-2," *Apoptosis*, vol. 11(3) 2006, 413-425.

Bubl, et al., "Dysphagia In Dermatologic Disease," *Dysphagia*, vol. 8(2) Apr. 2, 1993, 85-90.

Buckley, C. et al., "Pyoderma Gangrenosum with Severe Pharyngeal Ulceration," *Journal of the Royal Society of Medicine*, vol. 83 Sep. 1, 1990, 590-591.

Buelens, I. "Treatment of a Grade II Astrocytoma with Thalidomide (Phtalylglutamic Acide Imide) [Behandlung eines Astrocytoms II. Grades mit Thalidomide (N-Phthalylglutaminsaureimid)]," *Arzneimittel-Forschung*, vol. 17(5) May 1, 1967, 646-648.

Bullock, W. E. "The Clinical Significance of Erythema Nodosum," *Hospital Practice*, vol. 21(3) Mar. 15, 1986, 102E-2H, 102K-2L, 102Q-sR pas.

Burger, et al., "Epidermolysis Bullosa Acquisita, a Rate Late Complication of Allogeneicbone Marron Transplantation," *Bone Marrow Transplantation*, vol. 9(2) Feb. 1, 1992, 139-141.

Burgess, et al., "Possible Dissociation of the Heparin-binding and Mitogenic Activities of Heparin-binding (Acidic Fibroblast) Growth Factors-1-from Its Receptor-binding Activities by Site-directed Mutagenesis of a Single Lysine Residue," *The Journal of Cell Biology*, vol. 111 Nov. 1990, 2129-2138.

Burrows, N. P. "Thalidomide Modifies Disease," *British Medical Journal*, vol. 207(6909) Oct. 9, 1993, 939-940.

Calnan, et al., "Actinic Prurigo (Hutchison's Summer Prurigo)," *Clinical and Experimental Dermatology*, vol. 2(4) Dec. 1, 1977, 365-372.

Calos, Michele P. "The potential of extrachromosomal replicating vectors for gene therapy," *TIG*, vol. 12(11) Nov. 1996, 463-466.

Calvo, et al., "Inhibition of the Mammary Carcinoma Angiogenic Switch in C3(1)/SV40 Transgenic Mice by a Mutated Form of Human Endostatin," *International Journal of Cancer*, vol. 101 Jun. 2002, 224-234.

Cambie, et al., "Aromatic Steroids. Part I. Oxidation Products of 3-Methoxyestra-1,3,5(10)-triene- 17b-yl Acetate," *J. Chem Soc.* 1968, 2603-2608.

Cambie, et al., "Aromatic Steroids. Part II. Chromium Trioxide Oxidation of Some Oestro-1,3-5(10)-trienes," *Journal of the Chemical Society*, vol. 9 1969, 1234-1240.

Campbell, Ailsa M. "General Properties and applications of monoclonal antibodies," *Monoclonal Antibody Technology*, vol. 13 1984, 1-32.

Camus, et al., "A *Plasmodium falciparum* antigen that binds to host erythrocytes and merozoites," *Science*, vol. 230(4725) 1985, 553.

Cant, J. S. "Minor Ocular Abnormalities Associated with Thalidomide," *The Lancet* May 21, 1966, 1134.

Cao, Y. et al., "gro-B, a-C-X-C-Chemokine, is an Angiogenesis Inhibitor that Suppresses the Growth," *Journal of Experimental Medicine*, vol. 182 Hepatocyte Growth Factor HGF Dec. 1, 1995, 2069-2077.

Cao, Y. et al., "Human acidic fibroblast growth factor overexpressed in insect cells is not secreted into the medium," *Growth Factors*, vol. 3(1) 1990, 1-13.

Cao, Y. et al., "Kringle 5 Plasminogen is a Novel Inhibitor of Endothelial Cell Growth," *Journal of Biological Chemistry*, vol. 272(36) Sep. 5, 1997, 22924-22928.

Cao, Y. et al., "Kringle Domains of Human Angiostatin," *The Journal of Biological Chemistry*, vol. 271(46) Nov. 15, 1996, 29461-29467.

Cao, R. et al., "Suppression of angiogenesis and tumor growth by the inhibitor K1-5 generated by," *Proceedings of the National Academy*, vol. 96 Hepatocyte Growth Factor HGF May 1, 1999, 5728-5733.

Cardiff, R. D. "Protoneoplasia: The Molecular Biology of Murine Mammary Hyperplasia (Abstract only)," *Advances in Cancer Research*, vol. 42 Jan. 1, 1984, 167-1990.

Carmeliet, P. et al., "Molecular analysis of blood vessel formation and disease," *American Journal of Physiology*, vol. 273(5) Nov. 1, 1997, H2091-H2104.

Carmichael, et al., "Thalidomide: A Restricted Role," *The Lancet*, vol. 339 (8805) May 30, 1992, 1362.

Carothers, et al., "2-Methoxyestradiol induces p53-associated apoptosis of colorectal cancer cells," *Cancer Letters*, vol. 187 Jan. 2002, 77-86.

Carter, et al., "An inexpensive and simple method for DNA purifications on silica particles," *Nucleic Acids Research*, vol. 21(4) 1993, 1044.

Cashin, C. H. et al., "Angiogenesis and chronic inflammation," *Agents and Actions*, vol. 34 (3/4) Jan. 1, 1991, 332-338.

Casini, G. et al., "Preparazione di uno degli antipodi ottici della 2-Fralimmidoglutarimmide," *II Farmaco Edizione Scientifica*, vol. XIX (5) Mar. 1, 1964, 563-565.

Castagnetta, L. "Simple Approach to Measure Metabolic Pathways of Steroids in Living Cells," *Journal of Chromatography*, vol. 572 Dec. 6, 1991, 25-39.

Castellino, et al., "The kringle domains of human plasminogen," *Ciba Foundation Symposium 212—Plasminogen-Related Growth Factors*, vol. 212, discussion 60-5 1997, 46-65.

Caswell, L. R. et al., "Nitrophthaloyl and Aminophthaloyl Derivatives of Amino Acids," *Journal of Chemical and Engineering Data*, vol. 13(1) Jan. 1, 1968, 291-292.

Chamaon, et al., "Micromolar concentrations of 2-methoxyestradiol kill glioma cells by an apoptotic mechanism, without destroying their microtubule cytoskeleton," *Journal of Neuro-Oncology*, vol. 72 Jan. 2005, 11-16.

Chan, et al., "Identification of a Competitive HGF Antagonist Encoded by an Alternative Transcript," *Science*, vol. 254 Nov. 29, 1991, 1382-1385.

Chang, et al., "[32] Engineering for Protein Secretion in Gram-Positive Bacteria," *Methods in Enzymology*, vol. 153 1987, 507-516.

Chapon, et al., "Neuropathies Caused by Thalidomide," *Revue Neurologique*, vol. 141(1) Dec. 1, 1985, 719-728.

Chasserot-Golaz, et al., "Biotransformation of 17.beta-hydroxy-11. beta.-(4-dimethylaminophenyl) 17.alpha.1-propynyl-estra-4.9-diene-3-one (RU486) in Rat Hepatoma Variants (Identifier only)," *Biochemical Pharmacology*, vol. 46(11) 1993, 2100-2103.

Chatterjee, et al., "Idiotypic antibody immunotherapy of cancer," *Cancer Immunology and Ummunotherapy*, vol. 38(2) Feb. 1994, 75-82.

Chaudhry, A. "Effects of Prednisolone and Thalidomide on Induced Submandibular Gland Tumors in Hampsters," *Cancer Research*, vol. 27(9) Sep. 1, 1966, 1884-1886.

Chauhan, et al., "2-Methoxyestradiol and bortezomib/proteasome-inhibitor overcome dexamethasone-resistance in multiple myeloma cells by modulating Heat Shock Protein-27," *Apoptosis*, vol. 9 Jan. 1, 2004, 149-155.

Chauhan, et al., "2-Methoxyestradiol overcomes drug resistance in multiple myeloma cells," *Blood*, vol. 100(6) Sep. 15, 2002, 2187-2194.

Chauhan, et al., "Mechanisms of cell death and survival in multiple myeloma (MM): Therapeutic implications," *Apoptosis*, vol. 8(4) Jan. 2003, 337-343.

Chauhan, et al., "Superoxide-dependent and -independent mitochondrial signaling during apoptosis in multiple myeloma cells," *Oncogene*, vol. 22 Jan. 2003, 6296-6300.

Chen, et al., "A New Synthetic Route to 2- and 4-Methoxyestradiols by Nucleophilic Substitution," *Steroids*, vol. 47(1) Jan. 1986, 63-66.

Chen, C. et al., "A Strategy to Discover Circulating Angiogenesis Inhibitors Generated by Human," *Cancer Research*, vol. 55 Hepatocyte Growth Factor HGF Oct. 1, 1995, 4320-4233.

Chen, P. et al., "Genetic Mechanisms of Tumor Suppression by the Human p 53 Gene," *Science*, vol. 250 Dec. 1990, 1576-1579.

Chen, T. L. et al., "Plasma Pharmocokinetics and Urinary Excretion of Thalidomide after Oral Dosing in Healthy Male Volunteers," *The American Society for Pharmocology and Experimental Therapeutics*, vol. 17(4) Jan. 1, 1989, 402-405.

Chen, et al., "Synthesis of 11.beta.-(4-dimethylaminophenyl)-17.beta-hydroxy-17.alpha.- (1- propynyl) esta-4, 9-dien-3-one (RU486)(Identifier only)," *Nanjing Yaoxueyuan Xuebao*, vol. 17(4) 1986, 282-285.

Chen, et al., "The Carboxyl Terminus of Type VII Collagen Mediates Antiparallel-Dimer Formation and Constitutes a New Antigenic Epitope for EBA Autoantibodies," *The American Society for Biochemistry and Molecular Biology, Inc*. Mar. 27, 2001, 1-29.

Cheng, Pi-Wan "Receptor Ligand-Facilitated Gene Transfer. Enhancement of Liposome-Mediated Gene Transfer and Expression by Transferrin," *Human Gene Therapy*, vol. 7 Feb. 10, 1996, 275-282.

Chitnis, et al., "Identification of the erythrocyte binding domains of *Plasmodium vivax* and *Plasmodium knowlesi* proteins involved in erythrocyte invasion," *Journal of Experimental Medicine*, vol. 180(2) Aug. 1, 1994, 497-506.

Chng, et al., "Targeted Therapy in Multiple Myeloma," *Cancer Control*, vol. 12(2) Apr. 2005, 91-104.

Chodak, et al., "Increased Levels of Fibroblast Growth Factor-like Activity in Urine from Patients with Bladder or Kidney Cancer," *Cancer Research*, vol. 48 Apr. 15, 1988, 2083-2088.

Chosidow, O. "Sclerodermatous Chronic Graft-Versus-Host Disease: Analysis of Seven Cases," *Journal of the American Academy of Dermatology*, vol. 26(1) Jan. 1, 1992, 49-55.

Church, W. R. et al., "A Kringle-Specific Monoclonal Antibody," *Hybridoma*, vol. 13(5) Oct. 1, 1994, 423-429.

Claire, et al., "Synthesis of New 11B-Substituted Spirolactone Derivatives. Relationship with Affinity for Mineralocorticoid and Glucocorticoid Receptors," *Journal of the American Chemical Society*, vol. 36(16) Mar. 30, 1993, 2404-2407.

Clapp, C. et al., "The 16-Kilodalton N-terminal Fragment of Human Prolactin is a Potent Inhibitor of," *Endocrinology*, vol. 133 Hepatocyte Growth Factor HGF Mar. 1, 1993, 1292-1299.

Clare, J. J. et al., "Production of mouse epidermal growth factor in yeast: High-level secretion using *Pichia pastoris* strains containing multiple gene copies," *Gene*, vol. 105 1991, 205-212.

Claydon, et al., "Gastrointestinal Emergencies in HIV Infection," *Bailliere's Clinical Gastroenterology*, vol. 5(4) Dec. 1, 1991, 887-911.

Cleary, S. et al., "Purification and Characterization of Tissue Plasminogen Activator Kringle-2 Domain Expressed in *Escherica coli*," *Biochemistry*, vol. 28 1989, 1884-1891.

Clements, et al., "Kallikreins and Kinins in inflammatory-like events in the reproductive tract (Abstract only)," *Pharmacological Research*, vol. 35(6) Jun. 1997, 537-540.

Clemmenson, et al., "Thalidomide Neurotoxicity," *Archives of Dermatology*, vol. 120(3) Mar. 1, 1984, 338-341.

Cohen, Joel "Behind the Headlines of Endostatin's Ups and Downs," *Science*, vol. 283 Feb. 26, 1999, 1250-1251.

Cohen, et al., "Biological Effects of Prostate Specific Antigen as an Insulin-Like Growth Factor Binding Protein-3 Protease," *Journal of Endocrinology*, vol. 142 1994, 407-415.

Cohen, et al., "Novel Total Synthesis of (+)-Estrone 3-Methyl Ether, (+0-13b-Ehtyl-3-methoygona-1,3,5(10)-trien-17-one, and (+)-Equilenin e-Methyl Ether," *The Journal of Organic Chemistry*, vol. 40(6) Mar. 21, 1975, 681-685.

Collins, et al., "The Stability and Structure of Cholesterol-rich Codispersions of Cholesterol and Phosphatidylchlone," *Journal of Lipid Research*, vol. 23 1982, 291-198.

Collins, et al., "The Structure and Function of Estrogens. XI. Synthesis of (+/−)-7(8-11a) abeo-Estradiol and its 9,11-Didehydro Derivative," *Aust. Journal of Chemistry*, vol. 45(1) 1992, 71-97.

Colman, et al., "Basic Principles and Clinical Practice Second Edition," *Hemostatis and Thrombosis*, 20-21.

Colville-Nash, P. R. et al., "Angiogenesis and rheumatoid arthritis: Pathogenic and Therapeutic Implications," *Annals of Rheumatoid Diseases*, vol. 51 Jan. 1, 1992, 919-925.

Colville-Nash, et al., "The pharmacological modulation of angiogenesis in chronic granulomatous inflammation," *Journal of Pharmacology and Experimental Therapeutics (abstract to)*, vol. 274(3) Sep. 1995, 1463-1472.

Congy, et al., "Plasma Zinc Levels in Elderly Patients Hospitalized in Long Stay Units. Correlations with Other Nutritional Marks, Immunological Tests and Survival," *Semaine Des Hopitaux*, vol. 59(45) Dec. 8, 1983, 3105-3108.

Contrino, J. "In situ detection of tissue factor in vascular endothelial cells: Correlation with the malignant phenotype of human breast disease," *Nature Medicine*, vol. 2(2) Feb. 1996, 209-215.

Corey, et al., "Applications of N,N-Dimethylhydrazones to Synthesis. Use in Efficient, Positionally and Sterochemically Selective C-C Bond Formation; Oxidative Hydrolysis to Carbonyl Compounds," *Tetrahedon Letters*, vol. 1 1976, 3-6.

Corey, et al., "Facile Conversion of N,N-Dimethylhydrazones to Carbonyl Compounds by Cupric Ion-Catalyzed Hydrolysis," *Tetrahedron Letters*, vol. 41 1976, 3678-3668.

Costa, et al., "Aseptic Adenitis in Pyoderma Gangrenosum (Abstract only)," *Ann. Dermatol. Venereol.*, vol. 121(8) Jan. 1, 1994, 550-552.

Coviello, et al., "Scleroglucan: A Versatile Polysaccharide for Modified Drug Delivery," *Molecules*, vol. 10 Jan. 31, 2005, 6-33.

Crabbe, et al., "Additions of Difluorocarbene to an Enzyme System in a Steroid Molecule (identifier only)," *Journal of the American Chemical Society*, vol. 90(11) 1968, 2998-2999.

Crabbe, P. "Cotton effect of the styrene chromophore (Abstract only)," *Chem. Ind.*, vol. 27 1969, 917-918.

Crain, E et al., "The Effect of Thalidomide on Experimental Autoimmune Myasthenia Gravis," *Journal of Autoimmunity*, vol. 2(2) Apr. 1, 1989, 197-202.

Crawford, C. L. "Letter: Thalidomide in Erythema Leprosum," *The Lancet*, vol. 2(839) Nov. 24, 1973, 1201-1202.

Crawford, C. L. "Treatment of Erythema Nodosum Leprosum with Thalidomide," *The Lancet*, vol. 2(828) Sep. 8, 1973, 567-568.

Crawford, C. L. "Use of Thalidomide in Leprosy [Letter; comment]," *British Medical Journal*, vol. 302(6729) Jun. 29, 1991, 1603-1604.

Crum, R. et al., "A New Class of Steroids Inhibits Angiogenesis in the Presence of Heparin or a Heparin Fragment," *Science*, vol. 230 Dec. 20, 1985, 1375-1378.

Cummings, et al., "Apoptosis," *The American Journal of Surgical Pathology*, vol. 21(1) 1997, 88-101.

Cummings, et al., "Interspecies Cross-Reactivity of Monoclonal Antibodies to Various Epitopes of Human Plasminogen," *Archives of Biochemistry and Biophysics*, vol. 230(1) Apr. 1984, 306-315.

Cunningham, et al., "Dimerization of Human Growth Hormone by Zinc," *Science*, vol. 253 Aug. 2, 1991, 545-548.

Curti, Brendan D. "Physical barriers to drug delivery in tumors," *Critical Reviews in Oncology/Hematology*, vol. 14 1993, 29-39.

Cushman, et al., "Synthesis of Analogs of 2-Methoxyestradiol with Enhanced Inhibitory Effects on Tubulin Polymerization and Cancer Cell Growth," *Journal of Medicinal Chemistry*, vol. 40(15) 1997, 2323-2334.

Cushman, et al., "Synthesis, Antitubulin and Antimitotic Activity, and Cytotoxicity of Analogs of 2-Methoxyestradiol, an Endogenous Mammalian Metabolite of Estradiol that Inhibits Tubulin Polymerization by Binding to the Colchicine Binding Site," *Journal of Medicinal Chemistry*, vol. 38(12) Jun. 6, 1995, 2041-2049.

D'Amato, et al., "2-Methoxyestradiol, and Endogenous Mammalian Metabolite, Inhibits Tubulin Polymerization by Interacting at the Colchicine Site," *Proceedings of the National Academy of Science USA*, vol. 91 Apr. 26, 1994, 3964-3968.

D'Amato, et al., "Angiogenesis Inhibition in Age-Related Macular Degeneration," *Opthalmology*, vol. 102(9) Sep. 1, 1995, 1261-1262.

D'Amato, et al., "Microscopic Analysis of Retinal-Vessels Utilizing Flourescein-Labeled High-Molecular Weight Dextrans," *Investigative Ophthalmology and Visual Science*, vol. 33(4) Jan. 1, 1992, 1082.

D'Amato, R. J. et al., "Thalidomide is an Inhibitor of Angiogenesis," *Proceedings of the National Academy of Science USA*, vol. 91 Apr. 1, 1994, 4082-40085.

D'Andrea, et al., "Diferential Expression of Protease-Activated Receptors -1 and -2 in Stromal Fibroblasts of Normal, Benign, and Malignant Human Tissues," *The American Journal of Pathology*, vol. 158(6) Jun. 2001, 2031-2041.

D'Angelo, G. et al., "Activation of mitogen-activated protein knases by vascular endothelial growth factor and basic fibroblast growth factor in capillary endothelial cells is inhibited by the antiangiogenic factor 16-kDA N-terminal fragment of prolactin," *Proceedings of the National Academy of Science USA*, vol. 92 Jul. 1995, 6374-6378.

Dahut, et al., "Phase I Clinical Trial of Oral 2-Methoxyestradiol, an Antiangiogenic and Apoptotic Agent, in Patients with Solid Tumors," *Cancer Biology & Therapy*, vol. 5(1) Jan. 2006, e1-e6.

Dardik, R. et al., "The structure of endothelial cell thrombospondin—Characterization of the heparin-binding domains," *European Journal of Biochemistry*, vol. 168(2) Oct. 15, 1987, 347-355.

Dark, et al., "Combrestation A-4, an Agent that Displays Potent and Selective Toxicity Toward Tumor Vasculature," *Cancer Research*, vol. 37 Jan. 1, 1994, 1829-1837.

Date, "HGF/NK4 is a specific antagonist for pleiotrophic actions of hepatocyte growth factor," *FEBS Letters*, vol. 420, Issue 1 Oct. 1, 1997, 1-6.

Date, et al., "Inhibition of tumor growth and invasion by a four-kringle antagonist (HGF/NK4) for," *Oncogene*, vol. 17 Hepatocyte Growth Factor HGF Jun. 22, 1998, 3045-3054.

David-Bajar, K. M. "Subacute Cutaneous Lupus Erythematosus," *Journal of Investigative Dermatology*, vol. 100(1) Jan. 1, 1993, 2s-8s.

Davidson, et al., "The influence of the Nature of the Asparagine 289-linked Oligosaccharide on the Activation by Urokinase and Lysine Binding Properties of Natural and Recombinant Human Plasminogens," *The Journal of Clinical Investigation*, vol. 92 Jul. 1993, 249-254.

Davies, et al., "Pathobiology of Intimal Hyperplasia," *British Journal of Surgery*, vol. 81(4) Sep. 1994, 1254-1269.

Davoodpour, et al., "2-Methoxyestradiol-induced Apoptosis in Prostate Cancer Cells Requires Smad7," *The Journal of Biological Chemistry*, vol. 280(15) Apr. 15, 2005, 14773-14779.

Davoodpour, et al., "Effects of 2-methoxyestradiol on proliferation, apoptosis and PET-tracer uptake in human prostate cancer cell aggregates," *Nuclear Medicine and Biology*, vol. 31 Jan. 1, 2004, 867-874.

Dawling, et al., "In Vitro Model of Mammary Estrogen Metabolism: Structural and Kinetic Differences between Catechol Estrogens 2- and 4- Hydroxyestradiol," *Chem. Res. Toxicol.*, vol. 17 Jan. 1, 2004, 1258-1264.

Dawling, et al., "Methoxyestrogens Exert Feedback Inhibition on Cytochrome P450 and 1A1 and 1B1," *Cancer Research*, vol. 63 Jun. 15, 2003, 3127-3132.

Day, et al., "The effects of 2-substituted oestrogen sulphamates on the growth of prostate and ovarian cancer cells," *Journal of Steroid Biochemistry & Molecular Biology*, vol. 84 Jan. 2003, 317-325.

Dayhoff, et al., "A Model of Evolutionary Change in Proteins," *Atlas of Protein Sequence and Structure*, vol. 5 1972, 89-99.

De, A. U. "Possible Antineoplastic Agents I," *Journal of Pharmacological Science*, vol. 64(2) Feb. 1, 1975, 262-266.

De, A. U. "Possible Antineoplastic Agents. III. Synthesis of 6-alkyl-2-[4'methoxyphtalimido] and 6'alkyl-e-[3'-4'dimedhoxyphenyl]glutarimides (abstract only)," *Journal of Indian Chemical Society*, vol. 53(11) Jan. 1, 1976, 1122-1125.

De, A. U. et al., "Possible Antineoplastic Agents: Part IV-Synthesis and Antineoplastic Potency of N-Substituted a-(4,5-Dimethoxyphthalimido)glutarimides and N-Substituted B-(4-Bromophenyl)glutarimdes," *Indian Journal of Chemistry*, vol. 16B Jun. 1, 1978, 510-512.

De Bono, et al., "The Future of Cytotoxic Therapy: Selective Cytotoxicity Based on Biology is the Key," *Breast Cancer Research*, vol. 5(3) Mar. 27, 2003, 154-159.

Deans, et al., "Structural studies on a putative protective *Plasmodium knowlesi* merozoite antigen," *Molecular Biology and Parasitology*, vol. 26 1987, 155-166.

Debs, R. J. et al., "Regulation of Gene Expression in Vivo by Liposome-mediated Delivery of a Purified Transcription Factor," *The Journal of Biological Chemistry*, vol. 265(18) Jun. 25, 1990, 10189-10192.

Decock, K. "Treatment of Ulcerative Colitus," *British Medical Journal*, vol. 1 May 19, 1979, 1356.

Degen, et al., "Characterization of the cDNA Coding for Mouse Plasminogen and Localization of the Gene to Mouse Chromosome 17," *Genomics*, vol. 8 1990, 49-64.

Deklerk, et al., "New Methods of Treatment for Renal Allotransplants Using the Baboon as a Primate Experimental Model," *Journal of Urology*, vol. 102(5) Jan. 1, 1969, 532-540.

Delaglio, et al., "NMRPipe: A multidimensional spectral processing system based on UNIX pipes," *Journal of Biomolecular NMR*, vol. 6 1995, 277-293.

Delie, et al., "Polymeric Particulates to Improve Oral Bioavailability of Peptide Drugs," *Molecules*, vol. 10 Jan. 31, 2005, 65-80.

Demeester, et al., "Stress-Induced Fractal Rearrangement of the Endothelial Cell Cytoskeleton Causes Apoptosis," *Surgery*, vol. 124(2) Aug. 7, 1998, 368-371.

Deng, et al., "Strong incompatibility between derivatives of the *Streptomyces* multi-copy plasmid plJ101," *Mol. Gen. Genet.*, vol. 214 1988, 286-294.

Devaraj, et al., "The effects of alpha-tocopherol on critical cells in atherogenesis," *Current Opinion in Lipidology*, vol. 9(1) Feb. 1998, 11-15.

Dhanabal, et al., "Cloning, Expression, and in Vitro Activity of Human Endostatin," *Biochemical and Biophysical Research Communications*, vol. 258 Mar. 22, 1999, 345-352.

Dhanabal, et al., "Endostatin Induces Endothelial Cell Apoptosis," *The Journal of Biological Chemistry*, vol. 274(17) 1999, 11721-11726.

Dhanabal, et al., "Endostatin: Yeast Production, Mutants, and Antitumor Effect in Renal Cell Carcinoma," *Cancer Research*, vol. 59 Jan. 1, 1999, 189-197.

Dhodapkar, et al., "A Phase II Pilot Study of Anti-Angiogenesis Therapy Using Thalidomide in Patients with Multple Myeloma," *University of Arkansas for Medical Sciences*, vol. 98-003 1998, 1-15.

Dicken, C. H. "Malignant Pyoderma," *Journal of the American Academy of Dermatology*, vol. 13(6) Dec. 1, 1985, 1021-1025.

Dickens, et al., "Isolation and Characterization of a Gene from *Streptomyces* sp. Strain C5 that Convers the Ability To Convert Daunomycin to Doxorubicin on *Streptomyces lividans* TK24," *Journal of Bacteriology*, vol. 178(11) 1996, 3389-3395.

Dike, et al., "Geometric Control of Switching Between Growth, Apoptosis, and Differentiation During Angiogenesis Using Micropatterened Substrates," *In Vitro Cell. Dev. Biol.*, vol. 35 Sep. 1999, 441-448.

Dinbergs, et al., "Cellular Response to Transforming Growth Factor-b1 and Basic Fibroblast Growth Factor Depends on Release Kinetics and Extracellular Matrix Interactions," *The Journal of Biological Chemistry*, vol. 271(47) Nov. 22, 1996, 29822-29829.

Ding, et al., "Sex Hormone-Binding Globulin Mediates Prostate Androgen Receptor Action via a Novel Signaling Pathway (Abstract only)," *Endocrinology*, vol. 139(1) 1998, 213-218.

Ding, et al., "Zinc-dependent dimers observed in crystals of human endostatin," *Proceedings of the National Academy of Science USA*, vol. 95 Sep. 1, 1998, 10443-10448.

Dipaolo, "Effect of Thalidomide on a Variety of Transplantable Tumors," *Cancer Chemotherapy Reports*, vol. 29 May 1, 1963, 99-102.

Dipaolo, Joseph "In vitro Test Systems for Cancer Chemotherapy. II. Correlation of In Vitro Inhibition of Dehydrogenase and Growth with in Vivo Inhibition of Ehrlich Ascites Tumor," *P.S.E.B.M.*, vol. 114 Jan. 1, 1963, 384-387.

Dipaolo, et al., "Teratogenesis-oncogenesis: A Study of Possible Relationships," *Archives of Pathology*, vol. 81 Jan. 1, 1966, 3-23.

Dipaolo, et al., "Thalidomide: Effects on Ehrlich Ascites Tumor Cells in vitro," *Science*, vol. 144 Jun. 26, 1964, 1583.

Dixelius, et al., "Endostatin-induced tyrosine kinase signaling through the Shb adaptor protein regulates endothelial cell apoptosis," *Blood*, vol. 95(11) Jun. 1, 2000, 3403-3411.

Dixit, V. M. et al., "A monoclonal antibody against human thrombospondin inhibits platelet aggregation," *Proc. Natl. Acad. Sci. USA*, vol. 82 May 1985, 3472-3476.

Djavaheri-Mergny, et al., "TNFa Potentiates 2-Methoxyestradiol-Induced Mitochondrial Death Pathway," *Annals New York Academy of Sciences*, vol. 1010 Jan. 2003, 159-162.

Dobos, et al., "In Vitro and In Vivo Antitumor Effect of 2-Methoxyestradiol on Human Melanoma," *International Journal of Cancer*, vol. 112 Jan. 2004, 771-776.

Dolan, et al., "Glyhcophorin B as an EBA-175 independent *Plasmodium falciparum* receptor of human erythrocytes," *Molecular Biochemical and Parasitology*, vol. 64 1994, 55-63.

Donate, et al., "Molecular evolution and domain structure of plasminogen-related growth factors (HGF/SF and HGF1/MSP)," *Protein Science*, vol. 3 1994, 2378-2394.

Dong, et al., "Macrophage-Derived Metalloelastase Is Responsible for the Generation of Angiostatin in Lewis Lung Carcinoma," *Cell*, vol. 88(6) Mar. 21, 1997, 801-810.

Dorveaux, et al., "Le Traitement Actuell du Lupus Erythemateux Chronique," *Le Concours Med.* vol. 106(31) Aug. 9, 1984, 2957-2961.

Doutre, "Pyoderma Gangrenosum and Hemophaties," *Nouvelle Revue Francaise d'* vol. 29(4) Sep. 1, 1987, 251-254.

Dube, et al., "Agalactosyl IgG inflammatory bowel disease: correlation with C-reactive protein," *Gut* Apr. 11, 1990, 431-434.

Dubey, et al., "Cardiovascular Pharmacology of Estradiol Metabolites," *The Journal of Pharmacology and Experimental Therapeutics*, vol. 308(2) Jan. 2004, 403-409.

Dubey, et al., "Catecholamines Block the Antimitogenic Effect of Estradiol on Human Glomerular Mesangial Cells," *Hypertension*, vol. 42 Jan. 2003, 349-355.

Dubey, et al., "Methoxyestradiols Mediate the Antimitogenic Effects of Estradiol on Vascular Smooth Muscle Cells via Estrogen Receptor-Independent Mechanisms," *Biochemical and Biophysical Research Communications*, vol. 278 2000, 27-33.

Dubey, et al., "Mexthoxyestradiols Mediate the Antimitogenic Effects of Locally Applied Estradiol on Cardiac Fibroblast Growth," *Hypertension*, vol. 39 (Part 2) Feb. 2002, 412-417.

Dubey, et al., "Role of Methoxyestradiols in the Growth Inhibitory Effects of Estradiol on Human Glomerular Mesangial Cells," *Hypertension*, vol. 39 (Part 2) Feb. 2002, 418-424.

Dulbecco, et al., "Plaque Formation and Isolation of Pure Lines with Poliomayelitis Viruses," *J. Exp. Med*. vol. 99 (2): Jun. 1, 1953, 167-182.

Dulbecco, et al., "Plaque Production by the Polyoma Virus," *Letters to the Editors* 1959, 396-397.

Dunn, et al., "Bone Marrow Transplantation and Cataract Development," *Archives of Ophtalmology*, vol. 111(10) Oct. 1, 1993, 1367-1373.

Durani, et al., "Seco-Oestradiols and Some Non-Steroidal Oestrogens: Structural Correlates of Oestronenic Acid," *Journal of Steroid Biochemistry*, vol. 11 1979, 67-77.

Dvir, "Thin-layer Chromatography of DANSYL-oestrogens," *Journal of Chromatography*, vol. 52 Nov. 4, 1970, 505-506.

Dvorak, et al., "Melanoma. An ultrastructural study of the host inflammatory and vascular responses," *Journal of Investigative Dermatology*, vol. 75(5) Nov. 1980, 388-393.

Eberle, A. "Studies on melanotropin (MSH) receptors of melanophores and melanoma cells," *Biochemical Society Transactions*, vol. 9 1981, 37-39.

Edelberg, et al., "Neonatal Plasminogen Displays Altered Cell Surface Binding and Activation Kinetics—Correlation with Increased Glycosylation of the Protein," *The Journal of Clinical Investigation*, vol. 86(1) Jul. 1990, 107-112.

Eder, et al., "Synthese von Ostradiol (in German—No translation available)," *Chem. Ber.*, vol. 109 1976, 2948-2953.

Edsall, et al., "Effects of Altering the Electronics of 2-Methoxyestradiol on Cell Proliferation, on Cytotoxicity in Human Cancer Cell Cultures, and on Tubulin Polymerization," *Journal of Medicinal Chemistry*, vol. 47 Jan. 2004, 5126-5139.

Eger, K. et al., "Synthesis, Central Nervous System Activity and Teratogenicity of a Homothalidomide," *Ameimittelforschung Drug Research*, vol. 40(10) Jan. 1, 1990, 1073-1075.

Ehrlich, G. E. "Behcet's Disease: Current Concepts," *Comprehensive Therapy*, vol. 15(1) Jan. 1, 1989, 27-30.

Eide, et al., "Pathogenesis of generalized melanosis with melanuria and melanoptysis secondary to malignant melanoma," *Histopathology*, vol. 5(3) May 1991, 285-294.

Eisenbud, L. et al., "Recurrent Aphthous Stomatitis of the Behcet's Type: Successful Treatment with Thalidomide," *Oral Surgery, Oral Medicine and Oral Pathology*, vol. 64(3) Sep. 1, 1987, 289-292.

El-Naggar, A. M. et al., "Synthesis of Biologically Active 3,5-dinitrophthaloyl-and 3,5-diaminophthaloyl- Amino Acids and Dipeptide Derivatives (Abstract only)," *Indian Journal of Chemistry*, vol. 20B(1) Jan. 1, 1981, 514-517.

El-Tombary, "Synthesis. Uterotropic, and Antiuterotrophic Activities of some estradiol derivatives containing thiadiazole, thiazonline, and thiazolidinone moieties," *Arch. Pharm. Pharm. Med. Chem.*, vol. 330(9-10) 1997, 295-302.

El-Zaatari, et al., "Nucleotide sequence analysis and seroreactivities of the 65K heat shock protein from *Mycobacterium paratuberculosis*," *Clinical and Diagnostic Laboratory Immunology*, vol. 2(6) Jan. 1, 1995, 657-664.

Elia, et al., "Giant Esophageal Ulcer Treated with Steroids in AIDS Patient (2)," *Journal of Acquired Immune Deficiency Syndrome*, vol. 5(8) Jul. 1, 1992, 848-849.

Eliyahu, et al., "Polymers for DNA Delivery," *Molecules*, vol. 10 Jan. 31, 2005, 34-64.

Elvira, et al., "Covalent Polymer-Drug Conjugates," *Molecules*, vol. 10 Jan. 31, 2005, 114-125.

Emons, et al., "Modulation der hypophysaren Sekretion von Luteinisierendem Hormon (LH) durch Ostrogene," *Focus MHL*, vol. 3 1986, 221-228.

Endres, W. "Zur Acylierung von prim. Aminen durch Phthalimide," *Arch. Pharmaz*, vol. 305(72) Sep. 1972, 691-683.

Enjyoji, K. "Effect of Heparin on the Inhibition of Factor Xa by Tissue Factor Pathway Inhibitor: A Segment, Gly 212—Phe 243, of the third Kunitz Domain is a Heparin-Binding Site," *Biochemistry*, vol. 34(17) 1995, 5725-5735.

Epe, et al., "Microtubular Proteins as Cellular Targets for Carcinogenic Estrogens and Other Carcinogens," *Mechanisms of Chromosome Distribution and Aneuploidy, Prog. Clin. Biol. Res.* vol. 318 1989, 345-351.

Eravelly, J. et al., "Thalidomide in Weber-Christian Disease," *The Lancet*, vol. 1(8005) Jan. 29, 1977, 251.

Eriksson, et al., "Drug Exposure and Flow Cytometry Analysis in a Thalidomide Treatment Schedule That Prolongs Rat Cardiac Graft Survival," *Transplantation Proceedings*, vol. XXIV(6) Dec. 1, 1992, 2560-2561.

Eriksson, et al., "Synthesis and alkaline hydrolysis of some N-substituted phthalmides," *Acta Pharm. Suecica*, vol. 10 Jan. 1, 1973, 63-74.

Escuin, et al., "Both Microtubule-Stablizing and Microtubule-Destabilizing Drugs Inhibit Hypoxia-Inducible Factor-1a Accumulation and Activity by Disrupting Microtubule Function," *Cancer Research*, vol. 65(19) Oct. 1, 2005, 9021-9028.

Esterhay, R. "Specialty Rounds: Current concepts in the management of small cell carcinoma of the lung," *The American Journal of the Medical Sciences*, vol. 274(3) Nov. 1977, 232-245.

Evans, et al., "A Convergent Total Synthesis of +/– Colchicine and +/– Descaetamidoisocolchine," *Journal of the American Chemical Society*, vol. 103 Sep. 23, 1981, 5813-5821.

Evans, et al., "Inhibition of Prostate Cancer Neovascularization and Growth by Urokinase-Plasminogen Activator Receptor Blockade," *Cancer Research*, vol. 57 Aug. 15, 1997, 3594-3599.

Fabro, et al., "Teratogenic Activity of Thalidomide and Related Compounds," *Life Sciences*, vol. 3(9) Jan. 1, 1864, 987-992.

Fabro, S. "The Biochemical Basis of Chemical Teratogenesis," *Biochemical Basis of Thalidomide Teratogenicity* Jan. 1, 1981, 159-178.

Fabro, et al., "The Metabolism of Thalidomide: Some Biological Effects of Thalidomide and its Metabolites," *British Journal of Pharmacology and Chemotherapy*, vol. 25 Jan. 1, 1965, 352-362.

Fajardo, "Dual Role of Tumor Necrosis Factor-a in Angiogenesis," *American Journal of Pathology*, vol. 140(3) Mar. 1, 1992, 539-544.

Fan, et al., "Controlling the vasculature: angiogenesis, antiangiogenesis and vascular targeting of gene therapy," *Trends in Pharmacological Sciences*, vol. 16(2) Feb. 1995, 57-66.

Fanchenko, et al., "Characteristics of the guinea pig uterus estrogen receptor system (Abstract only)," *Byll. Eksp. Biol. Med.*, vol. 85(4) 1978, 467-470.

Fang, et al., "Cloning of the *Plasmodium vivax* Duffy Receptor," *Molecular Biochemical and Parasitology*, vol. 44 1991, 125-132.

Fantl, et al., "Characterisation of Monoclonal Antibodies Raised Against Testosterone," *Journal of Steroid Biochemistry*, vol. 19(5) 1983, 1605-1610.

Fantl, et al., "Production and Characterisation of a Monoclonal Antibody to Progesterone," *Journal of Steroid Biochemistry*, vol. 14 1981, 405-407.

Fantl, et al., "Simultaneous Production of Monoclonal Antibodies ot Dehydroepiandrosterone, Oestradiol, Progesterone and Testosterone," *Journal of Endocrinology*, vol. 100 1984, 367-376.

Faraj, et al., "Synthesis of new 10b-propargylic and 11B-allenic steroidal spirolactones," *Steroids*, vol. 56 Nov. 1, 1991, 558-561.

Faure, et al., "Chimotaxie Des Polynucleaires Neutrophils: Inhibition Par La Thalidomide," *Pathologie Biologie*, vol. 29(10) Dec. 1, 1981, 601-604.

Faure, et al., "Inhibition of PMN Leukocytes Chemotaxis by Thalidomide," *Archives of Dermatological Research*, vol. 269(3) Dec. 1, 1980, 275-280.

Fazal, et al., "Effect of blocking TNF-a on intracellular BCG (Bacillus Calmette Guerin) growth factor in human monocyte-derived macrophages," *FEMS Microbiology Immunology*, vol. 105 Jan. 1, 1992, 337-345.

Ferenczy, A. et al., "The cytodymanics of endometrial hyperplasia and carcinoma," *Annales de Pathologie*, vol. 3(3) Sep. 1983, 189-201.

Fesik, et al., "Heteronuclear Three-Dimensional NMR Spectroscopy. A Strategy for the Simplification of Homonuclear Two-Dimensional NMR Spectra," *Journal of Magnetic Resonance*, vol. 78 1988, 588-593.

Fetizon, et al., "Synthesis of 2-keto steroids (Abstract only)," *Bull. Soc. Chim. FR.*, vol. 8 1968, 3301-3306.

Fevig, et al., "A Short-Stereoselective Route to 16a-(Substituted-alkyl)estradiol Derivatives," *Journal of Organic Chemistry*, vol. 52 1987, 247-251.

Fickentscher, et al., "Stereochemical Properties and Teratogenic Activity of Some Tetrahydrophtalimides," *Molecular Pharmacology*, vol. 13 Jan. 1, 1977, 133-141.

Fidler, et al., "The Implications of Angiogenesis for the Biology and Therapy of Cancer Metastasis," *Cell*, vol. 79(2) Oct. 21, 1994, 185-1888.

Field, et al., "Effect of Thalidomide on the Graft versus Host Reaction," *Nature*, vol. 211(5055) Sep. 17, 1966, 1308-1310.

Figg, et al., "Inhibition of angiogenesis: treatment options for patients with metastic prostate cancer," *Investigational New Drugs*, vol. 20 Jan. 2002, 183-194.

Fisher, et al., "Induction of Terminal Differentiation in Cancer Cells as a Therapeutic Modality for Suppressing Tumor Growth: Studies Employing Human Melanoma," *Anticancer Research*, vol. 8 (5B) 1988, 1057.

Fishman, J. "Synthesis of 2-Methoxyestrogens," *Journal of the American Chemical Society*, vol. 80 Mar. 5, 1958, 1213-1216.

Fitzgerald, "Molecular Features of Colchicine Associated with Antimitotic Activity and Inhibition of Tubulin Polymerization," *Biochemical Pharmacology*, vol. 12(12) Jun. 15, 1976, 1383-1387.

Flohe, et al., "Studies on the Hypothetical Relationship of Thalidomide-induced Embryopathy and Collagen Biosynthesis," *Arzneimitte/Forschung (Germany West)*, vol. 31(2) Jan. 1, 1981, 315-320.

Fogler, et al., "Considerations for Angiogenic Tumor Models,", 301-316.

Folkman, et al., "Angiogenesis," *Journal of Biological Chemistry*, vol. 267(16) Jan. 1, 1992, 10931-10934.

Folkman, J. "Angiogenesis and Its Inhibitors," *Important Advances in Oncology* 1985, 42-62.

Folkman, J "Angiogenesis in Cancer, Vascular, Rheumatoid and other Disease," *Nature Medicine*, vol. 1(1) Jan. 1, 1995, 27-31.

Folkman, et al., "Angiogenesis Inhibition and Tumor Regression Caused by Heparin or a Heparin Fragment in the Presence of Cortisone," *Science*, vol. 221 Aug. 19, 1983, 719-725.

Folkman, Judah "Clinical Applications of Research on Angiogenesis," *The New England Journal of Medicine*, vol. 333(26) Dec. 28, 1995, 1757-1763.

Folkman, J et al., "Induction of Angiogenesis During the Transition from Hyperplasia to Neoplasia," *Nature*, vol. 339 May 4, 1989, 58-61.

Folkman, J et al., "Long-term Culture of Capillary Endothelial Cells," *Proceedings of the National Academy of Science USA*, vol. 76 Oct. 1, 1979, 5217-5221.

Folkman, J "Tumor angiogenesis and Tissue Factor," *Nature Medicine*, vol. 2 Feb. 1, 1996, 167-168.

Folkman, J. et al., "Tumor Angiogenesis: Therapeutic Implications," *New England Journal of Medicine*, vol. 285, No. 21 Hepatocyte Growth Factor HGF Nov. 18, 1971, 1182-1186.

Folkman, J et al., "Tumor Behavior in Isolated Perfused Organs in vitro Growth and Metastases of Biopsy Material and Rabbit Thryoid and Canine Intestinal Segment," *Annals of Surgery*, vol. 164(3) Sep. 1, 1966, 491-502.

Folkman, J "What is the Evidence that Tumors are Angiogenesis Dependent?," *Journal of the National Cancer Institute*, vol. 82(1) Jan. 3, 1990, 4-7.

Fornwald, et al., "Soluble Forms of the Human T Cell Receptor CD4 are Efficiently Expressed by *Strptomyces lividans*," *Bio/Technology*, vol. 11 Sep. 1993, 1031-1036.

Forsgren, M. et al., "Molecular cloning and characterization of a full-length cDNA clone for human plasminogen," *FEBS Letters*, vol. 213(2) Mar. 1987, 254-260.

Fotsis, et al., "The Endogenous Oestrogen Metabolite 2-Methoxyoestradiol Inhibits Angiogenesis and Suppresses Tumor Growth," *Nature*, vol. 368 Mar. 17, 1994, 237-239.

Francois, J "Embryological Pigment Epithelial Dystrophies," *Ophthalmologica*, vol. 172 Jan. 1, 1976, 417-433.

Franek, Milan "Structural Aspects of Steroid-Antibody Specificity," *Journal of Steroid Biochemistry*, vol. 28(1) 1987, 95-108.

Fraser, et al., "Angiogenesis and its control in the female reproductive system (Abstract only)," *British Medical Bulletin*, vol. 56(3) 2000, 787-797.

Friedlander, M. et al., "Definition of two angiogenic pathways by distint av integrins," *Science*, vol. 270 Dec. 1, 1995, 1500-1502.

Fries, et al., "Lipsomal Malaria Vaccine in Humans: A Safe and Potent Adjuvant Strategy," *Proceedings of the National Academy of Science USA*, vol. 89 Jan. 1992, 358-362.

Fujimoto, et al., "Increased Serum Levels of Basic Fibroblast Growth Factor in Patients with Renal Cell Carcinoma," *Biochemical and Biophysical Research Communication*, vol. 180(1) Oct. 15, 1991, 386-392.

Fujiwara, T. et al., "Induction of Chemosensitivity in Human Lung Cancer Cells i Vivo by Adenovirus-mediated Transfer of the Wild-Type p53 Gene," *Cancer Research*, vol. 54 May 1, 1994, 2287-2291.

Fuller, et al., "Application of Percent Labeled Mitosis (PLM) Analysis to the Investigation of Melanoma Cell Responsiveness to MSH Stimulation Throughout the Cell Cycle," *Experimental Cell Research*, vol. 126 1989, 183-190.

Fuller, et al., "Decay of Hormone Responsiveness in Mouse Melanoma Cells in Culture as a Function of Cell Density," *Journal of Cellular Physiology*, vol. 103 1980, 279-287.

Fuller, "Thalidomide, peripheral neuropathy and AIDS," *International Journal of STD & AIDS*, vol. 2(5) Sep. 1, 1991, 369-370.

Furner, et al., "Treatment of Subscute Cutaneous Lupus Erythematosus," *International Journal of Dermatology*, vol. 29(8) Oct. 1, 1990, 542-547.

Furukawa, et al., "Effect of Indole-3-Acetic Acid Derivatives on Neuroepithelium in Rat Embryos," *The Journal of Toxicological Sciences*, vol. 30(3) Jan. 2005, 165-174.

Gad, et al., "Thalidomide Induces Imbalances in T-Lymphocytes Sub-Popluations in the Circulating Blood of Healthy Males," *Leprosy Review*, vol. 56(1), Mar. 1985.

Gadosy, et al., "Generation, Characterization, and Deprotonation of Phenol Radical Cations," *Journal of Physical Chemistry*, vol. 103 1999, 8834-8839.

Gaetani, M "Studi Sull'Attivita Antitumorale Della Talidomide," *Giornale Italiano diu Chemioterapia*, 83-86.

Gandhi, et al., "Mannich Reaction of Estrone," *Journal of Indian Chem. Soc.*, vol. 39 1962, 306-308.

Gao, et al., "2-Methoxyestradiol-induced apoptosis in human leukemia cells proceeds through a reactive oxygen species and Akt-dependent process," *Oncogene*, vol. 24 Apr. 25, 2005, 3797A??3809.

Garcia, et al., "*Bartonella bacilliformis* Stimulates Endothelial Cells In Vitro and is Angiogenic In Vivo," *American Journal of Pathology*, vol. 136(5) May 1990, 1125-1135.

Gately, et al., "The mechanism of cancer-mediated conversion of plasminogen to the angiogenesis inhibitor angiostatin," *Proceedings of the National Academy of Sciences USA*, vol. 94(20) Sep. 30, 1997, 10868-10872.

Gavrieli, Y et al., "Identification of Programmed Cell Death in Situ via Specific Labeling of Nuclear DNA Fragmentation," *Journal of Cell Biology*, vol. 119 1992, 493-501.

Gehanno, et al., "Mouth and Pharyngeal Hyperalgesic Syndromes in AIDS," *Annales d' Oto-Laryngologie et de Chirugie Cervivo-faciale*, vol. 107(5) 1990, 311-313.

Genetech USA, "VEGF may be main cause of diabetic retinopahy (Abstract only)," *Biotechnology Newswatch* Oct. 17, 1994, 13-14.

Genvo, et al., "Treatment of Aphthosis with Thalidomide and with Colchicine," *Dermatologica*, vol. 168(4) Apr. 1984, 182-188.

Georghiou, et al., "HIV-associated oesophageal ulcers treated with thalidomide," *The Medical Journal of Australia*, vol. 152 Apr. 2, 1990, 382-383.

Gerlier, et al., "Liposomes as a Tool to Study the Role of Membrane Presentation in the immunogenicity of a MuLV-Related Tumor Antigen," *The Journal of Immunology*, vol. 131(1) Jul. 1983, 485-490.

Gershbein, L. "Effect of Transplanted Tumor and Various Agents on Liver Regeneration During Pregnancy," *P.S.E.B.M.*, vol. 126 1967, 88-92.

Gershbein, L. "Effect of Various Agents on Liver Regeneration and Walker Tumor Growth in Partially Hepatectomized Rats," *Cancer Research*, vol. 26(9) Sep. 1966, 1905-1908.

Gershbein, L. "The thalidomide analog. EM12, enhances 1,2-dimethylhydrazine-induction of rat colon adenocarcinomas," *Cancer Letters*, vol. 60(2) Nov. 1991, 129-133.

Getahun, et al., "Synthesis of Alkoxy-Substituted Diaryl Compounds and Correlation of Ring Separation with Inhibition of Tubulin Polymerization: Differential Enhancement of Inhibitory Effects Under Suboptimal Polymerization Reaction Conditions," *Journal of Medicinal Chemistry*, vol. 35(6) Mar. 20, 1992, 1058-1067.

Gherardi, et al., "Domain Structure of hepatocyte growth factor/scatter factor (HGF/SF) (Abstract only)," *Symposium on Plasminogen-related growth factors* Hepatocyte Growth Factor HGF Apr. 8, 1997, 5.

Ghigliotti, et al., "Thalidomide: Treatment of choise for aphthous ulcers in patients seropositive for human immunodeficiency virus," *Journal of the American Academy of Dermatology*, vol. 28(2) Feb. 1993, 271-272.

Gilani, S. H. "Cardiovascular Malformations in the Chick Embryo Induced by Thalidomide," *Toxicology and Applied Pharmacology*, vol. 25 1973, 77-83.

Gilbert, et al., "Production and Secretion of Proteins by *Streptomyces*," *Critical Reviews in Biotechnology*, vol. 15(1) 1995, 13-39.

Gilberts, et al., "Molecular evidence for two forms of Chrohn Disease," *Proceedings of the National Academy of Science USA*, vol. 91 Dec. 20, 1994, 12721-12724.

Gill, et al., "The Effects of Preparations of Human Chorionic Gonadotropin in AIDS-Related Kaposi's Sarcoma," *The New England Journal of Medicine*, vol. 335(17) Oct. 24, 1996, 1261-1269.

Gimbrone, M. A. et al., "Tumor dormancy in vivo by Prevention of Neovascularization," *Journal of Experimental Medine*, vol. 136 1972, 261-276.

Gimbrone, M. A. et al., "Tumor Growth and Neovascularization: An Experimental Model Using the Rabbit Cornea," *Journal of the National Cancer Institute*, vol. 52(2) Feb. 1974, 413-427.

Gissler, H. M. et al., "Enhanced Association of Plasminogen/Plamin with Lesional Epidermis of Bullous Pemphigold," *British Journal of Dermatology*, vol. 127 1992, 272-277.

Glaser, Vicki "Targeted Injectable Vestors Remain the Ultimate Goal in Gene Therapy," *Genetic Engineering News* Apr. 15, 1994, 8-9, 29.

Goihman-Yahr, et al., "Autoimmune Diseases and Thalidomide II. Adjuvant Disease, Experimental Allergic Encephalomyelitis and Experimental Allergic Neuritis of the Rat," *International Journal of Leprosy*, vol. 42(3) Jul. 9, 1974, 266-275.

Goihman-Yahr, et al., "Significance of Neutrophil Activation in Reactional Lepromatous Leprosy: Effects of Thalidomide in vivo and in vitro. Activation in Adjuvant Disease," *International Archives of Allergy Applications and Immunology*, vol. 57 1978, 317-332.

Gokmen-Polar, et al., "b-Tubulin Mutations are Associated with Resistance to 2-Methoxyestradiol in MDA-MB-435 Cancer Cells," *Cancer Research*, vol. 65(20) Oct. 15, 2005, 9406-9414.

Goldman, C. K. et al., "In vitro and in vivo gene delivery mediated by a synthetic polycationic amino polymer," *Nature Biotechnology*, vol. 15 May 1997, 462-466.

Gonzalez, et al., "Comparative study of experimental ocular melanoma using two implantation techniques of B16-F10 melanocytes," *Pigment Cell Research*, vol. 8(4) Aug. 1995, 173-179.

Gonzalez, et al., "Synthesis and Pharmacological Evaluation of 8a-Estradiol Derivatives," *Steroids*, vol. 40(2) Sep. 1982, 171-187.

Gonzalez-Gronow, et al., "Further Characterization of the Cellular Plasminogen Binding Site: Evidence That Plasminogen 2 and Lipoprotein a Compete for the Same Site," *Biochemistry*, vol. 28(6) Mar. 21, 1989, 2374-2377.

Gonzalez-Gronow, et al., "The role of carbohydrate in the function of human plasminogen: comparison of the protein obtained from molecular cloning and expression in *Escherichia coli* and COS cells," *Biochemica et Biophysica Acta*, vol. 1039 1990, 269-276.

Good, D. J. et al., "A Tumor Suppressor-dependent Inhibitor of Angiogenesis is Immunologically and," *Proceedings of the National Academy*, vol. 87 Hepatocyte Growth Factor HGF Sep. 1990, 6624-6628.

Goodall, T. et al., "Effect of Melanocyte Stimulating Hormone on Human Cultured Choroidal Melanocytes, Unveal Melanoma Cells, and Retinal Epithelial Cells," *Investigation Ophthalmology & Visual Science*, vol. 35(3) Mar. 1994, 826-837.

Goodman, et al., "Report of the National Cholesterol Education Program Expert Panel on Detection, Evaluation and Treatment of High Blood Cholesterol in Adults," *Archives of Internal Medicine*, vol. 148 Jan. 1988, 36-69.

Gooley, et al., "Secondary Structure and Zinc Ligation of Human Recombinant Short-Form Stromelysin by Multidimensional Heteronuclear NMR," *Biochemistry*, vol. 32 1993, 13098-13108.

Gorin, et al., "Thalidomide in hyperalgic pharyngeal ulceration of AIDS," *The Lancet*, vol. 335(8701) Jun. 2, 1990, 1343.

Gorin, et al., "Thalidomide May Cure AIDS Ulcers," *Nursing Times*, vol. 86(24) Jun. 13, 1990, 10.

Goulden, et al., "Linear prurigo simulating dermatitis artefacta in dominant dystrophic epidermolysis bullosa," *British Journal of Dermatology*, vol. 129(4) Oct. 1993, 443-446.

Grabstald, et al., "Clinical experiences with thalidomide in patients with cancer," *Clinical Pharmacology and Therapeutics*, vol. 6(3) Jan. 12, 1965, 298-302.

Grant, D. S. et al., "Scatter factor induces blood vessel formation in vivo," *Proceedings of the National Academy*, vol. 99 Hepatocyte Growth Factor HGF Mar. 1993, 1937-1941.

Grant, D. S. et al., "Two Different Laminin Domains Mediate the Differentiation of Human Endothelial Cells into Capillary-like Structures in Vitro," *Cell*, vol. 58 Sep. 8, 1989, 933-943.

Graybill, et al., "Treatment of murine Crytococcoisis with Liposome-Associated Amphotericin B," *The Journal of Infectious Diseases*, vol. 145(5) May 1982, 748-752.

Griffioen, et al., "Angiogenesis: Potentials for Pharmacologic Intervention in the Treatment of Cancer, Cardiovascular Diseases, and Chronic Inflammation," *Pharmacological Reviews*, vol. 52(2) 2000, 237-268.

Grinspan, D. "Significant response of oral aphthosis to thalidomide treatment," *Journal of the American Academy of Dermatology*, vol. 12(1) Jan. 1985, 85-90.

Grinspan, et al., "Treatment of aphthae with thalidomide," *Journal of the American Academy of Dermatology*, vol. 20(6) Jun. 1989, 1060-1063.

Gross, J. L. et al., "Increased Capillary Endothelial Cell Protease Activity in Response to Angiogenic Stimuli in vitro," *Proceedings of the National Academy of Science USA*, vol. 80 May 1983, 2623-2627.

Gross, et al., "Inhibition of Tumor Growth, Vascularization, and Collagenolysis in the Rabbit Cornea by Medroxyprogesterone," *Proceedings of the National Academy of Science USA*, vol. 78(2) Feb. 1981, 1176-1180.

Gross, J. L. et al., "Modulation of Solid Tumor Growth in vivo by cFGF," *Proceedings of the American Association of Cancer Research*, vol. 31 Mar. 1990, 79.

Grosshans, et al., "Thalidomide Therapy for Inflammatory Dermatoses," *International Journal of Dermatology*, vol. 23(9) Nov. 1984, 598-602.

Grzesiek, et al., "Amino acid type determination in the sequential assignment procedure of uniformly 13C/15N-enriched proteins," *Journal of Biomolecular NMR*, vol. 3 1993, 185-204.

Grzesiek, et al., "An Efficient Experiment for Sequential Backbone Assignment of Medium-Sized Isotopically Enriched Proteins," *Journal of Magnetic Resonance*, vol. 99 1992, 201-207.

Grzesiek, et al., "Correlating Backbone Amide and Side Chain Resonances in Larger Proteins by Multiple Relayed Triple Resonance NMR," *Journal of the American Chemical Society*, vol. 114 1992, 6191-6293.

Grzesiek, et al., "Correlation of Backbone Amide and Aliphatic Side-Chain Resonances in 13C/15N-Enriched Proteins by Isotopic Mixing of 13C Magnetization," *Journal of Magnetic Resonance, Ser. B 101* 1993, 114-119.

Grzesiek, et al., "Improved eD Triple-Resonance NMR Techniques Applied to a 31 kDa Protein," *Journal of Magnetic Resonance*, vol. 96 1992, 432-440.

Gui, et al., "2-Methoxyestradiol Induces Cell Cycle Arrest and Mitotic Cell Apoptosis in Human Vascular Smooth Muscle Cells," *Hypertension*, vol. 47 Dec. 27, 2005, 271-280.

Guidetti, et al., "Ricerche Sull'azione Immunodepressiva Della Talidomide E Del Prednisolone in Ratti Portatori Di Neoplasie Sperimentalmente Indotte," *Cancro*, vol. 22 1969, 503-512.

Gujjar, et al., "The Effect of Estradiol on *Candida albicans* Growth," *Annals of Clinical and Laboratory Science*, vol. 27(2) 1997, 151-156.

Guntert, et al., "Automated Stereospecific 1H NMR Assignments and Their Impact on the Precision of Protein Structure Determinations in Solution," *Journal of the American Chemical Society*, vol. 111 1989, 3997-4004.

Guntert, et al., "Efficient Computation of Three-dimensional Protein Structures in Solution from Nuclear Magnetic Resonance Data Using the Program DIANA and the Supporting Programs CALIBA, HABAS and GLOMSA," *Journal of Molecular Biology*, vol. 217 1991, 517-530.

Guntert, et al., "Structure Determination of the Antp(C39-S) Homeodomain from Nuclear Magnetic Resonance Data in Solution using a Novel Strategu for the Structure Calculation with the Programs DIANA, CALIBA, HABAS and GLOMSA," *Journal of Molecular Biology*, vol. 217 1991, 531-540.

Guntert, et al., "Torsion Angle Dynamics for NMR Structure Calculation with the New Program DYANA," *Journal of Molecular Biology*, vol. 273 1997, 283-298.

Gunzler, V. "Thalidomide in Human Immunodeficiency Virus (HIV) Patients," *Drug Experience*, vol. 7(2) 1992, 116-134.

Gunzler, V. "Thalidomide-A Therapy for the Immunological Consequences of HIV Infection?," *Medical Hypothesis*, vol. 30(2) Oct. 1989, 105-109.

Gunzler, W. A. et al., "The Primary Structure of High Molecular Mass Urokinase from Human Urine," *Hoppe-Seyler's Z. Physiol. Chem.*, vol. 363 Oct. 1982, 1155-1165.

Guo, et al., "Up-Regulation of Cdc2 Kinase and Cyclin A during Apoptosis of Endothelial Cells Induced by Angiogenic Inhibitor Kininostatin (Abstract No. 125)(Abstract only)," *Blood*, vol. 98(11)Pt.1, vol. 32A , 32A.

Gupta, S. et al., "A Potent Inhibitor of Endothelial Cell Proliferation is Generated by Proteolytic," *Proceedings of the National Academy*, vol. 92 Hepatocyte Growth Factor HGF Aug. 1995, 7799-7803.

Gupta, et al., "Antifertility Agents. XIV. Secosteroids. VII. Synthesis of 2a- and 2b, 6b dimethyl-eb-(p-hyroxyphenyl)-trans-bicyclo[4.3. 0]nonan-7 ones and some related compounds (Abstract only)," *Indian Journal of Chemistry*, vol. 13(7) 1975, 759-760.

Gupta, et al., "Studies in Antifertility Agents. Part XVIII.2a,6b-Diethyl-3b-(p-hydroxyphenyl) -trans-bicyclo[4.3.0]nonan-7b-ol (Abstract only)," *Indian Journal of Chemistry*, vol. 19B(10) 1980, 886-890.

Gura, Trisha "Cancer Models-Systems for Identifying New Drugs are Often Faulty," *Science*, vol. 278 Hepatocyte Growth Factor HGF Nov. 7, 1997, 1041-1042.

Gutierrez-Rodriguez, O. "Thalidomide—A Promising New Treatment for Rheumatoid Arthritis," *Arthritis and Rheumatism*, vol. 27(10) Oct. 1984, 1118-1121.

Gutierrez-Rodriguez, et al., "Treatment of Refractory Rheumatoid Arthritus—The Thalidomide Experience," *The Journal of Rheumatology*, vol. 16(2) Feb. 1989, 158-163.

Gutman, M. et al., "Failure of Thalidomide to inhibit Tumor Growth and Angiogenesis in Vivo," *Anticancer Research*, vol. 16 1996, 3673-3677.

Hass, A. F. "Angiolymphoid Hyperplasia with Eosinophila of the Hand," *Journal of Dermatologic Surgery and Oncology*, vol. 17 Sep. 1991, 731-734.

Hadley, et al., "Factors influencing invasion of erythrocytes by *Plasmodium falciparum* parasites: the effects of an N-acetyl-glucosamine neoglycoprotein and an anti-glycophorin antibody," *The American Journal of Tropical Medicine and Hygiene*, vol. 35(5) Sep. 1986, 898-905.

Hadley, et al., "Invasion of Erythrocytes by Malaria Parasites: A Cellular and Molecular Overview," *Ann. Rev. Microbiol.*, vol. 40 1986, 451-473.

Haffner, M. "Studies Involving Orphan Products for Treating/Diagnosing Women's Diseases," *Food and Drug Law Journal*, vol. 48 Jan. 1, 1993, 205-211.

Hagen, et al., "Inhibition of mitochondrial respiration by the anticancer agent 2-Methoxyestradiol," *Biochemical and Biophysical Research Communications*, vol. 322 Jan. 2004, 923-929.

Hahnel, et al., "The Specificity of the Estrogen Receptor of Human Uterus," *Journal of Steroid Biochemistry*, vol. 4 21-31, 1973.

Haldar, et al., "Bc12 is the Guardian of Microtubule Integrity," *Cancer Research*, vol. 57 Jan. 15, 1997, 229-233.

Hamel, et al., "Interactions of 2-Methoxyestradiol, an Endogenous Mammalian Metabolite, with Unpolymerized Tubulin and with Tubulin Polymers (Abstract only)," *Biochemistry*, vol. 35(4) 1996, 1304-1310.

Hammers, et al., "Introduction of a novel proliferation assay for pharmacological studies allowing the combination of BrdU detection and phenotyping," *Journal of Immunological Methods*, vol. 264 Jan. 2002, 89-93.

Hammond, B. et al., "Iris Color and Macular Pigment Optical Density," *Experimental Eye Research*, vol. 62(3) Mar. 1996, 293-297.

Hammond, et al., "Structure/function analyses of human sex hormone-binding blobulin: effects of zinc on steroid-binding specificity," *Steroid Biochemistry & Molecular Biology*, vol. 85 Jan. 2003, 195-200.

Hamza, M. "Behcet's disease, palmoplantar pustulosis and HLA-B27 treatment with thalidomide," *Clinical and Experimental Rheumatology*, vol. 8(4) Jul. 1, 1990, 427.

Hamza, M. "Treatment of Behcet's disease with thalidomide," *Clinical Theumatology*, vol. 5(3) Sep. 1, 1986, 365-371.

Han, et al., "Dehydroepiandrosterone and Dihydrotestosterone Recognition by Human Estrogenic 17B-Hydroxysteroid Dehydrogenase," *Journal of Biological Chemisty*, vol. 275 Iss 2 Jan. 14, 2000, 1105-1111.

Han, et al., "Synergism between the Anticancer Actions of 2-Methoxyestradiol and Microtubule-Disrupting Agents in Human Breast Cancer," *Cancer Research*, vol. 65(2) Jan. 15, 2005, 387-393.

Hanada, et al., "Carboxyl Terminal Basic Amino Acid Region of TFPI Prevents Proliferation of Human Smooth Muscle Cells by Inhibiting Activation of Map Kinase (Abstract only)," *Thrombosis and Haemostatis, Supplment* Jul. 2001.

Hanahan, et al., "Patterns and Emerging Mechanisms of the Angiogenic Switch during Tumorigenesis," *Cell*, vol. 86 Aug. 9, 1996, 353-364.

Handley, et al., "Chronic Bullous Disease of Childhood and Ulcerative Colitis," *Pediatric Dermatology*, vol. 10(3) Sep. 10, 1993, 256-258.

Handley, et al., "Chronic bullous disease of childhood and ulcerative colitis," *British Journal of Dermatology*, vol. 127(40) Jul. 1, 1992, 67-68.

Hanlon, et al., "Modeling Postradiation Prostate Specific Antigen Level Kinetics," *Cancer*, vol. 83(1) Jul. 1, 1998, 130-134.

Hara, et al., "Immunological Properties of Phosphatidycholesterol and its Homologue," *Chemistry and Physics of Lipids*, vol. 23 1979, 7-12.

Harindra, et al., *Papulo-Pruritic Eruption and Giant Ulceration of the Mouth: A Difficult Clinical Feature to Treat in the Patient Infected with Human Immunodeficiency Virus* Archives of Internal Medicine, vol. 152(9) Sep. 1, 1992, 1924.

Harris, A. "Antiangiogenesis for cancer therapy," *The Lancet*, vol. 349 May 1, 1997, 13-15.

Hartikka, et al., "An improved plasmid DNA expression vector for direct injection into skeletal muscle," *Human Gene Therapy*, vol. 7 1996, 1205-1217.

Hartley-Asp, et al., "Diethylstibestrol Induces Metaphase Arrest and Inhibits Microtubule Assembly," *Mutation Research*, vol. 143(4) Aug. 1985, 231-235.

Hasper, M. "Chronic Cutaneous Lupus Erythematosus," *Archives of Dermatology*, vol. 119 Oct. 1983, 812-815.

Hasper, et al., "Thalidomide in the Treatment of Chronic Discoid Lupus Erythematosus," *Acta Dermatovenereologica*, vol. 62(4) Sep. 1982, 321-324.

Hastings, et al., "Thalidomide in the treatment of erythema nodosum leprosum," *Clinical Pharmacology and Therapeutics*, vol. 11(4) Jul. 8, 1970, 481-487.

Hatfill, et al., "Induction of Morphological Differentiation in the Human Leukemic Cell Line K562 by Exposure to Thalidomide Metabolites," *Leukemia Research* vol. 15(2/3) May 1, 1990, 129-136.

Hawkins, Md., Michael J. "Clinical Trials of Antiangiogenic Agents," *Current Opinion in Oncology*, vol. 7 1995, 90-93.

Hawthorne, et al., "Antagonists of PAR2 on Human Skin Keratinocytes Identinfied Using a Microtitre Plate-Based Calcium Mobilsation Assay (Abstract only)," *13th International Symposium on Regulatory Peptides, Cairs, Queensland, Australia*, vol. 94(1-3) Oct. 22, 2000.

Hayashi, et al., "A Synthetic Peptide Inhibitor for a-Chemokines Inhibits the Growth of Melanoma Cell Lines," *Journal of Clinical Investigation*, vol. 99(11) Jun. 1997, 2581-2587.

He, et al., "A Versatile Synthesis of 2-Methoxyestradiol, and Endogenous Metabolite of Estradiol which inhibits Tubulin Polymerization by Binding to the Colchicine Binding Site," *Bioganic & Medicinal Chemistry Letters*, vol. 4(14) 1994, 1724-1728.

He, et al., "Novel Cytokine Release Inhibitors. Part II: Steroids," *Bioorganic & Medicinal Chemistry Letters*, vol. 8 1988, 2825-2828.

Heaton, et al., "Graft-versus-host disease following liver transplantation," *Journal of the Royal Society of Medicine*, vol. 15(5) Jun. 1992, 313-314.

Hejaz, et al., "Synthesis and Biological Activity of the Superestrogen (E)-17-Oximino 3-O-sulfamoyl-1,3,5(10)-estratriene: X-ray Crystal Structure of (E)-17-Oximino-3-hydroxy-1,3,5(10)-estratriene," *Journal of Medicinal Chemistry*, vol. 42(16) 1999, 3188-3192.

Hellberg, et al., "Disruption of b2-Integrin-Cytoskeleton Coupling Abolishes the Signaling Capacity of These Integrins on Granulocytes," *Biochemical and Biophysical Research Communications*, vol. 265(1) 1999, 164-169.

Hellman, et al., "Prolongation of Skin Homograft Survival by Thalidomide," *British Medical Journal*, vol. II Sep. 18, 1965, 687-689.

Helm, et al., "Comparative Teratological Investigation of Compounds Structurally and Pharmacologically Related to Thalidomide," *Arzneim.-Forsch./Drug Res.*, vol. 31(6) 1981, 941-949.

Hembrough, et al., "Novel Antagonists of PAR-2: Inhibition of Tumor Growth, Angiogenesis and Inflammation (Abstract only)," *Blood*, vol. 102(11) Nov. 16, 2003.

Hendler, S. "Immune Modulators Thalidomide," *The Oxygen Breakthrough*, 217-219.

Hendler, et al., "Thalidomide for Autoimmune Disease," *Medical Hypothesis*, vol. 10 1983, 437-443.

Heney, et al., "Thalidomide for Chronic Graft-Versus-Host Disease in Children," *The Lancet*, vol. 2(8623) Dec. 3, 1988, 1317.

Heney, et al., "Thalidomide in the treatment of graft-versus-host disease," *Biomedicine & Pharmacotherapy*, vol. 44(4) 1990, 199-204.

Heney, et al., "Thalidomide treatment for chronic graft-versus-host disease," *British Journal of Haematology*, vol. 78(1) May 1991, 23-27.

Hill, H. et al., "Melanin: A Two-Edged Sword?," *Pigment Cell Research*, vol. 19 1997, 158-161.

Himes, et al., "Action of the Vinca Alkaloids Vincristine, Vinblastine, and Desacetyl Vinblastine Amide on Microtubules in Vitro," *Cancer Research*, vol. 36 Oct. 1976, 3798-3802.

Hiscox, et al., "Interleukin-12, an Emergin Anti-Tumour Cytokine," *In Vivo*, vol. 11(2) Mar. 4, 1997, 125-132.

Ho, Shuk-Mei "Estrogens and Anti-Estrogens: Key Mediators of Prostate Carcinogenesis and New Therapeutic Candidates," *Journal of Cellular Biochemistry*, vol. 91 Jan. 1, 2004, 491-503.

Hodge, et al., "A Recombinant Vaccinia Virus Expressing Human Prostate-Specific Antigen (PSA): Safety and Immunogenicity in a Non-Human Primate," *Interntional Journal of Cancer*, vol. 63 1995, 231-237.

Hohenester, et al., "Crystal structure of the angiogenesis inhibitor endostatin at 1.5 A resolution," *The EMBO Journal*, vol. 17(6) 1998, 1656-1664.

Hohenester, et al., "Variable Zinc Coordination in Endostatin," *Journal of Molecular Biology*, vol. 297 2000, 1-6.

Hojyo, et al., "Actinic Pruigo," *International Journal of Dermatology*, vol. 31(5) May 1992, 372-373.

Holden, et al., "Mitotic Arrest by Benzimidazole Analogs in Human Lymphocyte Cultures," *Environmental Mutagenesis*, vol. 2 1980, 67-73.

Holker, et al., "The Reactions of Estrogens with Benzeneseleninic Anhydride and Hexamethyldisilazane," *J. Chem. Soc. Perkin Trans.*, vol. I 1982, 1915-1918.

Holm, et al., "Chronic Cutaneous Lupus Erythematosus Treated with Thalidomide," *Archives of Dermatology*, vol. 129 Dec. 1993, 1548-1550.

Holmgren, L. et al., "Dormancy of Micrometastases: Balanced Proliferation and Apoptosis in the Presence of Angiogensis Suppression," *Nature Medicine*, vol. 1(2) Feb. 1995, 149-153.

Homandberg, G. A. et al., "Heparin-Binding Fragments of Fibronectin are Potent Inhibitors of Endothelial Cell Growth," *American Journal of Pathology*, vol. 120 Sep. 1985, 327-332.

Hopfer, et al., "InVitro Antifungal Activities of Amphotericin B and Liposome-Encapsulated Amphotericin B," *Antimicrobial Agents and Chemotherapy*, vol. 25(3) Mar. 1984, 387-389.

Hopwood, et al., 1985.

Hori, A. et al., "Suppression of Solid Tumor Growth by Immunoneutralizing Monoclonal Antibody Against Human Basic Fibroblasts Growth Factor," *Cancer Research*, vol. 51 Nov. 15, 1991, 6180-6184.

Horuk, et al., "A receptor for the malarial parasite *Plasmodium vivax*: the erythrocyte chemokine receptor," *Science*, vol. 251 1993, 1182-1184.

Hostikka, et al., "The Complete Primary Structure of the a2 Chain of Human Type IV Collagen and Comparison with the a1 (IV) Chain," *The Journal of Biological Chemistry*, vol. 263(36) Dec. 25, 1988, 19488-19493.

Hou, et al., "2-Methoxyestradiol at low dose induces differentiation of myeloma cells," *Leukemia Research*, vol. 29 Jan. 2005, 1059-1067.

Hu, et al., "A novel regulatory function of proteolytically cleaved VEGF-2 for vascular endothelial and smooth muscle cells," *The FASEB Journal*, vol. 11 May 1997, 498-504.

Hu, et al., "Inhibition of Angiogenesis in Rats by IL-1 Receptor Antagonist and Selected Cytokine Antibodies," *Inflammation*, vol. 18(1) 1994, 45-58.

Hu, et al., "Neomycin inhibits angiogenin-induced angiogenesis (Abstract only)," *Proceedings of the National Academy of Sciences, USA*, vol. 95(17) 9791-9795, 1998.

Huang, et al., "Control of Cyclin D1, p27Kip1, and Cell Cycle Progression in Human Capillary Endothelial Cells by Cell Shape and Cytoskeleton Tension," *Molecular Biology of the Cell*, vol. 9 Nov. 1998, 3179-3193.

Huang, et al., "Superoxide Dismutase as a Target for the Selective Killing of Cancer Cells (Abstract only)," *Nature*, vol. 407(6802) Sep. 21, 2000, 390-395.

Huber, et al., "Tubulin Bindingn of Conformationally Restricted Bis-Aryl Compounds," *Bioorganic & Medicinal Chemistry Letters*, vol. 1(5) 1991, 243-246.

Ikegawa, et al., "Immunoaffinity extraction for liquid chromatographic determination of equilin and its metabolites in plasma (Abstract only)," *Biomed. Chromatogr.*, vol. 10(2) 1996, 73-77.

Ikura, et al., "Three-Dimensional NOESY-HMQC Spectroscopy of a 13C-Labeled Protein," *Journal of Magnetic Resonance*, vol. 86 1990, 204-209.

Imamura, et al., "Method for Manufacture of Dihydric Phenols (Abstract only)," *USPATFULL 76:20259 US 3,950,437*, Apr. 13, 1976.

Ingber, et al., "Control of Intracellular pH and Growth by Fibronectin in Capillary Endothelial Cells," *The Journal of Cell Biology*, vol. 1803-1811, May 15, 1990.

Ingber, D. "Drug News and Trial Developments," *AIDS Patient Care*, vol. 6(6) Dec. 1992, 288.

Ingber, Donald E. "Fibronectin Controls Capillary Endothelial Cell Growth by Modulating Cell Shape," *Proceedings of the National Academy of Science USA*, vol. 87 May 9, 1990, 3579-3583.

Ingber, et al., "How Does Extracellular matrix Control Capillary Morphogenesis?," *Cell*, vol. 58 Sep. 8, 1989, 803-205.

Ingber, D. et al., "Synthetic analogues of fumagillin that inhibit angiogenesis and suppress tumor growth," *Nature*, vol. 348 Dec. 6, 1990, 555-557.

Inoue, et al., "Molecular Mechanism of Diclofenac-Induced Apoptosis of Promyelocytic Leukemia: Dependency of Reactive Oxygen Species, AKT, BID, Cytochrome c, and Caspase Pathway," *Free Radical Biology & Medicine*, vol. 37(8) Jan. 1, 2004, 1290-1299.

Irache, et al., "Bioadhesive Properties of Gantrez Nanoparticles," *Molecules*, vol. 10 Jan. 31, 2005, 126-145.

Ireson, et al., "Pharmacokinetics and efficacy of 2-methoxyestradiol and 2-methoxyestradiol-bis-sulphamate in vivo in rodents," *British Journal of Cancer*, vol. 90 Jan. 1, 2004, 932-937.

Iriarte, et al., "Steroids (XCIV). Synthesis of 2-methyl and 1,2-dimethyl estrogens (Abstract only)," *Tetrahedon*, vol. 3 1958, 28-36.

Ishino, et al., "An Autopsy Case of Cerebral Form of v. Winiwater-Buerger's Disease with a Chronic Course of 12 years," *Folia Psychiatrica Neurologica Japonica*, vol. 27(3) 1973, 207-221.

Jackson, D. et al., "Stimulation and inhibition of angiogenesis by placental proliferin and proliferin-related protein," *Schience*, vol. 266 Dec. 2, 1994, 1581-1584.

Jacobson, et al., "Thalidomide for the Treatment of Oral Aphthous Ulcers in Patients with Human Immunodeficiency Virus Infection," *The New England Journal of Medicine*, vol. 336(1) May 22, 1987, 1487-1493.

Jacobson, et al., "The Diagnosis and Treatment of Leprosy," *Southern Medical Journal*, vol. 69(8) Aug. 1976, 979-985.

Jager, et al., "Clinical Observations in the Treatment of Leprosy Reaction with Cyclic Imides," *International Journal of Leprosy*, vol. 39(2) Apr. 6, 1971, 589.

Jaggers, et al., "Potent Inhibitory Effects of Steroids in an vitro Model of Angiogenesis (Abstract only)," *Journal of Endocrinology*, vol. 150(3) 1996, 457-464.

Jain, R. K. "Barriers to Drug Delivery in Solid Tumors," *Scientific American*, vol. 271 Jul. 1994, 58-65.

Jasmin, et al., "Renversement par la Thiamine et le pyridoxal de L'inhibition produite par L'hydroxy-3 Thalidomide Sur La Croissance D'Escherica Coli," *Canadian Journal of Microbiology*, vol. 12 1966, 333-336.

Jeltsch, "Hyperplasia of Lymphatic Vessels in VEGF-C Transgenic Mice," *Science*, vol. 276 May 30, 1997, 1423-1425.

Jenkins, et al., "Getting the glycosylation right: Implications for the biotechnology industry," *Nature Biotechnology*, vol. 14 Aug. 1996, 975-981.

Jenkins, et al., "Thalidomide, Orogential Ulcers, and Risk of Teratogenicity," *The Lancet*, vol. 1(8427) Mar. 2, 1985, 511.

Jennings, et al., "Effect of Actinomycin D on the Production of Acute Phase Protein in the Rabbit," *Experientia*, vol. 25 Mar. 15, 1969, 305-306.

Jeung, et al., "Thymidine phosphorylase suppresses apoptosis induced by microtubule-interfering agents," *Biochemical Pharmacology*, vol. 70 Jan. 2005, 13-21.

Jew, L. "Thalidomide in Erythema Nodosum Leprosum," *The Annals of Pharmacotherapy*, vol. 24(5) May 1990, 482-483.

Jhingran, et al., "STudies in Antifertility Agents—Part XLI: Secosteroids-x: Synthesis of Various Steroisomers of (=-)-2,6b-diethyl-7a-ethynyl-e-(p-hydroxyphenyl)-trans- bicyclo [4.3.0]nonan-7b-ol.," *Steroids*, vol. 42(6) 1983, 627-634.

Ji, et al., "Characterization of kringle domains of angiostatin as antagonists of endothelial cell," *The FASEB Journal*, vol. 12 Hepatocyte Growth Factor HGF Dec. 1998, 1731-1738.

Jin, et al., "Protease-Activated Receptor (PAR)-1 and PAR-2 Participate in the Cell Growth of Alveolar Capillary Endothelium in Primary Lung Adenocarcinomas," *Cancer*, vol. 97(3) Jan. 29, 2003, 703-713.

Joe, et al., "Inhibition of Human Malignant Glioma Growth In Vitro by Human Recombinant Plasminogen Kringles 1-3," *Int. J. Cancer*, vol. 82 1999, 694-699.

Johansson, H. et al., "Large scale recovery and purification of periplasmic recombinant protein from *E. coli* using expanded bed adsorption chromatography followed by new ion exchange media," *Journal of Biotechnolagy* 1996, 9-14.

Johansson, J. et al., "Surfactant Protein B: Disulfide Bridges, Structural Properties, and Kringle Similarities," *Biochemistry*, vol. 30(28) 1991, 6917-6921.

John, et al., "Novel Blycosylated Forms of Human Plasma Endostatin and Circulating Endostatin-Related Fragments of Collagen XV," *Biochemistry*, vol. 38(32) Aug. 10, 1999, 10217-10224.

Johnke, et al., "Thalidomide treatment of prurigo nodularis (abstract only)," *Ugeskrift for Laeger*, vol. 155(38) Sep. 20, 1993, 3028-3030.

Johnstone, A. et al., *Immunochemistry in Practice Second Edition*, Blackwell Scientific Publications, Oxford 1987, 30-47.

Jonsson, et al., "Chemical Structure and teratogenic properties I," *Acta Pharm. Suecica*, vol. 9(431) 1972, 431-446.

Jonsson, N. "Chemical structure and teratogenic properties III," *Acta Pharm. Suecica*, vol. 9 1972, 521-542.

Jonsson, N. "Chemical structure and teratogenic properties IV," *Acta Pharm. Suecica*, vol. 9 1972, 543-562.

Jorizzo, et al., "Thalidomide Effects in Behcet's Syndrome nad Pustular Vasculitis," *Archives of Internal Medicin*, vol. 146(5) May 1986, 878-881.

Josefsson, et al., "Suppression of Type II Collagen-Induced Arthritis by the Endogenous Estrogen Metabolite 2-Methoxyestradiol," *Arthritis & Rheumatism*, vol. 40(1) Jan. 1997, 154-163.

Joubert, et al., "Bax/Bcl-2 expression levels of 2-methoxyesteradiol-esposed esohageal cancer cells," *Biomedical Research*, vol. 105026(3) Jan. 2005, 131-134.

Joubert, et al., "Influence of prostaglandin A2 and 2-methoxyestradiol on Bax and Bcl-2 experssion levels in cervical carcinoma cells," *Biomedical Research*, vol. 26(2) Jan. 2005, 87-90.

Joussen, et al., "Effect of Thalidomide and structurally related compounds on corneal angiogenesis is comparable to their teratological potency (Abstract only)," *Graefes Arch Clin Exp Ophthalmol*, vol. 237(12) Dec. 1999, 954-961.

Jozsef, Timar "Beszamolo a Nemzeti Onkologiai Kutatas-fejlesztesi Konzorcium 2003. evi tevekenysegerol (Abstract in English)," *Magyaa Onkologusok Tarsasaga*, vol. 48 Jan. 2004, 75-79.

Juliano, et al., "Pharmacokinetic and Therapeutic Consequences of Liposomal Drug Delivery: Fluorodeoxyuridine and Amphotericin B as Examples," *Biology of the Cell*, vol. 47 1983, 39-46.

Jurand, A. "Early changes in limb buds of chick embryos after thalidomide treatment," *Journal of Embryology and Experimental Morphology*, vol. 16(2) Oct. 1966, 289-300.

Juret, et al., "Absence d'effet carcino-frenateur du Talidomide vis-a-vis de deux tumeurs greffees," *Societe de Biologie*, vol. 23 Feb. 23, 1963, 246-249.

Kabarity, et al., "Further investigations on the cytological effects of some contraceptives," *Mutation Research*, vol. 135 1984, 181-188.

Kaitin, K. "Graft-Versus-Host Disease," *The New England Journal of Medicine*, vol. 325(5) Aug. 1, 1991, 357-358.

Kamei, et al., "Effect of Allomelanin on Tumor Growth Suppression in vivo and on the Cell Cycle Phase," *Cancer Biotherapy and Radiopharmaceuticals*, vol. 12(4) Aug. 1997, 273-276.

Kamikubo, Y. et al., "Human Recombinant Tissue-Factor Pathway Inhibitor Prevents the Proliferation of Cultured Human Neonatal Aortic Smooth Muscle Cells," *FEBS Letters*, vol. 407 Jan. 1, 1997, 116-120.

Kamphaus, et al., "Canstatin, a Novel Matrix-derived inhibitor of Angiogenesis and Tumor Growth," *The Journal of Biological Chemistry*, vol. 275(2) Jan. 24, 2000, 1209-1213.

Kandel, J. et al., "Neovascularization is Associated with a Switch to the Export of bFGF in the Multistep," *Cell*, vol. 66 Hepatocyte Growth Factor HGF Sep. 20, 1991, 1095-1104.

Kaplan, et al., "TNF a regulation of HIV1: biology and therapy," *Research in Immunology*, vol. 145(8-9) 1994, 685-690.

Karwat, "Separation and Recovery of Hydrogen Sulfide from Hydrocarbon Mixture," *Caplus DE 1103310*, Sep. 2, 1959.

Kataoka, et al., "An Agent that Increases Tumor Suppressor Transgene Product Coupled with Systemic Transgene Delivery Inhibits Growth of Metastatic Lung Cancer in Vivo (Abstract only)," *Cancer Research*, vol. 58(21) Nov. 1998, 4761-4765.

Katsuta, et al., "Carcinogenesis in Tissue Culture III: Effects of the Second Treatments on DAB-Induced Proliferating Liver Cells of Normal Rats in Culture," *The Japanese Journal of Experimental Medicine*, vol. 35(4) 1965, 231-248.

Katz, et al., "Cloning and Expression of the Tyrosinase Gene from *Streptomyces antibioticus* in *Streptomyces lividans*," *Journal of General Microbiology*, vol. 129 1983, 2703-2714.

Kay, L. E. "Pulsed-Field Gradient-Enhanced Three-Dimensional NMR Experiment for Correlating 13Ca/b, 13C', and 1Ha Chemical Shifts in Uniformly 13C-Labeled Proteins Dissolved in H2O," *Journal of the American Chemical Society*, vol. 115 Mar. 10, 1993, 2055-2058.

Kay, et al., "Pure Absoption Gradient Enhanced Heteronuclear Single Quantum Correlation Spectroscopy with Improved Sensitivity," *Journal of the American Chemical Society*, vol. 114 1992, 10663-10665.

Kaytes, et al., "Homologies between the non-collagenous C-terminal (NC1) globular domains of the alpha 1 and alpha 2 subunits of type-IV collagen (Abstract only)," *Gene*, vol. 54(1) 1997, 141-146.

Keenan, et al., "Immunosuppressive Properties of Thalidomide Inhibition of In Vitro Lymphocyte Proliferation Alone and in Combination with Cyclosporine of FK506," *Transplantation*, vol. 52(5) Nov. 1991, 908-910.

Kehrel, B. "Platelet-collagen interactions," *Seminars in Thrombosis and Hemostatis*, vol. 21(2) 1995, 123-129.

Kelly, et al., "The Stimulation of Prostaglandin Production by Two Antiprogesterone Steroids in Human Endometrial Cells (Abstract only)," *Journal of Clinical Endocrinology Metabolism*, vol. 62(6) Jun. 1986, 1116-1123.

Kenyon, B. et al., "A Model of Angiogenesis in the Mouse Cornea," *Investigative Ophthalmology and Visual Science*, vol. 37(8) Jul. 1996, 1625-1632.

Kenyon, et al., "The discovery of new inhibitors of angiogenesis using an improved mouse corneal neovascularization model (No. 459-367)(abstract only)," 1994, S94.

Kerbel, Robert S. "A cancer therapy resistant to resistance," *Nature*, vol. 390 Nov. 27, 1997, 335-336.

Kesari, et al., "Externalization of Tropomysin Isoform 5 in Colon Epithelial Cells," *Clinical and Experimental Immunology*, vol. 118(2) Nov. 22, 1999, 219-227.

Khouri, R. K. et al., "Local Application of Tissue Factor Pathway Inhibitor (TFPI) Inhibits Intimal Hyperplasia Induced by Arterial Interventions," *Surgical Forum*, vol. 46 1995, 389-391.

Kieser, et al., "pIJ101, a Multi-Copy Broad Host-Range *Streptomyces* Plasmid: Functional Analysis and Development of DNA Cloning Fectors," *Mol. Gen. Genet.*, vol. 185 1982, 223-238.

Kim, K. J. et al., "Inhibition of Vascular Endothelial Growth Factor-induced Angiogenesis Suppresses Tumor Growth in Vivo," *Nature*, vol. 362 Apr. 29, 1993, 841-844.

Kim, et al., "Mass spectrometric measurement of differential reactivity of cysteine to localize protein-ligand binding sites. Application to tubulin-binding drugs," *Analytical Biochemistry*, vol. 332 Jan. 1, 2004, 376-383.

Kim, et al., "Molecular and Immunological Analysis of Genetic Prostate Specific Antigen (PSA) Vaccine," *Oncogene*, vol. 17 1998, 3125-3135.

King, Jr., Ralph P. "Novel Cancer Approach From Noted Scientist Hits Stumbling Block," *Wall Street Journal* Nov. 12, 1998, A1, A8.

Kinuya, et al., "Anti-angiogenic therapy and chemotherapy affect 99mTc sestamibi and 99mTc-HL91 accumulation differently in tumour xenograft," *Nuclear Medicine Communications*, vol. 26(12) Jan. 2006, 1067-1073.

Kinuya, et al., "Improved survival of mice bearing liver metastases of colon cancer cells treated with a combination of radioimmunotherapy and antiangiogenic therapy," *European Journal of Nuclear Medicine and Molecular Imaging*, vol. 31(7) Jul. 2004, 981-985.

Kitamoto, et al., "Vascular Endothelial Growth Factor is an Essential Molecule for Mouse Kidney Development: Glomerulogenesis and Nephrogenesi," *Journal of Clinical Investigation*, vol. 99(10) May 1997, 2351-2354.

Kiuru, et al., "Short synthesis of 2-Methoxyestradiol and 2-hydroxyestradiol," *Steroids*, vol. 68 Jan. 2003, 373-375.

Kivirikko, S. et al., "Primary Structure of the a1 Chain of Human Type XV Collagen and Exon-Intron Organization in the 3' Region of the Corresponding Gene," *Journal of Biological Chemistry*, vol. 269 Feb. 18, 1994, 4773-4779.

Klauber, et al., "Inhibition of Angiogenesis and Breast Cancer in Mice by the Microtubule Inhibitors 2-Methoxyestradiol and Taxol," *Cancer Research*, vol. 57 Jan. 1, 1997, 81-86.

Kligman, et al., "Topical tretinoin for photoaged skin," *Journal of the American Academy of Dermotology*, vol. 15 (4 Pt 2) Oct. 1986, 836-859.

Klimov, et al., "Cholesterol Metabolism in Rabbits with Resistance to Experimental Atherosclerosis Acquired by Immunological Treatment," *Vopr. Med. Khim*, vol. 6 1977, 803-807.

Klopstock, et al., "Antibodies Reacting with Steroid Haptens," *Journal of Immunology*, vol. 92 1964, 515-519.

Klug, et al., "Embryotoxic effects of thalidomide derivatives in the non-human primate *Callithrix jacchus*," *Archives of Toxicology*, vol. 68 1994, 203-205.

Knighton, D. et al., "Avascular and Vascular Phases of Tumour Growth in the Chick Embryo," *British Journal of Cancer*, vol. 35 1977, 347-356.

Knop, et al., "Thalidomide in the Treatment of sixty cases of chronic discoid lupus erythematosus," *British Journal of Dermatology*, vol. 108(4) Apr. 1983, 461-466.

Kobayashi, et al., "Production and Specificity of Antisera Raised Against 25-hydroxyvitamin D-3-[C-3]-bovind Albumin Conjugates," *Steroids*, vol. 57 1992, 488-493.

Koch, et al., "4 Thalidomide and Congeners as Anti-Inflammatory Agents," *Progress in Medicinal Chemistry*, vol. 22 1985, 166-242.

Koch, A. E. et al., "Interleukin-8 as a macrophage-derived mediator of angiogenesis," *Science*, vol. 258 Dec. 11, 1992, 1798-1801.

Koch, et al., "Teratology study of two isoglutamine derivatives," *Arch Toxicol.*, vol. 35(1) 1976, 63-68.

Koch, H. "The Arene Oxide Hypthesis of Thalidomide Action. Considerations on the Molecular Mechanism of Action of the "Classical" Teretogen," *Sci. Pharm.*, vol. 49 1981, 67-99.

Koch, H. "Uber die ZusammenhÄ?Ä☐nge zwischen chemischer Struktuf und biologischer AktivitÄ?Ä☐t bei Thalidomid und verwandten Verbindingen," *Scientia Pharmaceutica*, vol. 34(5) Dec. 31, 1966, 257-269.

Kohler, et al., "Zur EmbryotoxizatÄ?Ä☐t von N-Phthaloyl-DL-glutamine," *Z. Nayurforsch*, vol. 26b 1971, 857.

Kohno, et al., "Refolding of Recombinant Proteins," *Methods in Enzymology*. vol. 185 1990, 187-195.

Kole, et al., "Studies in Antifertility Agents. 11. Secosteroids.5. Systhesis of 9, 11-Secoestradiol," *Journal of Medicinal Chemistry*, vol. 18(7) 1975, 765-766.

Koradi, et al., "Molmol: A program for display and analysis of macromolecular structures," *Journal of Molecular Graphics*, vol. 14 1996, 51-55.

Korff, et al., "Blood vessel maturation in a 3-dimensional spheroidal coculture model: direct contact with smooth muscle cells regulates endothelial cell quiescence and abrogates VEGF responsiveness," *The FASEB Journal*, vol. 15 Feb. 1, 447-457.

Korff, et al., "Integration of Endothelial Cells in Multicellular Spheroids Prevents Apoptosis and Induces Differentiation," *The Journal of Cell Biology*, vol. 143(5) Nov. 30, 1998, 1341-1352.

Korff, et al., "Tensional forces in fibrillar extracellular matrices control directional capillary sprouting," *Journal of Cell Science*, vol. 112(19) Oct. 1999, 3249-3258.

Korn, et al., "The Second International Workshop on Scleroderma Research," *Matrix*, vol. 13(5) Sep. 1993, 427-429.

Kosfeld, M. D. et al., "Identification of a New Cell Adhesion Motif in Two Homologous Peptides from the COOH-terminal Cell Binding Domain on Human Thrombospondin," *The Journal of Biological Chemistry*, vol. 268(12) 1993, 8808-8814.

Kost, Christine et al., "Limited Plasmin Proteolysis of Vitronectin Characterization of the Adhesion Protein as Morpho-Regulatory and Angiostatin-Binding Factor," *European Journal of Biochemistry* vol. 236 Jan. 3, 1996, 682-688.

Kousteni, et al., "Reversal of Bone Loss in Mice by Nongenotypic Signaling of Sex Steroids," *Science*, vol. 298 Oct. 25, 2002, 843-846.

Kovacs, et al., "Steroids. XXIII. Synthesis of 2- and 4-hydroxy and 2,4- dihydroxy derivatives of estrone and estradiol (Abstract only)," *Acta Phys. Chem.* vol. 19(3) 1973, 287-290.

Koyama, et al., "Regulation and Function of an Activation-Dependent Epitope of the b1 Inegrins in Vascular Cells after Balloon Injury in Baboon Arteries and in Vitro," *American Journal of Pathology*, vol. 148(3) Mar. 1996, 749-761.

Kromhout, et al., "Serum Cholesterol and 25-year Incidence of and Mortality From Mycardial Infarcation and Cancer," *Archives of Internal Medicine*, vol. 148 May 1988, 1051-1055.

Kuba, et al., "HGF/NK4, a Four Kringle Antagonist of Hepatocyte Growth Factor, is an Angiogenesis Inhibitor that Suppresses Tumor Growth and Metatasis in Mice," *Cancer Research*, vol. 60 Dec. 1, 2000, 6737-6743.

Kubota, et al., "Role of Laminin and Basement Membrane in the Morphological Differentiation of Human Endo thelial Cells into Capillary-like Structures," *The Journal of Cell Biology*, vol. 107 1988, 1589-1598.

Kundu, et al., "Prurigo Nodularis in an HIV positive man," *Genitourinary Medicine*, vol. 71(2) Apr. 1995, 129-130.

Kurebayashi, et al., "Paradoxical Hormone Responses KPL-1 Breast Cancer Cells in vivo: a Significant Role of Angiogenesis in Tumor Growth (Abstract only)," *Oncology*, vol. 59(2) 2000, 158-165.

Kurkcuoglu, et al., "Thalidomide in the treatment of recurrent necrotic mucocutaneous aphthae," *British Journal of Dermatology*, vol. 112(5) May 1985, 632.

Kuzuya, et al., "Antioxidants Stimulate Endothelial Cell Proliferation in Culture," *Artery*, vol. 18(3) 1991, 115-124.

Laguchev, S. S. "Hormonal Regulation of Cell-Divisions in the Mammary Gland," *Path.-Biol.*, vol. 9(5-6) Mar. 1961, 638-640.

Lakhani, et al., "Determination of 2-methoxyestradiol in human plasma, using liquid chromatography/tandem mass spectrometry," *Rapid Commun. Mass Spectrum.*, vol. 19 Feb. 2005, 1176-1182.

Lakhani, et al., "Determination of the antiangiogenesis agent 2-methoxyestradiol in human plasma by liquid chromatography with ultraviolet radiation," *Journal of Chromatography B*, vol. 806 Jan. 1, 2004, 289-293.

Lalou, et al., "Interactions between Insulin-Like Growth Factor-1 (IGF-1) and the system of Plasminogen Activators and Their Inhibitors in the Control of IGF-Binding Protein-3 Production and Proteolysis in Human Osteosarcoma Cells," *Endocrinology*, vol. 135(6) 1994, 2318-2326.

Lambert, et al., "2-Methoxyestradiol Induces Caspase-Independent Mitochondria-Centered Apoptosis in DS-Sarcoma Cells," *International Journal of Cancer*, vol. 108 Jan. 2004, 493-501.

Lammertyn, et al., "Codon adjustment to maximise heterologous gene expression in Streptomyces lividans can lead to decreased mRNA stability and protein yield," *Mol. Gen. Genet.*, vol. 250 1996, 223-229.

Lampel, et al., "Cloning and Sequencing of a Gene Encoding a Novel Extracellular Neutral Proteinase from Streptomyces sp. Strain C5 and Expression of the Gene in Streptomyces lividans 1326," *Journal of Bacteriology*, vol. 174 May 1992, 2797-2808.

Lane, et al., "Treatment of Actinic Prurigo with Intermittent Short-Course Topical 0.05% Clobestral 17-Propionate," *Archives of Dermatology*, vol. 126(9) Sep. 1990, 1211-1213.

Langer, R. "New Methods of Drug Delivery," *Science*, vol. 249 Sep. 28, 1990, 1527-1533.

Languillon, J. "The Effects of Thalidomide on Leprosy Reaction," *International Journal of Leprosy and Other Mycobacterial Diseases*, vol. 39(2) Apr. 1971, 590-592.

Larsson, H. "Treatment of severe colitis in Behcet's syndrome with thalidomide (CG-217)," *Journal of Internal Medicine*, vol. 228(4) Oct. 1990, 405-407.

Lavallee, et al., "2-Methoxyestradiol Inhibits Proliferation and Induces Apoptosis Independently of Estrogen Receptors a and b," *Cancer Research*, vol. 62 Jul. 1, 2002, 3691-3697.

Lavallee, et al., "2-Methoxyestradiol Up-Regulates Death Receptor 5 and Induces Apoptosis through Activation of the Extrinsic Pathway," *Cancer Research*, vol. 63 Jan. 15, 2003, 468-475.

Lazar, et al., "Transforming Growth Factor a: Mutation of Aspartic Acid 47 and Leucine 48 Results in Different Biological Activities," *Molecular and Cellular Biology*, vol. 8(3) Mar. 1988, 1247-1252.

Le Bras, J. et al., "Activation and Regioselective Ortho-Functionalization of the A-Ring of B-Estradiol Promoted by "Cp*Ir": An Efficient Organometallic Procedure for the Synthesis of 2-Methoxyestradiol," *Organometallics*, vol. 16 1997, 1765-1771.

Ledo, E. "Photodermatosis. Part I: Photobiology, Photoimmunology, and Idiopathic Photodermatoses," *International Journal of Dermatology*, vol. 32(6) Jun. 1993, 387-396.

Leese, et al., "Anti-cancer activities of novel D-ring modified 2-substituted estrogen-3O-sulfamates," *Journal of Steroid Biochemistry and Molecular Biology*, vol. 94 Jan. 2005, 239-251.

Lehner, et al., "Thalidomide, Orogenital Ulcers, and the Risk of Teratogenesis," *The Lancet*, vol. 1(8423) Feb. 2, 1985, 288-289.

Lenicque, P. "Action of Thalidomide on the Induction of Tentacles in Regenerating Hydra littoralis," *Acta Zoologica* 1967, 127-139.

Leon, S.P. et al., "Genetic Aberrations in Human Brain Tumors," *Neurosurgery*, vol. 34(4) Apr. 1994, 708-722.

Lerch, Peter G. et al., "Localization of Individual Lysine-Binding Regions in Human Plasminogen and Investigations on Their Complex-Forming Properties," *European Journal of Biochemistry*, vol. 107 1980, 7-13.

Lesoon-Wood, L. A. et al., "Systemic Gene Therapy with p53 Reduces Growth and Metastases of a Malignant Human Breast Tumor in Nude Mice," *Human Gene Therapy*, vol. 6 Apr. 1995, 395-405.

Leu, et al., "Analysis of the promoter region of the melanin locus from Streptomyces antibioticus," *Gene*, vol. 84 1989, 267-277.

Levy, "Treatment of Erythema Nodosum Leprosum with Thalidomide," *The Lancet*, vol. 2(7824) Aug. 11, 1973, 324-325.

Lewis, Richard J. *Hawley's Condensed Chemical Dictionary* Jan. 1993, 577.

Lewis, Richard J. *Hawley's Condensed Chemical Dictionary* Jan. 1993, 128-129.

Lewis, et al., "Differential effects of 16a-hydroxyestrone and 2-Methoxyestradiol on cyclin D1 involving the transcription factor ATF-2 in MDF-7 breast cancer cells," *Journal of Molecular Endocrinology*, vol. 34 Jan. 2005, 91-105.

Li, J. et al., "(DN 103:65176) Catechol Formation of Fluoro- and Bromo-substituted Estradiols by Hamster Liver Microsomes. Evidence for Dehalogenation. (Abstract only)," *CAPLUS: Molecular Pharmacology*, vol. 27(5) 1985, 559-565.

Li, et al., "Antiproliferative activity and toxicity of 2-Methoxyestradiol in cervical cancer xenograft mice," *Int. J. Cynecol. Cancer*, vol. 15 Jan. 2005, 301-307.

Li, et al., "Antitumor Activities of 2-Methoxyestradiol on Cervical and Endometrial Cancers in Vitro and In Vivo," *Dissertations from the Faculty of Medicine—Uppsala*, vol. 1374 Jan. 2004.

Liang, et al., "A recombinant baculovirum-expressed *Plasmodium falciparum* receptor-bindingn domain of erythrocyte binding protein EBA-175 biologically mimcs native protein," *Infect Immun Jun.* vol. 68(6) 2000, 3564-3568.

Lichtenauer, et al., "Zur Behandlung des Prostata-Karzinoms," *Deutsches medizinisches Journal*, vol. 23 Jan. 1972, 248-249.

Lien, W. et al., "The blood supply of experimental liver metastases. II. A Microcirculatory study of the normal and tumor vessels of the liver with the use of perfused silicone rubber," *Surgery*, vol. 68(2) Aug. 1970, 334-340.

Lijnen, et al., "Generation of an Angiostatin-like Fragment from Plasminogen by Stromelysin-1 (MMP-3_," *Biochemistry*, vol. 37(13) Mar. 19, 1998, 4699-4702.

Lilja, et al., "Prostate-Specific Antigen in Serum Occurs Predominantly in Complex with a1-Antichymotrypsin," *Clinical Chemistry*, vol. 37(9) 1991, 1618-1625.

Limantsev, et al., "Effect of some estrogen structural analogs on the development of the mouse embryo (Abstract only)," *Akush Kinekol*, 1982, 55-56.

Lin, et al., "A comparative study on the effects of 2,3,7,8,-tetrochlorodibenzo-p-dioxin polychlorinated biphenyl126 and estrogen in human bronchial epithelial cells," *Toxicology and Applied Pharmacology*, vol. 195 Jan. 2004, 83-91.

Lin, et al., "Interactions of Tubulin with Potent Natural and Synthetic Analogs of the Antimitotic Agent Combretastatin: A Structure-Activity Study," *Molecular Pharmacology*, vol. 34(2) Aug. 1988, 200-208.

Lin, et al., "Structure Function Relationships in Glucagon: Properties of Highly Purified Des-His 1-Monoido- and [Des-Asn28Thr29](homoserine lactone27)-glucagon," *Biochemistry*, vol. 14(8) 1975, 1559-1563.

Lin, et al., "Tropomyosin Isoforms in Nonmuscle Cells," *Int. Rev. Cytol.*, vol. 170 1997, 1-38.

Lincoln, et al., "Conformation of Thiocolchicine and Two B-Ring-Modified Analogues Bound to Tubulin Studied with Optical Spectroscopy," *Biochemistry*, vol. 30(5) Feb. 5, 1991, 1179-1187.

Lindahl, A. "Coagulation Inhibition and Activation in Pancreatic Cancer," *Cancer*, vol. 70(8) Oct. 15, 1992, 2067-2072.

Lippert, et al., "The effects of A-ring and D-ring metabolites of estradiol on the proliferation of vascular endothelial cells," *Life Sciences*, vol. 67 2000, 1653-1658.

Lis, et al., "2-Methoxyestradiol inhibits proliferation of normal and neoplastic glial cells, and induces cell death, in vitro," *Cancer Letters*, vol. 213 Jan. 2004, 57-65.

Liu, et al., "Concentration-dependent mitogenic and antiproliferative actions of 2-methoxyestradiol in estrogen receptor-positive human breast cancer cells," *Steroid Biochemistry & Molecular Biology*, vol. 88 Jan. 1, 2004, 265-275.

Liu, et al., "Inhibitory action of ICI-182,780, an estrogen receptor antagonist, on BKCa channel activity in cultured endothelial cells of human coronary artery," *Biochemical Pharmacology*, vol. 66 Jan. 2003, 2053-2063.

Liu, et al., "Selective Insensitivity of ZR-75-1 Human Breast Cancer Cells to 2-Methoxyestradiol: Evidence for Type II 17b-Hydroxyestradiol Dehydrogenase as the Underlying Cause," *Cancer Research*, vol. 65(13) Jul. 1, 2005, 5802-5811.

Liu, et al., "Suppressive effects of 17b-estradiol on hepatic fibrosis in CCI4-induced rat model," *World Journal of Gastroenterology*, vol. 10(9) May 1, 2004, 1-11.

Liu, et al., "Total Synthesis of (+−) -D9(12)-Capnellene," *Tetrahedron Letters*, vol. 26(40) 1985, 4847-4850.

Lo, et al., "High level expression and secretion of Fc-X fusion proteins in mammalian cells," *Protein Engineering*, vol. 11(6) 1998, 495-500.

Lo, et al., "Treatment of Discoid Lupus Erythematosus," *International Journal of Dermatology*, vol. 28(8) Oct. 1989, 497-507.

Lokker, et al., "Generation and Characterization of a Competitive Antagonist of Human Hepatocyte Growth Factor, HGF/NK1," *The Journal of Biological Chemistry*, vol. 268(23) Aug. 15, 1993, 17145-17150.

Lokker, N. A. et al., "Mutational analysis and molecular modeling in the N-terminal kringle-containing domain of hepatocyte growth factor identifies amino acid side chains important for interaction with the c-met receptor," *Protein Engineering*, vol. 7(7) Jul. 1994, 895-903.

Lokker, et al., "Structure function analysis of hepatocyte growth factor: identification of variants that lack mitogenic activity yet retain high affinity receptor binding," *The EMBO Journal*, vol. 11(7) 1992, 2503-2510.

Londono, F. "Thalidomide in the Treatment of Actinic Pruigo," *International Journal of Dermatology*vol. 12(5) Sep. 10, 1973, 326-328.

Loozen, et al., "An approach to the synthesis of 7 beta-amino estrogens (Abstract only)," *Recl.: J.R. Neth. Chem.Soc.*, vol. 102(10) 1983, 433-437.

Lopez, et al., "Thalidomide as Therapy for Intestinal Chronic GVHD," *Bone Marrow Transplantation*, vol. 11(3) Mar. 1993, 251-252.

Lopez-Berestein, et al., "Effects of Sterols on the Therapeutic Efficacy of Liposome Amphotericin B in Murine Candidiasis," *Cancer Drug Delivery*, vol. 1(1) 1983, 37-42.

Lottering, et al., "17b-Estradiol Metabolites Affect Some Regulators of the MCF-7 Cell Cycle," *Cancer Letters*, vol. 110 1996, 181-186.

Lottering, et al., "Effects of the 17b-Estradiol Metabolites on Cell Cycle Events in MCF-7 Cells (Chemical Abstracts, 1992)," *Cancer Research*, vol. 52 Nov. 1, 1992, 5926-5932.

Louzir, et al., "Erythroleucemie chez un patient ayant une maladie de Behcet et traite au cours par thalidomide," *Annales de Medecine Inteme*, vol. 143(7) 1992, 479-480.

Lovell, et al., "Thalidomide in Actinic Prurigo," *British Journal of Dermatology*, vol. 108(4) Apr. 1983, 467-471.

Lovely, et al., "2-(Hydroxyalkyl)estradiols: Synthesis and Biological Evaluation," *Journal of Medicinal Chemistry*, vol. 39 1996, 1917-1923.

Lowe, et al., "Solubilisation, Refolding and Purification of Eukaryotic Proteins Expressed in *E. coli*," *Protein Purification: Micro to Macro Proceedinss of a Cetus-UCLA Symposium* Mar. 29, 1987, 429-442.

Lueprasitsakul, et al., "Effect of Thalidomide on the Incidence of Iodine-Induced and Spontaneous K1 Lumphoctic Thyroiditis and Spontaneous Diabetes Mellitus in the BB/W or Rat," *Acta Endocrino Logica*, vol. 123(1) Jul. 1990, 79-83.

Luers, H. "Failure of Mutagenic Action of Thalidomide In *Drosphilia*," *The Lancet*, vol. II(7258) Oct. 6, 1962, 1332.

Luginbuhl, et al., "The new program OPAL for molecular dynamics simulations and energy refinements of biological macromolecules," *Journal of Biomolecular NMR*, vol. 8 1996, 136-146.

Luo, et al., "Effect of Components of Crowth Ether Copper(I)Iodide Mixed Catalyst on Nucleophilic Substitution of Bromoestrogen (Abstract No. 195225)," *Chemical Abstracts*, vol. 111(21) Nov. 20, 1989, 818, col. 1.

Lupu, C. et al., "Thrombin Induces the Redistribution and Actue Release of Tissue Factor Pathway Inhibitor from Specific Granules within Human Endothelial Cells in Culture," *Arteriosclerosis, Thrombosis, and Vascular Biology*, vol. 15(11) Nov. 1995, 2055-2062.

Luu, et al., "Epitope mapping of monoclonal antibodies that block the binding of *Plasmodium falciparum* merozoite ligand EBA-175 (Abstract only)," *American Journal of Tropical Medicine and Hygiene*, vol. 61 (3)Supp. 1999, 492-493.

MacCarthy-Morrogh, et al., "Differential Effects of Estrone and Estrone-3-O-Sulfamate Derivatives on Mitotic Arrest, Apoptosis and Microtubule Assembly in Human Breast Cancer Cells," *Cancer Research*, vol. 60 Oct. 1, 2000, 5441-5450.

Magana-Garcia, M. "Antimalarials for Children," *Journal of American Academy of Dermatology*, vol. 30(3) Mar. 1994, 510.

Maione, T. E. et al., "Inhibition of Angiogenesis by Reocminant Human Platelet Factor-4 and RElated," *Science*, vol. 247 Hepatocyte Growth Factor HGF Jan. 5, 1990, 77-79.

Maione, T. E. et al., "Inhibition of Tumor Growth in Mice by an Analogue of Platelet Factor 4 That Lacks Affinity for Heparin and Retains Potents Angiostatic Activity," *Cancer Research*, vol. 51 Apr. 15, 1991, 2077-2083.

Makonkawkeyoon, et al., "Thalidomide Inhibits the Replication of Human Immunodeficiency Virus Type I," *Proceedings of the National Academy of Science*, vol. 90(13) Jul. 1, 1993, 5974-5978.

Manfredi, et al., "Taxol: An Antimitotic Agent with a New Mechanism of Action," *Pharmacology & Therapeutics*, vol. 25(1) 1984, 83-125.

Maran, et al., "2-Methoxyestradiol Induces Interferon Gene Expression and Apoptosis in Osteosarcoma Cells," *Bone*, vol. 30(2), Feb. 2002, 393-398.

Marin-Padilla, "Thalidomide Induced Alterations in the Blastocyst and Placenta of the Armadillo, *Dasypus Novemcinctus*, Including a Choriocarcinoma," *The American Journal of Pathology*, vol. 43(6) Oct. 1963, 999-1016.

Marion, et al., "Rapid Recording of 2D NMR Spectra without Phase Cycling. Application to the Study of Hydrogen Exchange in Proteins," *Journal of Magnetic Resonance*, vol. 85 1989, 393-399.

Mariyama, et al., "Complete Primary Structure of the Human a3(IV) Collagen Chain," *Journal of Biological Chemistry*, vol. 269(37) Sep. 16, 1994, 23013-23017.

Maro, et al., "Changes in Actin Distribution During Fertilization of the Mouse Egg," *Journal of Embryology and Experimental Morphology*, vol. 81 1984, 211-237.

Maro, et al., "Mechanism of Polar Body Formation in the Mouse Oocyte: An Interaction Between the Chromosomes, the Cytoskeleton and the Plasma Membrane," *Journal of Embryology and Experimental Morphology*, vol. 92 1986, 11-32.

Marshall, Eliot "Gene Therapy's Growing Pains," *Science*, vol. 269 Aug. 25, 1995, 1050-1055.

Marshall, E. "Setbacks for Endostatin," *Science*, vol. 295 Mar. 22, 2002, 2198-2199.

Marti, D. et al., "Expression, purification and characterization of the recombinant kringle 2 and kringle 3 domains of human plasminogen and analysis of their binding affinity for w-aminocarboxylic acids," *European Journal of Biochemistry*, vol. 219 1994, 455-462.

Mascaro, et al., "Thalidomide in the Treatment of Recurrent, Necrotic, and Giant Muccocutaneous Aphtae and Aphtosis," *Archives of Dermatology*, vol. 115 May 1979, 636-637.

Matsubara, et al., "Inhibition of Human Endothelial Cell Proliferation by Gold Compounds," *Journal of Clinical Investigation*, vol. 79 May 1987, 1440-1446.

Matsumoto, et al., "Cooperative Interaction between a- and B-Chains of Hepatocyte Growth Factor on c-Met Receptor Confers Ligand-induced Receptor Tyrosine Phosphorylation and Multiple Biological Responses," *The Journal of Biological Chemistry*, vol. 273(36) Sep. 4, 1998, 22913-22920.

Matsuyama, et al., "Cytokines and HIV Infection: is AIDS a Tumor Necrosis Factor Disease?," *AIDS*, vol. 5(12) 1991, 1405-1417.

Matukara, et al., "The Goodpasture antigen: common epitopes in the globular domains of collagen IV. (Abstract only)," *Nephron*, vol. 64(4) 1993, 532-539.

Mauad, "Melhoras Clinicas Obtidas em Doentes Cancerosos Avancados com Tratementa Pela Talidomida Associada a Hormonios," *Anais Paulistas Medicina e Cirurgia*, vol. LXXXVI(1) Jul. 1963, 15-39.

Maurice, et al., "The Effect of Thalidomide on Arachidonic Acid Metabolism in Human Polymorphonuclear Leukocytes and Platelets," *British Journal of Dermatology*, vol. 115(6) Dec. 1986, 677-680.

Mayol, et al., "Ethynylestradiol-Induced Cell Proliferation in Rat Liver Involvement of Specific Populations of Hepatocytes (Abstract only)," *Carcinogenesis*, vol. 13(12) 1992, 2381-2388.

McCance, S. G. et al., "Amino Acid Residues of the Kringle-4 and Kringle-5 Domains of Human Plasminogen that Stablize Their Interactions with w-Amino Acid Ligands," *Journal of Biological Chemistry*, vol. 269(51) Dec. 23, 1994, 32405-32410.

McCarthy, et al., "Thalidomide for the Therapy of Graft-versus-Host Disease Following Allogenic Bone *Marrow Transplantation*," *Biomedical Pharmacotherapy*, vol. 43(9) 1989, 693-697.

McGee, J. et al., "Simultaneous Expression of Tissue Factor and Tissue Factor Pathway Inhibitor by Human Monocytes. A Potential Mechanism for Localized Control of Blood Coagulation," *Journal of Experimental Medicine*, vol. 179 Jun. 1, 1994, 1847-1854.

McKenna, et al., "Linear IgA Disease, Oral Ulceration and Crohn's Disease," *British Journal of Dermatology*, vol. 127(40) Jul. 1992, 67-68.

McLachlan, A. D. "Gene Duplications in the Structural Evolution of Chymotrypsin," *Journal of Molecular Biology*, vol. 128 1979, 49-79.

McLean, J. W. et al., "cDNA Sequence of Human Apoliprotein(a) is Homologous to Plasminogen," *Nature*, vol. 330 Nov. 12, 1987, 132-137.

McPhee, et al., "Molecules After 10 Years: The Best is Yet to Come," *Molecules*, vol. 10 Jan. 31, 2005, 1-2.

Mehta, et al., "Liposomal Amphotericin B is Toxic to Fungal Cells But Not to Mammalian Cells," *Biochimica et Boiphysica Acta*, vol. 77 1984, 230-234.

Meikrantz, et al., "Apoptosis and the Cell Cycle," *Journal of Cellular Biochemistry*, vol. 58(2) Jun. 1995, 160-174.

Meise, et al., "Teratologische PrÅ?Å¼fung der Hydrolsenprodukte des Thalidomides," *Experientia*, vol. 29 1973, 426.

Meise, et al., "Zur Synthese und teratologischen PrÅ?Å¼fung einiger Thalidomidmetabolite," *Pharmazie*, vol. 27 1972, 418-419.

Menard, et al., "Quelques Metabolites Possibles de la Thalidomide," *Canadian Journal of Chemistry*, vol. 41 1963, 1722-1725.

Menhart, N. et al., "Construction, Expression and Purification of Recombinant Kringle 1 of Human Plasminogen and Analysis of Its Interaction with w-Amino Acides," *Biochemistry*, vol. 30 1991, 1948-1957.

Menhart, N et al., "Functional Independence of the Kringle 4 and Kringle 5 Regions of Human Plasminogen," *Biochemistry*, vol. 32 1993, 8799-8806.

Menon, I. A. et al., "Effects of Ultraviolet-visible Irradiation in the Presence of Melanin Isolated from Human Black or Red Hair upon Ehrlich Ascites Carcinoma Cells," *Cancer Research*, vol. 43(7) Jul. 1983, 3165-3169.

Meza, et al., "Managing the Gastrointestinal Complications of AIDS," *Drug Therapy*, vol. 23(11) Nov. 1993, 74-83.

Michel, et al., "Inhibition of synaptosomal high-affinity uptake of dopamine and serotonin by estrogen agonists and antagonists (Abstract only)," *Biochem. Pharmacol.*, vol. 36(19) 1987, 3175-3180.

Milia, et al., "Protease-activated Receptor-2 Stimulates Angiogenesis and Accelerates Hemodynamic Recovery in a Mouse Model of Hindlimb Ischemia (Abstract only)," *Circ. Res.*, vol. 91(4) 2002, 346-352.

Millauer, B. et al., "Glioblastoma Growth inhibited in vivo by a dominant-negative Flk-1 mutant," *Nature*, vol. 367 Feb. 10, 1994, 576-579.

Miller, et al., "Erythrocyte receptors for (*Plasmodium knowlesi*) malaria: Duffy blood group determinants," *Science*, vol. 189(4202) Aug. 15, 1975, 561-563.

Miller, "Synthesis and Structure-Activity Profiles of A-Homoestranes, the Estratropones," *Journal of Medicinal Chemistry*, vol. 40 1997, 3836-3841.

Miller, et al., "Treatment of Chronic Erythema Nodosum Leprosum with Cyclosporine A Produces Clinical and Immunohistologic Remission," *International Journal of Leprosy and Other Mycobacterial Diseases*, vol. 55(3) Sep. 1987, 441-449.

Miller, Thomas "Tubulin as a Therapeutic Target (Abstract only)," *Dissertations Abstracts International*, vol. 5907B 1998, 3454.

Miller, et al., "Zusammentreffen Einer Thalidomide-Induzierten Fehibidung mit Einem Maligen Lymphom Hohen Malidnitatsgrades," *Monatsschr. Kinderhelkd.*, vol. 128 1980, 27-29.

Mills, B. G. et al., "Cytokines Expressed in Multinucleated Cells: Paget's Disease and Giant Cell Tumors versus Normal Bone," *Calcified Tissue International*, vol. 61(1) Jul. 1997, 16-21.

Misery, et al., "Remission of Langerhans Cell Histiocytosis with Thalidomide Treatment," *Clinical and Experimental Dermatology*, vol. 18(5) Sep. 1993, 487.

Mishina, D. et al., "On the etiology of Crohn's disease," *Proceedings of the National Academy of Sciences of the United States of America*, vol. 93(18) Sep. 6, 1996, 9816-9820.

Misserilis, E. et al., "Angiogenesis is Associated with Collagenous Protein Synthesis and Degradation in the Chick Chorioallantoic Membrane," *Tissue and Cell*, vol. 22(4) 1990, 419-426.

Miura, et al., "Potentiating Effect of Thalidomide on Methylcholathrene Oncogenesis in Mice," *Experientia, vol. 26 Fasc. 3* Mar. 15, 1970, 305-306.

Miyachi, Y. "A Possible Mechanism of Action of Thalidomide on Rheumatoid Arthritis," *Arthritis and Rheumatism*, vol. 28(7) Jul. 1985, 836.

Miyachi, et al., "Effects of Thalidomide on the Generation of Oxygen Intermediates by Zymosan-Stimulated Normal Polymorphonuclear Leukocytes," *Dermatology Research*, vol. 274(3-4) 363-367, Dec. 1982.

Miyagi, Y. et al., "cDNA Cloning and mRNA Expression of a Serine Protease Inhibitor Secreted by Cancer Cells: Identification as Placental Protein 5 and Tissue Factor Pathway Inhibitor-2," *Journal of Biochemistry*, vol. 116 1994, 939-942.

Mizuno, et al., "Hairpin Loop and Second Kringle Domain are Essential Sites for Heparin Binding and," *The Journal of Biological Chemistry*, vol. 269 No. 2 Hepatocyte Growth Factor HGF Jan. 14, 1994, 1131-1136.

Mohri, et al., "Negative Effect of Thalidomide and Relative Substances on the Growth of HeLa Cells," *Chemical Pharmacology Bulletin*, vol. 16(11) 1968, 2289-2292.

Moldovan, et al., "Redox Changes of Cultured Endothelial Cells and Actin Dynamics," *Circulation Research*, vol. 86(5) Mar. 29, 2000, 549-557.

Mollendorff, W. V. "Wachstumsstorungen durch Geschlechtshormone, nach Untersuchgen an Gewebekulturen," Jun. 12, 1941, 187-2002.

Moncada, et al., "Thalidomide-Effect on T Cell Subsets as a Possible Mechanism of Action," *International Journal of Leprosy and other Mycobacterial Diseases*, vol. 53(2) Jun. 1985, 201-205.

Montgomery, et al., "Estrogen Effects on Tubulin Expressin and Taxane Mediated Cytotoxicity in Prostate Cancer Cells," *The Prostate*, vol. 9999 Jan. 2005, 1-10.

Mooberry, Susan "New insights into 2-Methoxyestradiol, a promising antiangiogenic and antitumor agent," *Current Opinions in Oncology*, vol. 15 Nov. 2003, 425-430.

Morales-Ruiz, et al., "Vascular Endothelial Growth Factor-Stimulated Actin Reorganization and Migration of Endothelial Cells Is Regulated via the Serine/Threonine Kinase Akt," *Circulation Research*, vol. 86(8) 2000, 892-896.

Morgan, et al., "Calcium and Oestrogen Interactions upon the Rat Thymic Lymphocyte Plasma Membrane (Chemical Abstracts, 1976)," *Biochemical and Biophysical Research Communications*, vol. 72(2) Sep. 20, 1976, 663-672.

Mori, et al., "The Activation of Type 1 and Type 2 Plasminogen by Type 1 and Type II Tissue Plasminogen Activator," *The Journal of Biological Chemistry*, vol. 270(7) Feb. 17, 1995, 3261-3267.

Morisaki, et al., "Steroids, L1. Aromatization reaction of the cross-conjugated dienone system by Zinc 9 (Abstract only)," *Chem. Pharm. Bull.*, vol. 14(8) 1966, 866-872.

Morosoli, et al., "Protein secretion in steptomycetes," *FEMS Microbiology Letters*, vol. 146 1997, 167-174.

Moser, et al., "Angiostatin binds ATP synthase on the surface of human endothelial cells," *Proceedings of the National Academy of Science, USA*, vol. 96 Mar. 1999, 2811-2816.

Moses, M. A. et al., "Identification of an Inhibitor of Neovascularization from Cartilage," *Science*, vol. 248 Jun. 15, 1990, 1408-1410.

Moses, et al., "Troponin I is Present in Human Cartilage and Inhibits Angiogenesis," *Proceedings of the National Academy of Science USA*, vol. 96(6) 1999, 2645-2650.

Moss, G. W. et al., "Hypothesis for a serine-protease-like domain at the COOH terminus of slowpoke calcium-activated protassium channels," *Journal of General Physiology*, vol. 108(6) Dec. 1996, 473-484.

Moulin, et al., "Treatment of Jessner-Kanof Disease with Thalidomide (Traitement de la Maladie de Jessner et Kanof par la Thalidomide)," *Annals de Dermatologie et due Venerologica*, vol. 198(110) 1983, 611-614.

Moyad, et al., "The Relationship of Tumor Angiogenesis and Race to Serum PSA Levels in Carcinoma of the Prostate (CaP) (Abstract only)," *The Journal of Urology-AUA 92nd Annual Meeting, vol. 157(4)Supp.* Apr. 14, 1997, 228.

Muckter, et al., "Thalidomide and Tumor," *Antimicrobial Agents and Chemotherapy*Oct. 1965, 531-538.

Mueck, et al., "Angiogenetic and anti-angiogenetic effects of estradiol and its metabolites (Abstract only)," *Journal of Clinical and Basic Cardiology*, vol. 4(2) 2001, 153-155.

Mueck, et al., "Chemotherapy of breast cancer-additive anticancerogenic effects by 2-Methoxyestradiol," *Life Sciences*, vol. 75 Jan. 2004, 1205-1210.

Mueck, et al., "Estradiol metabolism and malignant disease," *Maturitas*, vol. 43 Jan. 2002, 1-10.

Mueck, et al., "Estrogen-dependent Neoplasia—What is the Significance of Estradiol Metabolitse (English Abstract only)," *Zentralbi Gynakol*, vol. 125 Jan. 2003, 458-466.

Muhandiram, et al., "Gradient-Enhanced Triple-Resonance Three-Dimensional NMR Experiments with Improved Sensitivity," *Journal of Magnetic Resonance*, vol. Ser B., 103 1994, 203-216.

Mukhopadhyay, et al., "Induction of Apoptosis in Human Lung Cancer Cells after Wild-Type p53 Activation by Methoxyestradiol," *Oncogene*, vol. 14 1997, 379-384.

Mukhopadhyay, et al., "Two-dimensional gel analysis of apoptosis-specific p53 isoforms induced by 2-Methoxyestradiol in human lung cancer cells," *Apoptosis*, vol. 3 Jan. 1998, 421-430.

Mukhopadhyay, et al., "Wild-Type p53 and v-Src Expert Opposing Influences on Human Vascular Endothelial Growth Factor Gene Expression," *Cancer Research*, vol. 55 Dec. 15, 1995, 6161-6165.

Mukundan, et al., "Liver Regeneration in Oral Contraceptive Treated Female Rats—Effects of Moderate Malnutrition (Chemical Abstracts, 1984)," *Hormone and Metabolic Research*, vol. 16(12) 641-645, Dec. 1984.

Muller, et al., "Amino-Substituted Thalidomide Analogs: Potent Inhibitors of TNF-alfa Production," *Bioorganic & Medicinal Chemistry Letter*, vol. 9 1999, 1625-1630.

Mummery, et al., "Screening for Cytoxicity in Neuroblastoma Cells-I. Dependence of Growth Inhibition on the Presence of Serum," *Toxicology Letters*, vol. 18(3) Sep. 1983, 201-209.

Munro, et al., "Pyoderma Gangrenosum Associated with Behcet's Syndrome-Response to Thalidomide," *Clinical and Experimental Dermatology*, vol. 13(6) Nov. 1988, 408-410.

Muragaki, Y et al., "Mouse col18a1 is expressed in a tissue-specific manner as three alternative variants and is localized in basement membrane zones," *Proceedings of the National Academy of Science USA*, vol. 92 Sep. 1995, 8763-8767.

Muthukkaruppan, V. R. "Angiogenesis in the Mouse Cornea," *Science*, vol. 205 Sep. 28, 1979, 1416-1418.

Myers, et al., "Biochemical and Immunohistochemical Characterization of Human Type XXIX Define a Novel Class of Basement Membrane Zone Collagens," *American Journal of Pathology*, vol. 151(6) Dec. 1997, 1729-1740.

NAAFS, B "International Workshop on Leprosy Research, Treatment of Reactions and Nerve Damage," *International Journal of Leprosy and Other Mycobacterial Diseases*, vol. 64(4) Dec. 1996, Supp. S21-28.

NAAFS, et al., "Thalidomide Therapy An Open Trial," *International Journal of Dermatology*, vol. 24(2) Mar. 1985, 131-134.

Nadeau, et al., "AFM Study of a new Carrier Based on PLA and Salen Copolymers for Gene Therapy," *Molecules*, vol. 10 Jan. 31, 2005, 105-113.

Nakagawa-Yagi, et al., "Endogenous Estrogen Metabolite 2-Methoxyestradiol Induces Apoptotic Neuronal Cell Death in Vitro," *Life Sciences*, vol. 58(17) 1996, 1461-1467.

Nakamura, et al., "Studies on the Total Synthesis of dl-Colchiceine. I. Synthesis of 3-Hydroxy-9, 10, 11-trimethoxy-1,2,3,4,6,7-hexahydro-5H-dibenzo[a,c] cycloheptatrien-5-one," *Chemical and Pharmaceutical Bulletin*, vol. 10 1962, 281-290.

Nakao-Hayashi, et al., "Stimulatory effects of insulin and insulin-like growth factor I on migration and tube formation by vascular endothelial cells," *Atherosclerosis*, vol. 92 Feb. 1992, 141-149.

Nambara, T. et al., "DN 82:43650; Analytical Chemical Studies on Steroids. LXXIII. Synthesis of Epimeric 2-Hydroxyl-16-Chlorestrong Monomethyl Ethers (Abstract only)," *HCAPLUS-Chemical and Pharmaceutical Bulletin*, vol. 22(10) 1974, 2455-2457.

Nambara, et al., "Microbial transformation products derived from steroids. I. Synthesis of 1,2- and 3-dimethoxy-4-methylestratrienes (Abstract only)," *Chem. Pharm. Bull.* vol. 20(2) 1972, 336-342.

Nambara, et al., "Studies on Steroid Conjugates, III. New Synthesis of 2-Methoxyestrogens," *Chem. Pharm. Bulletin*, vol. 18(3) Mar. 1970, 474-480.

Nambara, et al., "Synthesis of 16b-Oxygenated Catechol Estrogen Methyl Ethers, New and Potential Metabolites," *Chemical & Pharmaceutical Bulletin*, vol. 23(7) Jul. 1975, 1613-1616.

Napolitano, et al., "11 Beta-Substituted Estradiol Derivatives. 2. Potential Carbon- 11 and Iodine-Labeled Probes for the Estrogen Receptor (Abstract only)," *Journal of Medicinal Chemistry*, vol. 38(14) Jul. 7, 1995, 2774-2779.

Narita, M. et al., "Two Receptor Systems are Involved in the Plasma Clearance of Tissue Factor Pathway Inhibitor in vivo," *Journal of Biological Chemistry*, vol. 270(42) Nov. 20, 1995, 24800-24804.

Narum, et al., "Antibodies against the *Plasmodium faciciparum* receptor binding domain of EBA-175 block invasion pathways that do not involve sialic acids," *Infection and Immunity*, vol. 68(4) 2000, 1964-1966.

Narum, et al., "Differential localization of full-length and processed forms of PF83/AMA-1 an apical membrane antigen of *Plasmodium falciparum* merozoites," *Molecular and Biochemical Parasitology*, vol. 67 1994, 59-68.

Narum, et al., "Inhibition of *Plasmodium falciparum* sialic acid-dependent (alternative pathway) invasion mediated by antibodies against EBA-175 REgion II (Abstract only)," *American Journal of Tropical Medicine and Hygiene*, vol. 61(3)Supp. 1999, 205-206.

Nelson, J et al., "Murine epidermal growth factor (EGF) fragment (33-42) inhibits both EGF- and laminin-dependent endothelial cell motility and angiogenesis," *Cancer Research*, vol. 55 Sep. 1, 1995, 3772-3776.

Neubert, et al., "Effect of Thalidomide-Derivatives on Limb Development in Culture," *Limb Development and Regeneration*, Part A 1983, 387-397.

Neubert, D. "Teratogenicity: Any Relationship to Carcinogenicity?," *Institute for Toxicology and Embryology*, 169-177.

Nevill, et al., "Thalidomide as therapy for intestinal chronic GVHD," *Bone Marrow Transplantation*, vol. 11(3) Mar. 1993, 251-252.

New, et al., "Antileishmanial Activity of Amphotericin and Other Antifungal Agents Entrapped in Liposomes," *Journal of Antimicrobial Chemotherapy*, vol. 8 1981, 371-381.

Newkome, et al., "Synthesis of Simple Hydrazones of Caronyl Compounds by an Exchange Reaction," *Journal of Organic Chemistry*, vol. 31 Mar. 1966, 677-681.

Newman, et al., "Inhibition of In Vitro Angiogenesis by 2-Methoxy- and 2-Ethyl-Estrogen Sulfamates," *International Journal of Cancer*, vol. 109 Jan. 2004, 533-540.

Nguyen, et al., "A Common Pharmacophore for a Diverse Set of Colchicine Site Inhibitors Using a Structure-Based Approach," *J. Med. Chem.*, vol. 48 Jan. 2005, 6107-6116.

Nguyen, M. "Elevated Levels of the Angiogenic Peptide Basic Fibroblast Growth Factor in Urine of Bladder Cancer Patients," *Journal of the National Cancer Institute*, vol. 85(3) Feb. 3, 1993, 241-242.

Nguyen, et al., "Elevated Levels of the Angiogenic Peptide Basic Fibroblast Growth Factor in Urine of Patients with a Wide Spectrum of Cancers," *Journal of the National Cancer Institute*, vol. 86(5) 1994, 356-361.

Nguyen, et al., "Pentosan inhibits angiogenesis in vitro suppresses prostate tumor growth in vivo," *Anticancer Research*, vol. 13(6A) Nov. 1993, 2143-2147.

Nguyen, M. et al., "Quantitation of Angiogenesis and Antiangiogenesis in the Chick Embryo Chorioallantoic Membrane," *Microvascular Research*, vol. 47 1994, 31-40.

Nicholson, et al., "Affinity and Kinetic Analysis of L-selectin (CD62L) Binding to Glycosylation-dependent Cell-adhesion Molecule-1," *Journal of Biological Chemistry*, vol. 273(2) Jan. 9, 1998, 763-770.

Nickisch, et al., "Aldosterone Antagonists. 2. New 7a-(Acetylhio)-15, 16-methylene Spriolactones," *Journal of Medicinal Chemistry*, vol. 30(8) 1987, 1403-1409.

Nickisch, et al., "Aldosterone Antagonists, 3, Synthesis and Activities of Steroidal 7a-(Alkoxycarbonyl)-15,16-methylene Spriolactones," *Journal of Medicinal Chemistry*, vol. 33(2) 1990, 509-513.

Nickisch, "Aldosterone Antagonists, 4, Synthesis and Activities of Steroidal 6.6-Ethylene-15, 16-methylene 17-Spriolactones," *Journal of Medicinal Chemistry*, vol. 34, No. 8 1991, 2464-2468.

Nicolas, et al., "Interferon Alfa Therapy in Severe Unresponsive Subacute Cutaneous Lupus Erythematosus," *New England Journal of Medicine*, vol. 321(22) Nov. 30, 1989, 1550-1551.

Nicolau, et al., "Thalidomide: Treatment of Severe Recurrent Aphthous Stomatis in Patients with AIDS," *DICP The Annals of Pharmacotherapy*, vol. 24(11) Nov. 1990, 1054-1056.

Nielsen, et al., "Thalidomide Enhances Superoxide Anion Release from Human Polymorphonuclear and Leukocytes," *Acta Pathologica Microbiologica Et Immunologica Scandinavica*, vol. 94(6) Dec. 1986, 233-237.

Niles, et al., "Control of Melanogenesis in Mouse Melanoma Cells of Varying Metastic Potential," *Journal of the National Cancer Institute* vol. 61 (2) Aug. 1978, 523-526.

Nishigaki, et al., "Anti-Proliferative Effect of 2-Methoxyestradiol on Cultured Smooth Muscle Cells from Rabbit Aorta," *Athersclerosis*, vol. 113 1995, 167-170.

Niwano, et al., "Inhibitory action of amyloid precuros protein against human Hagemanb factor (factor XII)," *Journal of Laboratory Clinical Medicine*, vol. 125(2) Feb. 1995, 252-256.

Niwayama, et al., "Potent Inhibition of Tumor Necrosis Factor-a- Production by Tetrafluorothalidomide and Tetrafluorophtalamides," *J. Med. Chem.* 1996, 3044-3045.

Novotny, W. F. "Purification and Characterization of the Lipoprotein-Associated Coagulation Inhibitor from Human Plasma," *Journal of Biological Chemistry*, vol. 264 Nov. 5, 1989, 18832-18837.

Numazawa, et al., "Efficient Synthesis of 2-Methoxy- and 4-Methoxy-Estrogens," *Journal of the Chemical Society* Jan. 1, 1983, 533-534.

Numazawa, et al., "Novel and Regiospecific Synthesis of 2-Amino Estrogens via Zincke Nitration," *Steroids*, vol. 41(5) 1983, 675-682.

O'Connell, et al., "A high quality nuclear magnetic resonance solution structure of peptide deformylase from *Escherica coli*: Application of an automated assignment strategy using GARANT," *Journal of Biomolecular NMR*, vol. 13 1999, 311-324.

O'Reilly, et al., "Angiostatin Induces and Sustains Dormancy of Human Primary Tumors in Mice," *Nature Medicine*, vol. 2(6) Jun. 1996, 689-692.

O'Reilly, et al., "Angiostatin: A Circulating Endothelial Cell Inhibitor That Suppresses Angiogenesis," *Cold Spring Harbor Symposia on . . .*, vol. LIX Hepatocyte Growth Factor HGF 1994, 471-482.

O'Reilly, et al., "Angiostatin: A Novel Angiogenesis Inhibitor that Mediates the Suppression of," *Cell*, vol. 79 Hepatocyte Growth Factor HGF Oct. 21, 1994, 315-328.

O'Reilly, et al., "Endogenous Inhibitors of Angiogenesis," *Proceedings of the American Association of Cancer Research*, vol. 37 Mar. 1996, 669.

O'Reilly, et al., "Endostation: An Endogenous Inhibitor of Angiogenesis and Tumor Growth," *Cell*, vol. 88 Jan. 24, 1997, 277-285.

O'Reilly, et al., "The Suppression of Tumor Metastases by a Primary Tumor," *79th Annual Clinical Congress—San Francisco—Surgical Form*, vol. XLIV 1993, 474-476.

Oberbaumer, et al., "Amino acid sequence of the non-collagenous globular domain (NC1) of the alpha 1 (IV) chain of basement membrane collagen as derived from complementary DNA. (Abstract only)," *European Journal of Biochemistry*, vol. 147(2) Mar. 1, 1985, 217-224.

Obeso, J et al., "Methods in Laboratory Investigation/A Hemangioendothelioma-Derived Cell Line: Its Use as a Model for the Study of Endothelial Cell Biology," *Laboratory: Investigation*, vol. 63(2) 1990, 259-269.

Ochi, "Methylmercury, but not Inorganic Mercury, Causes Abnormality of Centrosome Integrity (Multiple Foci of g-Tubulin), Multipolar Spindles and Multinucleated Cells without Microtubule Disruption in Cultured Chinese Hamster V79 Cells," *Toxicology*, vol. 175 2002, 111-121.

Ochs, et al., "Effect of Tumor Promoting Contraceptive Steroids on Growth and Drug Metabolizing Enzymes in Rat Liver (Abstract only)," *Cancer Research*, vol. 46(3) 1986, 1224-1232.

Ockenfels, et al., "Teratogene Wirkung von N-Phthalyl-L-asparaginsÅ?Åøure bei der Maus," *Arzneim-Forsch*, vol. 27(1) 1977, 126-128.

Oh, S. P. "Cloning of cDNA and Genomic DNA Encoding Human Type VIII Collagen and Localization of the a-1 (CVIII) Collagen Gene to Mouse Chromosome 10 and Human Chromosone 21," *Genomics*, vol. 19 1994, 494-499.

Oh, S. P. et al., "Isolation and Sequencing of cDNAs for Proteins with Multiple Domains of Gly-Xaa-Yaa Repeats Identify a Distinct Family of Collagenous Proteins," *Proceedings of the National Academy of Science USA*, vol. 91 May 1994, 4229-4233.

Oikawa, et al., "Eponemycin, A Novel Antibiotic is a Highly Powerful Angiogenesis Inhibitor," *Biochemistry and Biophysical Research Communications*, vol. 181(3) Dec. 31, 1991, 1070-1077.

Okigaki, et al., "Functional Characterization of Human Hepatocyte Growth Factor Mutants Obtained by Deletion of Structural Domains," *Biochemistry*, vol. 31 No. 40 Hepatocyte Growth Factor HGF Jan. 1, 1992, 9555-9561.

Oliver, et al., "Thalidomide Analogs Suppress Rat Collgen Arthritis (Abstract only)," *Arthritis & Rheumatism*, vol. 38(6) Supp Jun. 1995, R10.

Olsen, et al., "Alcohol Effects on y-Aminobutyric Acid Type A Receptors: Are Extrasynaptic Receptors in the Answer?," *Life Sciences 76* 2004, 1-8.

Omar, et al., "Synthesis, binding affinities and uterotryophic activity of some 2-substituted estradiol and ring-A-fused pyrone derivatives," *European Journal of Medicinal Chemistry*, vol. 29 1994, 25-32.

Oohashi, et al., "Isolation and Structure of the COL4A6 Gene Encoding the Human a6(IV) Collagen Chain and Comparison with Other Type IV Collagen Genes," *The Journal of Biological Chemistry*, vol. 270(45) Nov. 10, 1995, 26863-26867.

Oppolzer, et al., "177. The Enanthioselective Synthesis of (+)-Estradiol from 1,3-Dihydrobenzo[c] thiophene-2,2-dioxide by Successive Thermal SO2-Extrusion and Cycloaddition Reactions," *Helvetica Chimica Acta*, vol. 63 1980, 1703-1705.

Orlandi, et al., "A malaria invasion receptor, the 175-kilodalton erythrocite binding antigen of *Plasmodium falciparum* recognizes the terminal neu5Ac(2-3) gal-sequence of glycophorin A," *Journal of Cell Biology*, vol. 116 1992, 901-909.

Orlandi, et al., "Characterization of the 175-kilodalton erythrocte binding antigen of *Plasmodium falciparum*," *Mol Biochem Parasitol*, vol. 40 1990, 285-294.

Orzalesi, M. "II Danno Latrogeno in Neonatologica," *Ped. Med. Chir.*, vol. 14 1992, 105-112.

Osterud, B. et al., "Sites of Tissue Factor Pathway Inhibitor (TFPI) and Tissue Factor Expression under Physiologic and Pathologic Conditions," *Thrombosis and Haemostatis*, vol. 73 1995, 873-875.

Ostraat, et al., "Thalidomide Prolongs Graft Survival in Rat Cardiac Transplants," *Transplant Proc.*, vol. 24(6) Dec. 1992, 2624-2625.

Otani, et al., "Expressions of Angiopoietins and Tie2 in Human Choroidal Neovascular Membrane," *Investigative Ophthalmology & Visual Science*, vol. 40(9) Aug. 1999, 1912-1920.

Otsuka, et al., "A New Potent Angiogenesis Inhibitor, FR-118487," *Journal of Microbiology and Biotechnology*, vol. 1(3) 1991, 163-168.

Pakala, et al., "Modulation of Endothelial Cell Proliferation by Retinoid x Receptor Agonists," *European Journal of Pharmacology*, vol. 285(2/3) Sep. 1999, 255-261.

Paller, et al., "Proceedings of the Concurrent Sessions," *Pediatrics Dermatology*, vol. 9(4) Dec. 1992, 397-406.

Paquette, et al., "Activation of matrix metalloproteinase-2 and -9 by 2- and 4-hydroxyestradiol," *The Journal of Steroid Biochemistry & Molecular Biology*, vol. 87 Jan. 2003, 65-73.

Paradis, et al., "Expression and secretion of B-glucuronidase and Pertussis toxin S1 by *Streptomyces lividans*," *Appl. Microbiol. Biotechnol.*, vol. 45 1996, 646-651.

Parangi, S. et al., "Antiangiogenic Therapy of Transgenic Mice Impairs de novo Tumor Growth," *Proceedings of the National Academy of Science USA*, vol. 93 Mar. 1996, 2002-2007.

Park, et al., "Biodegradable Polymers for Microencapsulation of Drugs," *Molecules*, vol. 10 Jan. 31, 2005, 146-161.

Park, et al., "Development of liposome- and anti-HER2 immunoliposomeplasmid complexes for efficient and selective gene therapy," *Proceedings of the American Association for Cancer Research*, vol. 38 Mar. 1997, 342.

Parr, et al., "NK4, A New HGF/SF Variant, is an Antagonist to the Influence of HGF/SF on the Motility and Invasion of Colon Cancer Cells," *International Journal of Cancer*, vol. 85 2000, 563-570.

Parthasarathy, et al., "Antioxidant: A New Role for RU-486 and Related Compounds (Abstract only)," *Journal of Clinical Investigation*, vol. 94(5) Nov. 1994, 1990-1995.

Pasqualini, R. et al., "av Integrins as receptors for tumor targeting by circulating ligands," *Nature Biotechnology*, vol. 15 Jun. 1997, 542-546.

Pasqualini, R. et al., "Organ targeting in vivo using phage display peptide libraries," *Nature*, vol. 380 Mar. 28, 1996, 364-166.

Passaniti, A. et al., "Methods in Laboratory Investigation/A Simple, Quantitative Method for Assessing Angiogenesis and Antiangiogenic Agents Using Reconstituted Basement Membrane, Heparin, and Fibroblast Growth Factor," *Laboratory: Investigation*, vol. 67(4) 1992, 519-528.

Patey, et al., "Thalidomide et colite ulcereuse dans la maladie de Behcet," *Gastroenterolgie Clinique et Biologigue*, vol. 13(1) Apr. 1989, 104-110.

Patterson, et al., "Angiostatin-converting Enzyme Activities of Human Matrilysin (MMP-7) and Gelatinase B/Type IV Collagenase (MMP-9__," *The Journal of Biological Chemistry*, vol. 272(46) Nov. 14, 1997, 28823-28825.

Patz, A. "Retinal neovascularization: early contributions of Professor Michaelson and recent observations," *British Journal of Ophthalmology*, vol. 68 Jan. 1984, 42-46.

Paull, et al., "Identification of Novel Antimitotic Agents Acting at the Tubulin Level by Computer-assisted Evaluation of Differential Cytotoxicity Data," *Cancer Research*, vol. 52(14) Jul. 15, 1992, 3892-3900.

Pawelek, J. "Factors Regulating Growth and Pigmentation of Melanoma Cells," *The Journal of Investigative Dermatology*, vol. 66(4) 1976, 201-209.

Pawelek, J. et al., "Melanoma Cells Resistant to Inhibition of Growth by Melanocyte Stimulating Hormone," *Proceedings of the National Academy of Science*, vol. 72(3) Mar. 1975, 951-955.

Pawelek, et al., "Molecular Biology of Pigment Cells—Molecular Controls in Mammalian Pigmentation," *Yale Journal of Biology and Medicine*, vol. 46 1973, 430-443.

Pawelek, J. et al., "Molecular Controls in Mammalian Pigmentation," *Yale Journal of Biology & Medicine*, vol. 46 1973, 430-443.

Pearson, et al., "Treatment of Moderatly Severe Erythema Nodosum Leprosum with Thalidomide—A Double-Blind Controlled Trial," *Leprosy Review*, vol. 40(2) Aor-69, 111-116.

Pelicano, et al., "Inhibition of Mitochondrial Respiration," *The Journal of Biologicy Chemistry*, vol. 278(39) Sep. 26, 2003, 37832-37839.

Peng, et al., "Synthesis and Optical Properties of Novern Unsymmetrical Conjugated Dendrimers," *Journal of the American Chemical Society*, vol. 122 2000, 6619-6623.

Perez-Stable, Carlos "2-Methoxyestradiol and paclitaxel have similar effects on the cell cycle and induction of apoptosis in prostate cancer cells," *Cancer Letters*, vol. 231 Jan. 2006, 49-64.

Pert, et al., "Preparations of 2,4-disubstituted estradiols (Abstract only)," *Australian Journal of Chemistry*, vol. 42(3) 1989, 421-432.

Peters, et al., "17-Desoxy Estrogen Analogues," *Journal of Medicinal Chemistry*, vol. 32(7) 1989, 1642-1652.

Petersen, et al., "Characterization of the Gene for Human Plasminogen, a Key Proenzyme in the Fibrinolytic System," *The Journal of Biological Chemistry*, vol. 265(1) Apr. 15, 1990, 6104-6111.

Peterson, L. C. et al., "Inhibitory Properties of a Novel Human Kunitz-Type Protease Inhibitor Homologous to Tissue Factur Pathway Inhibitor," *Biochemistry*, vol. 35 Jan. 1, 1996, 266-272.

Peticlerc, et al., "New Functions for Non-collagenous Domains of Human Collagen Type IV," *The Journal of Biological Chemistry*, vol. 275(11) Mar. 17, 2000, 8051-8061.

Peyron, et al., "The Pharmacological Basis for the Treatment of Photodermatoses," *Biochimie*, vol. 68(6) Jun. 1986, 899-904.

Pfeiffer, et al., "Are catechol estrogens obligatory mediators of estrogen action in the central nervous system? I. Characterization of pharmacological probes with different receptor binding affinities and catechol estrogen formation rates (Abstract only)," *Journal of Endocrinology*, vol. 110(3) 1986, 489-497.

Pfeiffer, et al., "Interference with Microtubules and Induction of Micronuclei in vitro by Various Bisphenols," *Mutation Research*, vol. 390 1997, 21-31.

Pfordte, "Uber die Beeinflussung des Serumproperdinsystems Durch Verschiedene Arzneimittel," *Pharmazie*, vol. 26 1971, 301-302.

Phillips, et al., "Tumor Necrosis Factor Alpha (rh TNF) Fails to Stimulate Angiogenesis in the Rabbit Cornea," *The Anatomical Record*, vol. 245 1996, 53-56.

Pihlajaniemi, et al., "Two New Collagen Subgroups: Membrane-associated Collagens and Types XV and XVIII," *Progress in Nucleic Acid Research and Molecular Biology*, vol. 50 1995, 225-262.

Pilgrim, et al., "Proliferation kultivierter Endothelzellen unter dem Einfluß von Aprotinin und 4-Aminomethylbezoesaure (no translation)," *Biomedica Biochimica Acta*, vol. 45(8) 1986, 1015-1019.

Pittenger, et al., "Functional Properties of Non-Muscle Tropomyosin Isoforms," *Current Opinions in Cell Biology*, vol. 6(1) 1994, 96-104.

Placidi, et al., "Metabolic Drug Interactions Between Angiogenic Inhibitor, TNP-470 and Anticancer Agents in Primary Cultured Hepatocytes and Microsomes," *Drug Metabolism and Disposition*, vol. 27(5) 1999, 623-626.

Playfair, J.H. L. "Vaccines: Still Needed," *Immune Intervention*, vol. 1 1984, 1-12.

Plendel, et al., "Expression of Tissue Kallikrein and Kinin Receptors in Angiogenic Microvascular Endothelial Cells (Abstract only)," *Biol. Chem.*, vol. 381(11) 2000, 1103-1115.

Plum, et al., "Administration of a Liposomal FGF-2 Peptide Vaccine Leads to Abrogation of FGF-2-Mediated Angiogenesis and Tumor Development," *Vaccine*, vol. 19 (9-10) 2000, 1294-1303.

Plum, et al., "Vaccination with Peptide to the Heparin Binding Domain of bFGF Conjucated to Liposomes Inhibits bFGF Induced Neovascularization (Abstract only)," *Proceedings of the American Association for Cancer Research Annual.*, vol. 39 Mar. 1998, 8.

Poli, et al., "Tumor Necrosis Factor a Functions in an Autocrine Manner in the Induction of Human Immunodeficiency Virus Expression," *Proceedings of the National Academy of Science USA*, vol. 87(2) Jan. 1990, 782-785.

Polonski, T. "Circular Dichroism Spectra and Molecular Geometry of Six-Membered Ring Anhydrides and Imides," *J. Chem. Soc. Perkin Trans.*, vol. 1 1988, 639-648.

Ponting, et al., "Plasminogen: A Structural Review," *Blood Coagulation and Fibrinolysis*, vol. 3 1992, 605-614.

Pourati, et al., "Is Cytoskeltal Tension a Major Determinant of Cell Deformability in Adherent Endothelial Cells," *American Journal of Physiology*, vol. 274 (5Pt1) May 29, 1990, C1283-1289.

Powell, J. R. et al., "Amino Acid Sequence Analysis of the Asparagine-288 Region of the Carbohydrate Variants of Human Plasminogen," *Biochemistry*, vol. 22 1983, 923-927.

Powell, et al., "Investigation and Treatment of Orogenital Ulceration; studies on a Possible Mode of Action of Thalidomide," *British Journal of Dermatology, 113. Supp. 28* Jul. 1985, 141-144.

Powers, et al., "1H, 15N, 13C and 13 CO Assignments of Human Interleukin-4 Using Three-Dimensional Dougle- and Triple- Resonance Heteronuclear Magnetic Resonance Spectroscopy," *Biochemisty*, vol. 31 1992, 4334-4346.

Pozzi, et al., "Elevated matrix metalloprotease and angiostatin levels in integrin a1 knockout mice cause reduced tumor vascularization," *PNAS*, vol. 97(5) Feb. 29, 2000, 2202-2207.

Pribulda, et al., "2-Methoxyestradiol—A Novel Endogenous Chemotherapeutic and Antiangiogenic Agent-Chapter 21," *The New Angiotherapy* Nov. 2000, 1-21.

Pribulda, et al., "2-Methoxyestradiol: An endogenous antiangiogenic and antiproliferative drug candidate," *Cancer and Metastasis Reviews*, vol. 19 Jan. 1, 2000, 173-179.

Prigent, et al., "Sarcoidose cutanee Traitement par la Thalidomide," *La Presse Medicale*, vol. 12(47) Dec. 24, 1983, 3007.

Proenca, N. G. "Thalidomide: An Eclectic Medication in Dermatology (Abstract only)," *Rev. Paul. Med.*, vol. 107(1) Jan. 1989, 41-46.

Pryor, et al., "High-Level Expression of Soluble Protein in *Escherica coli* Using a His6-Tag and Maltose-Binding-Protein Double-Affinity Fusion System," *Protein Expression and Purification*, vol. 10 1997, 309-319.

Qadan, et al., "2-Methoxyestradiol Induces G2/M Arrest and Apoptosis in Prostate Cancer," *Biochemical and Biophysical Research Communications*, vol. 285(5) Jan. 2001, 1259-1266.

Qanungo, et al., "2-Methoxyestradiol induces mitochondria dependent apoptotic signaling in pancreatic cancer cells," *Oncogene*, vol. 21 Jan. 2002, 4149-4157.

Quesnel, et al., "Synthesis of PLA-b-PEG Multiblock Copolymers for Stealth Drug Carrier Preparation," *Molecules*, vol. 10 Jan. 31, 2005, 98-104.

Radeff, et al., "Recurrent Aphthous Ulcer in Patient Infected with Human Immunodeficiency Virus: Successful Treatment with Thalidomide," *Journal of the American Academy of Dermatology*, vol. 23(3) Pt. 1 Sep. 1990, 523-525.

Rainsford, K. D. "Disease-Modifying Antirheumatic and Immunoregulatory Agents," *Baillere's Clinical Rheumatology*, vol. 4(3) Dec. 1990, 405-432.

Rajan, et al., "A Clinical Study of Thalidomide Comparing Pre-Treatment and Post-Treatment Reactional Episodes and Corticosteroid Requirements," *Leprosy in India*, vol. 55(1) Jan. 1983, 111-116.

Rajkumar, et al., "Prevention of mammary carcinogenesis by short-term estrogen and progestin treatments," *Breast Cancer Research*, vol. 6(1) Nov. 11, 2003, R31-R37.

Ramanathan, et al., "Resistance to Paclitaxel is Proportional to Cellular Total Antioxidant Capacity," *Cancer Research*, vol. 65(18) Sep. 15, 2005, 8455-8460.

Randall, T. "Investigational New Drug (US) 'Orphan' Trials Now Use Thalidomide from Two Sources," *Journal of the American Medical Association*, vol. 263(11) Mar. 16, 1990, 1474.

Randall, T. "Thalidomide's Back in the News, but in more Favorable Circumstances," *Journal of the American Medical Association*, vol. 263(11) Mar. 16, 1990, 1467-1468.

Ranson, et al., "Phase II dose-finding trial of CAELYX TM (StealthÅ?Å® liposomal doxorubicin HCL) in the treatment of advanced breast cancer (XP004282899)(Abstract only)," *European Journal of Cancer*, vol. 33 Sep. 1997, S148.

Rao, et al., "A new, practical synthesis of 2-Methoxyestradiols," *Steroids*, vol. 67 Jan. 2002, 1065-1070.

Rao, et al., "A Novel, Two-Step Synthesis of 2-Methoxyestradiol," *Synthesis* Mar. 1, 1977, 168-169.

Rao, et al., "Mechanism of Antithrombin III Inhibition of Factor Vlla/Tissue Factor Activity on Cell Surfaces. Comparison with Tissue Factor Pathway Inhibitor/Factor Xa-Induced Inhibition of Factor Vlla/Tissue Factor Activity," *Blood*, vol. 83(1) Jan. 1, 1995, 121-129.

Rao, et al., "Structural Specificity of Estrogens in the Induction of Mitotic Chromatid Non-Disjunction in Hela Cells," *Experimental Cell Research*, vol. 48 1967, 71-81.

Rao, et al., "Synthesis and antimitotic activity of novel 2-Methoxyestradiol analogs," *Steroids*, vol. 67 Jan. 2002, 1079-1089.

Raobaikady, et al., "Inhibition of MCF-7 breast cancer proliferation and in vivo steroid sulphatase activity by 2-Methoxyestradiol-bis-sulphamate," *The Journal of Steroid Biochemistry & Molecular Biology*, vol. 84 Jan. 2003, 351-358.

Rastinejad, F. et al., "Regulation of the Activity of A New Inhibitor Of Angiogenesis By A Cancer," *Cell*, vol. 56 Hepatocyte Growth Factor HGF Feb. 10, 1989, 345-355.

Ravindra, R. "Effect of Estradiol on the vitro Assembly of Rat Brain Tubulin," *Journal of Indian Institute of Science*, vol. 64(3) Mar. 1983, 27-35.

Rehn, M. et al., "a1 (XVIII), a Collagen Chain with Frequent Interruptions in the Collagenous Sequence, a Distinct Tissue Distribution, and Honology with Type XV Collagen," *Proceedings of the National Academy of Science, USA*, vol. 91 May 1994, 4234-4238.

Rehn, M. et al., "Identification of three N-terminal ends of Type XVIII collagent chains and tissue-specific differences in the expression of the corresponding transcripts," *Journal of Biological Chemistry*, vol. 270 Mar. 3, 1995, 4705-4711.

Rehn, et al., "Interaction of endostatin with integrins implicated in angiogenesis," *PNAS*, vol. 98(3) Jan. 30, 2001, 1024-1029.

Rehn, et al., "Primary structure of the alpha 1 chain of mouse type XVIII collagen, partial structure of the corresponding gene, and comparison of the alpha 1 (XVIII) chain with its homologue, the alpha 1 (XV) collagen gene (Abstract only)," *Journal of Biological Chemistry*, vol. 269(10) 1994, 13929-13935.

Reiser, et al., "2-Methoxyestradiol Inhibits Normal and Angiotumor Endothelial Cell Proliferation and Cell Cycle," *Journal of Investigative Medicine*, vol. 45(7) Sep. 1997, 268A.

Rejante, M. R. et al., "Ligand specificity of human plasminogen kringle 4," *Biochemistry*, vol. 30 1991, 11081-11092.

Revuz, J. "Actualite Du Thalidomide," *Annales de Dermatologie et de Venereologica*, vol. 117(4) 1990, 313-321.

Revuz, et al., "Crossover Study of Thalidomide vs. Placebo in Severe Recurrent Aphthous Stomatitis," *Archives of Dermatology*, vol. 126(7) Jul. 1990, 923-927.

Rhoton, A. J. "Role for Thalidomide in Primary Biliary Cirrhosis Treatment," *Gastroenterology*, vol. 105(3) Sep. 1993, 956.

Riegman, et al., "Characterization of the Human Kallikrein Locus," *Genomics*, vol. 14 1992, 6-11.

Riley, P. A. "Melanogenesis: a Realistic Target for Antimelanoma Therapy?," *European Journal of Cancer*, vol. 27(9) Sep. 1991, 1172-1177.

Robbins, K. C. "Fibrinolysis: The Plasminogen-Plasmin Enzyme System," *Hemostatis and Thrombosis, Basic Principles and Pracice, 2nd Edition* 1995, 340-357.

Robbins, K. C. et al., "The primary structure of human plasminogen. I. The NH2-terminal sequences of human plasminogen and the S-carboxymethyl heavy (A) and light (B) chain derivatives of plasmin," *Journal of Biological Chemistry*, vol. 247(21) Nov. 10, 1972, 6757-6762.

Robinson, et al., "Safety and Pharmacokinetics of Intravitreal 2-Methoxyestradiol Implants in Normal Rabbit and Pharmacodynamics In a Rat Model of Choroidal Neovascularization," *Experimental Eye Research*, vol. 74 Jan. 2002, 309-317.

Roe, F.J. C. "Pathology Thalidomide and Neoplasia," *Nature*, vol. 200 Dec. 7, 1963, 1016-1017.

Roe, et al., "Tumour-Incidence in Progeny of Thalidomide-Treated Mice," *British Journal of Cancer* 1965, 331-333.

Romanelli, et al., "Ethyl-p-Dimethylaminophenylacetate," *Organic Synthesis*, vol. 5 Oct. 24, 1973, 552.

Rook, G. "Immunity to Viruses, Bacteria and Fungi," *Immunology* 1989, 16.14-16.15.

Rosen, et al., "Scatter Factor and Angiogenesis," *Advances in Cancer Research*, vol. 67 Hepatocyte Growth Factor HGF 1995, 257-279.

Rudd, et al., "The effects of variable glycosylation on the functional activities of ribonuclease, plasminogen and tissue plasminogen activator," *Biochmica et Biophysica Acta*, vol. 1248 1995, 1-10.

Rudinger, J. "Characteristics of the amino acids as components of a peptide hormone sequence," *Peptide Hormones, J.A. Parsons, Baltimore:University Park Press* Jun. 1976, 1-7.

Ruggenini, et al., "Talidomide e Tumori Sperimentali," *Cancro*, vol. 20 1967, 39-55.

Rustin, et al., "Pyoderma Gangrenosum Associated with Behcet's Disease: Treatment with Thalidomide," *Journal of the American Academy of Dermatology*, vol. 23(5) Pt. 1 Nov. 1990, 941-944.

Ryan, et al., "Thalidomide to Treat Esophageal Ulcer in AIDS (6)," *New England Journal of Medicine*, vol. 327(3) Jul. 16, 1992, 208-209.

Sage, E. H. et al., "Inhibition of Endothelial Cell Proliferation by SPARC is Mediated through a Ca2+ -Binding EF -Hand Sequence," *Journal of Cellular Biochemistry*, vol. 57 1995, 127-140.

Saiki, et al., "Inhibition of Tumor Angiogenesis by a Synthetic Cell-adhesive Polypeptide Containing the Arg-Gly-Asp (RGD) Sequence of Fibronectin, Poly(RGD)," *Jpn. J. Cancer Research*, vol. 81 1980, 668-675.

Sakakibara, Kyoichi "2-Hydroxy-1,3,5(10)-estratriene derivatives (Abstract only)(Identifier: XP-002186126)," *Chemical Abstracts*, vol. 60(1) Jan. 6, 1964.

Sakakibara, et al., "Effects of Diethylstibestrol and its Methl Ethers on Aneuploidy Induction and Microtubule Distribution in Chinese Hamster V79 cells," *Mutation Research*, vol. 263(4) Aug. 1991, 269-276.

Sakamoto, N. et al., "Inhibition of Angiogenesis and tumor growth by a synthetic laminin peptide. CDPGYIGSR-NH2," *Cancer Research*, vol. 51 Feb. 1, 1991, 903-906.

Salomon, Claudio J. "Macromolecules Applied to Pharmaceutical Chemistry," *Molecules*, vol. 10 Jan. 31, 2005, 3-5.

Salven, et al., "Serum Vascular Endothelial Growth Factor is Often Elevated in Disseminated Cancer," *Clinical Cancer Research*, vol. 3 May 1997, 647-651.

Samama, M. M. et al., "Mechanisms for the Antithrombotic Activity in Man of Law Molecular Weight Heparins (LMWHs)," *Haemostatis*, vol. 24 Jan. 1, 1994, 105-117.

Sambrook, J. et al., "Expression of Cloned Genes in *Escherichia coli*," *Molecular Cloning Second Edition* 1989, 17.37-37.41.

Sampaio, et al., "Prolonged Treatment with Recombinant Interferon Gamma Induces Erythema Nodosum Lepromatous Leprosy Patients," *Journal of Experimental Medicine*, vol. 175(6) Jun. 1, 1992, 1729-1737.

Sampaio, et al., "Thalidomide Selectivity Inhibits Tumor Necrosis Factor Alpha Production by Stimulated Human Monocytes," *Journal of Experimental Medicine*, vol. 173(3) Mar. 1, 1991, 699-703.

Santis, H. R. "Aphthous stomatitis and its management (Abstract only)," *Current Opinions Dent.*, vol. 1(6) Dec. 1991, 199-203.

Santos, D. et al., "In Vitro Tumor Necrosis Factor Production by Mononuclear Cells from Lepromatous Leprosy Patients and from Patients with Erythema Nodosum Leprosum," *Clinical Immunology and Immunopathology*, vol. 67(33) Jun. 1, 1993, 199-203.

Sarna, T. "New Trends in Photobiology (Invited Review)—Properties and Function of the Ocular Melanin—A Photobiophysical View," *J. Phochem. Photobiol. B: Biol.*, vol. 12, 1992, 215-258.

Sasaki, et al., "Structure, function and tissue forms of the C-terminal globular domains of collagen XVIII containing the angiogenesis inhibitor endostatin," *The EMBO Journal*, vol. 17(15) 1998, 4249-4256.

Sato, et al., "Anti-cholesterol Activity in Antisera Against Human Serum Lipoproteins," *Immunochemistry*, vol. 9(5) May 1972, 585-587.

Sato, et al., "Anticholeseremic Antibody," *Chemical Abstracts*, vol. 83(18) 1975, 152332m.

Sato, et al., "Autocrine Activities of Basic Fibroblast Growth Factor: Regulation of Endothelial Cell Movement, Plasminogen Activator Synthesis, and DNA Synthesis," *Journal of Cell Biology*, vol. 107(3) 1988, 1199-1205.

Sato, et al., "Disruptive Effect of Diethylstibestrol on Microtubules," *Gann*, vol. 75(12) Dec. 1984, 1046-1048.

Sato, "Effect of Estradiol and Ethynylestradiol on Microtubule Distribution in Chinese Hamster V79 Cells," *Chemical and Pharmaceutical Bulletin*, vol. 40(1) Jan. 1992, 182-184.

Sato, et al., "Effects of Hormone Deprivation and 2-Methoxyestradiol Combination Therapy on Hormone-Dependent Prostate Cancer in Vivo," *Neoplasia*, vol. 7(9) Sep. 2005, 838-846.

Sato, et al., "Effects of Hormone Deprivation and 2-Methoxyestraiol Combination Therapy on Hormone-Dependent Prostate Cancer in Vivo," *Neoplasia*, vol. 7(9) Sep. 2005, 838-846.

Sato, et al., "Increased Concentration of Vascular Endothelial Growth Factor/Vascular Permeability Factor in Cyst Fluid of Enlarging and Recurrent Thryoid Nodules," *Journal of Clinical Endocrinology and Metabolism*, vol. 82(6) 1997, 1968-1972.

Sato, et al., "Natural estrogens induce modulation of microtubules in Chinese hamster V79 cells in culture (Abstract only)," *Horm. Carcinog. II. Proceedings Int. Symp. 2nd (1996). Meeting Date 1994* 1996, 454-457.

Sattler, et al., "Novel strategies for sensitivity enhancement in heteronuclear multi-dimensional NMR experiments employing pulsed field gradients," *Journal of Biomolecular NMR*, vol. 5 1995, 11-22.

Sawada, et al., "Colchicine-Like Effect of Diethylstibestrol (DES) on Mammalian Cells," *Mutation Research*, vol. 57 May 1978, 175-182.

Schaeffer, et al., "Effect of Silver Oxide/Tricholorisocyanuric Acid Antimicrobial Urinary Drainage System on Catheter-Associated Bacteriura," *The Journal of Urology*, vol. 139(1) Jan. 1988, 69-73.

Schaller, et al., "Complete amino acid sequence of bovine plasminogen—Comparison with human plasminogen," *European Journal of Biochemistry*, vol. 149 1985, 267-278.

Schaller, J. et al., "Structural Aspects of the Plasminogen of Various Species," *Enzyme*, vol. 40 1988, 63-69.

Scherr, et al., "The Nonsteroidal Effects of Diethylstilbestrol: The Rationale for Androgen Deprivation Therapy without Estrogen Deprivation in the Treatment of Prostate Cancer," *The Journal of Urology*, vol. 170 Nov. 2003, 1703-1708.

Schiff, et al., "Tubulin: A Target for Chemotheraputic Agents," *Molecular Actions and Targets for Cancer Chemotherapeutic Agents* Jan. 1, 1981, 483-507.

Schmitt-John, et al., "Promoter constructions for efficient secretion expression in Streptomyces lividans," *Applied Microbiology and Biotechnology*, vol. 36 1992, 493-498.

Schulze-Osthoff, K. et al., "In Situ Detection of Basic Fibroblast Growth Factor by Highly Specific Antibodies," *American Journal of Pathology*, vol. 137(1) Jul. 1990, 85-92.

Schumacher, et al., "2-Methoxyestradiol induces p53 independent apoptosis and inhibits growth of lung metastases of pancreatic cancer (English summary p. 52)," *Langenbecks Arch Chir 1* Jan. 1998, 49-52.

Schumacher, et al., "The Metabolism of Thalidomide: The Fate of Thalidomide and Some of its Hydrolysis Products in Various Species," *British Journal of Dermatology*, vol. 25 1965, 338-351.

Schumacher, et al., "The Physiological Estrogen Metabolite 2-Methoxyestradiol Reduces Tumor Growth and Induces Apoptosis in Human Solid Tumors," *Cancer Research Clinical Oncology*, vol. 127 2001, 405-410.

Schutte, et al., "Additional Aspects of the Effect of Kallikrein on Cell Proliferation," *Kinogenases: Kallikrein Symposium Physiol. Prop. Pharmacol. Ration., 4th Edition* 1997, 161-177.

Schwartz, et al., "A superactive insulin: [B10-Aspartic acid]insulin(human)," *Proceedings of the National Academy of Science, USA*, vol. 84 Sep. 1987, 6408-6411.

Schweigerer, et al., "Angiogenesis and Angiogenesis Inhibitors in Paediatric Diseases," *European Journal of Pediatric*, vol. 151 1992, 472-476.

Scopes, Robert K. "Recombinant Proteins—Special Techniques," *Protein Purification—Principles and Practice*, Second Edition, Vol/Iss., 232-235.

Seaver, Sally "Monoclonal Antibodies in Industry: More Difficult than Originally Thought," *Genetic Engineering News*, vol. 14 Aug. 1994, 10 and 21.

Seeger, et al., "Different effects of estradiol and various antiestrogens on TNF-a-induced changes of biochemical markers for growth and invasion of human breast cancer cells," *Life Sciences*, vol. XX Jan. 2005, 1-5.

Seegers, et al., "Cyclic-AMP and Cyclic-GMP Production in MCF-7 Cells Exposed to Estradiol-17 Beta, Catecholestrogens and Methoxy-Estrogens in MCF-7 Cells (Meeting Abstract only)," *Joint MC1-1st Symposium, Third 1st International Symposium, Biology and Therapy of Breast Cancer* Sep. 25, 1989.

Seegers, J. C. et al., "Cytoxic Effects of Estradiol-17b, Catecholestradiols and Methoxyestradiols in Dividing MCF-7 and LeLa Cells," *Journal of Steroid Biochemistry*, vol. 32(6) Jun. 1989, 797-809.

Seegers, et al., "The Mammalian Metabolite, 2-methoxyestradiol, Affects P53 Levels and Apoptosis Induction in Transformed Cells but Not in Normal Cells (Abstract only)," *Journal of Steroid Biochemistry and Molecular Biology*, vol. 62(4) Jul. 1997, 253-267.

Seeliger, et al., "Proinflammatory Role of Proteinase-activated Receptor-2 in Humans and Mice During Cutaneous Inflammation in vivo," *The FASEB Journal*, vol. 17 Oct. 2003, 1871-1885.

Seng, et al., "Use of a monoclonal antibody specific for activated endotheilial cells to quantitate angiogenesis in vivo in zebrafish after drug treatment," *Angiogeneis*, vol. 7 Jan. 2004, 243-253.

Senger, et al., "Angiogenesis promoted by vascular endothelial growth factor: Regulation through a1b1 and a2b1 integrins," *Proceedings of the National Academy of Science USA*, vol. 94 Dec. 1997, 13612-13617.

Sengupta, et al., "Temporal targeting of tumour cells and neovasculature with a nanoscale delivery system," *Nature*, vol. 436 Jul. 28, 2005, 568-572.

Seno, et al., "Monoclonal Antibodies Against Human Basic Fibroblast Growth Factor," *Hybridoma*, vol. 8(2) 1989, 209-221.

Sevier, et al., "Monoclonal Antibodies in Clinical Immunology," *Clinical Chemistry*, vol. 27(11) 1981, 1797-1806.

Shackelford, et al., "#2865 Biochemical Properties and Cellular Effects of Prostate Specific Antigen (PSA)(Abstract only)," *Proceedings of the American Association for Cancer Research*, vol. 38 Mar. 1997, 428.

Shah, et al., "(+/−)-(N-alkylamino)benzazepine Analogs: Novel Dopamine D1 Receptor Antagonists (Abstract only)," *Journal of Medicinal Chemistry*, vol. 38(21) Oct. 13, 1995, 4284-4293.

Shah, et al., "Monocrotaline pyrrole-induced endothelial cell megalocytosis involves a Golgi blockage mechanism," *Am. J. Physiol. Cell Physiol.*, vol. 288 Nov. 23, 2004, C850-C862.

Shah, et al., "Synthesis and Enantiomeric Separation of 2-Phthalimidino-glutaric Acid Analogues: Potent Inhibitors of Tumor Metastasis," *Journal of Medicinal Chemistry*, vol. 42(16) 1999, 3014-3017.

Shannon, et al., "Inhibition of de Novo IgM Antibody Synthesis by Thalidomide as a Relevant Mechanism of Action in Leprosy," *Scandinavian Journal of Immunology*, vol. 13(6) 1981, 533-562.

Shannon, et al., "Thalidomide's Effectiveness in Erythema Nodosum Leprosum is Associated with a Decrease in CD+4 Cells in the Peripheral Blood," *Leprosy Review*, vol. 63(1) Mar. 1992, 5-11.

Sharp, et al., "Diethylstilboestrol: the Binding and Effects of Diethylstiboestrol upon the Polymerisation and Depolymerisation of Purified Microtubule Protein in vitro," *Carcinogenesis*, vol. 6(6) Jun. 1985, 865-871.

Shealy, et al., "D- and L- Thalidomide 1," *Chemistry and Industry*, vol. 24 Jun. 12, 1965, 1030-1031.

Shealy, et al., "Synthesis of D-and L-Thalidomide and Related Studies," *Journal of Pharmaceutical Sciences*, vol. 57 1968, 757-764.

Sheehan, N. J. "Thalidomide Neurotoxicity and Rheumatoid Arthritis," *Arthritis and Rheumatism*, vol. 29(10) 1986, 1296.

Sheikh, et al., "Overexpression of p21WAF1/CIP1 Induces Growth Arrest, Giant Cell Formration and Apoptosis in Human Breast Carcinome Cell Lines," *Oncogene*, vol. 11 1995, 1899-1905.

Shepard, et al., "Large-Scale Purification of Recombinant Human Angiostatin," *Protein Expression and Purification*, vol. 20 2000, 216-227.

Shepard, et al., "Purification of Recombinant Human Endostatin and Angiostatin from *Pichia pastoris* Fermentation Broth: Expanded Ben Adsoption Chromatography Method Development and Scale Up," *Abstracts of Papers American Chemical Society*, vol. 219(1-2) Mar. 26, 2000, BIOT 212.

Sherman, et al., "Thalidomide: A Twenty-Five Year Perspective," *Food Drug Cosmetic Law Journal*, vol. 41 1986, 458-466.

Sheskin, et al., "In Vivo Measurements of Iron, Copper and Zinc in the Skin of Prurigo Nodularis Patients with Thalidomide," *Dermatologica*, vol. 162(2) 1981, 86-90.

Sheskin, J. "The Treatment of Lepra Reaction in Lepromatous Leprosy. FIfteen Years Experience with Thalidomide," *International Journal of Dermatology*, vol. 19(6) Jul. 8, 1980, 318-322.

Shi, et al., "Encapsulation of Submicrometer-Sized Methoxyestradiol Crystals into Polymer Multilayer Capsules for Biological Applications," *Molecular Pharmaceutics*, vol. 3(2) 2006, 144-151.

Shi, G. et al., "Kringle Domains and Plasmin Denaturation," *Biochemical & Biophysical Research Communications*, vol. 178(1) Jul. 15, 1991, 360-368.

Shibata, et al., "Optimization of Protein Therapies by Polymer-Conjugation as an Effective DDS," *Molecules*, vol. 10 Jan. 31, 2005, 162-180.

Shim, et al., "Hydrazinocurcumin, A Novel Synthetic Curcumin Derivative, is a Potent Inhibitor of Endothelial Cell Proliferation (Abstract only)," *Caplus: Bioorganic & Medicinal Chemistry*, vol. 10(8) 2002, 2439-2444.

Shimada, et al., "Roles of p38- and c-jun NH2-terminal kinase-mediated pathways in 2-Methoxyestradiol-induced p53 induction and apoptosis," *Carcinogenesis*, vol. 24(6) Jan. 2003, 1067-1075.

Shimada, et al., "The Molecular Mechanism of Sensitization to Fas-Mediated Apoptosis by 2-Methoxyestradiol in PC3 Prostate Cancer Cells," *Molecular Carcinogenesis*, vol. 39 Jan. 1, 2004, 1-9.

Shishkina, et al., "Synthesis and Properties of condensed heterocyclic deratives of estra-4, 9-dien 17.beta.-ol-3-one (Abstract only)," *Khim.-Farm. Zh.*, vol. 8(1) 1974, 7-11.

Shizume, K. "Thirty-Fixe Years of Progress in the Study of MSH," *The Yale Journal of Biology and Medicine*, vol. 58 1985, 561-570.

Shuster, et al., "The Mechanics of Vascular Cell Motility," *Microcirculation*, vol. 5(4) Jun. 25, 1998, 239-257.

Sibonga, et al., "Evidence that 2-Methoxyestradiol suppresses proliferation and accelerates apoptosis in normal rat growth plate chondrocytes," *Journal of Cancer Research and Clinical Oncology*, vol. 128 Jan. 2002, 477-483.

Sidky, et al., "Inhibition of Angiogenesis by Interferons: Effects on Tumor- and Lymphocyte-induced Vascular Responses," *Cancer Research*, vol. 47 Oct. 1, 1987, 5155-5161.

Sidor, et al., "The Potential and Suitability of 2-Methoxyestradiol in Cancer Therapy," *Clinical Cancer Research*, vol. 11(16) Aug. 15, 2005, 6094-6096.

Siegbahn, A. "Cellular Consequences Upon Factor VIIa Binding to Tissue Factor (Abstract only)," *Haemostatis*, 30 Supp. 2 2000, 41-47.

Silkowski, et al., "Characterization of the Low Affinity Interaction Between Rat Cell Adhesion Molecules CD2 and CD48 by Analytical Ultracentrifugation," *European Biophysics Journal*, vol. 25(5/6) Jun. 17, 1997, 455-462.

Silverman, W. A. "Medical Inflation," *Perspectives in Biology and Medicine*, vol. 23(4) 1980, 617-637.

Sim, et al., "A Recombinant Human Angiostatin Protein Inhibits Experimental Primary and Metastatic Cancer," *Cancer Research*, vol. 57 Apr. 1, 1997, 1329-1334.

Sim, et al., "Angiostatin and Endostatin: Endogenous Inhibitors of Tumor Growth," *Cancer Metastasis Review*, vol. 19(1-2) 2000, 181-190.

Sim, B. Kim L. "Delineation of Functional Regions on *Plasmodium falciparum* EBA-175 by Antibodies Eluted from Immune Complexes," *Molecular and Biochemical Parasitology*, vol. 95 1988, 183-192.

Sim, et al., "Primary structure of the 175K *Plasmodium falciparum* erythrocyte binding antigen and identification of a peptide which elicits antibodies that inhibit malaria merozoite invasion," *Journal of Cellular Biology*, vol. 111(5 Pt 1) 1990, 1877-1884.

Sim, et al., "Receptor and ligand domains for invasion of erythrocytes by *Plasmodium falciparum*," *Science*, vol. 264 1994, 1941-1944.

Singh, et al., "Inhibition of deoxyglucose update in MCF-7 breast cancer cells by 2-methoxyestrone and 2-methoxyestrone-3-O-sulamate (Abstract only)," *Molecular and Cellular Endocrinology*, vol. 160(1-2) 2000, 61-66.

Singhal, et al., "Novel Therapies in Multiple Myeloma," *International Journal of Hermatology*, vol. 77 Jan. 9, 2003, 226-231.

Siracusa, et al., "The effect of microtubule- and microfilament-disrupting drugs on preimplantation mouse embryos (Abstract only)," *Journal of Embryology and Experimental Morphology*, vol. 60 Dec. 1980, 71-82.

Slominski, et al., "Inhibition of Melanogenesis for Melanoma Therapy," *Journal of Investigative Dermatology*, vol. 103(5) Nov. 1994, 742.

Smith, H. "Phytochrome transgenics: functional, ecological and biotechnological applications," *Seminars in Cell Biology*, vol. 5 1994, 315-325.

Smith, et al., "Studies on the Relationship Between the Chemical Structure and Embryotoxic Activity of Thalidomide and Related Compounds," *Chemical Structure and Embryopathy* 1965, 194-209.

Snellman, et al., "Type XIII Collagen Forms Homotrimers with Three Triple Helical Collagenous Domains and Its Association into Disulfide-bonded Trimers is Enhanced by Prolyl 4—Hydroxylase," *The Journal of Biological Chemistry*, vol. 275(12) Mar. 24, 2000, 8936-8944.

Sohndel, S. et al., "Recombinant gene expression and 1H NMR characteristics of the kringle (2+3) supermodule: spectroscopic/functional individuality of plasminogen kringle domains," *Biochemistry*, vol. 35(7) 1996, 2357-2364.

Soker, et al., "Neuropilin-1 is Expressed by Endothelial and Tumor Cells as an Isoform-Specific Receptor for Vascular Endothelial Growth Factor," *Cell*, vol. 92 Mar. 20, 1998, 735-745.

Sokoll, et al., "Prostate-Specific Antigen—Its Discovery and Biochemical Characteristics," *The Urologic Clinics of North America*, vol. 24(2) May 1997, 253-259.

Solovey, A. et al., "Sickle Cell Anemia as a Possible State of Enhanced Anti-Apoptotic Tone: Survival Effect of Vascular Endothelial Growth Factor on Circulating and Unanchored Endothelial Cells," *Blood*, vol. 93(1) Jun. 1, 1999, 3824-3830.

Sorensen, et al., "Endostatin reduces vascularization, blood flow, and growth in a rat gliosarcoma," *Neuro-Oncology*, vol. 4(1) 2000, 1-8.

Sottrup-Jensen, L. et al., "The Primary Structure of Human Plasminogen Isolation of Two Lysine-Binding Fragments and One "Mini-" Plasminogen (MW.38,000) by Elastase-Catalyzed-Specific Limited Proteolysis," *Progress in Chemical Fibrinolysis and Thrombolysis*, vol. 3 1978, 191-209.

Spencer-Green, G. "Retinoic Acid Effects on Endothelial Cell Function: Interaction with Interleukin 11," *Clinical Immunology and Immunopathology*, vol. 72(1) Jul. 1994, 53-61.

Spicer, et al., "Catecholestrogens Inhibit Proliferation and DNA Synthesis of Porcine Granulosa Cells in Vitro: Comparison with Estradiol, 5a-dihydrotestosterone, Gonadotropins and Catecholamines (Chemical Abstracts, 1989)," *Molecular and Cellular Endocrinology*, vol. 64 1989, 119-126.

Sprecher, C. A. et al., "Molecular cloning, expression, and partial characterization of a second human tissue-factor pathway inhibitor," *Proceedings of the National Academy of Science USA*, vol. 91 Apr. 1994, 3353-3357.

Spyriounis, et al., "Copper (II) complex of an estradiol derivative with potent antiinflammatory properties (Abstract only)," *Arch. Pharm.* vol. 324(9) 1991, 533-536.

Sreekrishna, et al., "High level expression of heterologous proteins in methylotropic yeast *Pichia pastoris*," *Journal of Basic Microbiology*, vol. 28(4) 1988, 265-278.

Srigley, J. R. "Small-Acinar Patterns in the Prostate Gland With Emphasis on Atypical Adenomatous Hyperplasia and Small-Acinar Carcinoma," *Seminars in Diagnostic Pathology*, vol. 5(3) Aug. 1988, 254-720.

Srivastava, A. et al., "The Prognostic Significance of Tumor Vascularity in Intermediate-Thickness (0.76-4.0 mm Thick) Skin Melanoma," *American Journal of Pathology*, vol. 133(2) Nov. 1988, 419-424.

Stafford, et al., "Colchicine and 2-methoxyestradiol Inhibit Human Angiogenesis," *Journal of Surgical Research*, vol. 125 Jan. 1, 2005, 104-108.

Standker, et al., "Isolation and characterization of the circulating form of human endostatin," *FEBS Letters*, vol. 420 1997, 129-133.

Staples, et al., "Structural Requirements for Steroid Inhibition of Sheep Lymphocyte Mitogenesis in vitro," *Steroids*, vol. 44(5) Nov. 1984, 419-433.

Starkov, et al., "Mono- and Dialkylation of Guaiacol by Olefins on KU-2 Cation Exchanger (Abstract only)," *Zhumal Prikladnoi Khimil*, vol. 41(3) 1968, 688-690.

Stathakis, et al., "Generation of Angiostatin by Reduction and Proteolysis of Plasmin-Catalysis By A Plasmin Reductase Secreted by Cultured Cells," *The Journal of Biological Chemistry*, vol. 272(3) Aug. 15, 1997, 20641-20645.

Steinhubl, S. R. et al., "Local Delivery of Tissue Factor Pathway Inhibitor (TFPI) to Reduce Neointimal Proliferation in the Porcine Coronary Balloon Injury Model (Abstract only)," *Journal of the Americal College of Cardiology*, vol. 29(2) Supp. A Feb. 1997, 97557.

Sternlicht, et al., "Colchicine Inhibition of Microtubule Assembly via Copolymer Formation," *The Journal of Biological Chemistry*, vol. 254(20) Oct. 25, 1979, 10540-10550.

Strieter, R. M. et al., "Interferong-indicible protein 10 (IP-10), a member of the C-X-C chemokine family, is an inhibitor of angiogenesis," *Biochemical & Biophysical Research Communications*, vol. 210 May 5, 1995, 51-57.

Strieter, R. M. et al., "The role of CXC chemokines as regulators of angiogenesis," *Shock*, vol. Jan. 1, 1995, 155-160.

Studier, W. F. et al., "Use of T7 RNA polymerase to direct expression of cloned genes," *Methods of Enzymology*, vol. 185 1990, 60-89.

Style, A. "Early Diagnosis and Treatment of Leprosy in the United States," *American Family Physician*, vol. 52(1) Jul. 1995, 172-178.

Sugiura, et al., "Effect of Thalidomide on Transplantable Mouse, Rat, and Hamster Tumors," *GANN*, vol. 55 Feb. 1964, 57-60.

Sulis, et al., "Nail Pigmentation Following Cancer Chemotherapy. A New Genetic Entity?," *European Journal of Cancer*, vol. 16 1980, 1517-1519.

Summers, et al., "Complete 1H and 13C Assignments of Coenzyme B12 through the Use of New Two-Dimensional NMR Experiments," *Journal of the American Chemical Society*, vol. 108 1986, 4285.

Sun, et al., "Antitumor Agents. 139. Synthesis and Biological Evaluation of Thicolchicine Analogs 5,6-Dihydro -6(2)-(acyloxy)-and 5,6-Dihydro-6(S)-[(aroyloxy) methyl]-1,2,3,-trimethoxy-9-(methylthio)-8H-cyclophepta[a]naphthalen-8-ones as Novel Cytotoxic and Antimitotic," *Journal of Medicinal Chemistry*, vol. 36(5) Mar. 5, 1993, 554-551.

Sunagawa, et al., "Synthesis of Colchicine; Synthesis of dl-Demethyoxydeoxy-hexahydrocolchicine," *Chemical & Pharmaceutical Bulletin*, vol. 9 1961, 81-83.

Sutherland, et al., "2-Methoxyestradiol Is an Estrogen Receptor Agonist That Supports Tumor Growth in Murine Xenograft Models of Breast Cancer," *Clinical Cancer Research*, vol. 11 Mar. 1, 2005, 1722-1732.

Suzuki, et al., "Growth Inhibition of multi-drug-resistant breast cancer cells by 2-Methoxyestradiol -bis-sulphamate and 2-ethyloestradiol-bis-sulphamate," *The Journal of Steroid Biochemistry & Molecular Biology*, vol. 84 Jan. 2003, 269-278.

Suzuki, H. "The History of Iatrogenic Diseases in Japan," *"First Dept. of Internal Medicine, Univ. of Envir. And Occup. Health,"* Kitakyushu, Japan, 35-40.

Swartz, et al., "Antibodies to cholesterol," *Proceedings of the National Academy of Science USA* Mar. 1988, 1902-1906.

Sweeney, et al., "A Phase II Multicenter, Randomized, Double-Blind, Safety Trial Assessing the Pharmacokinetics, Pharmacodynamics and Efficacy of Oral 2-Methoyestradiol Capsules in Hormone-Refractory Prostate Cancer," *Clinical Cancer Research*, vol. 11(18) Sep. 15, 2005, 6625-6633.

Swift, T. R. "Thalidomide in Erythema Nodosum Leprosum," *The Lancet*, vol. 2(7835) Oct. 27, 1973, 966.

Szydlowska, et al., "On the Application of Thalidomide as a Block of Functional Groups of Proteinsin Histochemical Investigations," *Folia Histochemica et Cytochemica*, vol. 16(3) Jan. 1, 1978, 233-240.

Szyperski, et al., "Determination of Scalar Coupling Constants by Inverse Fourier Transformation of In-Phase Mutliplets," *Journal of Magnetic Resonance*, vol. 99 1992, 552-560.

Takada, et al., "Physiology of Plasminogen: With Special Reference to Activation and Degradation," *Haemostatis*, vol. 18/S1/88 Jan. 1988, 25-35.

Takahashi, et al., "Effects of estrogens and metabolites on endometrial carcinogenesis in young adult mice initiated with N-ethyl-N'-nitro-N-nitrosoguanidine," *Cancer Letters*, vol. 211 Jan. 2004, 1-9.

Takanashi, et al., "Comparison of ex vivo Inhibitory Effect Between 2-Hydroxyestradiol and Its 17-Sulfate on Rat Hepatic Microsomal Lipid Peroxidation," *Lipids*, vol. 38(8) Jan. 2003, 847-854.

Takanashi, et al., "Metabolism of [6,7-3H, 35S] estradiol 17 sulfate in rats," *Steroids*, vol. 68 Jan. 2003, 383-392.

Takata, et al., "2-Methoxyestradiol Enhances p53 Protein Transduction Therapy-Associated Inhibition of the Proliferation of Oral Cancer Cells through the Suppression of NF-B Activity," *Acta Medica Okayama*, vol. 58(4) Jan. 2004, 181-187.

Takigawa, et al., "Tumor Angiogenesis and Polyamines: a-Difluoromethylomithine, an Irreversible Inhibitor of Ornithine Decarboxylase, Inhibits B16 Melanoma-induced Angiogenesis in Ovo and the Proliferation of Vascular Endothelial Cells in Vitro," *Cancer Research*, vol. 50 Jul. 1, 1990, 4131-4138.

Talarico, et al., "Protection of Mice Against Tumor Growth by Immunization with an Oncogene-Encoded Growth Factor," *Proceedings of the National Academy of Science USA*, vol. 87 Jun. 1990, 4222-4225.

Tamura, et al., "Combination Thalidomide and Cyclosporine for Cardiac Allograft Rejection. Comparison with Combination Methylprednisolone and Cyclosporine," *Transplantation*, vol. 49(1) Jan. 1990, 20-25.

Tanaka, et al., "Vascular Endothelial Growth Factor in Diabetic Retinopathy," *The Lancet*, vol. 349 May 24, 1997, 1520.

Tanaka, T. et al., "Viral vector-mediated transductions of a modified platelet factor 3 cDNA inhibits angiogenesis and tumor growth," *Nature Medicine*, vol. 3 Apr. 1997, 437-442.

Tarle, et al., "Correlation of Cell Proliferation Marker (TPS), Natural Killer (NK) Activity and Tumor Load Serotest (PSA) in Untreated and Treated Prostatic Tumors," *Anticancer Research*, vol. 13(1) Jan. 1993, 215-218.

Taylor, et al., "Amphotericin B in Liposomes: A Novel Therapy for Histoplasmosis," *Am. Rev. Respir. Dis.* vol. 125 1982, 610-611.

Taylor, S. et al., "Protamine is an Inhibitor of Angiogenesis," *Nature*, vol. 297 May 27, 1982, 307-312.

Teicher, et al., "Comparison of several antiangiogenic regimes alone and with cytotoxic therapies in the Lewis lung carcinoma," *Cancer Chemother Pharmacol.* vol. 38 1996, 169-177.

Teicher, B. A. et al., "Potentiation of cytotoxic cancer therapies by TNP-470 alone and with other antiangiogenic agents," *International Journal of Cancer*, vol. 57(6) 1994, 920-925.

Teppo, et al., "Thalidomide- Type Malformations and Subsequent Osteosarcoma," *The Lancet*, vol. II(8034) Aug. 20, 1977, 405.

Teranishi, M. "Methylation of Catechol Estrogen with Diazomethane," *Chemical and Pharmaceutical Bulletin*, vol. 31(9) Sep. 1983, 3309-3314.

Theophilus, S. "Treatment with Thalidomide in Steroid Dependency and Neuritis," *Leprosy in India*, vol. 52(3) Jul. 1980, 423-428.

Thomas, et al., "Effect of Thalidomide on Liver Regeneration in Rat," *Indian Journal of Experimental Biology*, vol. 10 Jul. 1972, 314-315.

Thomas, et al., "Lack of Thalidomide Induced Aplasia in Regenerating Tail of Lizard, Hemidactylus flavivirdis," *Indian Journal of Experimental Biology*, vol. 10 Jul. 1972, 316-317.

Thomas, et al., "Successful Treatment of Adult's Langerhans Cell Histiocytosis with Thalidomide," *Archives of Dermatology*, vol. 129(10) Oct. 1993, 1261-1264.

Tishler, et al., "Microtubule-Active Drugs Taxol, Vinblastine, and Nocodazole Increase the Levels of Transcriptionally Active p53," *Cancer Research*, vol. 55 Dec. 15, 1995, 6021-6025.

To, C. T. "The roles of hepatocyte growth factor/scatter factor and Met receptor in human cancers (Review)," *Oncology Reports*, vol. 5(5) Sep. 1998, 1013-1024.

Tofovic, et al., "Estradiol Metabolites Attenuate Monocrotaline-Induced Pulmonary Hypertension in Rats," *Journal of Cardiovascular Pharmacology*, vol. 46(4) Oct. 2005, 430-437.

Tofovic, et al., "Estradiol Metabolites Attenuate Renal and Cardiovascular Injury Induced by Chronic Nitric Oxide Synthase Inhibition," *Journal of Cardiovascular Pharmacology*, vol. 46(1) Jul. 2005, 25-35.

Tolsma, S. S. et al., "Peptides derived from two separate domains of the matrix protein thrombospondin- 1 have antiangiogenic activity," *Journal of Cell Biology*, vol. 122 Jul. 1993, 497-511.

Tomaszewski, et al., "Pharmacokinetics and range-finding toxicity studies of recombinant human Endostatin in cynomolgus monkeys," *Proceedings of the American Association for Cancer Research*, vol. 40 Mar. 1990.

Tomlinson, et al., "*Rhesus* Monkey Apoliproprotein (a)—Sequence, Evolution, and Sites of Synthesis," *Journal of Biological Chemistry*, vol. 264(10) Apr. 5, 1989, 5957-5965.

Tommila, P. et al., "Cortisone, heparin and argon laser in the treatment of corneal neovascularization," *Acta Opthalmologica*, vol. 68 Suppl. 182 1988, 89-92.

Tondury, Gian et al., "Zur Wirkung Der Sexualhormone Auf Wachstrum und Differenzierung (See English Summary p. 55)," *Cambridge Philosophical Society* Dec. 17, 1955, 28-58.

Torry, et al., "Angiogenesis in the Uterus: Potential Regulation and Relation to Tumor Angiogenesis," *American Journal of Reproductive Immunology*, vol. 27 1992, 171-179.

Traldi, et al., "L'impiego Dell' imide Dell'Acido N'ftalilglutammico (Talidomide) Nella Terapia Sintomatica del Vomito di Molti Pazienti Affeti da neoplasie Maligne o Causato Dalla Somministrazione di Cloridato di Mecloretamina," *Cancro*, vol. 18 1965, 336-341.

Trautman, J. R. "Treatment of Hansen's Disease," *Cutis*, vol. 18(1) Jul. 1976, 62-65.

Tremblay, et al., "A Convenient Synthetic Method for Alpha-Alkylation of Steroidal 17-Ketone: Preparation of 16b-(THOP-Heptyl)-Estradiol," *Synthetic Communications*, vol. 25(16) 1995, 2483-2495.

Tremblay, et al., "Synthesis of 16-(Bromoalkyl)-Estradiols Having Inhibitory Effect on Human Placental Estradiol 17b-Hydroxysteroid Dehydrogenase (17b-HSD Type 1)," *Bioorganic & Medicinal Chemistry*, vol. 3(5) 1995, 505-523.

Trusolino, et al., "Interactions between scatter factors and their receptors: hints for therapeutic," *The FASEB Journal*, vol. 12 Hepatocyte Growth Factor HGF Oct. 1998, 1267-1280.

Tsutsui, et al., "Comparision of Human Versus Syrian Hamster Cells in Culture for Induction of Nitotic Inhibition, Binucleation and Multinucleation, Following Treatment with Four Aneuploidogens," *Toxicology* in Vitro, vol. 4(1) 1990, 75-84.

Urakawa, et al., "Examination of a modified cell cycle synchronization method and bovine nuclear transfer using synchronized early G1 phase fibroblast cells," *Theriogeneology*, vol. 62 Jan. 2004, 714-728.

Utne, et al., "Synthesis of 2- and 4-Fluroestradiol," *Journal of Organic Chemistry*, vol. 33(6) Jun. 1968, 2469-2473.

Vaage, et al., "Tissue Distribution and Therapeutic Effect of Intravenous Free of Encapsulated Liposomal Doxorubicin on Human Prostate Carcinoma Xenografts," *Cancer*, vol. 73(5) Mar. 1, 1994, 1478-1484.

Vacca, et al., "Antiangiogenesis is Produced by Nontoxic Doses of Vinblastine," *Blood*, vol. 94(12) Dec. 15, 1999, 4143-4155.

Van Den Broek, H. "Treatment of Prurigo Nodularis with Thalidomide," *Archives of Dermatology*, vol. 116(5) May 1980, 571-572.

Van Der Eerden, et al., "Evidence for genomic and nongenomic actions of estrogen in growth plate regulation in female and male rats at the onset of sexual maturation," *Journal of Endocrinology*, vol. 175 Jan. 2002, 277-288.

Van Der Merwe, et al., "Affinity and Kinetic Analysis of the Interaction of the Cell Adhesion Molecules Rat CD2 and CD48," *EMBO Journal*, vol. 12(13) Dec. 20, 1993, 4945-4954.

Van Der Zypen, et al., "Induction of vascular haemostatis by ND:YAG laser light in melanin-rich and melanin-free tissue," *Doc Opthalmol.*, vol. 79(3) 1992, 221-239.

Van Duuresen, et al., "Effects of serval dioxin-like compounds on estrogen metabolism in the malignant MCF-7 and nontumorigenic MCF-10A human mammary epithelial cell lines," *Toxicology and Applied Pharmacology*, vol. 190 Jan. 2003, 241-250.

Van Geerestein, et al., "Structure of 11 beta-(4-(dimethylamino)phenyl)-17.beta.-bydroxy-17.alpha.-(2- propenyl) estra-4,9-dien-3-one (identifier only)," *Acta Crystallogr., Sect. C: Cryst. Struct. Commun.*, vol. C43(2) 1987, 319-322.

Van Meir, E. et al., "Release of an inhibitor of Angiogenesis upon Induction of Wild Type p53 Expression in Glioblastoma Cells," *Nature Genetics*, vol. 8 Oct. 1994, 171-176.

Van Tamelen, et al., "The Synthesis of Colchicine," *Tetrahedron*, vol. 14(1/2) Sep. 1961, 8-34.

Vandeputte, et al., "Vascular Tumors Induced by Polyoma Virus in Pregnant Rats," *Journal of the National Cancer Institute*, vol. 56(3) Mar. 1976, 517-521.

Vasilescu, et al., "Cercetari Privind Actiunea Talidomidei Asupra Celulelor Cultivate in Vitro," *Cerc. Fiziol.*, vol. 13(4) 1968, 293-300.

Verheul, et al., "Combination Oral Antiangiogenic Therapy with Talidomide and Sulindac Inhibits Tumor Growth in Rabbits," *British Journal of Cancer*, vol. 79(1) 1999, 114-118.

Verma, J. N. et al., "Adjuvant Effects of Liposomes Containing Lipid A: Enhancement of Liposomal Antigen Presentation and Recruitment of Macrophages (Abstract only)," *Infect. Immun.*, vol. 60(6) 1992, 2438-2444.

Vernes, et al., "*Plasmodium falciparum* strain-specific human antibody inhibits merozoite invasion of erythrocytes," *Am J Trop Med Hyg.* vol. 33(2) Mar. 1994, 197-203.

Vicente, et al., "In Vitro Activity of Thalidomide Against *Mycobacterium avium Complex*," *Archives of Internal Medicine*, vol. 153(4) Feb. 22, 1993, 534.

Viggiano, et al., "Trigeminal pain transmission requires reactive oxygen species production," *Brain Research*, vol. 1050 Jan. 1, 2005, 72-78.

Villa, et al., "Antimytotic Effect of Thalidomide and its Metabolites on the Chick Embryo Blood Cells," *Haematologica Latina*, vol. 6 1963, 217-221.

Villa, et al., "Cytological Effects of Thalidomide," *The Lancet*, vol. 1(7283) Mar. 30, 1963, 725.

Vladutiu, A. "Another Chance for Thalidomide?," *The Lancet*, vol. 1(7444) Apr. 30, 1966, 981-982.

Voest, E. E. et al., "Inhibition of Angiogenesis in Vivo by Interleukin 12," *Journal of the National Cancer Institute*, vol. 87 Apr. 19, 1995, 581-586.

Vogelsang, et al., "Thalidomide for the Treatment of Chronic Graft-versus-Host Disease," *The New England Journal of Medicine*, vol. 326 Apr. 16, 1992, 1055-1059.

Vogelsang, et al., "Thalidomide Induction of Bone Marrow Transplantation Tolerance," *Transplant Proc.* vol. 19(1) Pt. 3 Feb. 1987, 2658-2661.

Vogelsang, et al., "Therapy of Chronic Graft-v-Host Disease in a Rat Model," *Blood*, vol. 74(1) Jul. 1989, 507-511.

Vogelsang, et al., "Treatment and Prevention of Acute Graft-versus-Host Disease with Thalidomide in a Rat Model 1," *Transplantation*, vol. 41(5) May 1986, 644-647.

Vogt, et al., "Inhibition of Angiogenesis in Kaposi's Sarcoma by Captopril," *The Lancet*, vol. 349(9059) Apr. 19, 1997, 1148.

Vuister, et al., "Resolution Enhancement and Spectral Editing of Uniformly 13C-Enriched Proteins by Homonuclear Broadband 13C Decoupling," *Journal of Magnetic Resonance*, vol. 98 1992, 428-435.

Wadsworth, et al., "The Antigenic Action of Cholesterol," *Journal of Immunobiology*, vol. 29 1935, 135-149.

Wakui, et al., "Tumour Angiogenesis in Prostatic Carcinoma with and without Bone Marrow Metastasis: A Morphometric Study," *Journal of Pathology*, vol. 168 1992, 257-262.

Walz, D. A. et al., "Amino acid sequence of human prothrombin fragments 1 and 2," *Proceedings of the National Academy of Science*, vol. 74 May 1977, 1969-1973.

Wang, et al., "A Simple Quantitative Method for Evaluation of Angiogenesis Activity," *Assay and Drug Development Technologies*, vol. 2(1) Jan. 2004, 31-38.

Wang, Z. et al., "An Optimized Synthesis of 2-Methoxyestradiol, a Naturally Occurring Human Metabolite with Anticancer Activity," *Synth. Commun.*, vol. 28(23) 1998, 4431-4437.

Wang, et al., "Photoaffinity labeling of human placental estradiol 17.beta.-dehydrogenase with 2- and 4-azidoestrone, 2- and 4-azidoestradiol (Abstract only)," *Shengwu Huaxue Zazhi*, vol. 8(6) 1992, 715-718.

Wang, et al., "Synthesis of B-Ring Homologated Estradiol Analogues that Modulate Tubulin Polymerization and Microtubule Stability," *Journal of Medicinal Chemistry*, vol. 43 2000, 2419-2429.

Warshawsky, I. et al., "The Carboxy Terminus of Tissue Factor Pathway Inhibitor is Required for Interacting with Hepatoma Cells in Vitro and in Vivo," *The American Society for Clinical Investigation*, vol. 95 Apr. 1995, 1773-1782.

Warshawsky, I. et al., "The low density lipoprotein receptor-related protein mediates the cellular degradation of tissue factor pathway inhibitor," *Proceedings of the National Academy of Science USA*, vol. 91 Jul. 1994, 6664-6668.

Wassef, et al., "Phosphate-Binding Specificities of Monoclonal Antibodies Against Phosphoinsitides in Liposomes," *Molecular Immunology*, vol. 21(10) 1984, 863-868.

Watanabe, "A Sensitive Enzyme Immunoassay for Human Basic Fibroblast Growth Factor," *Biochemical and Biophysical Research Communications*, vol. 175(1) Feb. 28, 1991, 229-235.

Waters, M. F. "An Internally-Controlled Double Blind Trial of Thalidomide in Severe Erythema Nodosum Leprosum," *Leprosy Review*, vol. 42(1) Mar. 1971, 26-42.

Waters, et al., "Treatment of Ulcerative Colitis with Thalidomide," *British Medical Journal*, vol. 1(6166) Mar. 24, 1979, 792.

Waters, M. "Use of Thalidomide in Leprosy," *British Medical Journal*, vol. 303(6800) Aug. 24, 1991, 470.

Webb, et al., "Cell-Surface Expression and Purification of Human CD-4 Produced in Baculovirus-Infected Insect Cells (Abstract only)," *Proceedings of the National Academy of Science* (USA), vol. 86(20) 1989, 7731-7735.

Weidner, N. et al., "Tumor Angiogenesis and Metastasis-Correlation in Invasive Breast Carcinoma," *New England Journal of Medicine*, vol. 324(1) Jan. 3, 1991, 1-8.

Weidner, N. et al., "Tumor Angiogenesis Correlates with Metastasis in Invasive Prostate Carcinoma," *American Journal of Pathology*, vol. 143(2) Aug. 1993, 401-409.

Weidner, N. et al., "Tumor angiogenesis: A New Significant and Independent Prognostic Indicator in Early-Stage Breast Carcinoma," *Journal of the National Cancer Institute*, vol. 84 Dec. 16, 1992, 1875-1887.

Weinstat=Saslow, D. L. et al., "Transfection of Thrombospondin 1 Complementary DNA into a Human Breast Carcinoma Cell Line Reduces Primary Tumor Growth, Metastatic Potential, and Angiongenesis," *Cancer Research*, vol. 54 1994, 6504-6511.

Weissleder, et al., "MR Imaging and Scintigraphy of Gene Expression through Melanin Induction," *Radiology*, vol. 204 1997, 425-429.

Weiter, et al., "Relationship of Senile Macular Degeneration to Ocular Pigmentation," *American Journal of Ophthalmology*, vol. 99 Feb. 1985, 185-187.

Welsch, et al., "Staphylostatic Activity of Some New Diphenols, Napthols, and Chalcones (Abstract only)," *Experientia*, vol. 11 1955, 350-351.

Werkmeister, et al., "Characterization of a Monoclonal Antibody Against Native Human Type I Collagen," *European Journal of Biochemistry*, vol. 187 1990, 439-443.

Wesolowski, et al., "Effect on Light on a Murine Model of Retinopathy of Prematurity (Abstract only)," *Invest. Opthalmology and Visual Science*, vol. 33(4) 1992, 1281.

Wheeler, et al., "Mitotic Inhibition and Aneuploidy Induction by Naturally Occurring and Synthetic Estrogens in Chinese Hamster Cells in Vitro," *Mutation Research*, vol. 171 Jul. 1986, 31-41.

Wheeler, et al., "Mitotic Inhibition and Chromosome Displacement Induced by Estradiol in Chinese Hamster Cells (Chemical Abstracts, 1986)," *Cell Motility and the Cytoskeleton*, vol. 7(3) 1987, 235-247.

White, et al., "Treatment of Pulmonary Hemangiomatosis with Recombinant Interferon Alfa-2a," *The New England Journal of Medicine*, vol. 32(18) May 4, 1989, 1197-1200.

Wiese, et al., "Induction of the Estrogen Specific Mitogenic Response of MCF-7 Cells by Selected Analogues of Estradiol-17b: A 3D QSAR Study," *Journal of Medicinal Chemistry*, vol. 40 1997, 3659-3669.

Williams, K. M. "Enantiomers in Arthritic Disorders," *Parmacology and Therapeutics*, vol. 46(2) 1990, 273-295.

Williams, et al., "Thalidomide Hypersensitivity in AIDS," *The Lancet*, vol. 337(8738) Feb. 16, 1991, 436-437.

Wiman, B. et al., "On the Specific Interaction Between the Lysine-Binding Sites in Plasmin and Complementary Sites in a2-Antiplasmin and Fibinogen," *Biochimica et Biophysica Acta.*, vol. 579 1979, 142-154.

Winkelmann, et al., "Thalidomide Treatment of Prurigo Nodularis," *Acta Dermato-Venereologica*, vol. 64(5) 1984, 412-417.

Wiseman, et al., "Mechanism of Inhibition of Lipid Peroxidation by Tamoxifen and 4-hydroxytamoxifen Introduced to Liposomes," *FEBS Letters*, vol. 274 (1.2) Nov. 1990, 107-110.

Wishart, et al., "1H, 13C and 15N chemical shift referencing in biomolecular NMR," *Journal of Biomolecular NMR*, vol. 6 1995, 135-140.

Wolff, et al., "Direct Gene Transfer into Mouse Muscle in vivo (Abstract only)," *Science*, vol. 247 (4949 Pt 1) 1990, 1465-1468.

Wolpert, L. "Mechanisms of Limb Development and Malformation," *British Medical Bulletin*, vol. 32(1) 1976, 65-70.

Wong, et al., "Cytotoxic Melanin Precurser, 5, 6-Dihydroxyindole, from the Folkloric Anti-Cancer Plan Rhaphidophoro Korthalsii," *Natural Product Letters*, vol. 9 1996, 137-140.

Wood, et al., "2-MeOE2bisMATE induces caspase-despendent apoptosis in CAL51 breast cancer cells and overcomes resistance to TRAIL via cooperative activation of caspases," *Apoptosis*, vol. 9 Jan. 2004, 323-332.

Wood, et al., "The Potential Use of Thalidomide in the Therapy of Graft-versus-Host Disease—A Review of Clinical and Laboratory Information," *Leukemia Research*, vol. 14(5) 1990, 395-399.

Woodyatt, P. B. "Thalidomide (Letter to the Editor)," *The Lancet*, vol. 1 Apr. 7, 1962, 750.

Wright, et al., "Codon usage in the G+C=rich Stroptomyces genome," *Gene*, vol. 113 1992, 55-65.

Wu, et al., "Interaction of Plasminogen and Fibrin in Plasminogen Activation," *Journal of Biological Chemistry*, vol. 265(32) Nov. 15, 1990, 19658-19664.

Wu, et al., "Supression of Tumor Growth with Recombinant Murine Angiostatin," *Biochemical and Biophysical Research Communications*, vol. 236 1997, 651-654.

Wu, et al., "The Binding of Plasminogen Fragments to Cultured Human Umbilical Vein Endothelial Cells," *Biochemistry and Biophysical Research Communications*, vol. 188(1) Oct. 30, 1992, 703-711.

Wuest, et al., "Teratological Studies in the Thalidomide Field," *Life Sciences*, vol. 5 1966, 393-396.

Wulff, et al., "Development of Polyneuropathy During Thalidomide Therapy," *British Journal of Dermatology*, vol. 112(4) Apr. 1985, 475-480.

Wurtz, et al., "Three-Dimensional Models of Estrogen Receptor Ligand Binding Domain Complexes, Based on Related Crystal Structures and Mutational and Structure-Activity Relationship Data," *Journal of Medicinal Chemistry*, vol. 41 1998, 1803-1814.

Xin, et al., "Kringle 1 of Human Hepatocyte Growth Factor Inhibits Bovine Aortic Endothelial Cell," *Biochemical and Biophysical*, vol. 277 Hepatocyte Growth Factor HGF 2000, 186-190.

Xu, M. et al., "Gene Therapy with P53 and a Fragment of Thrombospondin I Inhibits Human Breast Cancer in Vivo," *Molecular Genetics and Metabolism*, vol. 63 1998, 103-109.

Xu, M. et al., "In Vivo Gene Therapy with a Cationic Polymer Markedly Enhances the Antitumor Activity of Antiangiogenic Genes," *Molecular Genetics and Metabolism*, vol. 64 1998, 001-005.

Xu, M. et al., "Parental Gene Therapy with p53 Inhibits Human Breast Tumors in Vivo Through a Bystander Mechanism Without Evidence of Toxicity," *Human Gene Therapy*, vol. Jan. 20, 1997, 177-185.

Yamaguchi, et al., "The cloning and sequencing of alpha 1 (VIII) collagen cDNAs demonstrate that type VIII collagen is a short chain collagen and contains triple-helical and carboxyl-terminal non-triple-helical domains similar to those of type X collagen (Abstract only)," *Journal of Biological Chemistry*, vol. 264(27) Sep. 25, 1989, 16022Å??16029.

Yang, et al., "Constutively active FOX04 inhibits Akt activity, regulates p27 Kip1 stability, and suppresses HER2-medicated tumorigenicity," *Oncogene*, vol. 24 Jan. 1, 2005, 1924-1935.

Yang, Ning-Sun "Gene Transfer into Mammalian Somatic Cells In Vivo," *Critical Reviews in Biotechnology*, vol. 12 No. 4 Hepatocyte Growth Factor HGF 1992, 335-356.

Yasuda, et al., "Accelerated Differentiation in seminiferous tubules of fetal mice prenatally exposed to ethinyl estradiol (Abstract only)," *Anat. Embryol. (Berl.)*, vol. 174(3) 1986, 289-2999.

Yazici, et al., "Practical Treatment Recommendations for Pharmacotherapy of Behcet's Syndrome," *Drugs*, vol. 42(5) Nov. 1991, 196-804.

Yell, et al., "Diagnosis and management of systemic lupus erythematosus," *British Medical Journal*, vol. 307(6909) Oct. 9, 1993, 939.

Yoshimura, T. et al., "Cloning, Sequencing, and Expression of Human Macrophange Stimulating Protein (MSP, MST1) Confirms MSP as a Member of the Framily of Kringle Proteins and Locates the MSP Gene on Chromosome 3," *The Journal of Biological Chemistry*, vol. 268(21) Jul. 25, 1993, 15461-15468.

You, et al., "Purification and characterizatno of recombinant murine endostatin in *E. coli,*" *Experimental and Molecular Medicine*, vol. 31(4) Dec. 1999, 197-202.

Youle, et al., "Thalidomide in Hyperalgic Pharyngeal Ulceration in AIDS," *The Lancet*, vol. 335(8705) Jun. 30, 1990, 1591.

Youle, et al., "Treatment of Resistant Aphthous Ulceration with Thalidomide in Patients Positive for HIV Antibody," *British Medical Journal*, vol. 298(6671) Feb. 18, 1989, 432.

Yue, et al., "2-Methoxyestradio, an Endogenous Estrogen Metabolite, Induces Apoptosis in Endothelial Cells and Inhibits Angiogenesis: Possible Role for Stress-Activated Protein Kinase Signaling Pathway and Fas Expression," *Molecular Pharmacology*, vol. 51 1997, 951-952.

Zabrenetzky, V. et al., "Expression of the Extracellular Matrix Molecule Thromospondin Inversely Correlates With Malignant Progression in Melanoma, Lung and Breast Carcinoma Cell Lines," *Int. J. Cancer*, vol. 59 1994, 191-195.

Zacharia, et al., "2-Hydroxyestradiol Is A Prodrug of 2-Methoxyestradiol," *Journal for Pharmacology and Experimental Therapeutics*, vol. 62505 Feb. 10, 2004, 1-25.

Zacharia, et al., "Methoxyestradiols Mediate the Antimitogenic Effects of 17b-Estradiol," *Circulation*, vol. 108 Dec. 16, 2003, 2974-2978.

Zacharia, et al., "Methylation of 2 Hydroxyestradiol in Isolated Organs," *Hypertension*, vol. 42 Jan. 2003, 82-87.

Zalc, et al., "Immunogenic Properties of Glucosylceramide," *Molecular Immunology*, vol. 16 1979, 297-300.

Zaman, et al., "Analysis of the site for second-strained initiation during replication of the Stroptomyces plasmid pKJ101," *Journal of General Microbiology*, vol. 139 1993, 669-576.

Zetter, Bruce R. "Angiogenesis and Tumor Metastasis," *Annu. Rev. Med.*, vol. 49 Jan. 1, 1998, 407-424.

Zhang, et al., "Detection of 1,2,4-benzenetriol induced aneuploidy and microtubule disruption by flourescence in situ hybridization and immunocytochemistry," *Mutation Research*, vol. 320 1994, 315-327.

Zhang, et al., "The noncollagenous Domain 1 of Type X Collagen," *The Journal of Biological Chemistry*, vol. 274(32) Aug. 6, 1999, 22409-22413.

Zhang, et al., "Tumor suppressor ARF inhibits HER-2/neu-mediated oncogenic growth," *Oncogene*, vol. 23 Jan. 2004, 7132-7143.

Zhou, et al., "2-Methoxyestradiol induces cell cycle arrest and apoptosis of nasopharyngeal carcinoma cells," *Acta Pharmacologica Sinica*, vol. 25(11) Nov. 2004, 1515-1520.

Zhou, et al., "Complete primary structure of the sixth chain of human basement membrane collagen, alpha 6(IV). Isolation of the cDNAs for alpha 6(IV) and comparison with five other type IV collagen chains. (Abstract only)," *The Journal of Biological Chemistry*, vol. 269(18) May 6, 1994, 13193-13199.

Zhu, et al., "NADPH-dependent metabolism of 17B-estradiol and estrone to polar and nonpolar metabolites by human tissues and cytochrome P450 isoforms," *Steroids*, vol. 70 Jan. 1, 2005, 225-244.

Zhu, N. et al., "Systemic Gene Expression After Intravenous DNA Delivery into Adult Mice," *Science*, vol. 261 Jul. 9, 1993, 209-211.

Ziche, et al., "Nitric Oxide Synthase Lies Downstream from Vascular Endothelial Growth Factor-induced but not Basic Fibroblast Growth Factor-Induced Angiogenesis," *Journal of Clinical Investigation*, vol. 99(11) Jun. 1, 1997, 2652-2634.

Zoubine, et al., "2-Methoxyestradiol-Induced Growth Suppression and Lethality in Estrogen-Responsive MCF-7 Cells May Be Mediated by Down Regulation of p34cdc2 and Cyclin B1 Expression (Abstract only)," *International Journal of Oncology*, vol. 15(4) Oct. 1999, 639-646.

Zwart, D. "Treatment of Grade II Astrocytoma with Thalidomide," *Arzneim.-Forsch.*, vol. 16(12) 1966, 1688-1689.

\* cited by examiner

THERAPEUTIC ANTIANGIOGENIC ENDOSTATIN COMPOSITIONS

CROSS REFERENCE TO PRIOR RELATED CASES

This application is a continuation of and claims priority to U.S. Ser. No. 10/042,347 filed Jan. 11, 2002 (now abandoned), which is a divisional of and claims priority to U.S. Ser. No. 09/315,689 filed May 20, 1999 (now U.S. Pat. No. 6,346,510), which claims priority to provisional application 60/106,343 filed Oct. 30, 1998, and is a continuation-in-part of U.S. patent application Ser. No. 09/154,302 filed Sep. 16, 1998, now U.S. Pat. No. 6,630,448 which is a divisional of U.S. patent application Ser. No. 08/740,168 filed Oct. 22, 1996, now U.S. Pat. No. 5,854,205 which claims priority to provisional application Ser. No. 60/005,835 filed Oct. 23, 1995, provisional application Ser. No. 60/023,070 filed Aug. 2, 1996, and provisional application Ser. No. 60/026,263 filed Sep. 17, 1996. Each of the above-referenced applications is incorporated herein in its entirety.

This invention may have been made in part by funds from NIH grants RO1-CA64481 and PO1-CA45548. The U.S. government may have certain rights in this invention.

TECHNICAL FIELD

This application relates to a novel inhibitor of angiogenesis useful for treating angiogenesis-related diseases, such as angiogenesis-dependent cancer. The invention further relates to a novel composition and method for curing angiogenesis-dependent cancer. In addition, the present invention relates to diagnostic assays and kits for endostatin measurement, to histochemical kits for localization of endostatin, to molecular probes to monitor endostatin biosynthesis, to antibodies that are specific for the endostatin, to the development of peptide agonists and antagonists to the endostatin receptor, and to cytotoxic agents linked to endostatin peptides.

BACKGROUND OF THE INVENTION

Several lines of direct evidence now suggest that angiogenesis is essential for the growth and persistence of solid tumors and their metastases (Folkman, 1989; Hori et al., 1991; Kim et al., 1993; Millauer et al., 1994). To stimulate angiogenesis, tumors up-regulate their production of a variety of angiogenic factors, including the fibroblast growth factors (FGF and BFGF) (Kandel et al., 1991) and vascular endothelial cell growth factor/vascular. permeability factor (VEGF/VPF). However, many malignant tumors also generate inhibitors of angiogenesis, including angiostatin and thrombospondin (Chen et al., 1995; Good et al., 1990; O'Reilly et al., 1994). It is postulated that the angiogenic phenotype is the result of a net balance between these positive and negative regulators of neovascularization (Good et al., 1990; O'Reilly et al., 1994; Parangi et al., 1996; Rastinejad et al., 1989). Several other endogenous inhibitors of angiogenesis have been identified, although not all are associated with the presence of a tumor. These include, platelet factor 4 (Gupta et al., 1995; Maione et al., 1990), interferon-alpha, interferon-inducible protein 10 (Angiolillo et al., 1995; Strieter et al., 1995), which is induced by interleukin-12 and/or interferon-gamma (Voest et al., 1995), gro-beta (Cao et al., 1995), and the 16 kDa N-terminal fragment of prolactin (Clapp et al., 1993). The only known angiogenesis inhibitor which specifically inhibits endothelial cell proliferation is angiostatin (O'Reilly et al. 1994).

Angiostatin is an approximately 38 kiloDalton (kDa) specific inhibitor of endothelial cell proliferation. Angiostatin is an internal fragment of plasminogen containing at least three of the five kringles of plasminogen. Angiostatin has been shown to reduce tumor weight and to inhibit metastasis in certain tumor models. (O'Reilly et al., 1994). As it is used hereinafter, the term "angiostatin" refers to angiostatin as described above; peptide fragments of angiostatin that have endothelial cell proliferation inhibiting activity; and analogs of angiostatin that have substantial sequence homology (as defined herein) to the amino acid sequence of angiostatin, which have endothelial cell proliferation inhibiting activity.

SUMMARY OF THE INVENTION

The present invention relates to a novel protein inhibitor, and method for its use. The protein is a potent and specific inhibitor of endothelial proliferation and angiogenesis. Systemic therapy with the inhibitor causes a nearly complete suppression of tumor-induced angiogenesis, and it exhibits strong anti-tumor activity.

The inhibitory protein has a molecular weight of approximately 18,000 to approximately 20,000 Daltons (18 to 20 kDa) and is capable of inhibiting endothelial cell proliferation in cultured endothelial cells. The protein can be further characterized by its preferred N-terminal amino acid sequence, the first twenty (20) of which are as follows:

```
                                          (SEQ ID NO:1)
His Thr His Gln Asp Phe Gln Pro Val Leu
 1   2   3   4   5   6   7   8   9  10

His Leu Val Ala Leu Asn Thr Pro Leu Ser
11  12  13  14  15  16  17  18  19  20
```

A preferred endothelial cell proliferation inhibitor of the invention is a protein having the above-described characteristics, and which can be isolated and purified from the murine hemangioendothelioma cell line EOMA. This inhibitory protein has been named endostatin.

The present invention provides methods and compositions for treating diseases and processes mediated by undesired and uncontrolled angiogenesis by administering to a human or animal with the undesired angiogenesis a composition comprising a substantially purified endostatin or endostatin derivative in a dosage sufficient to inhibit angiogenesis. The present invention is particularly useful for treating or for repressing the growth of tumors. Administration of endostatin to a human or animal with prevascularized metastasized tumors prevents the growth or expansion of those tumors.

The present invention also includes diagnostic methods and kits for detection and measurement of endostatin in biological fluids and tissues, and for localization of endostatin in tissues. The diagnostic method and kit can be in any configuration well known to those of ordinary skill in the art. The present invention also includes antibodies specific for the endostatin and antibodies that inhibit the binding of antibodies specific for the endostatin. These antibodies can be polyclonal antibodies or monoclonal antibodies. The antibodies specific for endostatin can be used in diagnostic kits to detect the presence and quantity of endostatin which is diagnostic or prognostic for the occurrence or recurrence of cancer or other diseases mediated by angiogenesis. Antibodies specific for endostatin may also be administered to a human or animal to passively immunize the human or animal against endostatin, thereby reducing angiogenic inhibition.

The present invention also includes diagnostic methods and kits for detecting the presence and quantity of antibodies that bind endostatin in body fluids. The diagnostic method and kit can be in any configuration well known to those of ordinary skill in the art.

The present invention also includes endostatin peptide fragments that can be labeled isotopically or with other molecules or proteins for use in the detection and visualization of endostatin binding sites with state of the art techniques, including, but not limited to, positron emission tomography, autoradiography, flow cytometry, radioreceptor binding assays, and immunohistochemistry.

These endostatin peptides also act as agonists and antagonists at the endostatin receptor, thereby enhancing or blocking the biological activity of endostatin. Such peptides are used in the isolation of the endostatin receptor.

The present invention also includes endostatin, endostatin fragments, endostatin antisera, or endostatin receptor agonists and antagonists linked to cytotoxic agents for therapeutic and research applications.

The present invention includes molecular probes for the ribonucleic acid and deoxyribonucleic acid involved in transcription and translation of endostatin. These molecular probes provide means to detect and measure endostatin biosynthesis in tissues and cells.

A surprising discovery is that various forms of recombinant endostatin protein can serve as sustained release anti-angiogenesis compounds when administered to a tumor-bearing animal. A preferred form of the sustained release compound is un-refolded recombinantly produced endostatin.

Additionally, the present invention encompasses nucleic acid sequences comprising corresponding nucleotide codons that code for the above disclosed amino acid sequence and for endostatin and endothelial cell proliferation inhibiting peptide fragments thereof.

The present invention also relates to methods of using the endostatin protein and peptide fragments, corresponding nucleic acid sequences, and antibodies that bind specifically to the inhibitor and its peptides, to diagnose endothelial cell-related diseases and disorders.

The invention further encompasses a method for identifying receptors specific for endostatin, and the receptor molecules identified and isolated thereby.

The invention also relates to a method for identifying novel enzymes capable of releasing endostatin from collagen type XVIII, and other molecules containing an endostatin amino acid sequence, and peptides thereof. Such endostatin producing enzymes are also an aspect of the invention.

An important medical method is a new form of birth control, wherein an effective amount of endostatin is administered to a female such that uterine endometrial vascularization is inhibited and embryo implantation cannot occur, or be sustained.

A particularly important aspect of the present invention is the discovery of a novel and effective method for treating angiogenesis-related diseases, particularly angiogenesis-dependent cancer, in patients, and for curing angiogenesis-dependent cancer in patients. The method unexpectedly provides the medically important result of inhibition of tumor growth and reduction of tumor mass. The method relates to the co-administration of the endostatin of the present invention and another anti-angiogenesis compound, preferably angiostatin. Accordingly, the present invention also includes formulations containing endostatin, and optionally angiostatin, which are effective for treating or curing angiogenesis-dependent cancers.

Accordingly, it is an object of the present invention to provide a composition comprising an endostatin protein.

It is another object of the present invention to provide a method of treating diseases and processes that are mediated by angiogenesis.

It is yet another object of the present invention to provide a diagnostic or prognostic method and kit for detecting the presence and amount of endostatin in a body fluid or tissue.

It is yet another object of the present invention to provide a method and composition for treating diseases and processes that are mediated by angiogenesis including, but not limited to, hemangioma, solid tumors, leukemia, metastasis, telangiectasia psoriasis scleroderma, pyogenic granuloma, myocardial angiogenesis, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

It is another object of the present invention to provide a composition for treating or repressing the growth of a cancer.

It is an object of present invention to provide a method for detecting and quantifying the presence of an antibody specific for an endostatin in a body fluid.

Still another object of the present invention is to provide a composition consisting of antibodies to endostatin that are selective for specific regions of the endostatin molecule.

It is another object of the present invention to provide a method for the detection or prognosis of cancer.

It is another object of the present invention to provide a composition for use in visualizing and quantitating sites of endostatin binding in vivo and in vitro.

It is yet another object of the present invention to provide a composition for use in detection and quantification of endostatin biosynthesis.

It is yet another object of the present invention to provide a therapy for cancer that has minimal side effects.

Still another object of the present invention is to provide a composition comprising endostatin or an endostatin peptide linked to a cytotoxic agent for treating or repressing the growth of a cancer.

These and other objects, features and advantages of the present invention will become apparent after a review of the following detailed description of the disclosed embodiments and the appended claims.

Conditioned media collected from confluent EOMA cells or base media was applied to bovine capillary endothelial cells with 1 ng/ml bFGF in a 72 hour proliferation assay. Endothelial cell proliferation was inhibited by the EOMA conditioned media. Each bar represents the mean±SEM.

Figure 2:
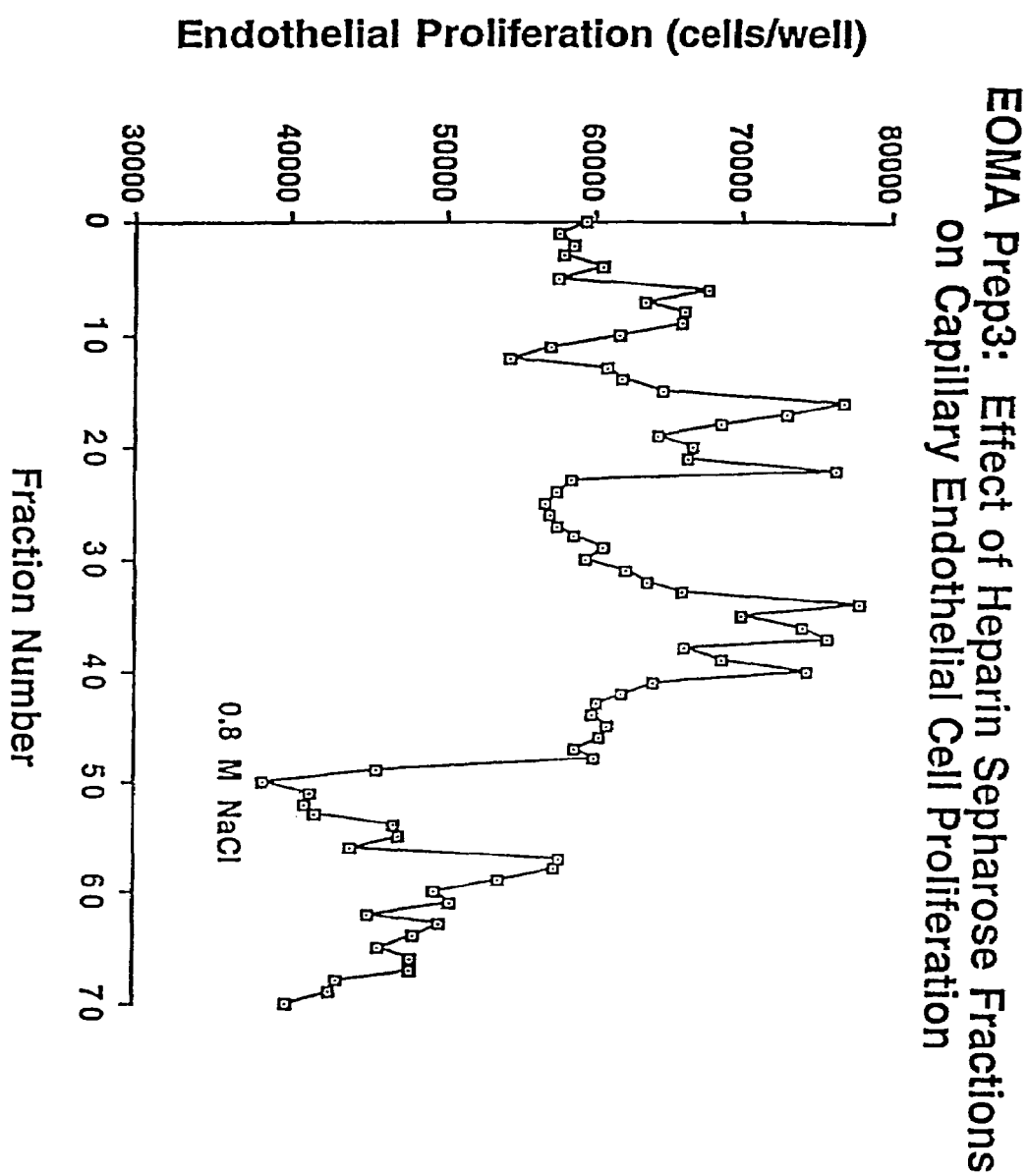

FIG. 2: Purification of an Inhibitor of Endothelial Proliferation from EOMA Conditioned Media.

Conditioned media collected from confluent EOMA cells was fractionated on a heparin sepharose column. Endothelial proliferation inhibiting activity eluted at approximately 0.8M NaCl.

Figure 3:
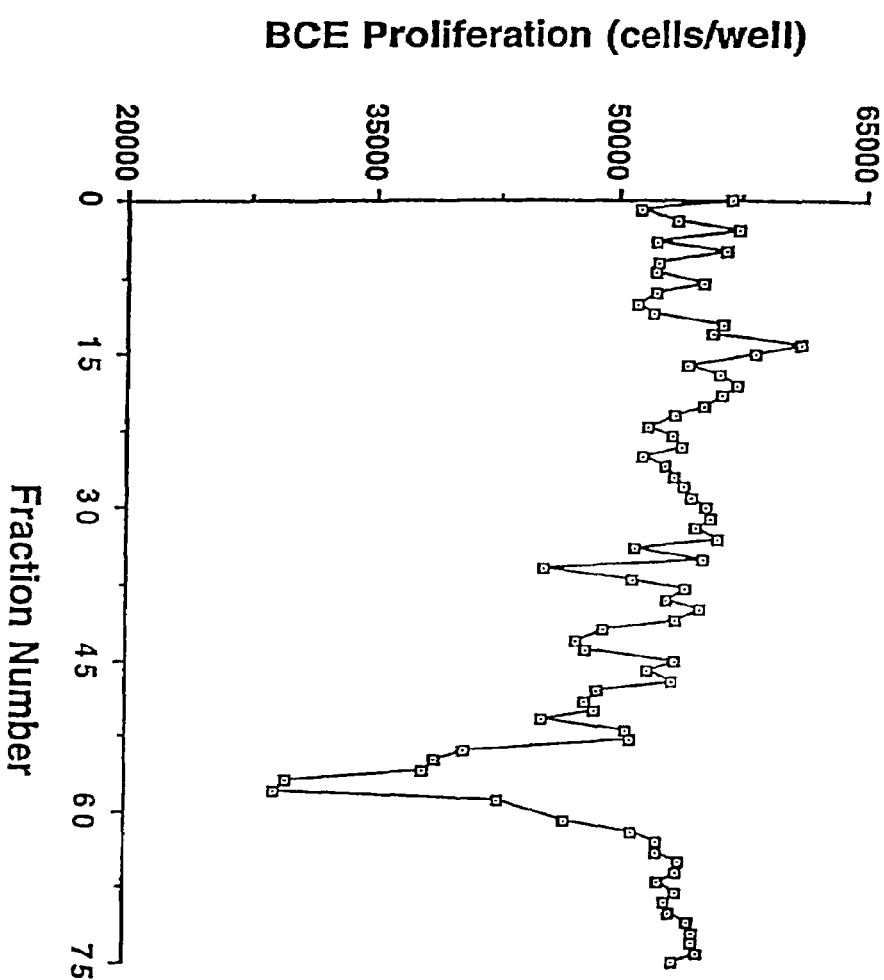

FIG. 3: Purification of an Inhibitor of Endothelial Proliferation by Gel Filtration.

Purified inhibitor from heparin sepharose column chromatography was applied to a gel filtration column and eluted as a single peak.

Figure 4:
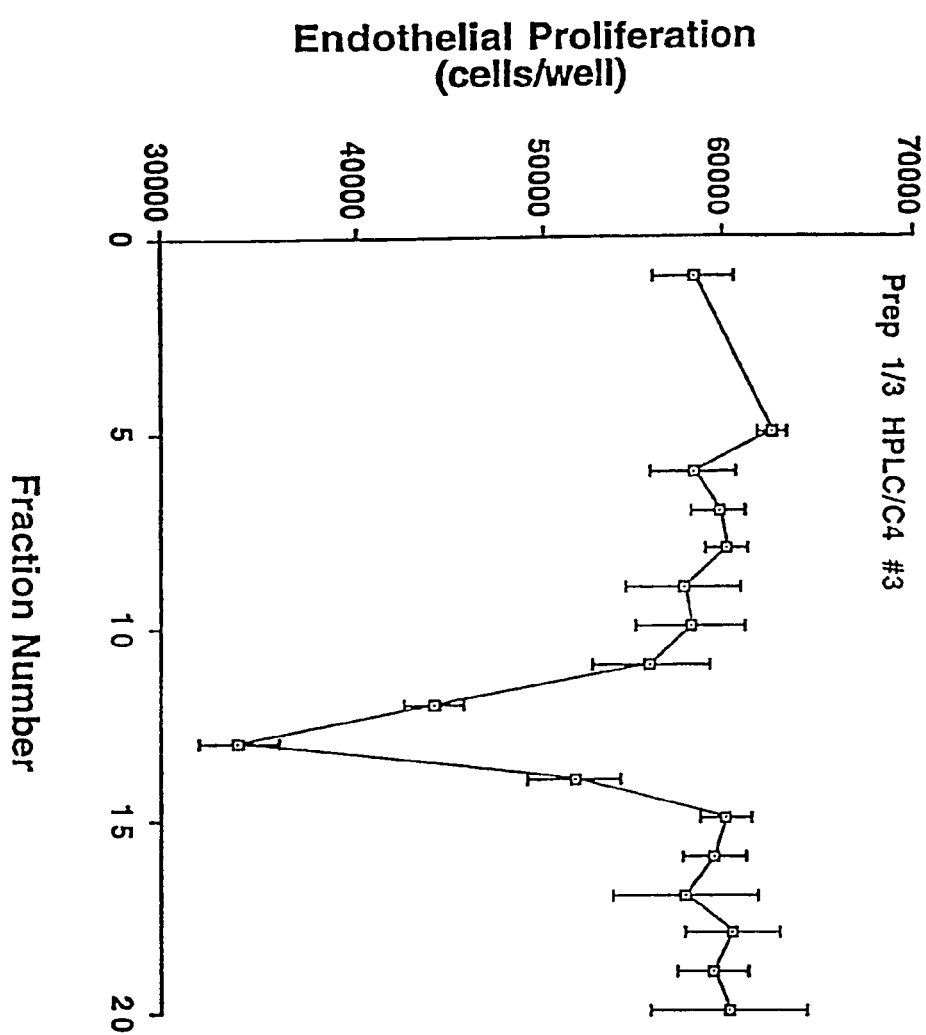

FIG. 4: Purification of Inhibitor of Endothelial Cell Proliferation by Reversed Phase Column Chromatography.

Inhibitor purified by heparin sepharose and gel filtration chromatography was applied to a reverse phase column. The inhibitor eluted as a single band from the column at approximately 45% of the acetonitrile.

Figure 5:
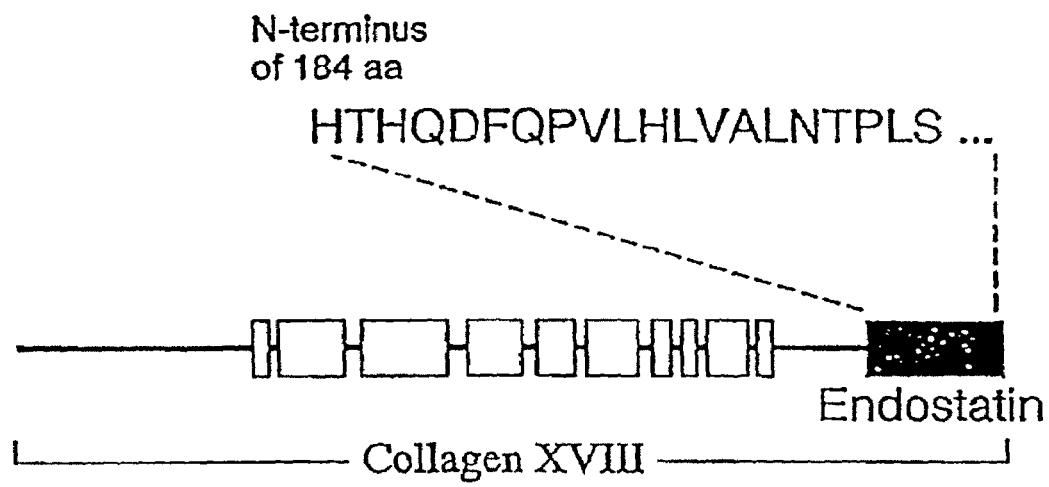

FIG. 5: N-terminal Amino Acid Sequence of An Inhibitor of Endothelial Cell Proliferation.

The N-terminal sequence of the purified inhibitor of endothelial cell proliferation is shown in relation to a schematic diagram of collagen type 18. The N-terminal sequence revealed identity of the inhibitor to an approximately 20 kDa C-terminal fragment (shown in solid shading) for collagen type XVIII. The open boxes represent the collagenase domains of collagen type XVIII.

Figure 6:
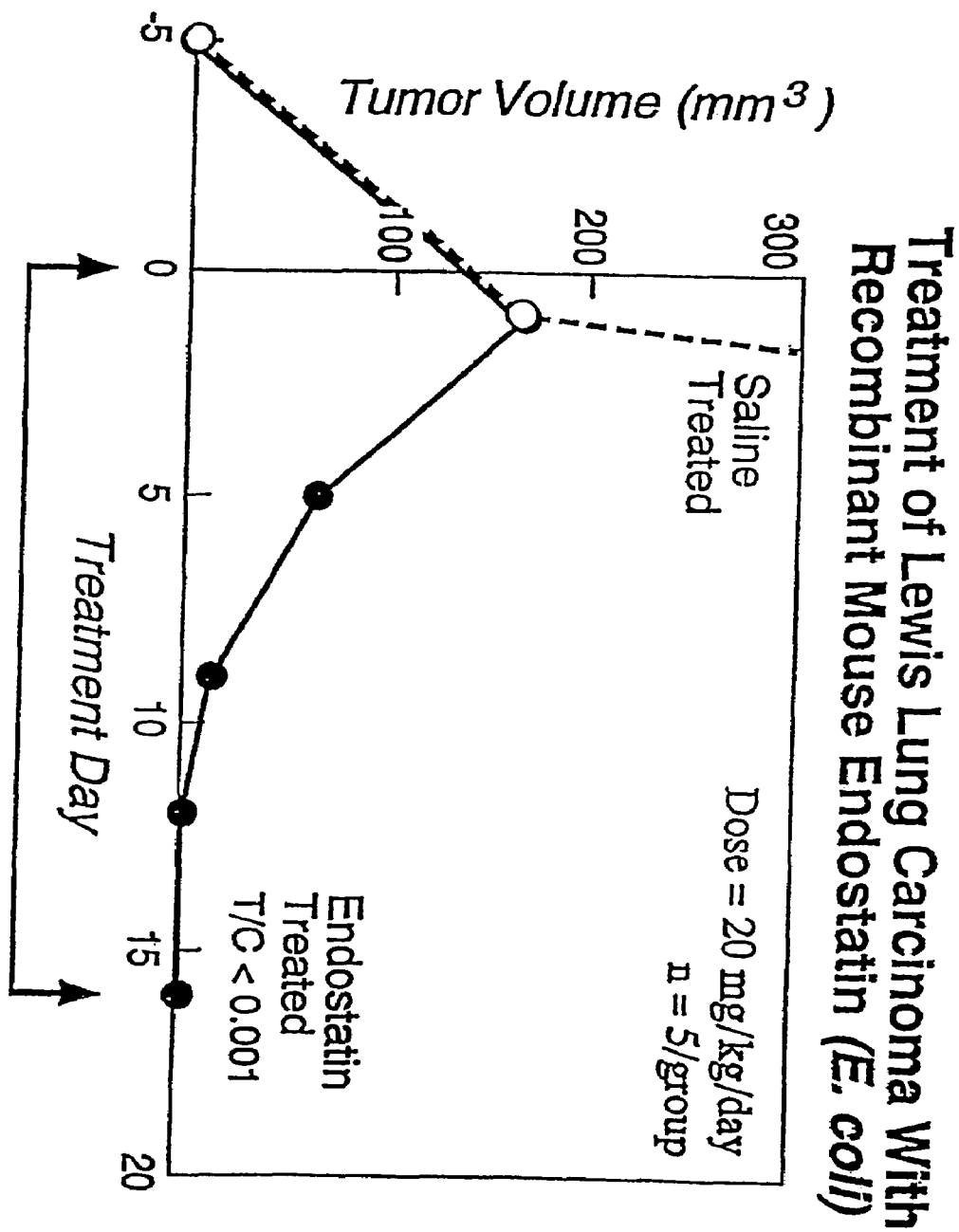

FIG. 6: Treatment of Lewis Lung Carcinoma With Recombinant Mouse Endostatin Inhibitor.

Recombinant inhibitor produced in *E. coli* was administered to mice seeded with Lewis lung carcinoma that had achieved a tumor volume of approximately 150 mm$^3$. The inhibitor was administered at 20 mg/kg/day. Tumor mass regressed to non-detectable levels after approximately 12 days of treatment.

FIG. 7A-C: Systemic Therapy with Recombinant Endostatin Regresses Lewis Lung Carcinoma Primary Tumors.

FIG. 7A. Mice were implanted subcutaneously on the dorsum with Lewis lung carcinoma cells. Systemic therapy with recombinant mouse endostatin (20 mg/kg/day) was begun when tumors were approximately 200 mm$^3$ (1% of body weight). Tumors in the mice treated with endostatin inhibitor rapidly regressed and were inhibited by >99% relative to saline-treated controls. Each point represents mean±SEM for 5 mice. The experiment was repeated with comparable results.

FIG. 7B. Representative treated and untreated tumor-bearing mice after 11 days of systemic therapy with endostatin. Saline-treated mice (right) had rapidly growing red tumors with ulcerated surfaces. Endostatin treated mice (left) had small pale residual tumors (arrow).

FIG. 7C. Residual disease in endostatin treated mice. Three of the five endostatin treated mice were sacrificed after 16 days of therapy. Autopsy revealed small white residual tumors at the site of the original primary implantation (arrows).

Figure 8:
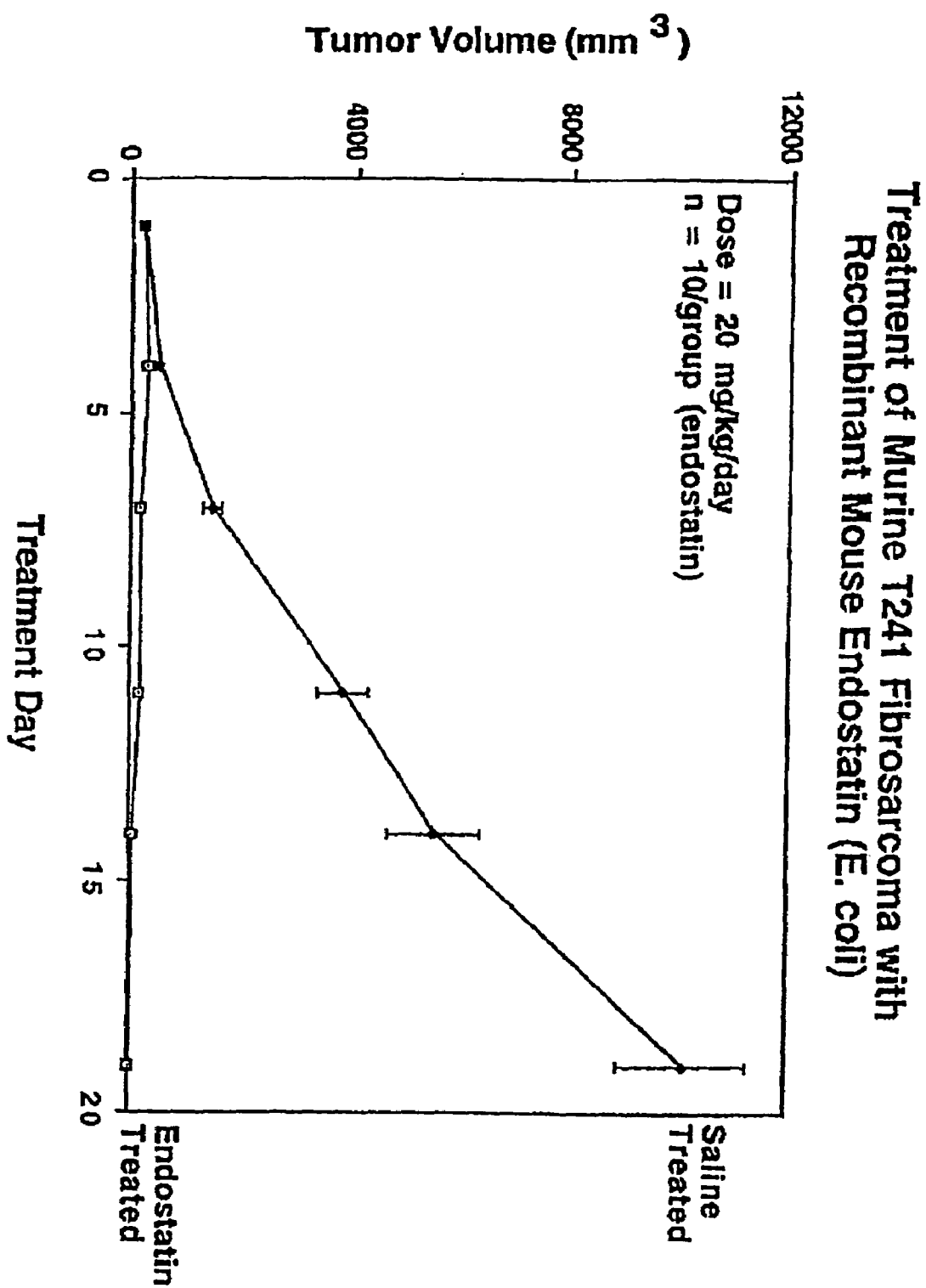

FIG. 8: Treatment of Murine T241 Fibrosarcoma with Recombinant Mouse Endostatin from *E. coli*

Mice were seated with T241 Fibrosarcoma cells. Control mice were treated with saline. Experimental mice were treated with 20 mg/kg/day of recombinant mouse Endostatin directed from *E. coli*.

Figure 9:
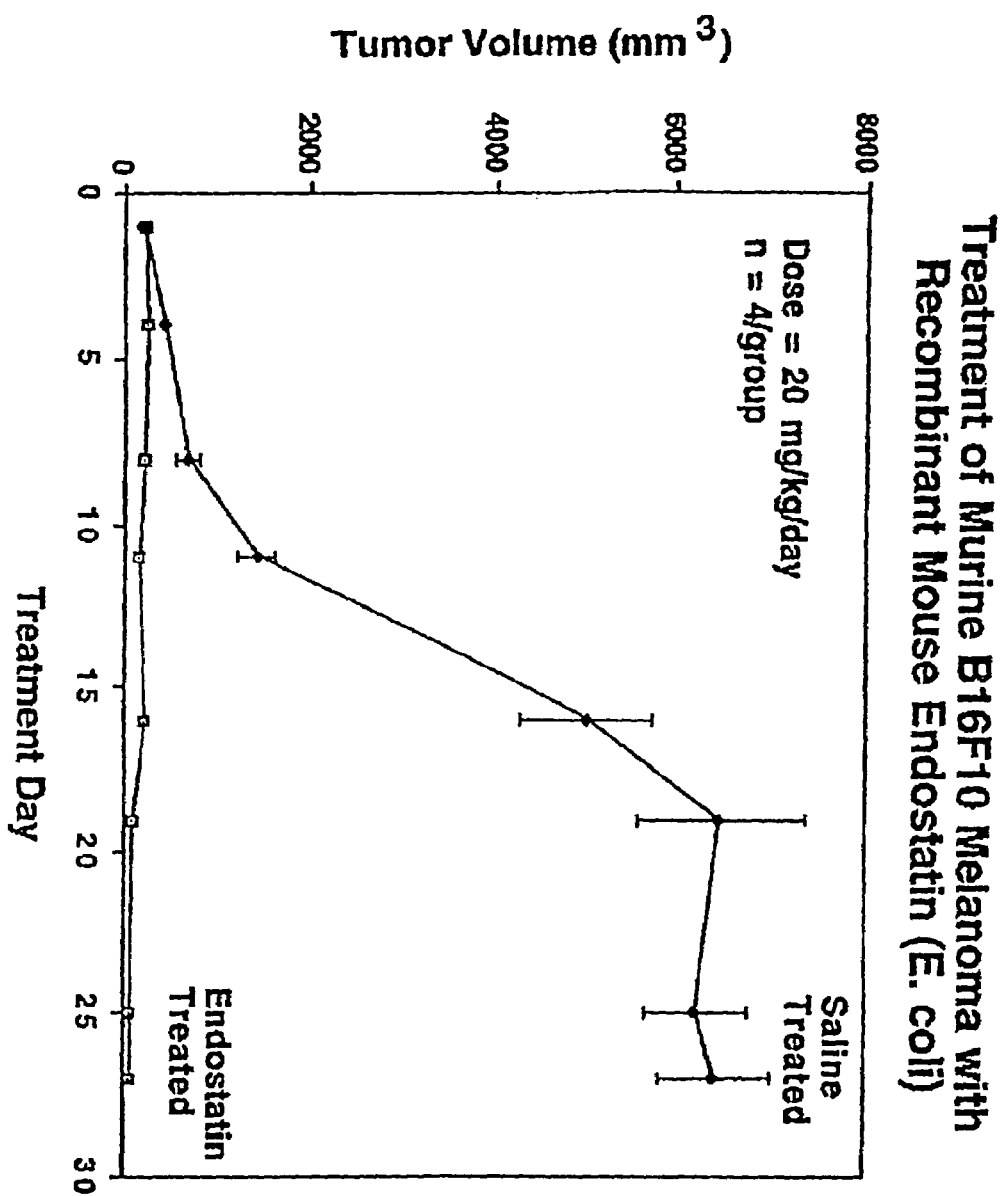

FIG. 9: Treatment of Murine B16F10 Melanoma with Recombinant Mouse Endostatin from *E. coli*

Mice were seated with Murine B16F10 melanoma cells. Control animals were treated with saline. Experimental animals were treated with 20 mg/kg/day of recombinant mouse Endostatin direct from *E. coli*.

Figure 10:
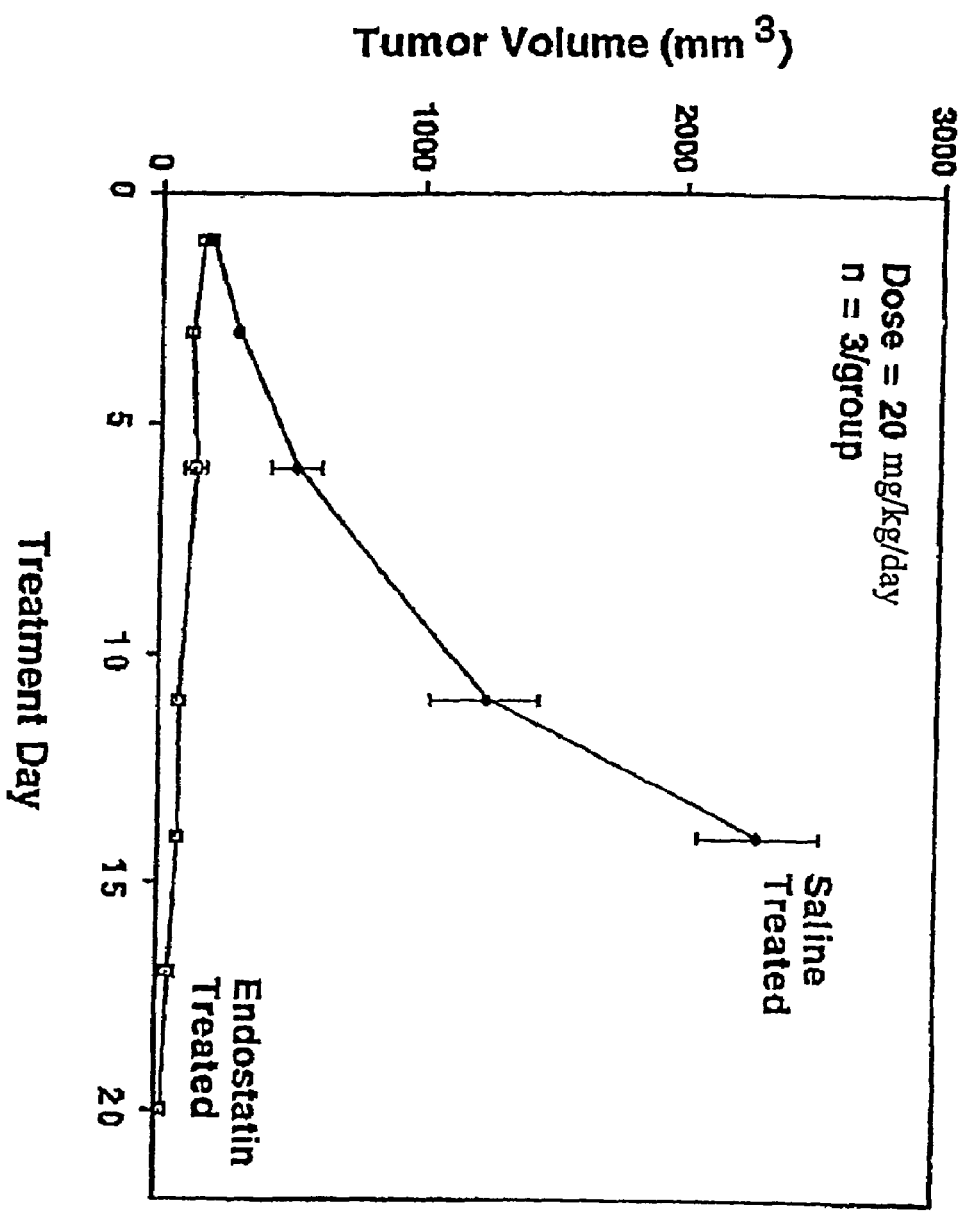

FIG. 10: Treatment of EOMA Hemangioendothelioma with Recombinant Mouse Endostatin from *E. coli*

Mice were seated with EOMA hemangioendothelioma cells. Control animals were treated with saline. Experimental animals were treated with 20 mg/kg/day of Recombinant Mouse Endostatin direct from *E. coli*.

Figure 11:
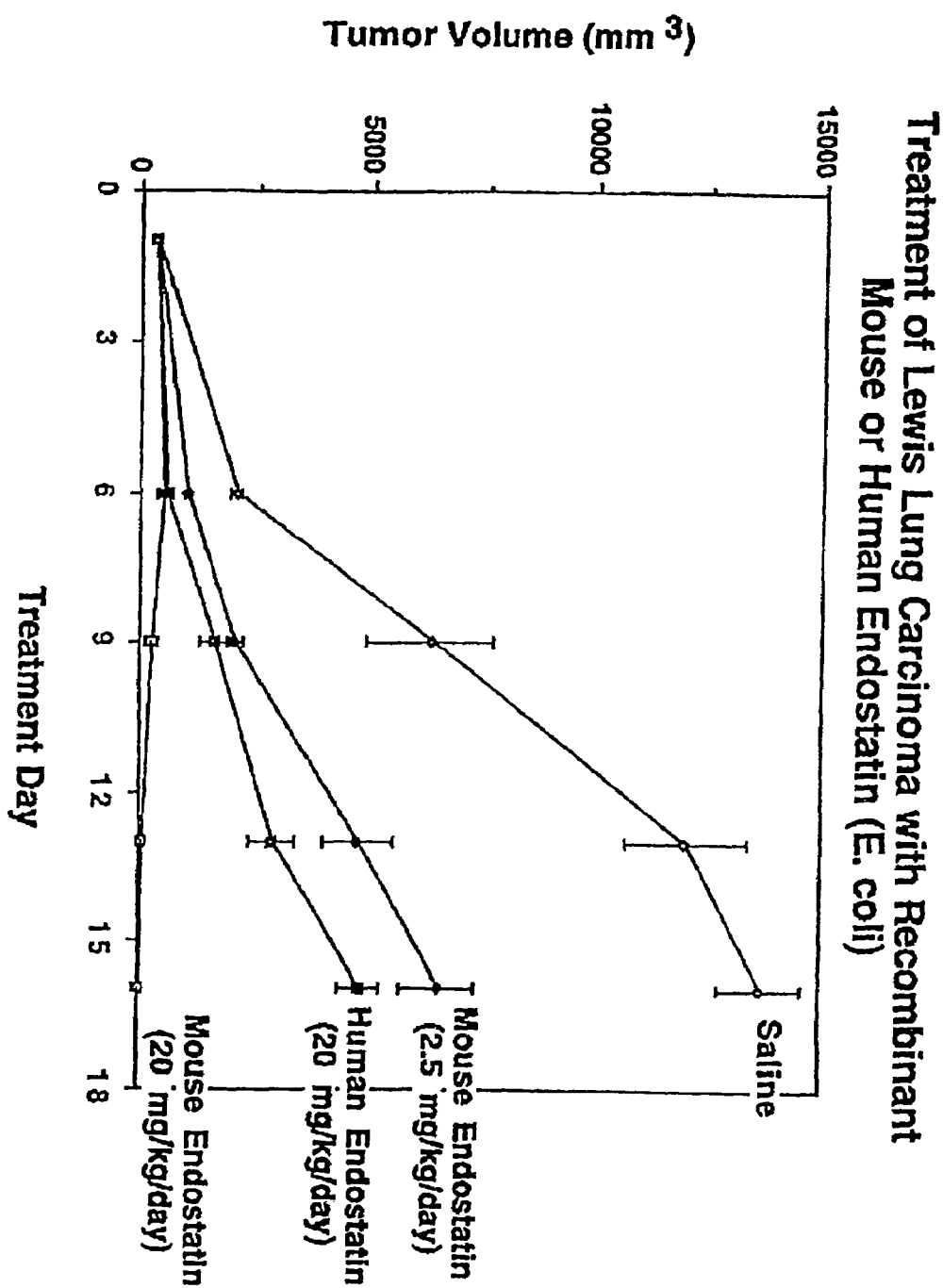

FIG. 11: Treatment of Lewis Lung Carcinoma with Recombinant Mouse or Human Endostatin direct from *E. coli*.

Mice were seated with Lewis Lung Carcinoma cells. Control animals were treated with saline. Experimental animals were treated with Recombinant Endostatin derived from the mouse sequence or Recombinant Endostatin direct from the human sequence, wherein both Endostatins were produced recombinantly in the *E. coli*. Mouse Endostatin was administered at either 20 mg/kg/day or 2.5 mg/kg/day, and Human Endostatin was administered at 20 mg/kg/day.

Figures 12A, 12B, 12C:
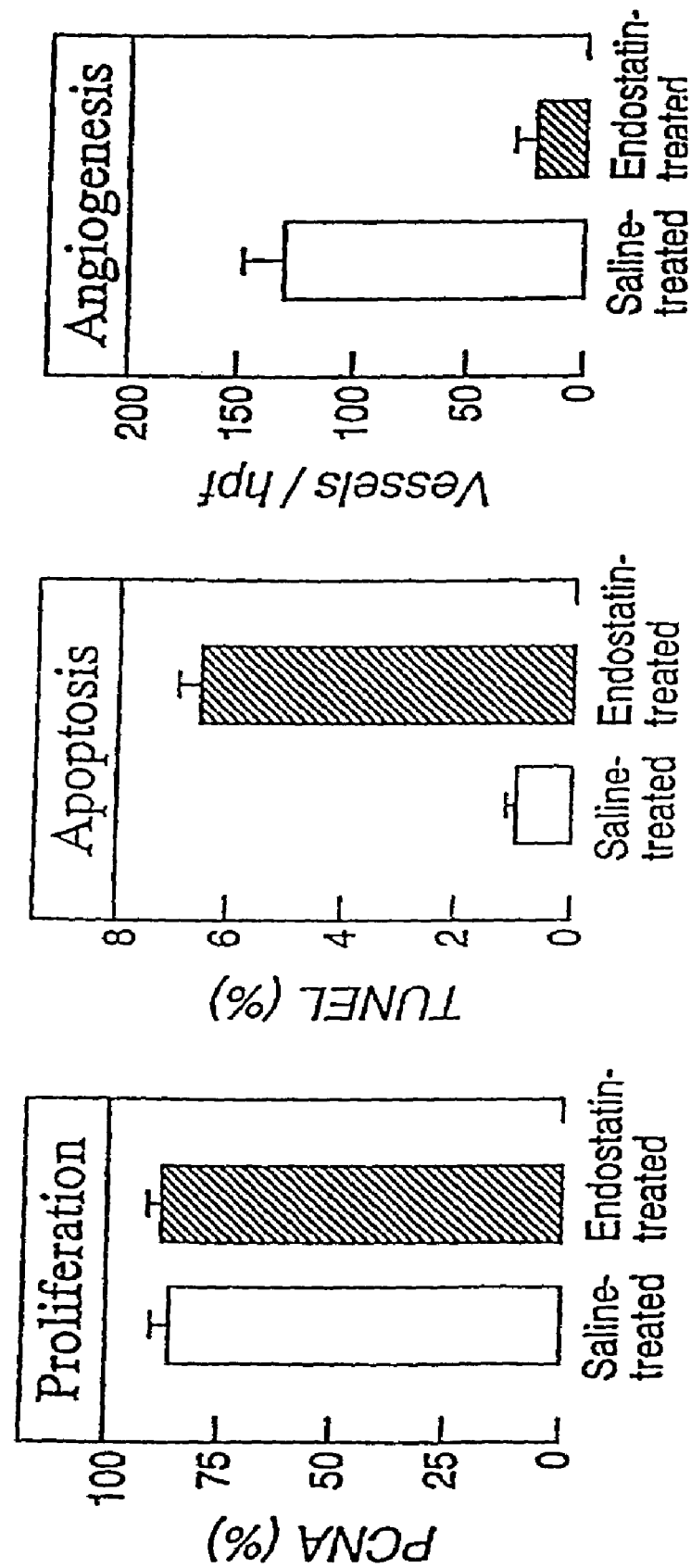

FIG. 12A-C: Endostatin Results in an Inhibition of Angiogenesis and an Increase in Apoptosis of Lewis Lung Carcinoma Primary Tumors.

Histological sections of tumors from saline versus endostatin treated mice implanted with Lewis lung carcinomas were analyzed for proliferation (PCNA), apoptosis (TUNEL), and angiogenesis (vWF). There was no significant difference in the proliferative index of tumor cells (FIG. 12A) in treated versus untreated tumors. In contrast, the apoptotic index of the tumor cells (FIG. 12B) increased 8-fold (p<0.001) in the endostatin treated mice. Vessel density (FIG. 12C) was determined by counting the number of capillary blood vessels per high-power field (HPF) in sections stained with antibodies against vWF. Angiogenesis was almost completely suppressed in the residual microscopic tumors of the endostatin treated mice (p<0.001).

Figure 13:
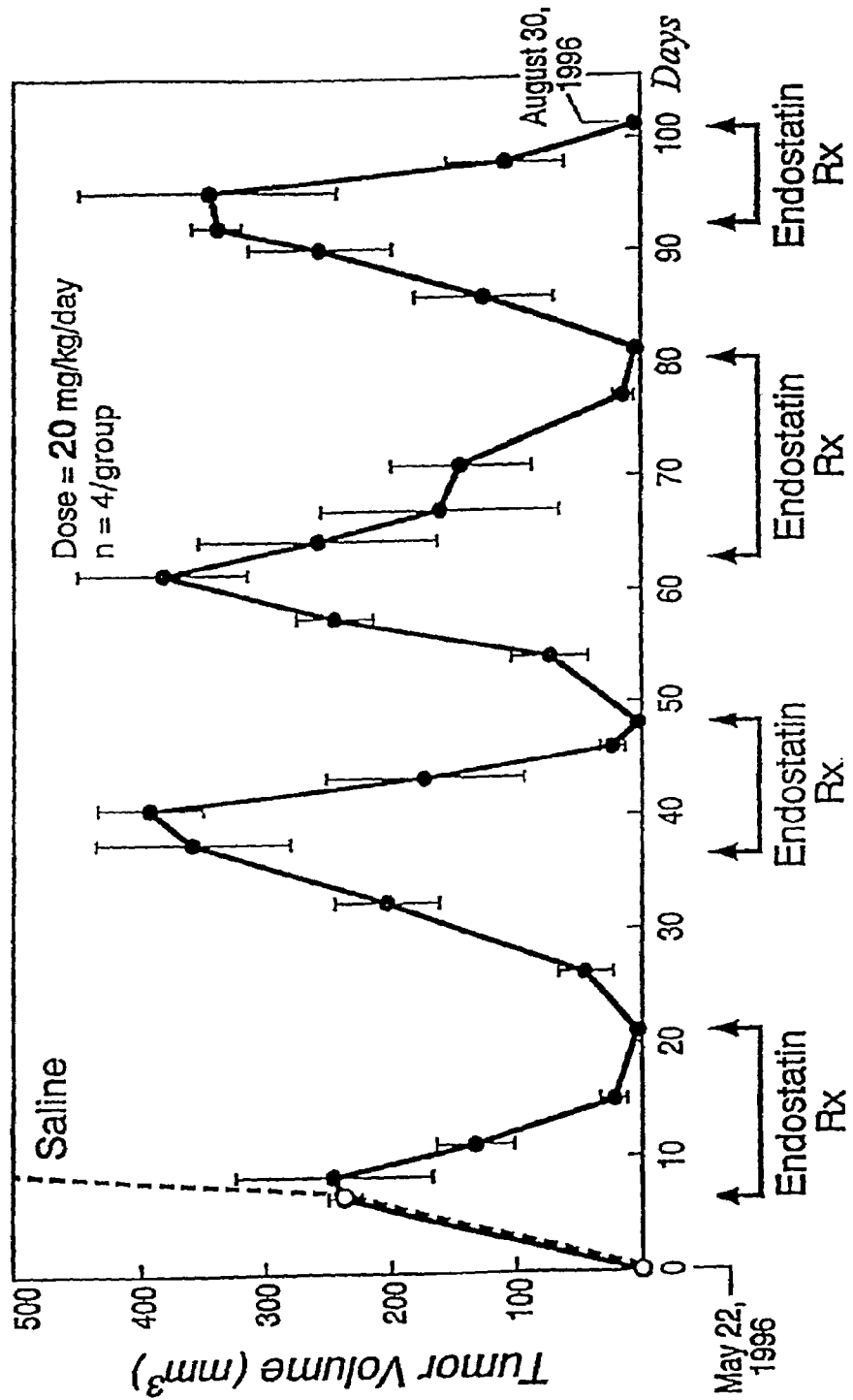

FIG. 13: Cycle Dormancy Therapy of Lewis Lung Carcinoma with Recombinant Mouse Endostatin From *E. Coli*.

Mice were implanted subcutaneously on the dorsum with Lewis lung carcinoma cells. Systemic therapy with recombinant mouse inhibitor (endostatin), administered at a dose of 20 mg/kg/day, was begun when tumors were approximately 200 mm$^3$ (1% of body weight). Tumors in the mice treated with the endostatin inhibitor rapidly regressed to essentially non-detectable levels after approximately 15 days of therapy. When treatment was terminated the tumor volume increased rapidly and was subsequently treatable to the same non-detectable levels by re-initiation of treatment. The peaks and valleys in the figure show the cycling effect of inhibition with endostatin.

Figure 14:
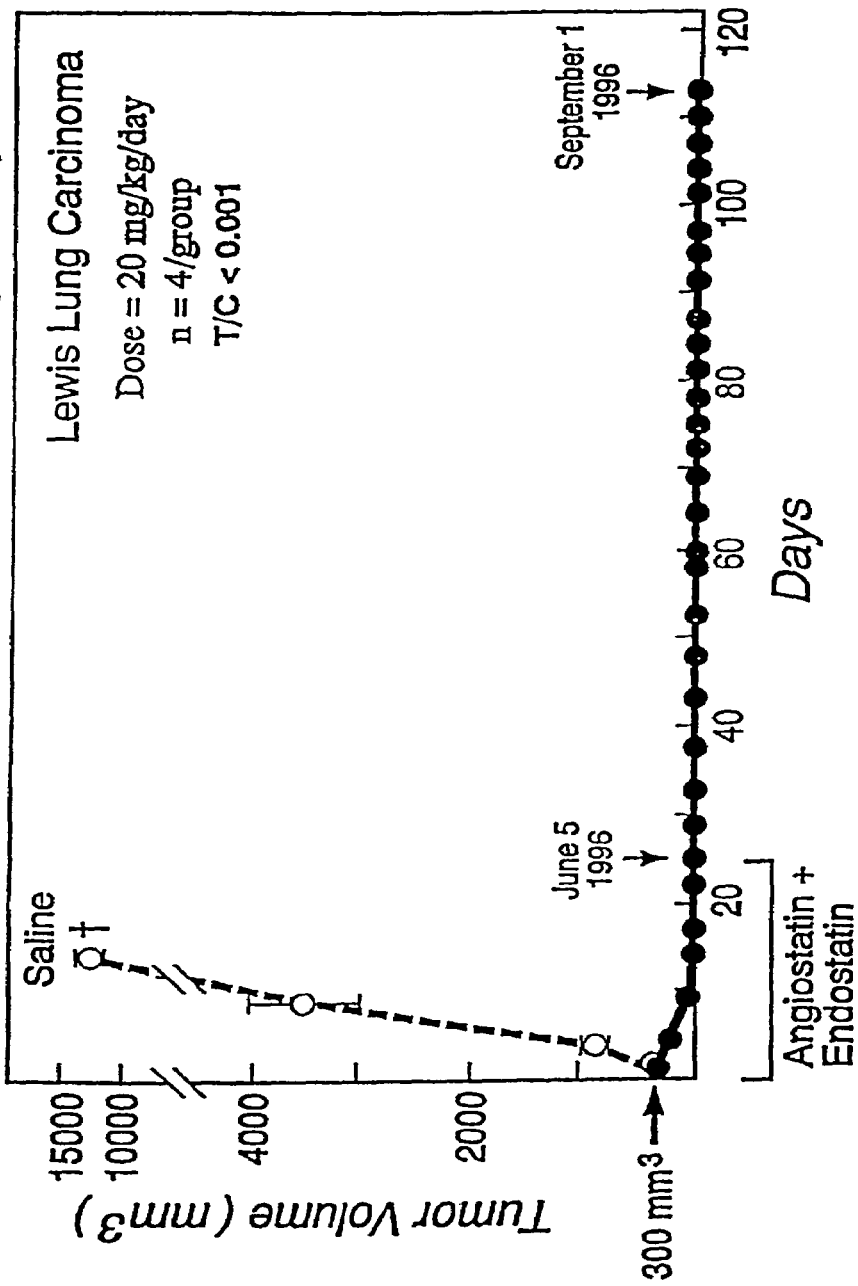

FIG. 14: Combination Therapy with Recombinant Mouse Angiostatin and Endostatin from *E. Coli*.

Mice were implanted subcutaneously on the dorsum with Lewis lung carcinoma cells. Systemic therapy with a combination of recombinant mouse endostatin (20 mg/kg/day) and recombinant mouse angiostatin (20 mg/kg/day) was begun when tumors were approximately 300 mm$^3$. Tumors in the mice treated with the combination therapy rapidly regressed to essentially non-detectable levels in about 15 days. Importantly, the regressed tumors remained dormant and did not increase in size or mass after treatment was stopped. This is an unexpected result of substantial medical significance.

DETAILED DESCRIPTION OF THE INVENTION

Applicants have discovered a new class of protein molecules that have the ability to inhibit endothelial proliferation when added to proliferating endothelial cells in vitro. Accordingly, these protein molecules have been functionally defined as endostatins, however, it is to be understood that this functional definition is no way limits the bioactivity of endostatins to inhibition of endothelial cell growth in vitro or in vivo. Many other functions of endostatins are likely.

The term "endostatin" refers to a protein that is preferably 18 kDa to 20 kDa in size as determined by non-reduced and reduced gel electrophoresis, respectively. The term endostatin also includes precursor forms of the 18 kDa to 20 kDa protein. The term endostatin also includes fragments of the 18 kDa to 20 kDa protein and modified proteins and peptides that have a substantially similar amino acid sequence, and which are capable inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "endostatin" includes shortened proteins or peptides wherein one or more amino acid is removed from either or both ends of endostatin, or from an internal region of the protein, yet the resulting molecule retains endothelial proliferation inhibiting activity. The term "endostatin" also includes lengthened proteins or peptides wherein one or more amino acid is added to either or both ends of endostatin, or to an internal location in the protein, yet the resulting molecule retains endothelial proliferation inhibiting activity. For example, molecules with tyrosine added in the first position can be labeled with $^{125}$iodine for use in assays. Labeling with other radioisotopes may be useful in providing a molecular tool for destroying the target cell containing endostatin receptors. Other labeling with molecules such as ricin may provide a mechanism for destroying cells with endostatin receptors.

"Substantial sequence homology" means at least approximately 70% homology between amino acid residue sequence in the endostatin analog sequence and that of endostatin, preferably at least approximately 80% homology, more preferably at least approximately 90% homology.

Also included in the definition of the term endostatin are modifications of the endostatin protein, its subunits and peptide fragments. Such modifications include substitutions of naturally occurring amino acids at specific sites with other molecules, including but not limited to naturally and non-naturally occurring amino acids. Such substitutions may modify the bioactivity of endostatin and produce biological or pharmacological agonists or antagonists. The term endostatin also includes an N-terminal fragment of endostatin consisting of the sequence of the first 20 N-terminal amino acids which is shown in SEQ ID NO:1 and is shown in Table 1. This sequence of the first 20 N-terminal amino acids corresponds to a C-terminal fragment of newly identified collagen type XVIII.

Table 1 shows the correspondence of 3 letter and 1 letter amino acid designations.

TABLE 1

| Amino Acid | Residue | Abbreviation |
|---|---|---|
| 1 | HIS | H |
| 2 | THR | T |
| 3 | HIS | H |
| 4 | GLN | Q |
| 5 | ASP | D |
| 6 | PHE | F |
| 7 | GLN | Q |
| 8 | PRO | P |
| 9 | VAL | V |
| 10 | LEU | L |
| 11 | HIS | H |
| 12 | LEU | L |
| 13 | VAL | V |
| 14 | ALA | A |
| 15 | LEU | L |
| 16 | ASN | N |
| 17 | THR | T |
| 18 | PRO | P |
| 19 | LEU | L |
| 20 | SER | S |

The N-terminal amino acid sequence of endostatin corresponds to an internal 20 amino acid peptide fragment found in mouse collagen alpha 1 type XVIII starting at amino acid 1105 and ending at amino acid 1124. The N-terminal amino acid sequence of the inhibitor also corresponds to an internal 20 amino acid peptide fragment found in human collagen alpha 1 type XVIII starting at amino acid 1132 and ending at amino acid 1151.

Endostatin can be isolated from murine hemangioendothelioma EOMA. Endostatin may be produced from recombinant sources, from genetically altered cells implanted into animals, from tumors, and from cell cultures as well as other sources. It is anticipated that endostatin is made in cells of the nervous system. Endostatin can be isolated from body fluids including, but not limited to, serum, urine and ascites, or synthesized by chemical or biological methods (e.g. cell culture, recombinant gene expression, peptide synthesis, and in vitro enzymatic catalysis of precursor molecules to yield active endostatin). Recombinant techniques include gene amplification from DNA sources using the polymerase chain reaction (PCR), and gene amplification from RNA sources using reverse transcriptase/PCR.

Endostatin specifically and reversibly inhibits endothelial cell proliferation. The inhibitor protein molecules of the invention are useful as a birth control drug, and for treating angiogenesis-related diseases, particularly angiogenesis-dependent cancers and tumors. The protein molecules are also useful for curing angiogenesis-dependent cancers and tumors. The unexpected and surprising ability of these novel compounds to treat and cure angiogenesis-dependent cancers and tumors answers a long felt unfulfilled need in the medical arts, and provides an important benefit to mankind.

Important terms that are used herein are defined as follows. "Cancer" means angiogenesis-dependent cancers and tumors, i.e. tumors that require for their growth (expansion in volume and/or mass) an increase in the number and density of the blood vessels supplying them with blood. "Regression" refers to the reduction of tumor mass and size.

The endothelial proliferation inhibiting proteins of the present invention can be made by automated protein synthesis methodologies-well known to one skilled in the art. Alternatively, endothelial proliferation inhibiting proteins, or endostatins, of the present invention may be isolated from larger known proteins, such as human alpha 1 type XVIII collagen and mouse alpha 1 type XVIII collagen, proteins that share a common or similar N-terminal amino acid sequence. Examples of other potential endostatin source materials having similar N-terminal amino acid sequences include *Bos taurus* pregastric esterase, human alpha 1 type 15 collagen, NAD-dependent formate dehydrogenase (EC 1.2.1.2) derived from *Pseudomonas* sp., s11459 hexon protein of bovine adenovirus type 3, CELF21D12 2 F21d12.3 *Caenorhabditis elegans* gene product, VAL1 TGMV AL1 protein derived from tomato golden mosaic virus, s01730 hexon protein derived from human adenovirus 12, *Saccharomyces cerevisiae*. For example, peptides closely related to endostatin may be derived from BOVMPE 1 pregastric esterase (*BOS TAURUS*) gene sequence corresponding to amino acids 502 to 521, and collagen alpha 1 type 15 from humans beginning at amino acid 316 ending at 335.

Proteins and peptides derived from these and other sources, including manual or automated protein synthesis, may be quickly and easily tested for endothelial proliferation inhibiting activity using a biological activity assay such as the bovine capillary endothelial cell proliferation assay. Other bioassays for inhibiting activity include the chick CAM assay, the mouse corneal assay, and the effect of administering isolated or synthesized proteins on implanted tumors. The chick CAM assay is described by O'Reilly, et al. in "Angiogenic Regulation of Metastatic Growth" *Cell*, vol. 79 (2), Oct. 21, 1994, pp. 315-328, which is hereby incorporated by reference in its entirety. Briefly, 3 day old chicken embryos with intact yolks are separated from the egg and placed in a petri dish. After 3 days of incubation, a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Applicants' invention also encompasses nucleic acid sequences that correspond to and code for the endothelial proliferation-inhibiting protein molecules of the invention, and to monoclonal and polyclonal antibodies that bind specifically to such protein molecules. The biologically active protein molecules, nucleic acid sequences corresponding to the proteins, and antibodies that bind specifically to the proteins of the present invention are useful for modulating endothelial processes in vivo, and for diagnosing and treating endothelial cell-related diseases, for example by gene therapy.

Nucleic acid sequences that correspond to, and code for, endostatin and endostatin analogs can be prepared based upon the knowledge of the amino acid sequence, and the art recognized correspondence between codons (sequences of three nucleic acid bases), and amino acids. Because of the degeneracy of the genetic code, wherein the third base in a codon may vary yet still code for the same amino acid, many different possible coding nucleic acid sequences are derivable for any particular protein or peptide fragment.

Nucleic acid sequences are synthesized using automated systems well known in the art. Either the entire sequence may be synthesized or a series of smaller oligonucleotides are made and subsequently ligated together to yield the full length sequence. Alternatively, the nucleic acid sequence may be derived from a gene bank using oligonucleotides probes designed based on the N-terminal amino acid sequence and well known techniques for cloning genetic material.

The present invention also includes the detection of endostatin in body fluids and tissues for the purpose of diagnosis or prognosis of angiogenesis-mediated diseases such as cancer. The present invention also includes the detection of endostatin binding sites and receptors in cells and tissues. The present invention also includes methods of treating or preventing angiogenic diseases and processes including, but not limited to, arthritis and tumors by stimulating the production of endostatin, and/or by administering substantially purified endostatin, or endostatin agonists or antagonists, and/or endostatin antisera or antisera directed against endostatin antisera to a patient. Additional treatment methods include administration of endostatin, endostatin fragments, endostatin antisera, or endostatin receptor agonists and antagonists linked to cytotoxic agents. It is to be understood that the endostatin can be animal or human in origin. Endostatin can also be produced synthetically by chemical reaction or by recombinant techniques in conjunction with expression systems. Endostatin can also be produced by enzymatically cleaving different molecules, including endostatin precursors, containing sequence homology or identity with segments of endostatin to generate peptides having anti-angiogenesis activity.

Passive antibody therapy using antibodies that specifically bind endostatin can be employed to modulate endothelial-dependent processes such as reproduction, development, and wound healing and tissue repair. In addition, antisera directed to the Fab regions of endostatin antibodies can be administered to block the ability of endogenous endostatin antisera to bind endostatin.

Antibodies specific for endostatin and endostatin analogs are made according to techniques and protocols well known in the art. The antibodies may be either polyclonal or monoclonal. The antibodies are utilized in well know immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva, and mucus.

The proteins, nucleic acid sequences and antibodies of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention. Angiogenesis-related diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helobacter pylori*).

The endothelial cell proliferation inhibiting proteins can be used as a birth control agent by reducing or preventing uterine vascularization required for embryo implantation. Thus, the present invention provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possibly a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that endostatin administration will interfere with normal enhanced vascularization of the placenta, and also with the development of vessels within a successfully implanted blastocyst and developing embryo and fetus.

Conversely, blockade of endostatin receptors with endostatin analogs that act as receptor antagonists may promote endothelialization and vascularization. Such effects may be desirable in situations of inadequate vascularization of the uterine endometrium and associated infertility, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

A surprising discovery is that un-refolded and non-soluble recombinant endostatin is also a potent anti-angiogenesis compound which serves as a sustained release depot when administered to a patient.

The present invention also relates to methods of using endostatin and endothelial cell proliferation inhibiting peptide fragments of endostatin, nucleic acid sequences corresponding to endostatin and active peptide fragments thereof, and antibodies that bind specifically to endostatin and its peptides, to diagnose endothelial cell-related diseases and disorders.

The invention further encompasses a method for identifying endostatin-specific receptors, and the receptor molecules identified and isolated thereby.

The present invention also provides a method for quantitation of endostatin receptors.

A particularly important aspect of the present invention is the discovery of a novel and effective method for treating and curing angiogenesis-dependent cancer in patients. It was unexpectedly found that the co-administration of endostatin and angiostatin in an amount sufficient to inhibit tumor growth and cause sustainable regression of tumor mass to microscopic size cures angiogenesis-dependent cancer. Accordingly, the present invention also includes formulations effective for treating or curing angiogenesis-dependent cancers and tumors.

More particularly, recombinant mouse endostatin, from insect cells or *E. coli*, potently inhibits angiogenesis and the growth of metastases and primary tumors. In a novel method of sustained release, the *E. coli*-derived recombinant endostatin was administered as an un-refolded suspension in an amount sufficient to inhibit angiogenesis, thereby inhibiting tumor growth. Tumor mass was reduced when recombinant endostatin was administered in an amount sufficient to cause regression of the tumor. Primary tumors of 1-2% of body weight regressed by greater than 150-fold to become microscopic dormant lesions when treated by endostatin. Immunohistochemical analysis of the dormant tumors revealed blocked angiogenesis accompanied by high proliferation of the tumor cells balanced by a high rate of tumor cell apoptosis. There was no evidence of toxicity in any of the mice treated with endostatin.

It is contemplated as part of the present invention that endostatin can be isolated from a body fluid such as blood or urine of patients or the endostatin can be produced by recombinant DNA methods or synthetic peptide chemical methods that are well known to those of ordinary skill in the art. Protein purification methods are well known in the art and a specific example of a method for purifying endostatin, and assaying for inhibitor activity is provided in the examples below. Isolation of human endogenous endostatin is accomplished using similar techniques.

One example of a method of producing endostatin using recombinant DNA techniques entails the steps of (1) identifying and purifying an endostatin as discussed above, and as more fully described below, (2) determining the N-terminal amino acid sequence of the purified inhibitor, (3) synthetically generating a DNA oligonucleotide probe that corresponds to the N-terminal amino acid sequence, (4) generating a DNA gene bank from human or other mammalian DNA, (5) probing the gene bank with the DNA oligonucleotide probe, (6) selecting clones that hybridize to the oligonucleotide, (7) isolating the inhibitor gene from the clone, (8) inserting the gene into an appropriate vector such as an expression vector, (9) inserting the gene-containing vector into a microorganism or other expression system capable of expressing the inhibitor gene, and (10) isolating the recombinantly produced inhibitor. The above techniques are more fully described in laboratory manuals such as "Molecular Cloning: A Laboratory Manual" Second Edition by Sambrook et al., Cold Spring Harbor Press, 1989.

The gene for endostatin may also be isolated from cells or tissue (such as tumor cells) that express high levels of endostatin by (1) isolating messenger RNA from the tissue, (2) using reverse transcriptase to generate the corresponding DNA sequence and then (3) using PCR with the appropriate primers to amplify the DNA sequence coding for the active endostatin amino acid sequence.

Yet another method of producing endostatin, or biologically active fragments thereof, is by peptide synthesis. Once a biologically active fragment of an endostatin is found using the assay system described more fully below, it can be sequenced, for example by automated peptide sequencing methods. Alternatively, once the gene or DNA sequence which codes for endostatin is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, for example the N-terminal 20 amino acids, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for agonistic and antagonistic activity in vitro and in vivo. Peptide fragments that possess high affinity binding to tissues can be used to isolate the endostatin receptor on affinity columns. Isolation and purification of the endostatin receptor is a fundamental step towards elucidating the mechanism of action of endostatin. This isolation facilitates development of drugs to modulate the activity of the endostatin receptor, the final pathway to biological activity. Isolation of the receptor enables the construction of nucleotide probes to monitor the location and synthesis of the receptor, using in situ and solution hybridization technology.

Endostatin is effective in treating diseases or processes that are mediated by, or involve, angiogenesis. The present invention includes the method of treating an angiogenesis mediated disease with an effective amount of endostatin or endostatin agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Endostatin is useful in the treatment of disease of excessive or abnormal stimulation of endothelial cells. These diseases include, but are not limited to, intestinal adhesions, atherosclerosis, scleroderma, and hypertrophic scars, i.e., keloids. Endostatin can be used as a birth control agent by preventing vascularization required for blastocyst implantation and for development of the placenta, the blastocyst, the embryo and the fetus.

The synthetic peptide fragments of endostatin have a variety of uses. The peptide that binds to the endostatin receptor with high specificity and avidity is radiolabeled and employed for visualization and quantitation of binding sites using autoradiographic and membrane binding techniques. This application provides important diagnostic and research tools. Knowledge of the binding properties of the endostatin receptor facilitates investigation of the transduction mechanisms linked to the receptor.

In addition, labeling these peptides with short lived isotopes enables visualization of receptor binding sites in vivo using positron emission tomography or other modern radiographic techniques in order to locate tumors with endostatin binding sites.

Systematic substitution of amino acids within these synthesized peptides yields high affinity peptide agonists and antagonists to the endostatin receptor that enhance or diminish endostatin binding to its receptor. Such agonists are used to suppress the growth of micrometastases, thereby limiting the spread of cancer. Antagonists to endostatin are applied in situations of inadequate vascularization, to block the inhibitory effects of angiostatin and possibly promote angiogenesis. This treatment may have therapeutic effects to promote wound healing in diabetics.

Endostatin peptides are employed to develop affinity columns for isolation of the endostatin receptor from cultured tumor cells. Isolation and purification of the endostatin receptor is followed by amino acid sequencing. Next, nucleotide probes are developed for insertion into vectors for expression of the receptor. These techniques are well known to those skilled in the art. Transfection of the endostatin receptor into tumor cells enhances the responsiveness of these cells to endogenous or exogenous endostatin and thereby decrease the rate of metastatic growth.

Cytotoxic agents, such as ricin, are linked to endostatin, and high affinity endostatin peptide fragments, thereby providing a tool for destruction of cells that bind endostatin. These cells may be found in many locations, including but not limited to, micrometastases and primary tumors. Peptides linked to cytotoxic agents are infused in a manner designed to maximize delivery to the desired location. For example, ricin-linked high affinity endostatin fragments are delivered through a cannula into vessels supplying the target site or directly into the target. Such agents are also delivered in a controlled manner through osmotic pumps coupled to infusion cannulae. A combination of endostatin antagonists may be co-applied with stimulators of angiogenesis to increase vascularization of tissue. This therapeutic regimen provides an effective means of destroying metastatic cancer.

According to the present invention, endostatin may be used in combination with other compositions and procedures for the treatment of diseases. For example, a tumor may be treated conventionally with surgery, radiation or chemotherapy combined with endostatin and then endostatin may be subsequently administered to the patient to extend the dormancy of micrometastases and to stabilize any residual primary tumor.

The endostatin of the present invention also can be used to generate antibodies that are specific for the inhibitor. The antibodies can be either polyclonal antibodies or monoclonal antibodies. These antibodies that specifically bind to the endostatin can be used in diagnostic methods and kits that are well known to those of ordinary skill in the art to detect or quantify the endostatin in a body fluid or tissue. Results from these tests can be used to diagnose or predict the occurrence or recurrence of a cancer and other angiogenesis mediated diseases.

The endostatin also can be used in a diagnostic method and kit to detect and quantify antibodies capable of binding endostatin. These kits would permit detection of circulating endostatin antibodies which indicates the spread of micrometastases in the presence of endostatin secreted by primary tumors in situ. Patients that have such circulating anti-endostatin antibodies may be more likely to develop tumors and cancers, and may be more likely to have recurrences of cancer after treatments or periods of remission. The Fab fragments of these anti-endostatin antibodies may be used as antigens to generate anti-endostatin Fab-fragment antisera which can be used to neutralize the removal of circulating endostatin by anti-endostatin antibodies.

Another aspect of the present invention is a method of blocking the action of excess endogenous endostatin. This can be done by passively immunizing a human or animal with antibodies specific for the undesired endostatin in the system. This treatment can be important in treating abnormal ovulation, menstruation and placentation, and vasculogenesis. This provides a useful tool to examine the effects of endostatin removal on metastatic processes. The Fab fragment of endostatin antibodies contains the binding site for endostatin. This fragment is isolated from endostatin antibodies using techniques known to those skilled in the art. The Fab fragments of endostatin antisera are used as antigens to generate production of anti-Fab fragment serum. Infusion of this antiserum against the Fab fragments of endostatin prevents endostatin from binding to endostatin antibodies. Therapeutic benefit is obtained by neutralizing endogenous anti-endostatin antibodies by blocking the binding of endostatin to the Fab fragments of anti-endostatin. The net effect of this treatment is to facilitate the ability of endogenous circulating endostatin to reach target cells, thereby decreasing the spread of metastases.

It is to be understood that the present invention is contemplated to include any derivatives of the endostatin that have endothelial inhibitory activity. The present invention includes the entire endostatin protein, derivatives of the endostatin protein and biologically-active fragments of the endostatin protein. These include proteins with endostatin activity that have amino acid substitutions or have sugars or other molecules attached to amino acid functional groups. The present invention also includes genes that code for endostatin and the endostatin receptor, and to proteins that are expressed by those genes.

The proteins and protein fragments with the endostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the endostatin may be incorporated into biodegradable polymers allowing for sustained release of the compound, the polymers being implanted in the vicinity of where drug delivery is desired, for example, at the site of a tumor or implanted so that the endostatin is slowly released systemically. Osmotic minipumps may also be used to provide controlled delivery of high concentrations of endostatin through cannulae to the site of interest, such as directly into a metastatic growth or into the vascular supply to that tumor. The biodegradable polymers and their use are described, for example, in detail in Brem et al., J. Neurosurg. 74:441-446 (1991), which is hereby incorporated by reference in its entirety.

The dosage of the endostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the endostatin can be administered. A more preferable range is 1 mg/kilogram to 100 mg/kilogram with the most preferable range being from 2 mg/kilogram to 50 mg/kilogram. Depending upon the half-life of the endostatin in the particular animal or human, the endostatin can be administered between several times per day to once a week. It is to be understood that the present invention has application for both human and veterinary use. The methods of the present invention contemplate single as well as multiple administrations, given either simultaneously or over an extended period of time.

The endostatin formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The endostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Different peptide fragments of the intact endostatin molecule can be synthesized for use in several applications including, but not limited to the following; as antigens for the development of specific antisera, as agonists and antagonists active at endostatin binding sites, as peptides to be linked to cytotoxic agents for targeted killing of cells that bind endostatin. The amino acid sequences that comprise these peptides are selected on the basis of their position on the exterior regions of the molecule and are accessible for binding to antisera. The amino and carboxyl termini of endostatin, as well as the mid-region of the molecule are represented separately among the fragments to be synthesized. The amino terminus distal to the 20th amino acid and carboxyl termini of endostatin may contain or be modified to contain tyrosine and lysine residues and are labeled with many techniques. A tyrosine or lysine is added to fragments that do not have these residues to facilitate labeling of reactive amino and hydroxyl groups on the peptide. These peptide sequences are compared to known sequences using sequence data banks to determine potential sequence homologies. This information facilitates elimination of sequences that exhibit a high degree of sequence homology to other molecules, thereby enhancing the potential for high specificity in the development of antisera, agonists and antagonists to endostatin.

Peptides can be synthesized in a standard microchemical facility and purity checked with HPLC and mass spectrophotometry. Methods of peptide synthesis, HPLC purification and mass spectrophotometry are commonly known to those skilled in these arts.

Peptides and endostatin are also produced in recombinant E. coli, as described below, or in insect or yeast expression systems, and purified with column chromatography.

Endostatin and endostatin derived peptides can be coupled to other molecules using standard methods. The amino terminus distal to the 20th amino acid and the carboxyl terminus of endostatin may both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Endostatin peptides are chemically coupled to isotopes, enzymes, carrier proteins, cytotoxic agents, fluorescent molecules and other compounds for a variety of applications. The efficiency of the coupling reaction is determined using different techniques appropriate for the specific reaction. For example, radiolabeling of an endostatin peptide or protein with $^{125}$I is accomplished using chloramine T and Na $^{125}$I of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted Na $^{125}$I is separated from the labeled endostatin peptide. The peptide fractions with the highest specific radioactivity are stored for subsequent use such as analysis of the ability to bind to endostatin antisera.

Another application of peptide conjugation is for production of polyclonal antisera. For example, endostatin peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum against endostatin can be generated. After peptide synthesis and purification, both monoclonal and polyclonal antisera are raised using established techniques known to those skilled in the art. For example, polyclonal antisera may be raised in rabbits, sheep, goats or other animals. Endostatin peptides conjugated to a carrier molecule such as bovine serum albumin, or endostatin itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes. The serum is removed, aliquoted, and stored at 4° C. for immediate use or at −20 to −90° C. for subsequent analysis.

All serum samples from generation of polyclonal antisera or media samples from production of monoclonal antisera are analyzed for determination of titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. Endostatin peptides are coupled to the gel in the affinity column. Antiserum samples are passed through the column and anti-endostatin antibodies remain bound to the column. These antibodies are subsequently eluted, collected and evaluated for determination of titer and specificity.

The highest titer endostatin antisera is tested to establish the following; a) optimal antiserum dilution for highest specific binding of the antigen and lowest non-specific binding, b) the ability to bind increasing amounts of endostatin peptide in a standard displacement curve, c) potential cross-reactivity with related peptides and proteins, including endostatin related species, d) ability to detect endostatin peptides in extracts of plasma, urine, tissues, and in cell culture media.

Kits for measurement of endostatin are also contemplated as part of the present invention. Antisera that possess the highest titer and specificity and can detect endostatin peptides in extracts of plasma, urine, tissues, and in cell culture media are further examined to establish easy to use kits for rapid, reliable, sensitive, and specific measurement and localization of angiostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit, the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An endostatin RIA is illustrated below. After successful radioiodination and purification of endostatin or an endostatin peptide, the antiserum possessing the highest titer is added at several dilutions to tubes containing a relatively constant amount of radioactivity, such as 10,000 cpm, in a suitable buffer system. Other tubes contain buffer-or pre-immune serum to determine the non-specific binding. After incubation at 4° C. for 24 hours, protein A is added and the tubes are vortexed, incubated at room temperature for 90 minutes, and centrifuged at approximately 2000-2500×g at 4° C. to precipitate the complexes of antibody bound to labeled antigen. The supernatant is removed by aspiration and the radioactivity in the pellets counted in a gamma counter. The antiserum dilution that binds approximately 10 to 40% of the labeled peptide after subtraction of the non-specific binding is further characterized.

Next, a dilution range (approximately 0.1 pg to 10 ng) of the endostatin peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled endostatin peptide by the unlabeled endostatin peptide (standard) provides a standard curve. Several concentrations of other endostatin peptide fragments, plasminogen, endostatin from different species, and homologous peptides are added to the assay tubes to characterize the specificity of the endostatin antiserum.

Extracts of various tissues, including but not limited to, primary and secondary tumors, Lewis lung carcinoma, cultures of endostatin producing cells, placenta, uterus, and other tissues such as brain, liver, and intestine, are prepared using extraction techniques that have been successfully employed to extract endostatin. After lyophilization or Speed Vac of the tissue extracts, assay buffer is added and different aliquots are placed into the RIA tubes. Extracts of known endostatin producing cells produce displacement curves that are parallel to the standard curve, whereas extracts of tissues that do not produce endostatin do not displace radiolabeled endostatin from the endostatin antiserum. In addition, extracts of urine, plasma, and cerebrospinal fluid from animals with Lewis lung carcinoma are added to the assay tubes in increasing amounts. Parallel displacement curves indicate the utility of the endostatin assay to measure endostatin in tissues and body fluids.

Tissue extracts that contain endostatin are additionally characterized by subjecting aliquots to reverse phase HPLC. Eluate fractions are collected, dried in Speed Vac, reconstituted in RIA buffer and analyzed in the endostatin RIA. The maximal amount of endostatin immunoreactivity is located in the fractions corresponding to the elution position of endostatin.

The assay kit provides instructions, antiserum, endostatin or endostatin peptide, and possibly radiolabeled endostatin and/or reagents for precipitation of bound endostatin—endostatin antibody complexes. The kit is useful for the measurement of endostatin in biological fluids and tissue extracts of animals and humans with and without tumors.

Another kit is used for localization of angiostatin in tissues and cells. This endostatin immunohistochemistry kit provides instructions, endostatin antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This endostatin immunohistochemistry kit permits localization of endostatin in tissue sections and cultured cells using both light and electron microscopy. It is used for both research and clinical purposes. For example, tumors are biopsied or collected and tissue sections cut with a microtome to examine sites of endostatin production. Such information is useful for diagnostic and possibly therapeutic purposes in the detection and treatment of cancer.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Identification of an Inhibitor of Capillary Endothelial Cell Proliferation from Hemangioendothelioma Cells A murine hemangioendothelioma cell line, EOMA (Obeso et al., 1990), was evaluated for evidence of the production of inhibitors of endothelial cell proliferation. Many of the known endogenous inhibitors of angiogenesis inhibit the in vitro proliferation of endothelial cells.

Figure 1:
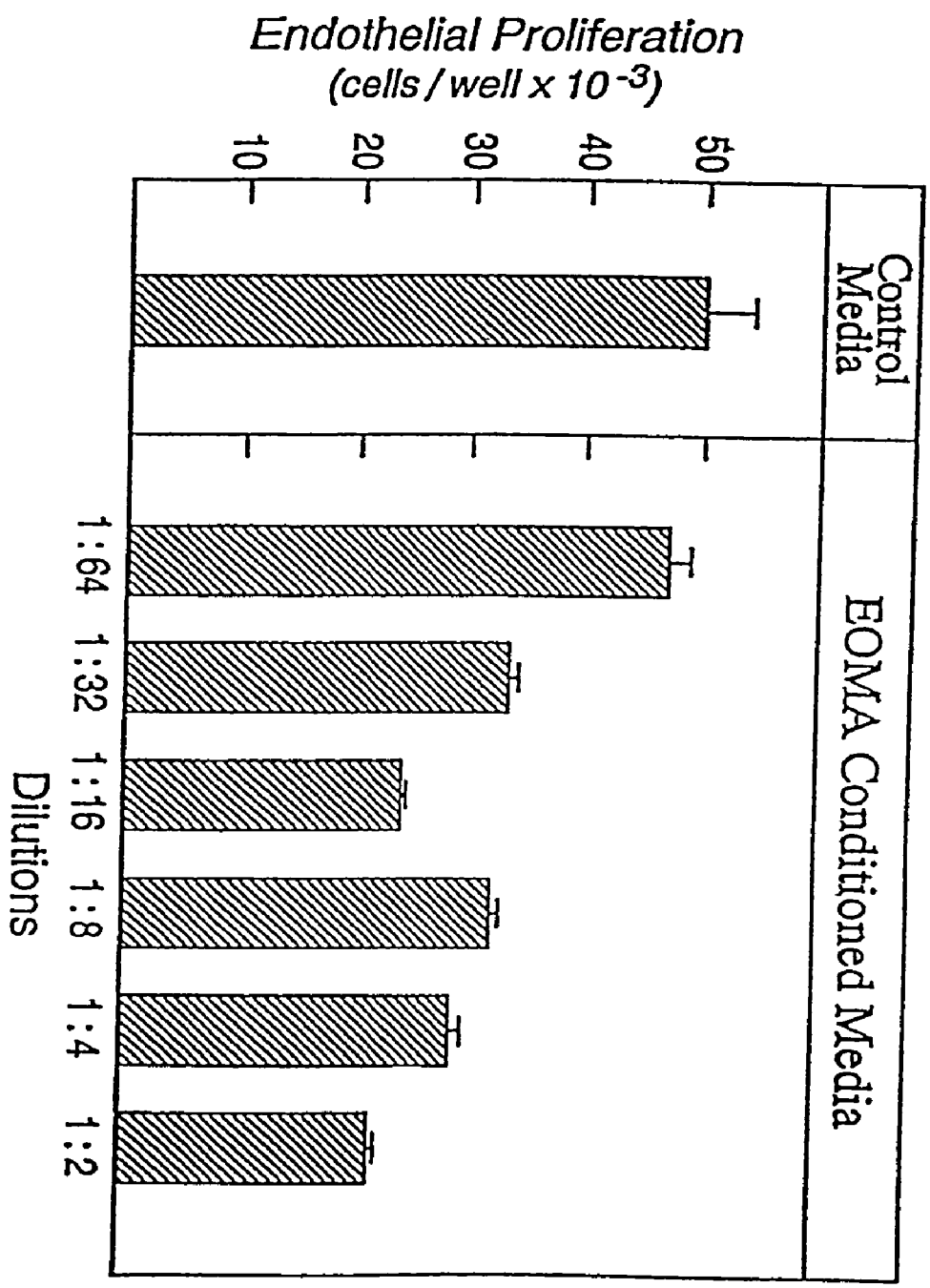
FIG. 1: Inhibition of Capillary Endothelial Cell Proliferation by Conditioned Media from EOMA Cells.

Conditioned Media Collection: Cells of the murine hemangioendothelioma cell line EOMA were maintained in DMEM supplemented with 10% bovine calf serum (BCS) and 1% glutamine-penicillin-streptomycin (GPS) in a 37° C. and 10% $CO_2$ incubator. Conditioned media from EOMA cells (i.e. culture media used to grow EOMA cells) was applied to bovine capillary endothelial cells, stimulated with bFGF, in a 72 hour proliferation assay. The conditioned media reversibly inhibited the proliferation of capillary endothelial cells as compared to controls. The pattern of inhibition was consistent with the presence of inhibitory and stimulatory activity of endothelial cell proliferation (FIG. 1).

EXAMPLE 2

Inhibitory Activity of Endothelial Cell Proliferation is not Due to Angiostatin

To determine if the inhibitor of capillary endothelial cell proliferation produced by the EOMA cells was angiostatin, pooled conditioned media was applied to a lysine column (lysine conjugated to Sepharose™ chromatography beads). Lysine Sepharose binds angiostatin and has been used for its purification (O'Reilly et al., 1996). The endothelial cell inhibitory activity was found only in the flow through fraction and not in the bound fraction (data not shown). The lack of binding of the inhibitory activity to lysine Sepharose suggested that the novel inhibitor of endothelial cell proliferation was not angiostatin.

EXAMPLE 3

Purification of a 20 kDa Protein from the Conditioned Media of EOMA Cells which Specifically Inhibits Endothelial Cell Proliferation Because several angiogenesis inhibitors have an affinity for heparin, we applied the flow-through from the lysine Sepharose column to a heparin Sepharose column. The inhibitory activity bound heparin with relatively high affinity and was eluted with 0.6-0.8 M NaCl in 10 mM Tris pH 7.4, as shown in FIG. 2. To further purify the inhibitory activity, the sample was concentrated and applied to a gel filtration (Bio-Rad Bio-Gel P-100 fine gel or Pharmacia Sephacryl S-200HR gel) column (see FIG. 3), followed by several cycles of reverse-phase HPLC with a C4 column. The inhibitory activity was eluted from the C4 column with 40-45% acetonitrile in 0.1% trifluoroacetic acid, as exemplified by FIG. 4. After the final C4 column, the inhibitory activity was associated with a protein of molecular mass of approximately 20 kDa (reduced) or 18 kDa (non-reduced), by SDS-PAGE, purified to apparent homogeneity.

With respect to Examples 2 and 3, lysine Sepharose, heparin Sepharose, Sephacryl S-200 HR gel (Pharmacia, Uppsala, Sweden), Bio-Gel P-100 fine polyacrylamide gel (Bio-Rad Laboratories, Richmond, Calif.), and a SynChropak RP-4 (100×4.6 mm) C4 reverse-phase column (Synchrom, Inc., Lafayette, Ind.) were prepared according to the manufacturers recommendations. A heparin-Sepharose column (50×2.5 cm) was equilibrated with 50 mM NaCl 10 mM Tris-HCl pH 7.4. Pooled conditioned media was applied and the column was washed with the equilibration buffer. The column was eluted with a continuous gradient of 50 mM-2 M NaCl in 10 mM Tris-HCl at pH 7.4 (200 ml total volume) followed by 100 ml of 2 M NaCl in 10 mM Tris-HCl at pH 7.4. Fractions were collected and an aliquot of each was applied to capillary endothelial cells. Fractions which inhibited their proliferation were dialyzed (MWCO=6,000-8,000) against PBS and concentrated using a 4000 MWCO Nanospin concentrator (Gelman Sciences, Ann Arbor, Mich.).

A Bio-Gel P-100 column or a Sephacryl S-200 HR column (75×1.5 cm) was equilibrated with PBS. The sample from heparin Sepharose chromatography was applied and the column was fluted with the equilibration buffer. Fractions were collected and an aliquot of each was applied to endothelial cells. Fractions which inhibited endothelial proliferation were concentrated-and dialyzed as above.

A SynChropak RPG (100×4.6 mm) column was equilibrated with $H_2O$/0.1% trifluoroacetic acid (TFA). HPLC-grade reagents (Pierce, Rockford, Ill.) were used. The sample from gel filtration chromatography was applied to the column and the column was fluted with a gradient of acetonitrile in 0.1% TFA at 0.5 ml/minute and fractions were collected. An aliquot of each was evaporated by vacuum centrifugation, resuspended in PBS, and applied to capillary endothelial cells. Inhibitory activity was further purified to apparent homogeneity by at least two subsequent cycles on the SynChropak C4 column.

To further characterize the 20 kDa inhibitor, we tested it on several cell lines of endothelial and non-endothelial origin. For the BCE assay, bovine capillary endothelial cells were obtained and grown as previously described (Folkman et al., 1979). For the proliferation assay, cells were washed with PBS and dispersed in a 0.05% solution of trypsin. A cell suspension (25,000 cells/ml) was made with DMEM+10% BCS+1% GPS, plated onto gelatinized 24-well culture plates (0.5 mewed), and incubated (37° C., 10% $CO_2$) for 24 hours. The media was replaced with 0.25 ml of DMEM+5% BCS+ 1% GPS and the test sample applied. After 20 minutes of incubation, media and bFGF were added to obtain a final volume of 0.5 ml of DMEM+5% BCS+1% GPS+1 ng/ml bFGF. After 72 hours, cells were dispersed in trypsin, resuspended in Hematall (Fisher Scientific, Pittsburgh, Pa.), and counted by Coulter counter.

Non-Endothelial Cell Proliferation Assays

Bovine aortic smooth muscle (SMC), bovine retinal pigment epithelial (RPE), mink lung epithelial (MLE), Lewis lung carcinoma (LLC), and EOMA cells and 3T3 fibroblasts were maintained in a 10% CO2 and 37° C. incubator. For the proliferation assays, cells were washed with PBS and were dispersed in a 0.05% solution of trypsin. Optimal conditions for the cell proliferation assays were established for each different cell type. Fetal calf serum (FCS) was used for the RPE, MLE, and LLC cells and BCS was used for the other cell types. A cell suspension (20,000 cells/ml for SMC, RPE, MLE; 15,000 cells/ml for 3T3; 10,000 cells/ml for LLC, EOMA) was made with DMEM+10% bovine serum+1% GPS, plated onto 24-well culture plates (0.5 ml/well), and incubated (37° C., 10% C02) for 24 hours. The media was replaced with 0.5 ml of DMEM+5% bovine serum+1% GPS and the test sample applied. After 72 hours, cells were dispersed in trypsin, resuspended in Hematall (Fisher Scientific, Pittsburgh, Pa.), and counted by Coulter counter.

Only endothelial cells were significantly inhibited, as shown in Table 2.

TABLE 2

EFFECT OF ENDOSTATIN ON ENDOTHELIAL AND NON-ENDOTHELIAL CELL PROLIFERATION

| INHIBITED | NON-INHIBITED |
| --- | --- |
| Bovine capillary endothelial cells | Bovine aortic smooth muscle cells Bovine retinal pigment epithelial cells 3T3 fibroblasts Mink lung epithelial cells EOMA hemangioendothelioma cells Lewis Lung carcinoma cells |

The inhibition was first observed at doses of 100 ng/ml with maximal inhibition observed at doses of 600 ng/ml or greater. No significant inhibition was seen for cells of non-endothelial origin at doses 1 log unit higher than those used to inhibit capillary endothelial cell proliferation (data not shown).

EXAMPLE 4

Microsequence Analysis of the 20 kDa Protein Reveals Identity to a Fragment of Collagen XVIII The 20 kDa inhibitor of capillary endothelial cell proliferation from the conditioned media was purified to homogeneity, as described in the above examples, resolved by SDS-PAGE, electroblotted onto PVDF (Bio-Rad, Richmond, Calif.), detected by Ponceau S stain, and excised from the membrane. N-terminal sequence was determined by automated Edman degradation on a PE/ABD Model 470A protein sequencer (Foster City, Calif.) operated with gas-phase delivery of trifluoracetic acid.

Sequence library searches and alignments were performed against combined GenBank, Brookhaven Protein, SWISS-PROT, and PIR databases. Searches were performed at the National Center for Biotechnology Information through the use of the BLAST network service.

Microsequence analysis of the inhibitor revealed identity to a C-terminal fragment of collagen XVIII. The molecular cloning and sequence of collagen XVIII was first described by Olsen and his coworkers and by Rehn and Pihlajaniemi (Oh et al., 1994; Rehn and Pihlajaniemi, 1994). Collagen XVIII is a novel collagen which consists of an N-terminal region with 3 splice variants (Muragaki et al., 1995; Rehn and Pihlajaniemi, 1995), a series of collagen-like domains with interruptions, and a 35 kDa C-terminal non-collagenous (NC1) domain. An 18-amino acid N-terminal microsequence analysis of the purified inhibitor of endothelial cell proliferation confirms that it is identical to a C-terminal fragment of this NCl domain (FIG. 5). We have named this inhibitory fragment of collagen XVIII "endostatin" and it is included in the group of molecules that have endostatin activity.

EXAMPLE 5

Recombinant Mouse Endostatin (*Baculovirus* or *E. coli*) Inhibits Endothelial Cell Proliferation In Vitro and Angiogenesis In Vivo The endothelial proliferation cell inhibitor of the present invention can be recombinantly expressed in any system used to express proteins. Non-limiting examples of such expressions systems include bacterial expression systems, yeast expression systems and insect viral expression systems.

Recombinant mouse endostatin was expressed using the BacPAK baculovirus expression system (CLONTECH Laboratories) following the manufacturer's protocol. Briefly, a cDNA fragment encoding the signal sequence and C-terminal part (endostatin region) of mouse collagen XVIII was inserted into the pBacPAK8 transfer vector. BacPAK6 viral DNA (expression vector) and plasmid DNA of the pBacPAK8-endostatin clone (modified transfer vector) were then co-transfected into insect Sf21 cells and media containing expressed mouse endostatin was collected. The BacPAK6 was first digested with BSU36 enzyme to make it incompetent for independent replication. The media containing expressed mouse endostatin was applied to a 1.5×40 cm heparin Sepharose column which had been equilibrated with 50 mM NaCl 10 mM Tris pH 7.4. The column was washed with the equilibration buffer and was then eluted sequentially with 0.2 M NaCl, 0.4 M NaCl, 0.6 M NaCl, and 1 M NaCl in 10 mM Tris pH 7.4. All chromatography was performed at 4° C. The 0.6 M NaCl eluant (which inhibited bovine capillary endothelial cells in a 72 hour proliferation assay) was dialyzed (6-8000 MWCO) against PBS and then reapplied to the heparin Sepharose column. The column was eluted with a gradient of 50 mM NaCl—1.2 M NaCl in 10 mM Tris pH 7.4. An aliquot of each fraction was applied to bovine capillary endothelial cells as above and fractions which inhibited proliferation were pooled, dialyzed against PBS, and concentrated using a Nanospin Plus (Gelman Sciences) centrifugal concentrator (MWCO=10,000). SDS-PAGE of the concentrated sample revealed a discrete band of apparent $M_r$ of 20 kDa.

Expression and Purification of Recombinant Mouse Endostatin from *E. coli*

The C-terminal part of the cDNA of collagen XVIII was used to amplify the cDNA of mouse endostatin which was cloned into the pETKH1 vector (pET11d derivative) (Studier et al., 1990). Induction resulted in the production of a fusion protein carrying the amino acid sequence MARRASVGTD (SEQ ID NO:2) (RRAS=protein kinase A recognition sequence) and 6 histidine residues at the N-terminus followed by the sequence of mouse endostatin (pTB01#8). The pTB01#8 plasmid was transformed into BL21:DE3 and the fusion protein was purified on $Ni^{+2}$-NTA-beads as described (QiaExpressionist Handbook, Qiagen). Briefly, *E. coli* were grown until an $O.D._{600}$ of 0.8-0.9 and expression of the fusion protein was then induced for 3 hours with 1 mM IPTG. The bacteria were pelleted and resuspended in 8 M urea, 10 mM Tris-HCl pH 8.0 containing 10 mM imidazole and incubated for 1 hour at room temperature. The suspension was centrifuged for 15 minutes at 20,000 g and the supernatant incubated with the $Ni^{+2}$-NTA beads for 1 hour at room temperature. The suspension was transferred into a column and washed with 8 M urea, 0.1 M Na-phosphate, 10 mM Tris-HCl pH 6.25 containing 10 mM imidazole. The protein was eluted with the same buffer containing 250 mM imidazole. The fractions containing endostatin were extensively dialyzed against PBS. During dialysis, the endostatin precipitated. The precipitated endostatin was resuspended in PBS, the protein concentration was adjusted to 2-4 mg/ml, and the endostatin was stored at $-20°$ C. until use. For the mouse studies, endostatin was delivered as a suspension in PBS. For the chick chorioallantoic assay, endostatin was further dialyzed against water and then lyophilized.

Recombinant mouse endostatin was produced in both baculovirus and *E. coli* expression systems. Using sequential heparin Sepharose chromatography, recombinant mouse endostatin was purified to apparent homogeneity from insect cell media. $Ni^{+2}$-NTA-agarose was used to purify the *E. coli*-derived mouse endostatin.

SDS-PAGE revealed a discrete band of approximately 20 kDa or approximately 22 kDa (reduced) purified to apparent homogeneity for baculovirus and *E. coli*-derived recombinant endostatins, respectively (data not shown). Both were dialyzed against PBS prior to use. After dialysis, the material from the *E. coli* system precipitated and was delivered as a suspension for subsequent in vivo studies. Recombinant endostatin from baculovirus specifically inhibited the proliferation of bovine capillary endothelial cells in a dose-dependent fashion. The inhibition was seen at doses of 100 ng/ml with maximal inhibition observed at doses above 600 ng/ml. No significant inhibition of proliferation of cells of non-endothelial origin or of the EOMA cells was observed when endostatin was tested at doses up to one log unit higher than those used to inhibit endothelial cell proliferation.

The precipitated (un-refolded) material was not testable in vitro, because of its insolubility. However, a small percentage was soluble in PBS during dialysis and this fraction was used for the endothelial cell assays. Furthermore, after refolding, it was soluble and inhibited endothelial proliferation (data not shown). When this soluble material was applied to endothelial cells, it was found to be inhibitory at concentrations comparable to both the native and baculovirus-derived endostatin.

To test for the ability of recombinant mouse endostatin to inhibit in vivo angiogenesis, we used the chick chorioallantoic membrane (CAM) assay (Folkman, 1985; Nguyen et al., 1994 which are incorporated herein by reference). Briefly, three day old fertilized white Leghorn eggs (Spafas, Norwich, Conn.) were cracked, and embryos with intact yolks were placed in 100×20 mm petri dishes (Folkman, 1985). After 3 days of incubation ($37°$ C. and 3% $CO_2$), a methylcellulose (Fisher Scientific, Fair Lawn, N.J.) disc containing endostatin was applied to the CAM of individual embryos. The discs were made by desiccation of endostatin in 10 μl of 0.45% methylcellulose (in $H_2O$) on teflon rods. After 48 hours of incubation, embryos and CAMs were observed by means of a stereomicroscope.

At doses of 10-20 μg/10 μl disc, there was potent inhibition of in vivo angiogenesis for both the *E. coli* and the baculovirus-derived endostatins in all of the tested CAMs (n=5/group). The *E. coli* derived-endostatin precipitate gradually dissolved over 5 days and produced a sustained antiangiogenic effect on the implanted CAMs. In contrast, the soluble baculovirus-derived endostatin dissolved within 24 hours and gave a maximal antiangiogenic effect within a period of 48 hours. There was no evidence of toxicity in any of the chick embryos tested.

Human Endostatin was produced recombinantly using similar methods.

EXAMPLE 6

Recombinant Mouse Endostatin Inhibits the Growth of Metastases

Because tumor growth is angiogenesis dependent, we treated Lewis lung carcinoma metastases systematically with recombinant mouse endostatin expressed in the baculovirus system. Animals with Lewis lung carcinomas of 600-1200 $mm^3$ tumors were sacrificed and the skin overlying the tumor was cleaned with betadine and ethanol. In a laminar flow hood, tumor tissue was excised under aseptic conditions. A suspension of tumor cells in 0.9% normal saline was made by passage of viable tumor tissue through a sieve and a series of sequentially smaller hypodermic needles of diameter 22- to 30-gauge. The final concentration was adjusted to 1×107 cells/ml and the suspension was placed on ice. After the site was cleaned with ethanol, the subcutaneous dorsa of mice in the proximal midline were injected with 1×106 cells in 0.1 ml of saline.

When tumors were 1500 $mm^3$ in size, approximately 14 days after implant, the mice underwent surgical removal of the tumor. The incision was closed with simple interrupted sutures. From the day of operation, mice received daily intraperitoneal injections of recombinant (baculovirus) mouse endostatin or saline. Mice received 0.3 mg/kg/day of endostatin once daily via subcutaneous injection. When the control mice became sick from metastatic disease (i.e., after 13 days of treatment), all nice were sacrificed and autopsied. Lung surface metastases were counted by means of a stereomicroscope at 4× magnification.

The growth of Lewis lung carcinoma metastases was almost completely suppressed by the systemic administration of endostatin at a dose of 0.3 mg/kg/day given subcutaneously (7±3 metastases/mouse, n=4, p<0.001). In contrast, in mice treated with saline after removal of a Lewis lung carcinoma primary tumor, lung metastases grew rapidly (77±7 metastases/mouse). Lung weight, which reflects tumor burden, was 240±25 mg in the endostatin treated mice versus 760±30 mg in the control mice (p<0.001). Further, there was no weight loss or evidence of toxicity in any of the mice treated with endostatin.

EXAMPLE 7

Recombinant Mouse Endostatin Inhibits the Growth of Primary Tumors

The yield of endostatin from the baculovirus system was lower than that of the E. coli system, i.e. 1-2 mg/liter versus 30-40 mg/liter. We therefore used E. coli-derived endostatin to study the effect of endostatin therapy on primary tumor growth. We produced recombinant mouse endostatin from E. coli in sufficient quantity to treat Lewis lung carcinoma primary tumors. The endostatin was administered as a suspension of the precipitated purified protein to mice bearing Lewis lung carcinomas of at least 100-200 mm$^3$. The protein was purified by conventional means but was not refolded prior to its administration to the mice. The injected precipitate was slowly resorbed over 24-48 hours.

We are unaware of any precedent for the use of an injected depot of non-refolded recombinant protein as a sustained-release method in animals. Nevertheless, endostatin gradually resorbed in vivo and proved to have potent antiangiogenic activity which resulted in prolonged anti-tumor and antiangiogenic activity. Therefore, these data suggest a novel general method for the controlled release of recombinant proteins. Based on this rationale, we have delivered non-refolded recombinant angiostatin from E. coli with similar success.

Accordingly, an aspect of the invention is the administration of recombinant endostatin or endostatin analogs in an un-refolded state so as to provide a sustained release depot of endothelial cell proliferation inhibiting protein over a period of at least 8 hours, desirably at least 12 hours, more desirably at least 24 hours or at least 48 hours, depending on the patient and the disease to be treated. Optionally recombinant and un-refolded angiostatin is administered to similarly provide a sustained release depot of protein capable of releasing angiostatin protein over a period of at least 8 hours, desirably at least 12 hours, more desirably at least 24 hours or at least 48 hours, depending on the patient and the disease to be treated.

Mice were implanted with Lewis lung carcinomas as described above. Tumors were measured with a dial-caliper and tumor volumes were determined using the formula width$^2$× length×0.52, and the ratio of treated to control tumor volume (T/C) was determined for the last time point. After tumor volume was 100-200 mm$^3$ (0.5-1% of body weight), which occurred within 3-7 days, mice were randomized into two groups. One group received recombinant mouse endostatin (E. coli) as a suspension in PBS injected subcutaneously at a site distant from the tumor once daily. The other group received comparable injections of the vehicle alone. The experiments were terminated and mice were sacrificed and autopsied when the control mice began to die.

Figure 7:
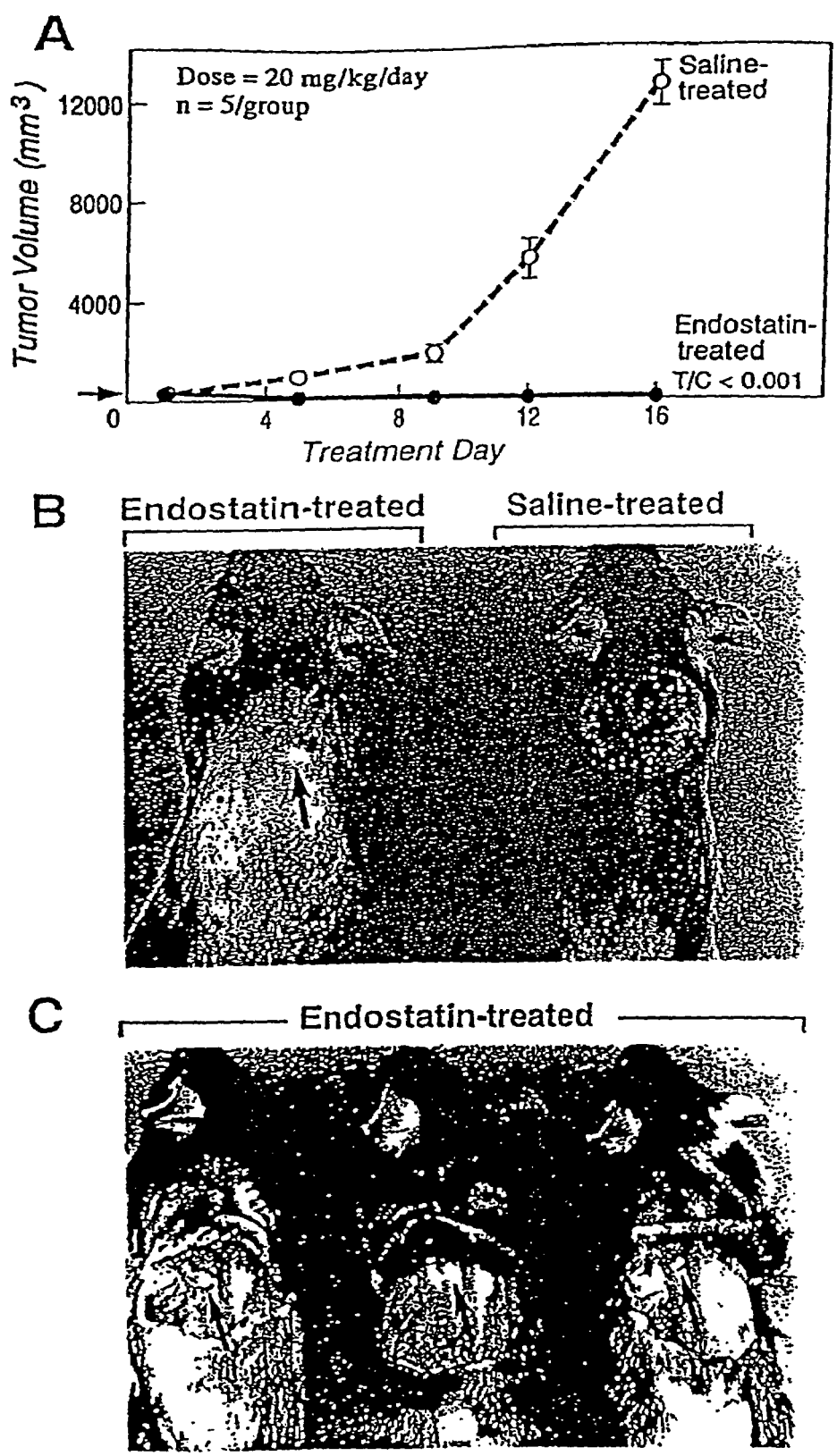

The growth of Lewis lung primary tumors was potently suppressed by systemic therapy with endostatin. Increasing the dose of endostatin was associated with improved efficacy (data not shown). At a dose of 10 mg/kg, tumor growth was inhibited by 97% as compared to control mice treated with vehicle alone. At a dose of 20 mg/kg given once daily, in two separate experiments, there was an almost complete regression of established primary tumors (>99% inhibition, p<0.001). These surprising and unexpected results are shown in FIGS. 6 and 7.

FIGS. 8, 9, 10 and 11 demonstrate the effectiveness of recombinant mouse endostatin for inhibiting tumor growth in a variety of different tumor models. Also demonstrated is the effectiveness of endostatin derived from human for inhibiting tumor growth.

Immunohistochemical analysis (FIG. 12) of the residual small tumors showed a potent inhibition of angiogenesis in the endostatin treated tumors. Further, the proliferative index of tumors in the endostatin and saline treated mice was at the same high level in both groups while the apoptotic index increased 8-fold after endostatin therapy. Thus, endostatin therapy results in a similar pattern of tumor dormancy to the one we have previously described for angiostatin (Holmgren et al., 1995; O'Reilly et al., 1996). Further, there was no evidence of drug-related toxicity in any of the treated mice.

After discontinuation of endostatin therapy, a tumor recurred at the primary site within 5-14 days, became vascularized, and eventually killed the mice (data not shown). Notably, we found that E. coli-derived recombinant mouse endostatin with a C-terminal polyhistidine tag, which was expressed. purified and administered in a comparable fashion to the N-terminal tagged product described above did not inhibit angiogenesis in the CAM assay and had no effect on the growth of Lewis lung carcinomas (data not shown). These data argue strongly that the anti-tumor and antiangiogenic activity of recombinant endostatin are due to the specific structure of endostatin and not to a contaminant in the sample.

FIG. 13 shows the results of cycled treatment of Lewis lung carcinoma with recombinant mouse endostatin derived from E. coli. These results clearly show reproducible endostatin-dependent regression of tumor mass, followed by tumor growth after termination of endostatin treatment.

These results show that a murine hemangioendothelioma produces a novel and specific 20 kDa inhibitor of endothelial cell proliferation in vitro which is also a potent inhibitor of angiogenesis and tumor growth in vivo. The N-terminal sequence of this inhibitor, endostatin, is identical to a C-terminal fragment of collagen XVIII. Systemic administration of recombinant endostatin potently inhibits angiogenesis, maintains metastases at a microscopic size, and regresses primary tumors to less than 1 mm$^3$, a reduction of over 150-fold. For as long as mice are treated there is no re-growth of tumors, no evidence of drug resistance, and no toxicity. It is interesting to note that some fragments of the C-terminal domain of collagen type XVIII that are longer than endostatin do not inhibit endothelial cell proliferation (data not shown).

Endostatin was discovered by the same strategy employed to find angiostatin (O'Reilly et al.,1994), i.e., isolation from a tumor. While it is counter-intuitive that tumors should be a source of angiogenesis inhibitors, the results reported here seem to validate this approach.

This leads to the question of why angiogenesis inhibitors should be present in tumors that are angiogenic. One possibility is that an inhibitor could be 'left-over' after down-regulation of its production by a tumor cell undergoing the switch to the angiogenic phenotype. This appears to be the case for thrombospondin produced by Li-Fraumeni cells in which the second allele for p53 is mutated or deleted (Dameron et al., 1994).

A second possibility is that the proteolytic activity which accompanies tumor growth, and which is an important component of capillary blood, vessel growth, may also mobilize circulating angiogenesis inhibitors from precursor proteins which are not inhibitory themselves. Angiostatin for example, inhibits angiogenesis and endothelial cell proliferation while plasminogen does not (O'Reilly et al., 1996; O'Reilly et al., 1994). For endostatin, a similar pattern is revealed.

Histology of tumors which regressed under endostatin therapy showed perivascular cuffing of tumor cells surrounding one or more microvessels in which angiogenesis was blocked. Tumor cells displayed high proliferation balanced by high apoptosis, with no net gain in tumor size. These data are consistent with a model of a new type of tumor dormancy recently proposed (Holmgren et al., 1995), Furthermore, endostatin inhibited proliferation of endothelial cells in vitro, but had no effect on Lewis lung carcinoma cells, or other cell types including smooth muscle, epithelium, fibroblasts, and the EOMA cell line from which it was purified.

The fact that a specific inhibitor of endothelial cell proliferation can regress a tumor to a microscopic size and hold it in a dormant state, despite the fact that the tumor cells are refractory to the inhibitor from the outset, indicates that the endothelial population can exert powerful growth regulatory control over the tumor cells.

The results with endostatin support the theory (Folkman, 1996) that for therapeutic purposes, it is fruitful to think about a tumor in terms of two distinct cell populations: a tumor cell population and an endothelial cell population, each of which can stimulate growth of the other. Growth of each cell population may be optimally inhibited by agents which selectively or specifically target that cell type, i.e., cytotoxic chemotherapy and antiangiogenic therapy. Furthermore, combined treatment of both cell populations may be better than treatment of either cell type alone.

To test this theory mice seeded with Lewis lung carcinomas, and bearings tumors which had attained a size of approximately 300 mm$^3$, were treated with a combination therapy comprising angiostatin and endostatin, each at a dose of 20 mg/kg/day for 25 days. Tumors regressed to microscopic levels by about day 10 of treatment. A completely unexpected finding was that tumors remained regressed and dormant for approximately three months, even after all treatment was terminated, as is shown in FIG. 14. Experiments of longer duration indicate that an initial treatment of tumor with a combination of angiostatin and endostatin causes a very long term dormancy, the actual period of which is unknown at this time.

Such long term dormancy is considered a cure to one skilled in the art. For example, the NIH guideline for determining when a treatment is effective as a cancer cure, is that the tumor remain dormant (i.e. not increasing in size) for ten times the normal doubling time of the tumor. The dormancy length achieved using a combination of endostatin and angiostatin far exceeds this criteria.

Accordingly, an important aspect of the invention is a composition comprising a combination of angiostatin and endostatin, or an endostatin analog, in amounts sufficient to cause long term dormancy, or cure, of angiogenesis-dependent cancers when administered to patients with angiogenesis-dependent cancers. Administration can be systemically, for example by injection, in which case the dosage is determined depending upon the patient and the particular cancer, but which generally is at least 0.2 mg/kg/day, desirably at least 2.0 mg/kg/day, more desirably at least 20 mg/kg/day. Generally, the composition is administered daily for at least 10 days, desirably at least 20 days, more desirably at least 25 days. Alternative systemic administration routes include, orally where the composition is formulated, for example into coated microbeads, to protect the protein from inactivating digestive environments; transdermally; and via pump.

Alternatively, different dosages and treatment periods can be used if the composition is administered locally to an angiogenesis-dependent site, such as a tumor. Such administration may be, for example, surgical implantation or local injection into, or near by, the site.

EXAMPLE 8

Isolation of the Putative Receptor for Endostatin

Both endostatin and angiostatin appear to be specific inhibitors of endothelial cell proliferation. Therefore, it is likely that endostatin binds to specific structures exclusively expressed on the surface of endothelial cells. We are not aware of the existence of any other specific inhibitors of endothelial cell proliferation.

Identifying and isolating proteins which specifically bind to endostatin is accompanied by methods well known in the art, for example by affinity chromatography and expression cloning.

Affinity Chromatography

Bovine Capillary Endothelial cells (BCE) are radiolabeled with [$^{35}$S]-methionine, total cell and membrane extracts prepared and applied to affinity columns prepared with endostatin. As a negative control, fibroblast protein extracts are isolated in a similar way. Bound proteins are eluted from the column using a NaCl gradient and the different fractions are analyzed using standard SDS-PAGE and autoradiography. This procedure yields proteins that are tightly bound to the endostatin column and present only in the endothelial cell derived fractions. Comparing the gel electrophoretic patterns of the two cell types reveals expressed proteins unique to the BCE cells. Protein sequences subsequently are determined and corresponding gene(s) cloned. A cDNA library of bovine capillary endothelial cells, is prepared and screened with a degenerative oligo based PCR technique to locate the cDNA(s) of the endostatin-specific binding protein(s). Hybridization using degenerative oligonucleotides to the corresponding cDNA, is also used to identify genes of endostatin binding proteins. Another approach is to raise antibodies against the peptide sequences with methods described earlier in the Detailed Description and immunoscreen the same library.

Expression Cloning.

A cDNA library of BCE cells is prepared. Poly-A mRNA is isolated from BCE cells whose proliferation has previously been inhibited by endostatin. These cells express an endostatin binding protein. The corresponding cDNA library is transfected into cells allowing high expression of the various cDNAs. Binding activity of endostatin to cells which express the receptor protein on the surface is used as a positive selection of these cells. To select for these cells, purified endostatin is labeled with biotin and consequently detected using either streptavidin coupled magnetic-beads or FACS sorting. Alternatively, an antibody against endostatin is used for screening. After selection of the positive cells, the corresponding plasmids are isolated, amplified and transfected again into high expression cells. After several rounds of positive selection, plasmids are analyzed for identical inserts using endonuclease digestion and PCR. Using these data, complementation groups are formed, sequenced and analyzed with the BLAST network program. In addition to computer analysis, individual cDNAs are re-transfected into-high expression cells and tested for endostatin binding activity under different conditions (e.g., competition with non-labeled endostatin, time-course of binding, Scatchard analysis, etc. in other words the use of "classical" receptor characterization procedures known to those skilled in the art).

EXAMPLE 9

Determination of the Minimal Region of the Mouse Endostatin Protein Responsible for its Antiangiogenic Activity Different PCR primers are designed, the corresponding cDNAs cloned into the *E. coli* expression system, and the different endostatin fragments purified to homogeneity. The full length cDNA is cut from both the N- and C-terminus. As a first screen, the capillary endothelial proliferation assay and the chick embryo assay are used to determine the residual activity compared to the full length fragment.

EXAMPLE 10

Determination of the Putative Enzyme(s) Which May Release Endostatin from Collagen XVIII Collagen XVIII belongs to the non-fibrillar collagen type family and can be found in three different splicing variants encoding for proteins with 1315-, 1527-, and 1774 amino acid residues (Rehn, *PNAS* 91:4234, 1994). The difference is caused by alterations in the N-terminal part of the gene and therefore all three splicing variants could potentially be the source of endostatin which itself is a fragment of the non-collagenous domain 11 (NC11). The function of collagen XVIII is not known, but because its message is substantially expressed in highly vascularized organs, a role in perivascular matrix assembly and/or structure has been proposed (Oh, et al., *Genomics,* 19:494, 1994). A first clue about the function of collagen XVIII came from the purification of endostatin as a potent inhibitor of endothelial cell proliferation.

From this preliminary data and from our initial observation that endostatin was purified from conditioned medium of a hemangioendothelioma (EOMA), we asked whether the enzyme(s) which release endostatin from collagen XVIII could be identified.

The last 325 amino acid residues, encoding for the NC11 domain, are expressed in *E. coli* and the insect cell baculovirus system, the purified protein is used as a substrate to identify enzymes that clone this region of collagen XVIII. By PCR, a cDNA fragment encoding the NC11 domain is cloned into an *E. coli* expression vector (pET series) which allows high expression of the target protein after induction with IPTG. Alternatively, a vector suitable for insect cell expression is used. The proteins are tagged with the $HIS_6$-Tag located on the C-terminus for purification using $Ni^{2+}$-NTA-beads. An $Ni^{2+}$-NTA-alkaline phosphatase conjugate can detect the C-terminus by Western blotting. Another construct is made which not only has a $HIS_6$-Tag on the C-terminus, but will also encode the hemaglutinin HA-tag on the N-terminus. This is detected by Western blotting with an HA-specific monoclonal antibody. The N- and C-terminus of the protein followed after incubation with EOMA supernatant and different metalloproteinase extracts.

Cleavage product is detected by SDS-PAGE analysis or Western blotting, the protein is re-purified using the $Ni^{2+}$-NTA beads, eluted with imidazole, dialyzed against PBS and tested for inhibitor activity in the various in vitro and in vivo assays (e.g., endothelial cell proliferation, chick embryo, and mouse corneal assay). If the purified cleavage product shows inhibitory activity, N-terminal amino acid sequencing is performed and compared to the original starting sequence of endostatin obtained from the EOMA supernatant. Accordingly, the cleavage procedure can be scaled up to purify sufficient protein for testing in tumor-bearing mice, and to compare this activity to that of the full length NC11 domain.

EXAMPLE 11

Sequence of Human Endostatin Protein

Based on the data revealed in the above examples, and the publicly available protein sequences of human collagen XVIII (Oh, et al., *Genomics,* 19:494, 1994), the following is an example of a functional human endostatin protein of the present invention. This is the carboxy terminal protein of human collagen XVIII, starting at the amino-terminal end position 1132, as correlating to the murine fragment of SEQ ID NO:1 above.

Human Endostatin protein sequence,

```
182 aa
HSHRDFQPVLHLVALNSPLSGGMRGIRGADFQCFQQA    (SEQ ID NO:3)

RAVGLAGTRAFLSSRLQDLYSIVRRADRAAVPIVNLK

DELLFPSWEALFSGSEGPLKPGARIFSFDGKDVLRHP

TWPQKSVWHGSDPNGRRLTESYCETWRTEAPSATGQA

SSLLGGRLLGQSAASCHHAYIVLCIENSFMTAS
```

Furthermore, based on publicly available gene sequences for human collagen XVIII, the following is a representative gene encoding for the above endostatin protein.

Human Endostatin gene sequence,

```
546 bp
CACAGCCACCGCGACTTCCAGCCGGTGCTCCACCTGG    (SEQ ID NO:4)

TTGCGCTCAACAGCCCCCTGTCAGGCGGCATGCGGGG

CATCCGCGGGGCCGACTTCCAGTGCTTCCAGCAGGCG

CGGGCCGTGGGGCTGGCGGGCACCTTCCGCGCCTTCC

TGTCCTCGCGCCTGCAGGACCTGTACAGCATCGTGCG

CCGTGCCGACCGCGCAGCCGTGCCCATCGTCAACCTC

AAGGACGAGCTGCTGTTTCCCAGCTGGGAGGCTCTGT

TCTCAGGCTCTGAGGGTCCGCTGAAGCCCGGGGCACG

CATCTTCTCCTTTGACGGCAAGGACGTCCTGAGGCAC

CCCACCTGGCCCCAGAAGAGCGTGTGGCATGGCTCGG

ACCCCAACGGGCGCAGGCTGACCGAGAGCTACTGTGA

GACGTGGCGGACGGAGGCTCCCTCGGCCACGGGCCAG

GCCTCCTCGCTGCTGGGGGGCAGGCTCCTGGGGCAGA

GTGCCGCGAGCTGCCATCACGCCTACATCGTGCTCTG

CATTGAGAACAGCTTCATGACTGCCTCC
```

As described above, amino acid substitutions may occur in the sequence of endostatin, which still yield a functional endostatin protein. For example, when the above gene sequence is recombinantly expressed, an observable doublet of protein results, both versions of which are functional endostatin proteins. In addition to the above endostatin protein, the following endostatin variant occurs, which is the former protein minus the first four amino acids. This demonstrates the variability of functional endostatin protein molecules.

Alternate Human Endostatin protein sequence,

```
178 aa
DFQPVLHLVALNSPLSGGMRGIRGADFQCFQQARAVG  (SEQ ID NO:5)

LAGTFRAFLSSRLQDLYSIVRRADRAAVPIVNLKDEL

LFPSWEALFSGSEGPLKPGARIFSEDGKDVLRHPTWP

QKSVWHGSDPNGRRLTESYCETWRTEAPSATGQASSL

LGGRLLGQSAASCHHAYIVLCIENSFMTAS
```

Furthermore, based on publicly available gene sequences for human collagen XVIII, the following is a representative gene encoding for the above alternate endostatin protein.

Alternate Human Endostatin gene sequence,

```
534 bp
GACTTCCAGCCGGTGCTCCACCTGGTTGCGCTCAACA  (SEQ ID NO:6)

GCCCCCTGTCAGGCGGCATGCGGGGCATCCGCGGGGC

CGACTTCCAGTGCTTCCAGCAGGCGCGGGCCGTGGGG

CTGGCGGGCACCTTCCGCGCCTTCCTGTCCTCGCGCC

TGCAGGACCTGTACAGCATCGTGCGCCGTGCCGACCG

CGCAGCCGTGCCCATCGTCAACCTCAAGGACGAGCTG

CTGTTTCCCAGCTGGGAGGCTCTGTTCTCAGGCTCTG

AGGGTCCGCTGAAGCCCGGGGCACGCATCTTCTCCTT

TGACGGCAAGGACGTCCTGAGGCACCCCACCTGGCCC

CAGAAGAGCGTGTGGCATGGCTCGGACCCCAACGGGC

GCAGGCTGACCGAGAGCTACTGTGAGACGTGGCGGAC

GGAGGCTCCCTCGGCCACGGGCCAGGCCTCCTCGCTG

CTGGGGGGCAGGCTCCTGGGGCAGAGTGCCGCGAGCT

GCCATCACGCCTACATCGTGCTCTGCATTGAGAACAG

CTTCATGACTGCCTCC
```

REFERENCES

The following references are hereby incorporated by reference herein in their entirety.

Angiolillo, A. L., Sgadari, C., Taub, D. D., Liao, F., Farber, J. M., Miaheshwari, S., Kleinman, H. K., Reaman, G. H., and Tosato, G. (1995). Human interferon-inducible protein 10 is a potent inhibitor of angiogenesis in vivo. J. Exp. Med. 182, 155-162.

Cao, Y., Chen, C., Weatherbee, J. A., Tsang, M., and Folkman, J. (1995). Gro-beta, a C—X—C chemokine, is an angiogenesis inhibitor that suppresses the growth of Lewis lung carcinoma in mice. J. Exp. Med. 182, 2069-2077.

Chen, C., Parangi, S., Tolentino, M. J., and Folkman, J. (1995). A strategy to discover circulating angiogenesis inhibitors generated by human tumors. Cancer Res. 55, 4230-4233.

Clapp, C., Martial, J. A., Guzman, R. C., Rentier-Delrue, F., and Weiner, R. I. (1993). The 16-kilodalton N-terminal fragment of human prolactin is a potent inhibitor of angiogenesis. Endocrinology 133, 1292-1299.

Dameron, K. M., Volpert, O. V., Tainsky, M. A., and Bouck, N. (1994). Control of angiogenesis in fibroblasts by p53 regulation of thrombospondin-1. Science 265, 1582.

Folkman, J. (1996). Tumor angiogenesis and tissue factor. Nature Med. 2, 167-168.

Folman, J. (1989). What is the evidence that tumors are angiogenesis dependent?. J. Natl. Cancer Inst. 82, 4-6.

Folkman, J. (1985). Angiogenesis and its inhibitors. In Important Advances in Oncology 1985, V. T. DeVita, S. Hellman, and S. Rosenberg, eds. (Philadelphia: J.B. Lippincott Company), pp. 42-62.

Folkman, J., Haundenschild, C. C., and Zetter, B. R. (1979). Long-term culture of capillary endothelial cells. Proc. Natl. Acad. Sci. USA 76, 5217-5221.

Gavrieli, Y., Sherman, Y., and Ben-Sasson, S. A. (1992). Identification of programmed cell death in situ via specific labeling of nuclear DNA fragmentation. J. Cell Biol. 119, 493-501.

Good, D. J., Polverini, P. J., Rastinejad, F., Le Beau, M. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc. Nat. Acad. Sci. USA. 87, 6624-6628.

Grant, D. S., Tashiro, K.-I., Sequi-Real, B., Yamada, Y., Martin, G. R., and Kleinman, H. K. (1989). Two different laminin domains mediate the differentiation of human endothelial cells into capillary-like structures in vitro. Cell 58, 933-943.

Gross, J. L., Moscatelli, D., and Rifkin, D. B. (1983). Increased capillary endothelial cell protease activity in response to angiogenic stimuli in vitro. Proc. Natl. Acad. Sci. USA 80, 2623-2627.

Gupta, S. K., Hassel, T., and Singh, J. P. (1995). A potent inhibitor of endothelial cell proliferation is generated by proteolytic cleavage of the chemokine platelet factor 4. Proc. Natl. Acad. Sci. USA 92, 7799-7803.

Holmgren, L., O'Reilly, M. S., and Folkman, J. (1995). Dormancy of micrometastases: balanced proliferation and apoptosis in the presence of angiogenesis suppression. Nature Med. 1, 149-153.

Homandberg, G. A., Williams, J. E., Grant, D., B., S., and Eisenstein, R. (1985). Heparin-binding fragments of fibronectin are potent inhibitors of endothelial cell growth. Am. J. Path. 120, 327-332.

Hori, A., Sasada, R., Matsutani, E., Naito, K., Sakura, Y., Fujita, T., and Kozai, Y. (1991). Suppression of solid tumor growth by immunoneutralizing monoclonal antibody against human basic fibroblast growth factor. Cancer Res. 51, 6180-6184.

Kandel, J., Bossy-Wetzel, E., Radvany, F., Klagsburn, M., Folkman, J., and Hanahan, D. (1991). Neovascularization is associated with a switch to the export of bFGF in the multistep development of fibrosarcoma. Cell 66, 1095-1104.

Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841-844.

Maione, T. E., Gray, G. S., Petro, J., Hunt, A. J., Donner, A. L., Bauer, S. I., Carson, H. F., and Sharpe, R. J. (1990). Inhibition of angiogenesis by recombinant human platelet factor-4 and related peptides. Science 247, 77-79.

Millauer, B., Shawver, L. K., Plate, K. H., Risau, W., and Ullrich, A. (1994). Glioblastoma growth inhibited in vivo by a dominant-negative Flk-1 mutant. Nature 367, 576-579.

Muragaki, Y., Timmons, S., Griffith, C. M., Oh, S. P., Fadel, B., Quertemmous, T., and Olsen, B.-R. (1995). Mouse col18a1 is expressed in a tissue-specific manner as three alternative variants and is localized in basement membrane zones. Proc. Natl. Acad. Sci. USA 92, 8763-8767.

Nelson, J., Allen, W. E., Scott, W. N., Bailie, J. R., Walker, B., and McFerran, N. V. (1995). Murine epidermal growth factor (EGF) fragment (33-42) inhibits both EGF- and laminin-dependent endothelial cell motility and angiogenesis. Cancer Res. 55, 3772-3776.

Nguyen, M., Shing, Y., and Folkman, J. (1994). Quantitation of angiogenesis and antiangiogenesis in the chick embryo chorioallantoic membrane. Microvascular Res. 47, 31-40.

O'Reilly, M. S., Holmgren, L., Chen, C. C., and Folkman, J. (1996). Angiostatin induces and sustains dormancy of human primary tumors in mice. Nature Med. 2, 689-692.

O'Reilly, M. S., Holmgren, L., Shing, Y., Chen, C., Rosenthal, R. A., Moses, M., Lane, W. S., Cao, Y., Sage, E. H., and Folkman, J. (1994). Angiostatin: A novel angiogenesis inhibitor that mediates the suppression of metastases by a Lewis lung carcinoma. Cell 79, 315-328.

Obeso, J., Weber, J., and Auerbach. R. (1990). A hemangioendothelioma-derived cell line: its use as a model for the study of endothelial cell biology. Lab. Invest. 63, 259-269.

Oh, S. K., Kamagata, Y., Muragaki, Y., Timmons, S., Ooshima, A., and Olsen, B. R. (1994). Isolation and sequencing of cDNAs for proteins with multiple domains of GlyXaa-Yaa repeats identify a distinct family of collagenous proteins. Proc. Natl. Acad. Sci. USA 91, 4229-4233.

Oh, S. K., Warman, M. L., Seldin, M. F., Cheng, S. D., Knoll, J. H. M., Timmons, S., and Olsen, B. R. (1994). Cloning of cDNA and Genomic DNA Encoding Human Type XVIII Collagen and Localization of the α 1 (SVIII) Collagen Gene to Mouse Chromosome 10 and Human Chromosome 21. Genomics 19, 494-499.

Parangi, S., O'Reilly, M., Christofori, G., Holmgren, L., Grosfeld, J., Folkman, J., and Hanahan, D. (1996). Antiangiogenic therapy of transgenic mice impairs de novo tumor growth. Proc. Natl. Acad. Sci. USA 93, 2002-2007.

Rastinejad, F., Polverini, P. J., and Bouck, N. P. (1989). Regulation of the activity of a new inhibitor of angiogenesis by a cancer suppressor gene. Cell 56, 345-355.

Rehn, M., and Pihlajaniemi, T. (1994). al (XVIII), a collagen chain with frequent interruptions in the collagenous sequence, a distinct tissue distribution, and homology with type XV collagen. Proc. Natl. Acad. Sci. USA 91, 4234-4238.

Rehn, M., and Pihlajaniemi, T. (1995). Identification of three N-terminal ends of type XVIII collagen chains and tissue-specific differences in the expression of the corresponding transcripts. J. Biol. Chem. 270, 4705-4711.

Sage, E. H., Bassuk, J. A., Vost, J. C., Folkman. M. J., and Lane, T. F. (1995). Inhibition of endothelial cell proliferation by SPARC is mediated through a Ca (2+)-binding EF-hand sequence. J. Cell Biochem. 57, 127-140.

Sakamato, N., Iwahana, M., Tanaka, N. G., and Osaka, 8. (1991). Inhibition of angiogenesis and tumor growth by a synthetic laminin peptide, $CDPGYIGSR-NH_2$. Cancer Res. 51, 903-906.

Strieter, R. M., Kunkel, S. L., Arenberg, D. A., Burdick, M. D., and Polverini, P. J. (1995). Human interferon-inducible protein 10 (IP-10), a member of the C-X-C chemokine family, is an inhibitor of angiogenesis. Biochem. Biophys. Res. Comm. 210, 51-57.

Studier, W. F., Rosenberg, A. H., Dunn, J. J., and Dudendorf, J. W. (1990). Use of T7 RNA polymerase to direct expression of cloned genes. Methods Enzymol. 85, 60-89.

Teicher, B. A., Holden, S. A., Ara, G., Sotomayor, E. A., and Dong, H. Z. (1994). Potentiation of cytotoxic cancer therapies by TNP-470 alone and with other antiangiogenic agents, Int. J. Cancer 57, 1-6.

Tolsma, S. S., Volpert, O. V., Good, D. J., Frazier, W. A., Polverini, P. J., and Bouck, N. (1993). Peptides derived from two separate domains of the matrix protein thrombospondin-1 have antiangiogenic activity. J. Cell Biol. 122, 497-511.

Voest, E. E., Kenyon, B. M., O'Reilly, M. S., Truitt, G., D'Amato, R. J., and Folkman, J. (1995). Inhibition of angiogenesis in vivo by interleukin 12. J. Natl. Cancer Inst. 87, 581-586.

The invention claimed is:

1. A pharmaceutical composition comprising an isolated nucleic acid molecule that comprises a coding region encoding a polypeptide that inhibits endothelial cell proliferation, wherein the coding region encoding the polypeptide that inhibits endothelial cell proliferation consists of the nucleotide sequence set forth in SEQ ID NO: 4.

2. The pharmaceutical composition of claim 1, formulated as a sustained release for a period of at least 8 hours.

3. The composition of claim 1, administered to an individual for the treatment of an angiogenesis-related disease.

4. The composition of claim 1, wherein the angiogenesis-related disease is an angiogenesis-dependent cancer.

5. The composition of claim 1, wherein the nucleic acid molecule encodes an endostatin protein or an angiogenic inhibitory peptide fragment thereof.

6. The composition of claim 5, wherein the endostatin protein or angiogenic inhibitory peptide fragment thereof is a fragment of a C-terminal non-collagenous region of a non-fibrillar collagen protein.

7. The composition of claim 6, wherein the collagen protein comprises collagen type XVIII.

8. The composition of claim 5, wherein the endostatin protein or angiogenic inhibitory peptide fragment thereof is a human endostatin protein or peptide fragment.

9. The composition of claim 5, wherein the endostatin protein or angiogenic inhibitory peptide fragment thereof binds to a heparin affinity column and does not bind to a lysine affinity column.

10. The composition of claim 1 further comprising a vector comprising the isolated nucleic acid molecule.

11. The composition of claim 1 wherein the isolated nucleic acid molecule further comprises a nucleotide sequence encoding an angiostatin protein, wherein the angiostatin protein has an amino acid sequence of a fragment of a kringle region of plasminogen.

12. The composition of claim 11 further comprising a vector comprising the isolated nucleic acid molecule.

13. An isolated nucleic acid that comprises a coding region encoding a polypeptide that inhibits endothelial cell proliferation, wherein the coding region encoding the polypeptide that inhibits endothelial cell proliferation consists of the nucleotide sequence set forth in SEQ ID NO: 4.

14. A vector comprising the isolated nucleic acid of claim 13.

* * * * *

SEQUENCE LISTING

```
<160> NUMBER OF SEQ ID NOS: 6

<210> SEQ ID NO 1
<211> LENGTH: 20
<212> TYPE: PRT
<213> ORGANISM: Murinae sp.

<400> SEQUENCE: 1

His Thr His Gln Asp Phe Gln Pro Val Leu His Leu Val Ala Leu Asn
1               5                   10                  15

Thr Pro Leu Ser
            20

<210> SEQ ID NO 2
<211> LENGTH: 10
<212> TYPE: PRT
<213> ORGANISM: Murinae sp.

<400> SEQUENCE: 2

Met Ala Arg Arg Ala Ser Val Gly Thr Asp
```

-continued

```
1               5                   10
```

<210> SEQ ID NO 3
<211> LENGTH: 182
<212> TYPE: PRT
<213> ORGANISM: Homo sapiens

<400> SEQUENCE: 3

| His | Ser | His | Arg | Asp | Phe | Gln | Pro | Val | Leu | His | Leu | Val | Ala | Leu | Asn |
|---|---|---|---|---|---|---|---|---|---|---|---|---|---|---|---|
| 1 | | | | 5 | | | | | 10 | | | | | 15 | |

| Ser | Pro | Leu | Ser | Gly | Gly | Met | Arg | Gly | Ile | Arg | Gly | Ala | Asp | Phe | Gln |
|---|---|---|---|---|---|---|---|---|---|---|---|---|---|---|---|
| | | | 20 | | | | | 25 | | | | | 30 | | |

| Cys | Phe | Gln | Gln | Ala | Arg | Ala | Val | Gly | Leu | Ala | Gly | Thr | Phe | Arg | Ala |
|---|---|---|---|---|---|---|---|---|---|---|---|---|---|---|---|
| | | | 35 | | | | | 40 | | | | | 45 | | |

| Phe | Leu | Ser | Ser | Arg | Leu | Gln | Asp | Leu | Tyr | Ser | Ile | Val | Arg | Arg | Ala |
|---|---|---|---|---|---|---|---|---|---|---|---|---|---|---|---|
| | 50 | | | | | 55 | | | | | 60 | | | | |

| Asp | Arg | Ala | Ala | Val | Pro | Ile | Val | Asn | Leu | Lys | Asp | Glu | Leu | Leu | Phe |
|---|---|---|---|---|---|---|---|---|---|---|---|---|---|---|---|
| 65 | | | | | 70 | | | | | 75 | | | | | 80 |

| Pro | Ser | Trp | Glu | Ala | Leu | Phe | Ser | Gly | Ser | Glu | Gly | Pro | Leu | Lys | Pro |
|---|---|---|---|---|---|---|---|---|---|---|---|---|---|---|---|
| | | | | 85 | | | | | 90 | | | | | 95 | |

| Gly | Ala | Arg | Ile | Phe | Ser | Phe | Asp | Gly | Lys | Asp | Val | Leu | Arg | His | Pro |
|---|---|---|---|---|---|---|---|---|---|---|---|---|---|---|---|
| | | | 100 | | | | | 105 | | | | | 110 | | |

| Thr | Trp | Pro | Gln | Lys | Ser | Val | Trp | His | Gly | Ser | Asp | Pro | Asn | Gly | Arg |
|---|---|---|---|---|---|---|---|---|---|---|---|---|---|---|---|
| | | | 115 | | | | | 120 | | | | | 125 | | |

| Arg | Leu | Thr | Glu | Ser | Tyr | Cys | Glu | Thr | Trp | Arg | Thr | Glu | Ala | Pro | Ser |
|---|---|---|---|---|---|---|---|---|---|---|---|---|---|---|---|
| | 130 | | | | | 135 | | | | | 140 | | | | |

| Ala | Thr | Gly | Gln | Ala | Ser | Ser | Leu | Leu | Gly | Gly | Arg | Leu | Leu | Gly | Gln |
|---|---|---|---|---|---|---|---|---|---|---|---|---|---|---|---|
| 145 | | | | | 150 | | | | | 155 | | | | | 160 |

| Ser | Ala | Ala | Ser | Cys | His | His | Ala | Tyr | Ile | Val | Leu | Cys | Ile | Glu | Asn |
|---|---|---|---|---|---|---|---|---|---|---|---|---|---|---|---|
| | | | | 165 | | | | | 170 | | | | | 175 | |

| Ser | Phe | Met | Thr | Ala | Ser |
|---|---|---|---|---|---|
| | | | 180 | | |

<210> SEQ ID NO 4
<211> LENGTH: 546
<212> TYPE: DNA
<213> ORGANISM: Homo sapiens

<400> SEQUENCE: 4

| cacagccacc | gcgacttcca | gccggtgctc | cacctggttg | cgctcaacag | ccccctgtca | 60 |
|---|---|---|---|---|---|---|
| ggcggcatgc | ggggcatccg | cggggccgac | ttccagtgct | tccagcaggc | gcgggccgtg | 120 |
| gggctggcgg | gcaccttccg | cgccttcctg | tcctcgcgcc | tgcaggacct | gtacagcatc | 180 |
| gtgcgccgtg | ccgaccgcgc | agccgtgccc | atcgtcaacc | tcaaggacga | gctgctgttt | 240 |
| cccagctggg | aggctctgtt | ctcaggctct | gagggtccgc | tgaagcccgg | ggcacgcatc | 300 |
| ttctcctttg | acggcaagga | cgtcctgagg | caccccacct | ggccccagaa | gagcgtgtgg | 360 |
| catggctcgg | accccaacgg | cgcaggctg | accgagagct | actgtgagac | gtggcggacg | 420 |
| gaggctccct | cggccacggg | ccaggcctcc | tcgctgctgg | ggcaggct | cctggggcag | 480 |
| agtgccgcga | gctgccatca | cgcctacatc | gtgctctgca | ttgagaacag | cttcatgact | 540 |
| gcctcc | | | | | | 546 |

<210> SEQ ID NO 5
<211> LENGTH: 178
<212> TYPE: PRT
<213> ORGANISM: Homo sapiens

```
<400> SEQUENCE: 5

Asp Phe Gln Pro Val Leu His Leu Val Ala Leu Asn Ser Pro Leu Ser
1               5                   10                  15

Gly Gly Met Arg Gly Ile Arg Gly Ala Asp Phe Gln Cys Phe Gln Gln
            20                  25                  30

Ala Arg Ala Val Gly Leu Ala Gly Thr Phe Arg Ala Phe Leu Ser Ser
        35                  40                  45

Arg Leu Gln Asp Leu Tyr Ser Ile Val Arg Arg Ala Asp Arg Ala Ala
    50                  55                  60

Val Pro Ile Val Asn Leu Lys Asp Glu Leu Leu Phe Pro Ser Trp Glu
65                  70                  75                  80

Ala Leu Phe Ser Gly Ser Glu Gly Pro Leu Lys Pro Gly Ala Arg Ile
                85                  90                  95

Phe Ser Phe Asp Gly Lys Asp Val Leu Arg His Pro Thr Trp Pro Gln
            100                 105                 110

Lys Ser Val Trp His Gly Ser Asp Pro Asn Gly Arg Arg Leu Thr Glu
            115                 120                 125

Ser Tyr Cys Glu Thr Trp Arg Thr Glu Ala Pro Ser Ala Thr Gly Gln
    130                 135                 140

Ala Ser Ser Leu Leu Gly Gly Arg Leu Leu Gly Gln Ser Ala Ala Ser
145                 150                 155                 160

Cys His His Ala Tyr Ile Val Leu Cys Ile Glu Asn Ser Phe Met Thr
                165                 170                 175

Ala Ser

<210> SEQ ID NO 6
<211> LENGTH: 534
<212> TYPE: DNA
<213> ORGANISM: Homo sapiens

<400> SEQUENCE: 6
gacttccagc cggtgctcca cctggttgcg ctcaacagcc ccctgtcagg cggcatgcgg      60
ggcatccgcg gggccgactt ccagtgcttc cagcaggcgc gggccgtggg gctggcgggc    120
accttccgcg ccttcctgtc ctcgcgcctg caggacctgt acagcatcgt gcgccgtgcc    180
gaccgcgcag ccgtgcccat cgtcaacctc aaggacgagc tgctgtttcc cagctgggag    240
gctctgttct caggctctga gggtccgctg aagcccgggg cacgcatctt ctcctttgac    300
ggcaaggacg tcctgaggca ccccacctgg ccccagaaga gcgtgtggca tggctcggac    360
cccaacgggc gcaggctgac cgagagctac tgtgagacgt ggcggacgga ggctccctcg    420
gccacgggcc aggcctcctc gctgctgggg ggcaggctcc tggggcagag tgccgcgagc    480
tgccatcacg cctacatcgt gctctgcatt gagaacagct tcatgactgc ctcc          534
```